US012790315B2

(12) United States Patent
Liu et al.

(10) Patent No.: US 12,790,315 B2
(45) Date of Patent: Nov. 10, 2026

(54) PYRIDYL-CONTAINING COMPOUND

(71) Applicant: CHIA TAI TIANQING PHARMACEUTICAL GROUP CO., LTD., Lianyungang (CN)

(72) Inventors: Fei Liu, Lianyungang (CN); Hongjiang Xu, Lianyungang (CN); Yan Peng, Lianyungang (CN); Wei Shi, Lianyungang (CN); Jiawei Zhou, Lianyungang (CN); Jiajia Gu, Lianyungang (CN)

(73) Assignee: CHIA TAI TIANQING PHARMACEUTICAL GROUP CO., LTD., Lianyungang (CN)

( * ) Notice: Subject to any disclaimer, the term of this patent is extended or adjusted under 35 U.S.C. 154(b) by 304 days.

(21) Appl. No.: 18/703,482

(22) PCT Filed: Oct. 28, 2022

(86) PCT No.: PCT/CN2022/128251
§ 371 (c)(1),
(2) Date: Apr. 22, 2024

(87) PCT Pub. No.: WO2023/072248
PCT Pub. Date: May 4, 2023

(65) Prior Publication Data

US 2025/0002472 A1 Jan. 2, 2025

(30) Foreign Application Priority Data

Oct. 29, 2021 (CN) ......................... 202111269381.X
Mar. 10, 2022 (CN) ......................... 202210233624.2
Jul. 19, 2022 (CN) ......................... 202210849103.X
Oct. 18, 2022 (CN) ......................... 202211274771.0

(51) Int. Cl.

| | |
|---|---|
| ***C07D 401/14*** | (2006.01) |
| ***A61K 31/4439*** | (2006.01) |
| ***A61K 31/444*** | (2006.01) |
| ***A61K 31/4709*** | (2006.01) |
| ***A61K 31/4725*** | (2006.01) |
| ***A61K 31/506*** | (2006.01) |
| ***A61P 35/00*** | (2006.01) |
| ***C07D 413/14*** | (2006.01) |
| ***C07D 471/04*** | (2006.01) |

(52) U.S. Cl.
CPC ........ *C07D 401/14* (2013.01); *A61K 31/4439* (2013.01); *A61K 31/444* (2013.01); *A61K 31/4709* (2013.01); *A61K 31/4725* (2013.01); *A61K 31/506* (2013.01); *A61P 35/00* (2018.01); *C07D 413/14* (2013.01); *C07D 471/04* (2013.01)

(58) Field of Classification Search
CPC .................................................... C07D 401/14
See application file for complete search history.

(56) References Cited

FOREIGN PATENT DOCUMENTS

| | | | |
|---|---|---|---|
| CN | 105339358 | A | 2/2016 |
| CN | 110592141 | A | 12/2019 |
| CN | 112538069 | A | 3/2021 |
| CN | 112566902 | A | 3/2021 |
| CN | 113045550 | A | 6/2021 |
| CN | 113248474 | A | 8/2021 |
| JP | 2016-522266 | A | 7/2016 |
| WO | 2013/019548 | A1 | 2/2013 |
| WO | 2014/144772 | A1 | 9/2014 |
| WO | 2017/117529 | A1 | 7/2017 |
| WO | 2020/092965 | A1 | 5/2020 |
| WO | 2021/252900 | A1 | 12/2021 |

OTHER PUBLICATIONS

Dec. 16, 2022 International Search Report issued in International Patent Application No. PCT/CN2022/128251.
Crochiere et al., "A method for quantification of exportin-1 (XPO1) occupancy by Selective Inhibitor of Nuclear Export (SINE) compounds", Oncotarget, vol. 7, No. 2, pp. 1863-1877.
M. Nazaki et al., Medicinal Chemistry., 1st Edition, Kagaku Dojin Co., LTD., 1995, pp. 98-99.

*Primary Examiner* — Golam M Shameem
(74) *Attorney, Agent, or Firm* — Oliff PLC

(57) ABSTRACT

A pyridyl-containing compound represented by formula I and a preparation method therefor, and the use thereof in the preparation for a drug for treating tumors.

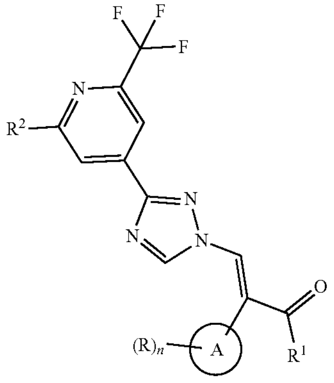

I

20 Claims, No Drawings

PYRIDYL-CONTAINING COMPOUND

CROSS-REFERENCE TO RELATED APPLICATIONS

The present application claims the benefits and priority of the Chinese Patent Application No. 202111269381.X filed with China National Intellectual Property Administration on Oct. 29, 2021, the Chinese Patent Application No. 202210233624.2 filed with China National Intellectual Property Administration on Mar. 10, 2022, the Chinese Patent Application No. 202210849103.X filed with China National Intellectual Property Administration on Jul. 19, 2022, and the Chinese Patent Application No. 202211274771.0 filed with China National Intellectual Property Administration on Oct. 18, 2022, the content of each of which is incorporated herein by reference in its entirety.

TECHNICAL FIELD

The present application belongs to the field of pharmaceutical chemistry, provides a pyridinyl-containing compound (an exportin inhibitor) and a preparation method therefor, and relates to use thereof for preparing a medicament for treating tumors.

BACKGROUND

Exportin-1 (also known as CRM-1 and XPO-1) has become a key "carrier" protein for transporting some crucial growth-regulatory proteins and tumor suppressor factors from the nucleus to the cytoplasm of eukaryotic cells. When efflux of the exportin-1 becomes abnormally high (e.g., due to the production of overexpressed XPO-1), depletion of these nuclear regulator factors can trigger a wide variety of diseases.

XPO1 is the sole nuclear export factor transporting tumor suppressor factors (e.g., p53, p27, FOXO1, and IkB), and it is overexpressed in various solid tumors and hematological malignant tumors (e.g., GBM, ovarian cancer, pancreatic cancer, cervical cancer, AML, MM, CLL, and NHL). Here, the main key point of XPO1 for carcinogenesis is overexpression of the XPO1 protein in multiple types of cancer cells, and its association with the proliferated cell cycle, depleting tumor suppressor proteins (e.g., p53, p27, FOXO1, and IkB) in the cell nucleus, which allows growth of cancer cells (e.g., M. L. Crochiere et al., Oncotarget v.7, pages 1863-1877 (2015)). Generally, selective inhibitor of nuclear export (SINE) compounds are a class of small molecules that inhibit nuclear export of cargo proteins by covalently binding to cysteine at position 528 (Cys528) in the cargo-binding pocket of exportin 1 (XPO1, also known as chromosome maintenance protein 1 (CRM1)) and exert anti-proliferative effects. The interaction between XPO1 and the activated small G-protein Ran (Ran-GTP) in the nucleus facilitates the binding to cargo proteins that comprise short amino acid sequences of hydrophobic residues known as a nuclear export signal (NES). According to preclinical results, many inflammatory, neurodegenerative and autoimmune diseases also involve similar pathologies. Thus, for example, glucocorticoids are widely used anti-inflammatory and immunomodulatory drugs, the efficacy/mechanism of action of which is based primarily on the restoration of sufficient steroid-activated glucocorticoid receptors (GRs) to interfere with the overactivity of transcription factors such as NF-κB in the cell nucleus.

Nowadays, although drugs that inhibit diseases caused by excessive efflux of XPO-1 have been demonstrated to have clinical efficacy by the U.S. FDA, new drug therapies are still urgently needed for many diseases.

SUMMARY

The present application provides a compound of formula I, a pharmaceutically acceptable salt thereof, or a stereoisomer thereof:

I

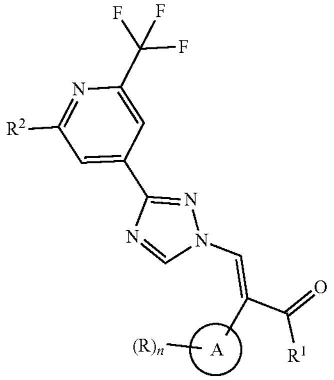

wherein, $R^1$ is selected from the group consisting of —$NH_2$, $C_{1-6}$ alkyl-O—, $C_{1-6}$ alkyl-NH—, and ($C_{1-6}$ alkyl)$_2$N—;

ring A is selected from the group consisting of a $C_{6-10}$ aromatic ring group and a 5- to 10-membered heteroaromatic ring group;

R is selected from the group consisting of halogen, CN, OH, $NH_2$, $C_{1-6}$ alkyl, $C_{1-6}$ alkyl-O—, $C_{1-6}$ alkyl-S—, $C_{1-6}$ haloalkyl-O—, $C_{1-6}$ haloalkyl-S—, $C_{1-6}$ haloalkyl, $C_{1-6}$ alkyl substituted with 3- to 10-membered heterocycloalkyl, $R^a$NH—, and $(R^a)_2$N—;

$R^a$ is selected from the group consisting of $C_{1-6}$ alkyl, $C_{3-10}$ cycloalkyl, and 3- to 10-membered heterocycloalkyl, and $R^a$ is optionally substituted with one or more groups selected from the group consisting of halogen, CN, OH, $NH_2$, $C_{1-6}$ alkyl, $C_{1-6}$ alkyl-O—, and 5 to 6-membered heterocycloalkyl;

n is selected from the group consisting of 0, 1, 2, 3, and 4;

$R^2$ is selected from the group consisting of cyclopropyl and trifluoromethyl.

In some embodiments, $R^1$ is selected from the group consisting of —$NH_2$, $C_{1-4}$ alkyl-O—, $C_{1-4}$ alkyl-NH—, and ($C_{1-4}$ alkyl)$_2$N—.

In some embodiments, $R^1$ is selected from the group consisting of —$NH_2$, $C_{1-3}$ alkyl-O—, $C_{1-3}$ alkyl-NH—, and ($C_{1-3}$ alkyl)$_2$N—.

In some embodiments, $R^1$ is selected from the group consisting of —$NH_2$, isopropyl-O—, and methyl-NH—. In some embodiments, $R^1$ is selected from the group consisting of —$NH_2$ and isopropyl-O—. In some embodiments, $R^1$ is selected from —$NH_2$.

In some embodiments, ring A is selected from the group consisting of phenyl and a 5- to 10-membered heteroaromatic ring group. In some embodiments, ring A is selected from the group consisting of 5-, 6-, 7-, 8-, 9-, and 10-membered heteroaromatic ring groups. In some embodiments, ring A is selected from the group consisting of 5- to 6-membered and 9- to 10-membered heteroaromatic ring groups. In some embodiments, ring A is selected from the group consisting of 6- and 10-membered heteroaromatic ring groups. In some embodiments, ring A is selected from a 10-membered heteroaromatic ring group. In some embodiments, ring A is selected from the group consisting of 5- to 6-membered heteroaromatic ring groups.

In some embodiments, ring A is selected from a 6-membered heteroaromatic ring group.

In some embodiments, ring A is selected from the group consisting of pyrimidinyl, pyridinyl, pyrazolyl, isoxazolyl, oxazolyl, quinolyl, indazolyl, pyridazinyl, thiazolyl, furanyl, pyranyl, thienyl, pyrrolyl, pyrazinyl, isothiazolyl, oxazolyl, indolyl, naphthyridinyl, isoquinolyl, quinazolinyl, and benzofuranyl.

In some embodiments, ring A is selected from the group consisting of pyrimidinyl, pyridinyl, pyrazolyl, isoxazolyl, quinolyl, indazolyl, naphthyridinyl, and isoquinolyl. In some specific embodiments, ring A is selected from the group consisting of pyrimidinyl and pyridinyl; in some specific embodiments, ring A is selected from pyrimidinyl; in some specific embodiments, ring A is selected from pyridinyl; in some specific embodiments, ring A is selected from the group consisting of pyrazolyl and isoxazolyl; in some specific embodiments, ring A is selected from the group consisting of quinolyl, indazolyl, naphthyridinyl, and isoquinolyl; in some specific embodiments, ring A is selected from the group consisting of quinolyl and naphthyridinyl.

In some embodiments, ring A is selected from the group consisting of

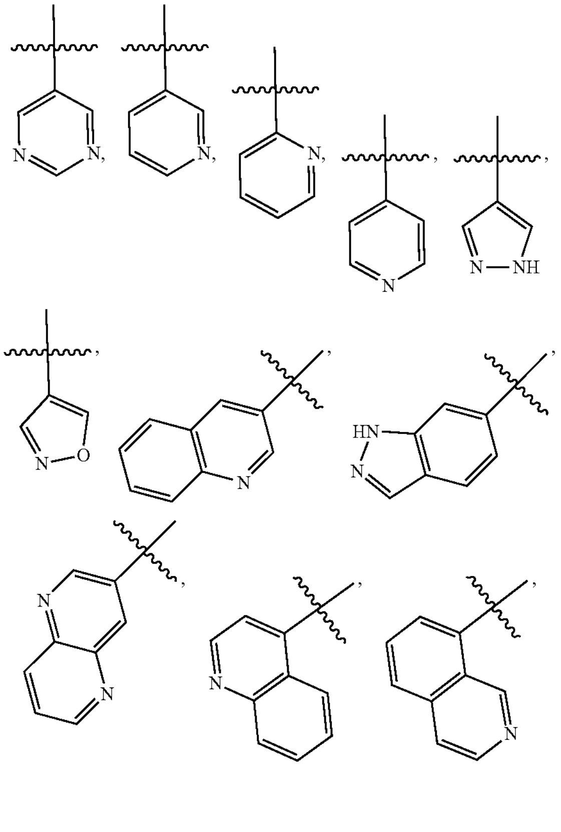

-continued

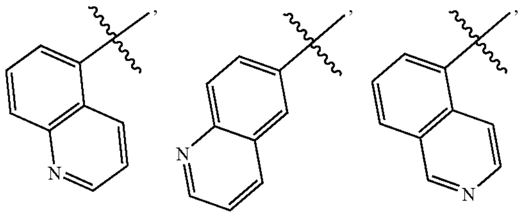

and

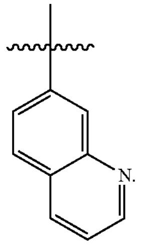

In some embodiments, ring A is selected from the group consisting of

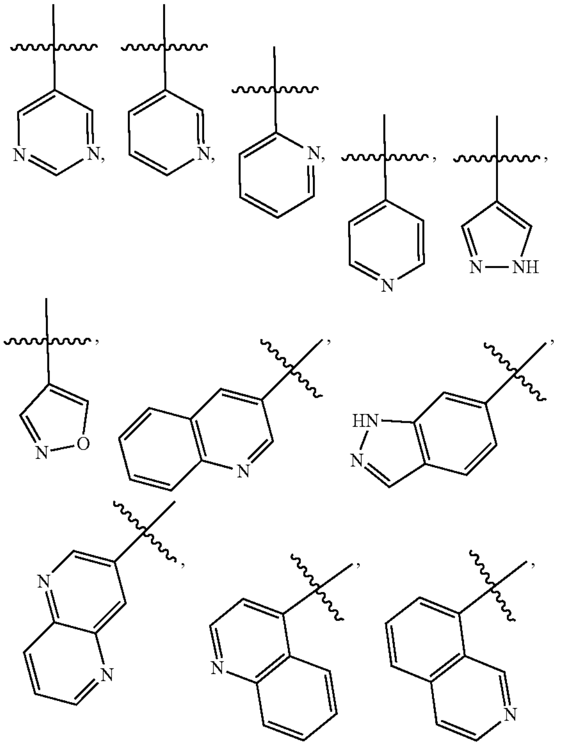

and

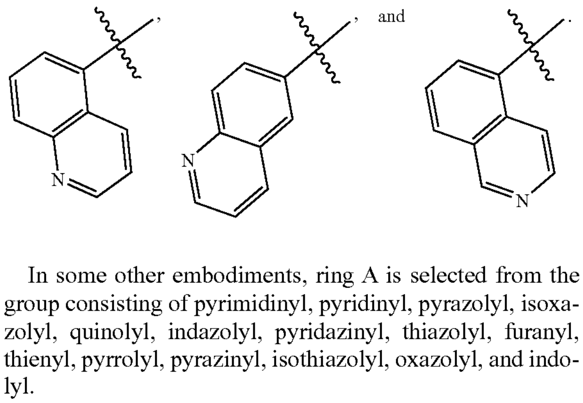

In some other embodiments, ring A is selected from the group consisting of pyrimidinyl, pyridinyl, pyrazolyl, isoxazolyl, quinolyl, indazolyl, pyridazinyl, thiazolyl, furanyl, thienyl, pyrrolyl, pyrazinyl, isothiazolyl, oxazolyl, and indolyl.

In some other embodiments, ring A is selected from the group consisting of pyrimidinyl, pyridinyl, pyrazolyl, isoxazolyl, quinolyl, and indazolyl.

In some other embodiments, ring A is selected from the group consisting of

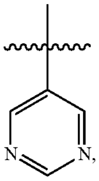,
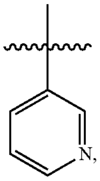,
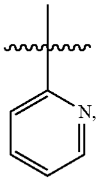,
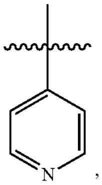,
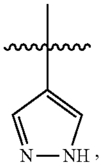,
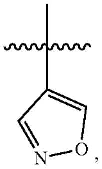,
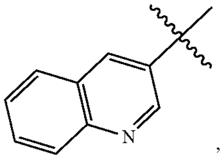, and
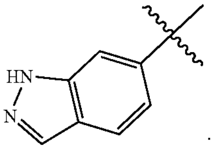.

In some other embodiments, ring A is selected from the group consisting of

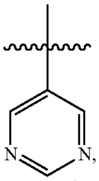,
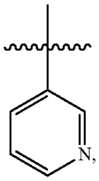,
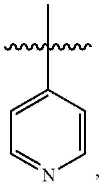,
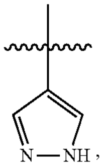,
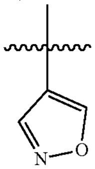,
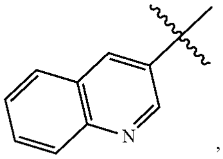, and
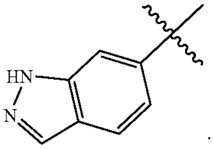.

In some embodiments, R is selected from the group consisting of halogen, CN, OH, $NH_2$, $C_{1-4}$ alkyl, $C_{1-4}$ alkyl-O—, $C_{1-4}$ alkyl-S—, $C_{1-4}$ haloalkyl-O—, $C_{1-4}$ haloalkyl-S—, $C_{1-4}$ haloalkyl, $R^aNH$—, and $(R^a)_2N$—.

In some embodiments, R is selected from the group consisting of halogen, CN, OH, $NH_2$, $C_{1-3}$ alkyl, $C_{1-3}$ alkyl-O—, $C_{1-3}$ alkyl-S—, $C_{1-3}$ haloalkyl-O—, $C_{1-3}$ haloalkyl-S—, $C_{1-3}$ haloalkyl, $R^aNH$—, and $(R^a)_2N$—. In some embodiments, R is selected from the group consisting of fluorine, chlorine, CN, OH, $NH_2$, $C_{1-3}$ alkyl, $C_{1-3}$ alkyl-O—, $C_{1-3}$ haloalkyl, and $R^aNH$—.

In some embodiments, R is selected from the group consisting of fluorine, CN, $NH_2$, methyl, methoxy, trifluoromethyl, and $R^aNH$—.

In some embodiments, $R^a$ is selected from the group consisting of $C_{1-4}$ alkyl, $C_{3-6}$ cycloalkyl, and 3- to 6-membered heterocycloalkyl, and $R^a$ is optionally substituted with one or more groups selected from the group consisting of halogen, CN, OH, $NH_2$, and 5- to 6-membered heterocycloalkyl.

In some embodiments, $R^a$ is selected from the group consisting of $C_{1-3}$ alkyl, $C_{5-6}$ cycloalkyl, and 5- to 6-membered heterocycloalkyl, and $R^a$ is optionally substituted with one or more groups selected from the group consisting of halogen, CN, OH, $NH_2$, and 5- to 6-membered heterocycloalkyl.

In some embodiments, $R^a$ is selected from the group consisting of $C_{1-3}$ alky and 5- to 6-membered heterocycloalkyl, and $R^a$ is optionally substituted with one or more groups selected from the group consisting of halogen, CN, OH, $NH_2$, and 5- to 6-membered heterocycloalkyl.

In some embodiments, $R^a$ is selected from the group consisting of $C_{1-3}$ alkyl and 6-membered heterocycloalkyl, and $R^a$ is optionally substituted with one or more groups selected from the group consisting of fluorine, chlorine, bromine, CN, OH, $NH_2$, and 6-membered heterocycloalkyl.

In some embodiments, $R^a$ is selected from the group consisting of methyl, ethyl, propyl, and tetrahydropyranyl, and $R^a$ is optionally substituted with one or more fluorine or dioxane.

In some embodiments, $R^a$ is selected from the group consisting of $FCH_2CH_2$—, $F_2CHCH_2$—, $F_3CCH_2$—, $CF_3CH(CH_3)$—, $CH_3CF_2CH_2$—, tetrahydropyranyl, and dioxane-$CH_2$—.

In some embodiments, R is selected from the group consisting of fluorine, CN, $NH_2$, methyl, methoxy, trifluoromethyl,

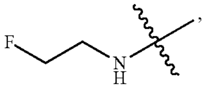,
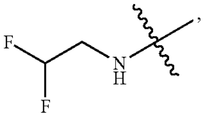,
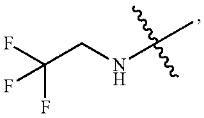,
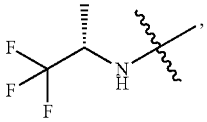,
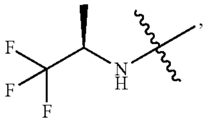,
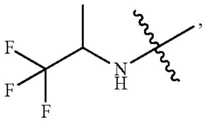,
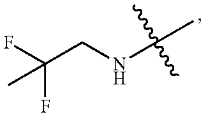,
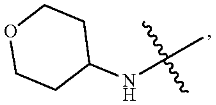,
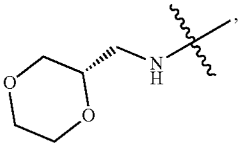,
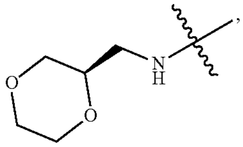, and
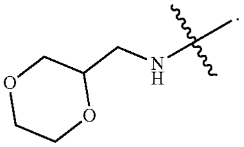.

In some embodiments, n is selected from the group consisting of 0, 1, 2, and 3.

In some embodiments, n is selected from the group consisting of 0, 1, and 2.

In some embodiments, n is selected from the group consisting of 0 and 1. In some embodiments, n is selected from 0. In some embodiments, n is selected from 1.

In some embodiments, $R^2$ is selected from cyclopropyl.

In some embodiments, structural unit

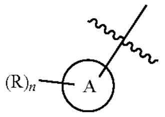

is selected from the group consisting of

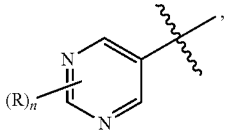 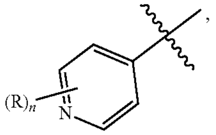

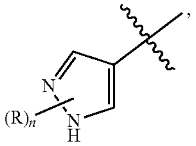 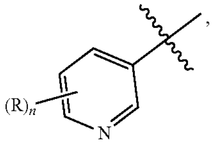

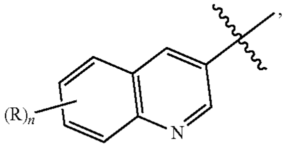 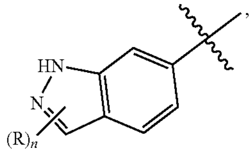

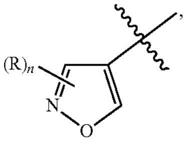 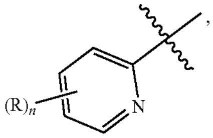

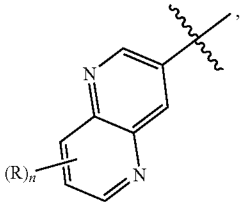 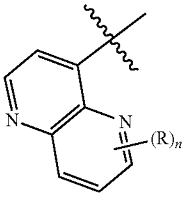 ,

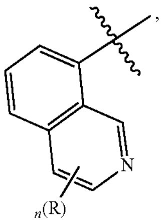 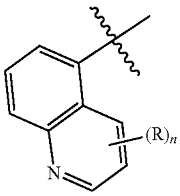 ,

-continued

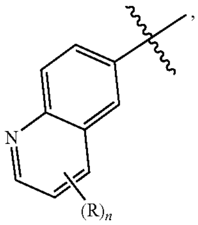 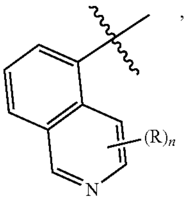 , and

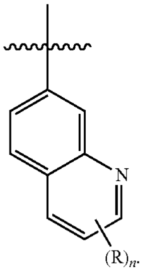

In some embodiments, structural unit

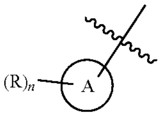

is selected from the group consisting of

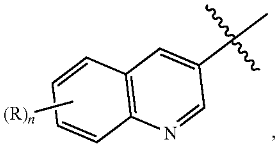 , 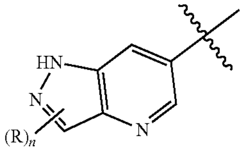 ,

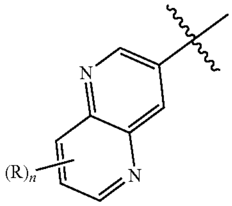 , 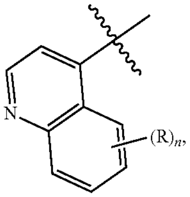

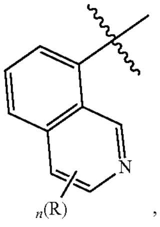 , 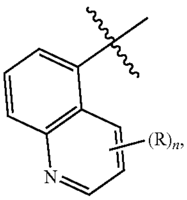

-continued
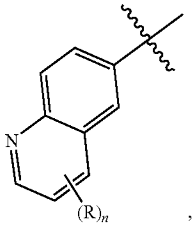
,
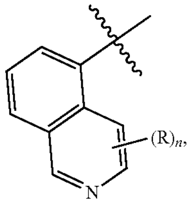
and
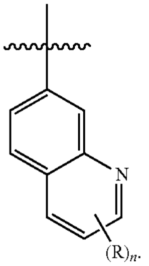
In some embodiments, structural unit
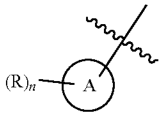
is selected from the group consisting of
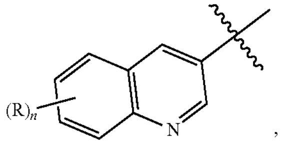
,
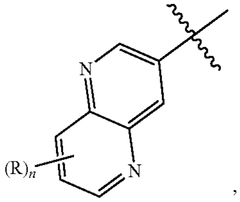
,
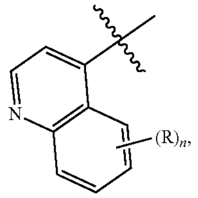
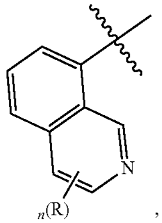
,
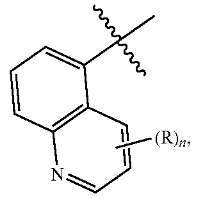
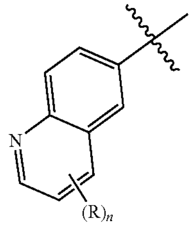
,
-continued
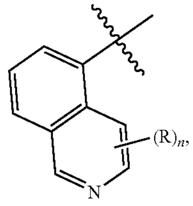
and
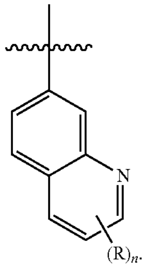
In some embodiments, structural unit
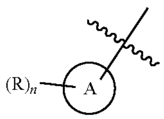
is selected from the group consisting of
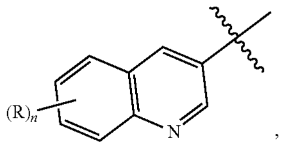
,
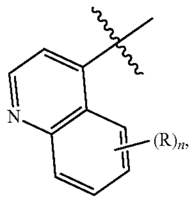
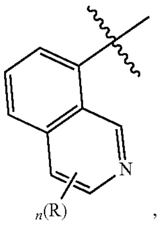
,
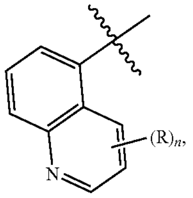
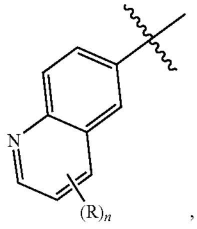
,
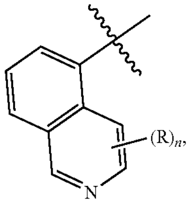
and
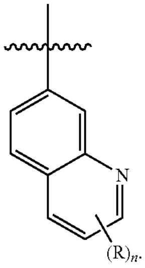

In some embodiments, structural unit
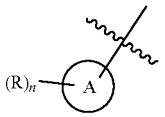
is selected from
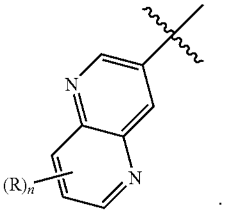
In some embodiments, structural unit
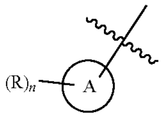
is selected from the group consisting of
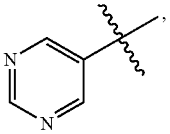,
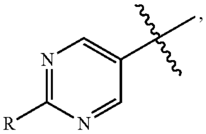,
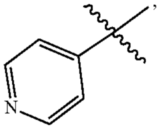,
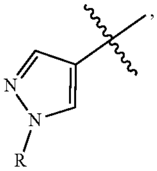,
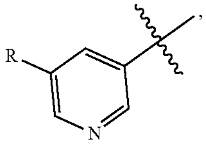,
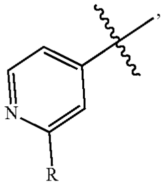,
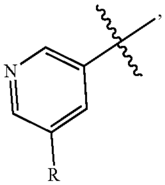,
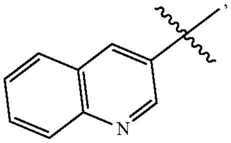,
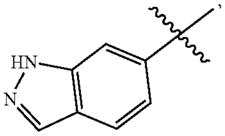,
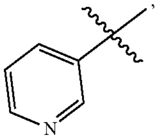,
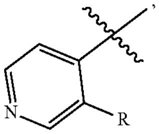,
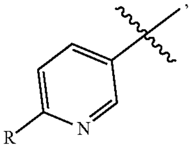,
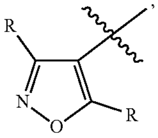,
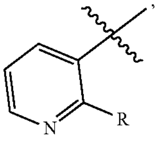,
-continued
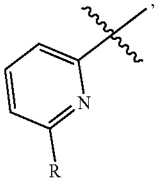,
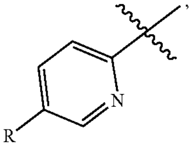,
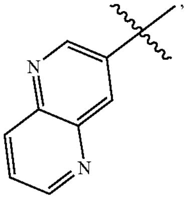,
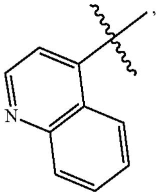,
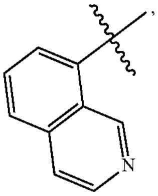,
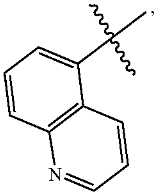,
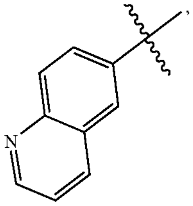,
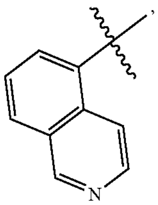, and
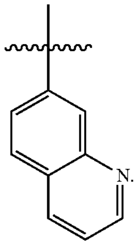.
In some embodiments, structural unit
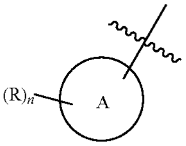
is selected from the group consisting of
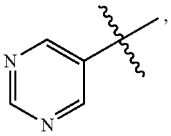,
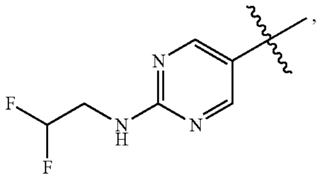,
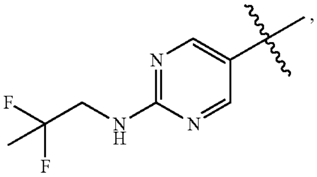,
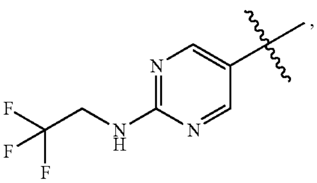, -continued
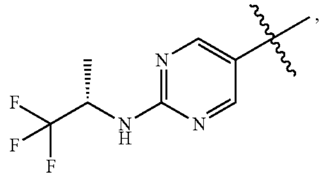,
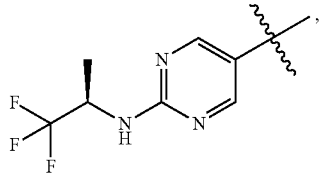,
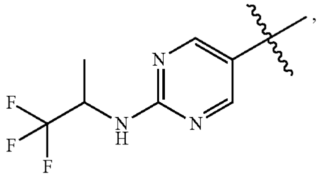, 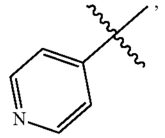,
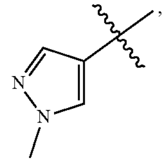, 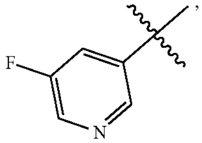, 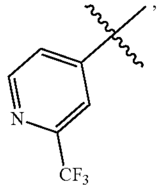,
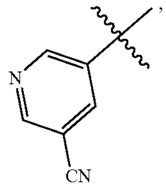, 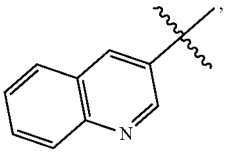,
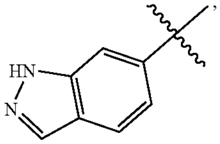, 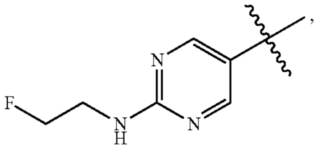,
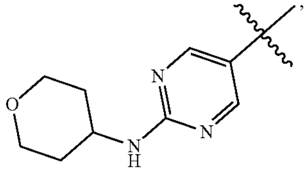,
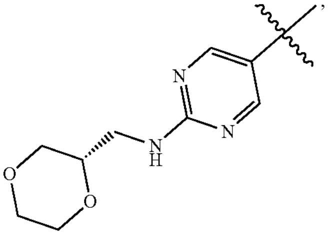,
-continued
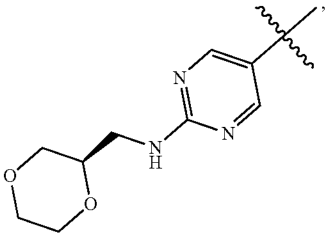,
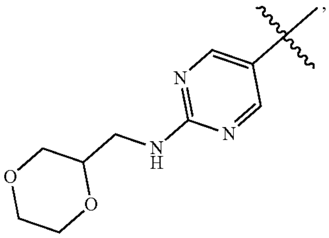, 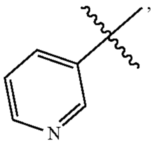,
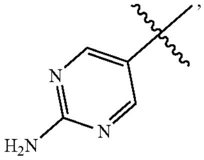, 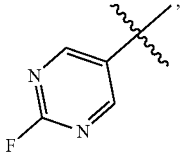,
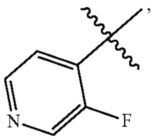, 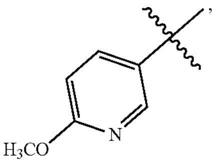,
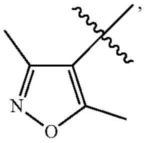, 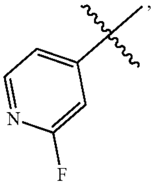, 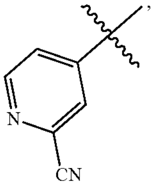,
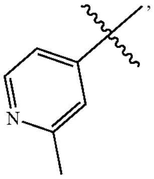, 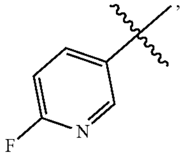, 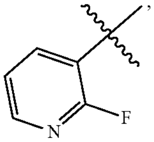,
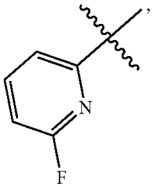, 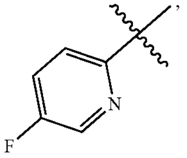, 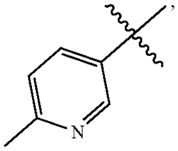,
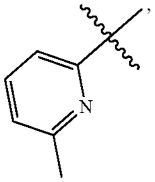, 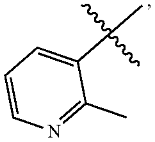, -continued
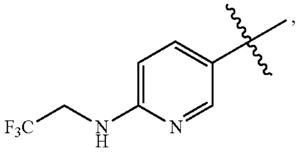
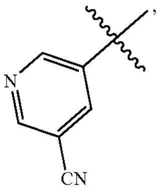
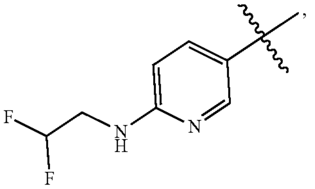
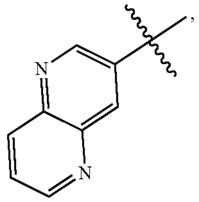
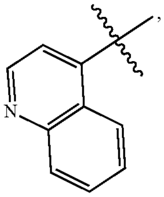
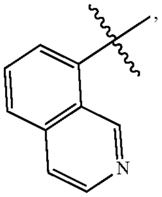
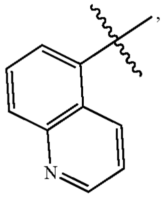
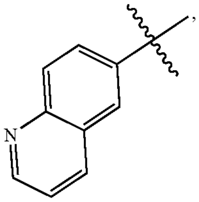
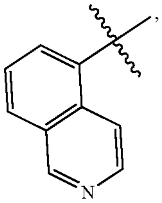
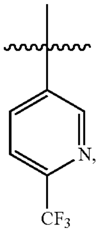
and
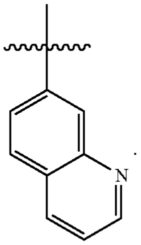
In some other embodiments, structural unit
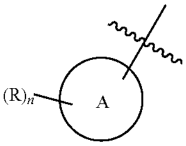
is selected the group consisting of
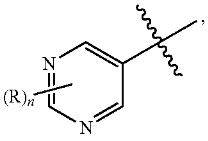
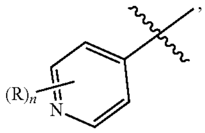
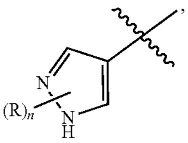
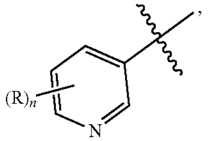
-continued
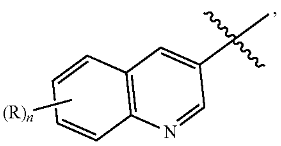
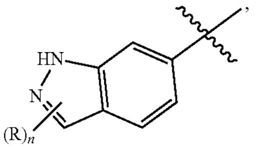
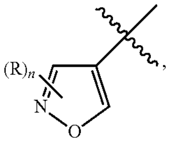
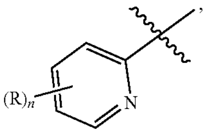
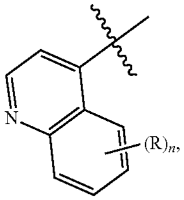
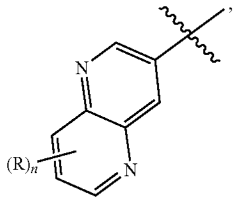
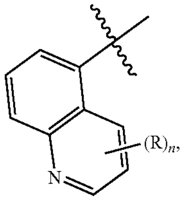
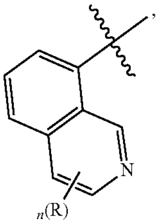
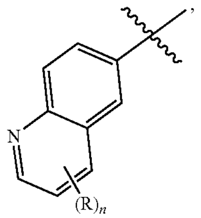
and
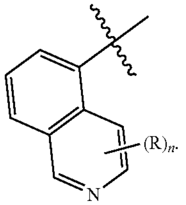
In some other embodiments, structural unit
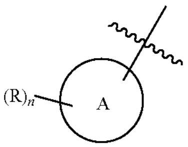

is selected from the group consisting of
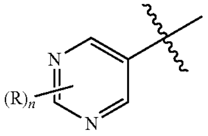,
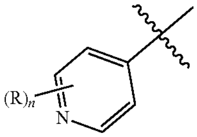,
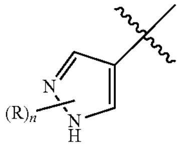,
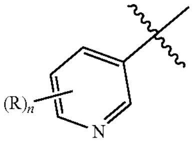,
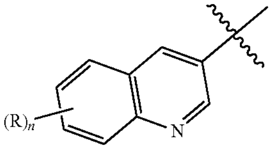,
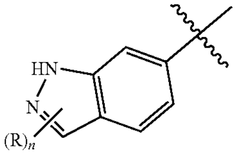,
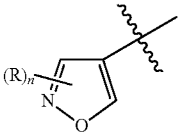, and
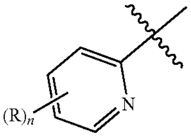.
In some embodiments, structural unit
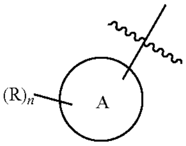
is selected from the group consisting of
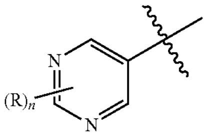,
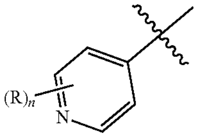,
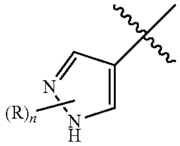,
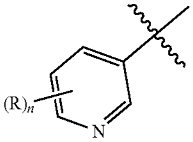,
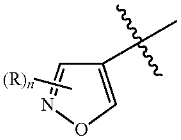, and
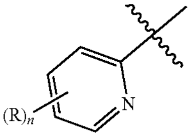.
In some embodiments, structural unit
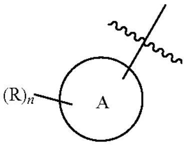
is selected from the group consisting of
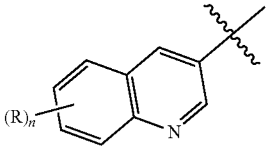,
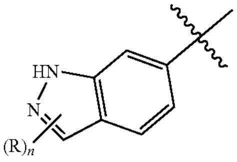,
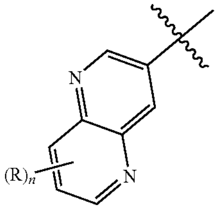,
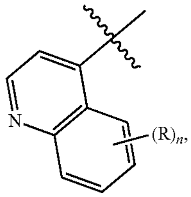
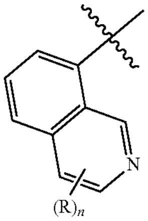,
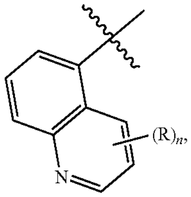
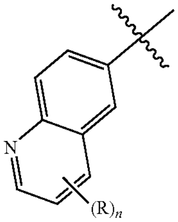, and
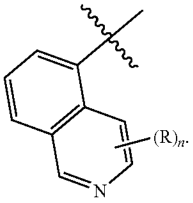
In some embodiments, structural unit
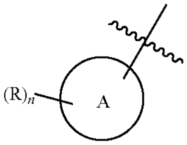
is selected from the group consisting of
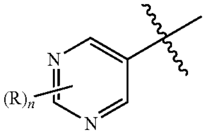,
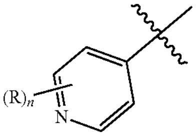,
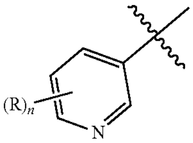, and
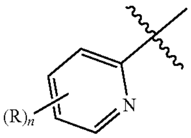.

In some embodiments, structural unit
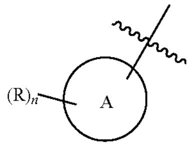
is selected from
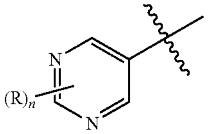
.
In some embodiments, structural unit
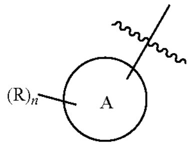
is selected from
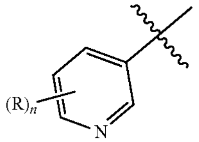
.
In some embodiments, structural unit
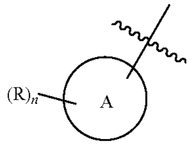
is selected from the group consisting of
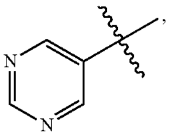,
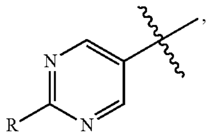,
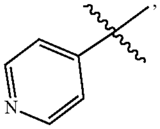,
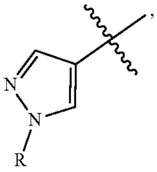,
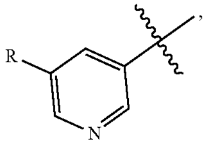,
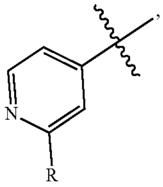,
-continued
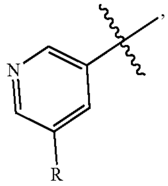,
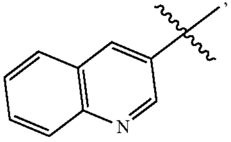,
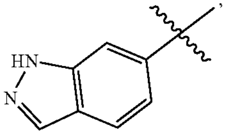,
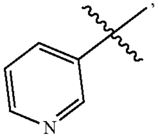,
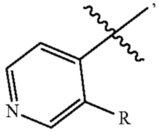,
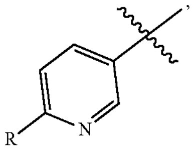,
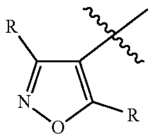,
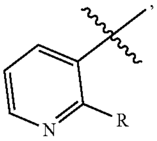,
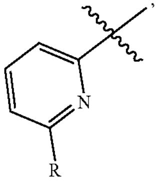,
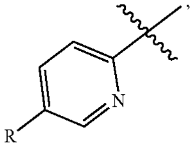,
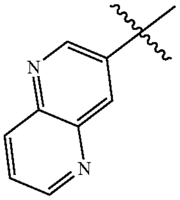,
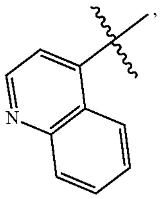,
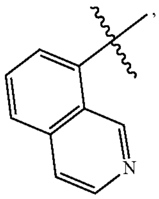,
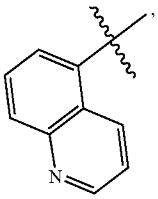,
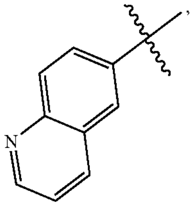, and
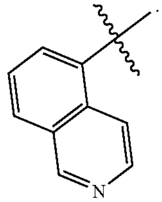.
In some other embodiments, structural unit
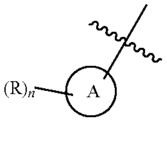
is selected from the group consisting of
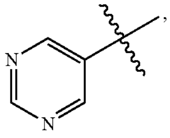,
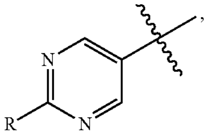,
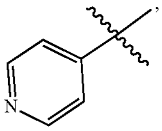, -continued
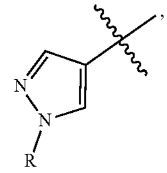
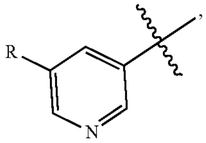
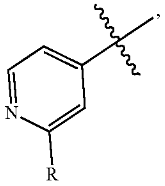
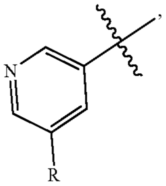
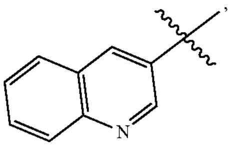
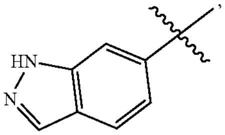
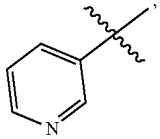
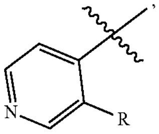
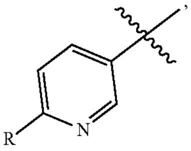
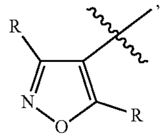
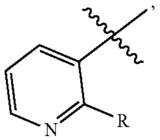
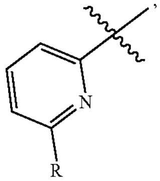
and
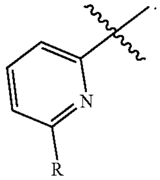
In some embodiments structural unit
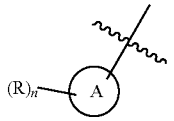
is selected from the group consisting of
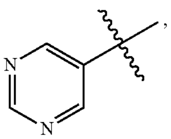
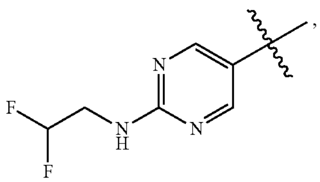
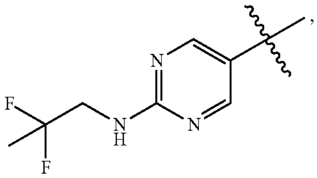
-continued
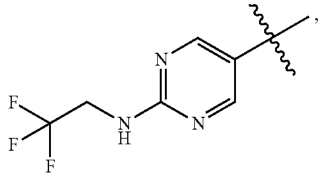
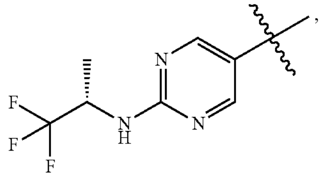
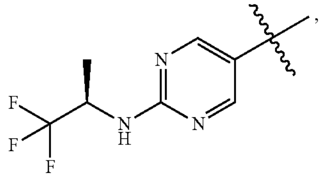
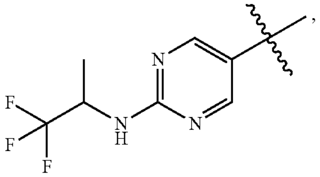
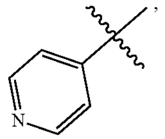
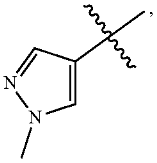
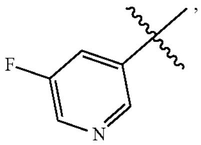
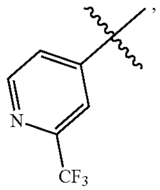
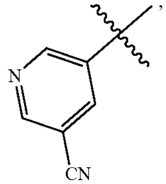
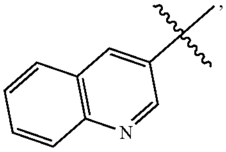
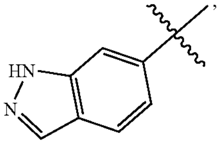
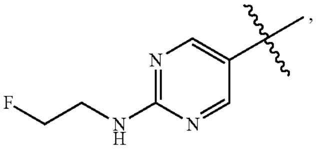
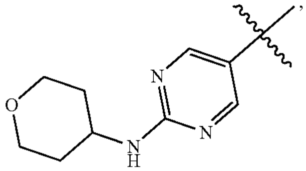
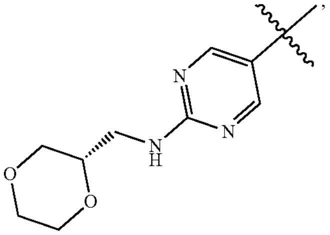

-continued
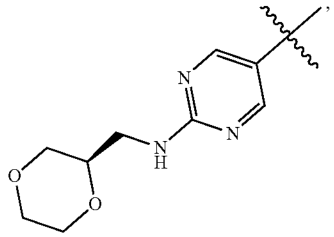
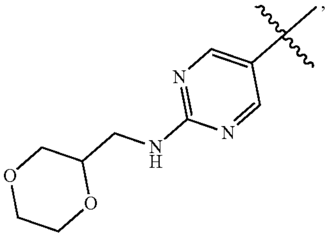
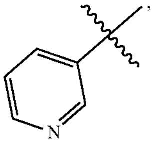
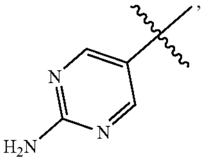
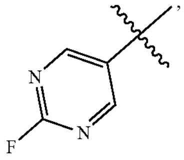
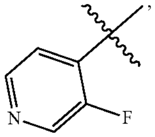
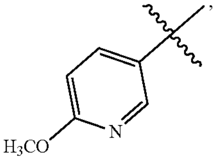
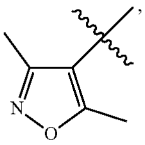
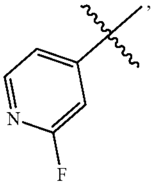
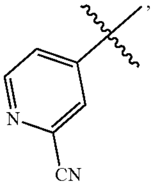
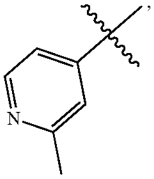
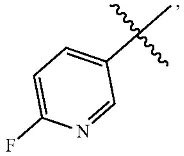
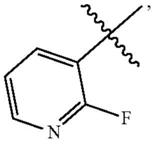
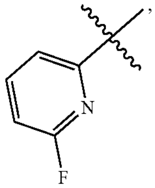
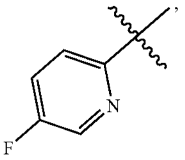
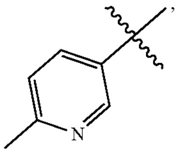
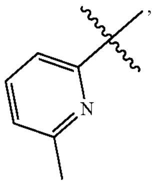
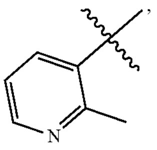
-continued
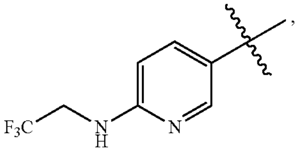
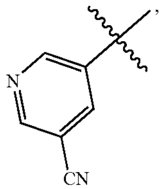
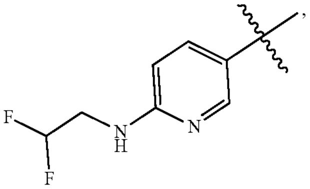
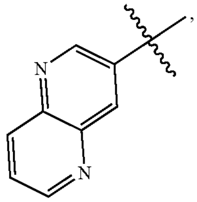
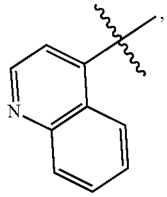
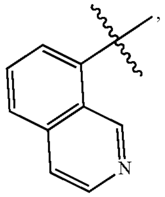
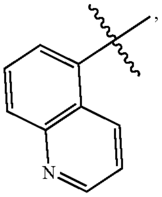
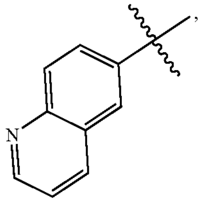
and
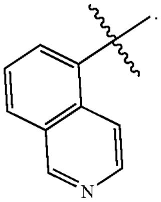
In some other embodiments, structural unit
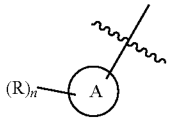
is selected from the group consisting of
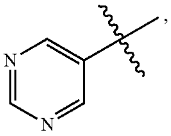
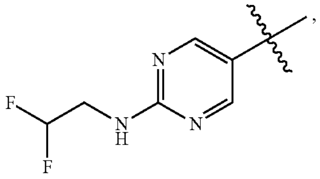
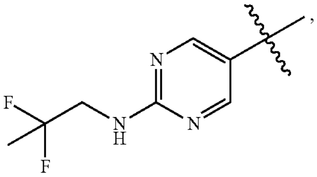

-continued
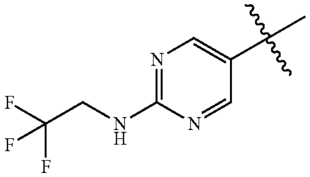,
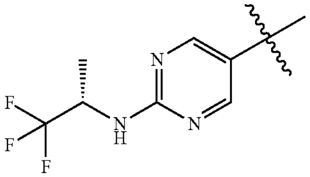,
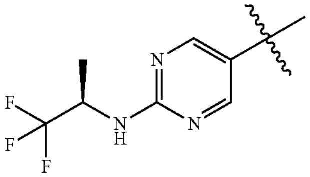,
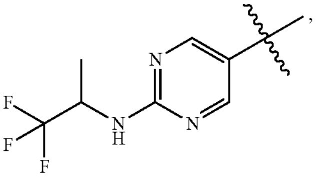,
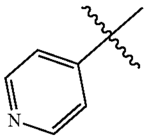,
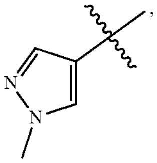,
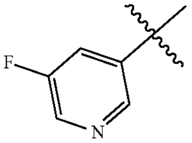,
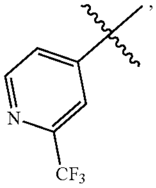,
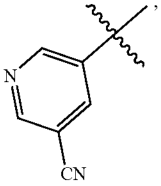,
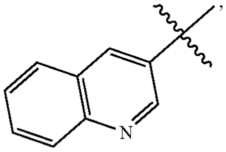,
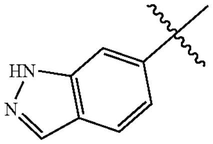,
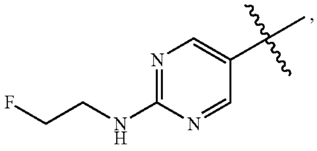,
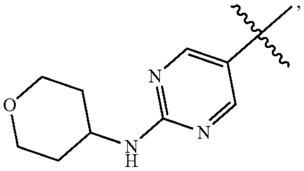,
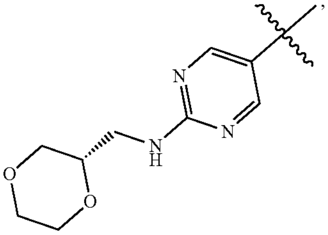,
-continued
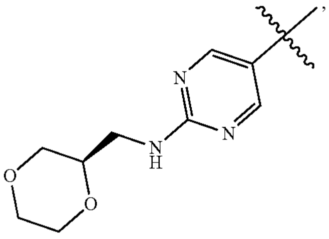,
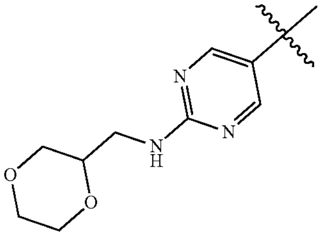,
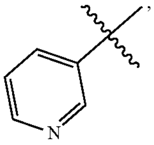,
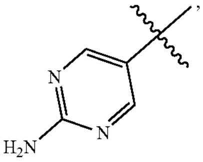,
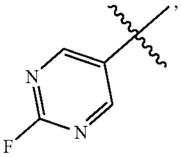,
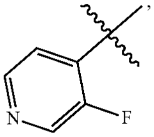,
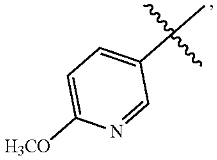,
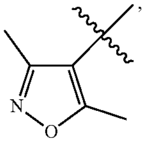,
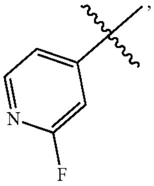,
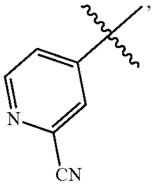,
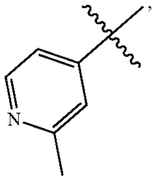,
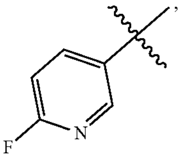,
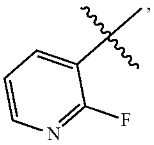,
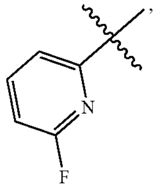,
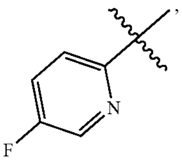,
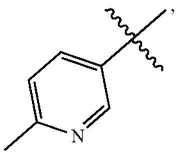,
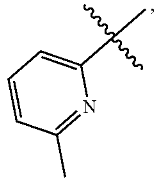,
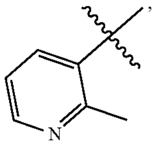, and -continued

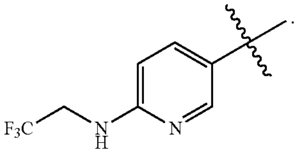

In some other embodiments, structural unit

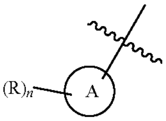

is selected from the group consisting of

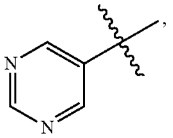
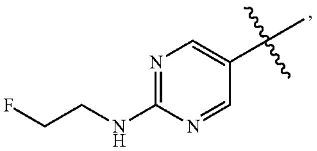
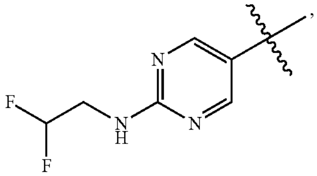
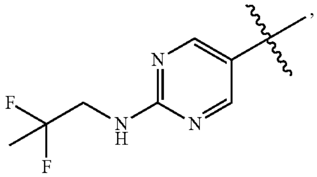
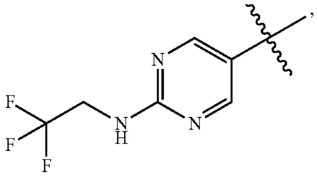
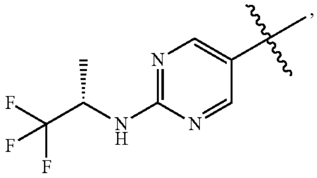
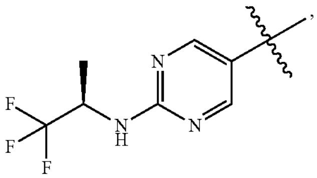

-continued

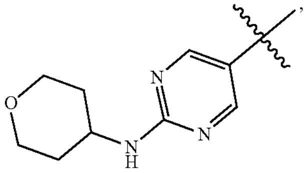
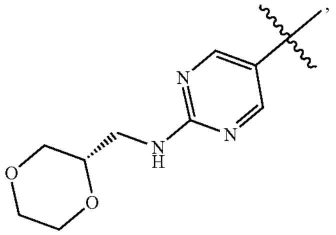
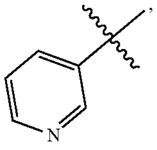
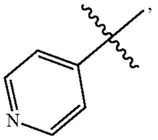
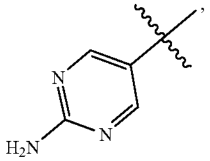
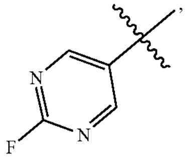
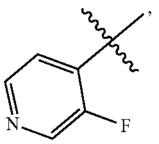
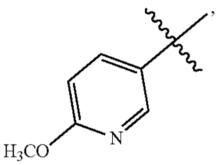
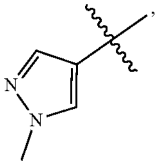
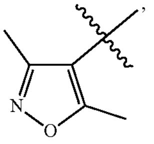
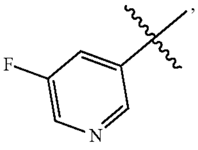
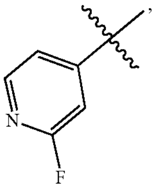
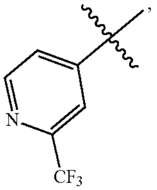
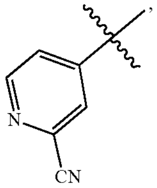
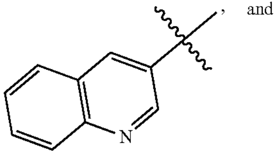

and

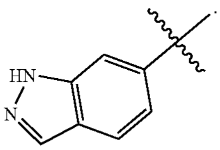

In some embodiments, the compound of formula I, the pharmaceutically acceptable salt thereof, or the stereoisomer thereof is selected from the group consisting of a compound of formula I-1 or I-2, a pharmaceutically acceptable salt thereof, or a stereoisomer thereof,

I-1

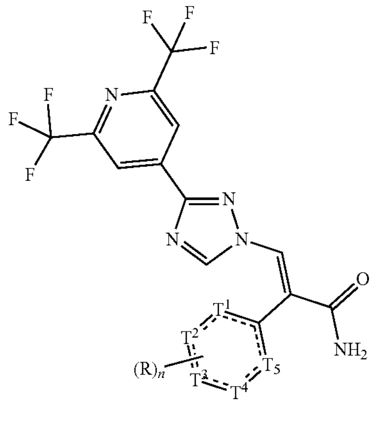

I-2

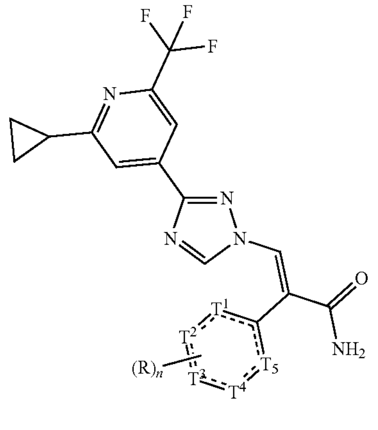

wherein R and n are as described in the present application;

$T^1$, $T^2$, $T^3$, $T^4$, and $T^5$ are each independently selected from the group consisting of a bond, O, S, N, and CH, no more than one of which is selected from a bond and at least one of which is selected from N;

 represents a single bond or double bond.

In some embodiments, $T^1$, $T^2$, $T^3$, $T^4$, and $T^5$ are each independently selected from the group consisting of N and CH, at least one of which is selected from N.

In some embodiments, $T^2$ and $T^4$ are selected from N, and $T^1$, $T^3$, and $T^5$ are selected from CH.

In some embodiments, $T^3$ is selected from N, and $T^1$, $T^2$, $T^4$, and $T^5$ are selected from CH.

In some embodiments, $T^2$ is selected from N, and $T^1$, $T^3$, $T^4$, and $T^5$ are selected from CH.

In some embodiments, structural unit

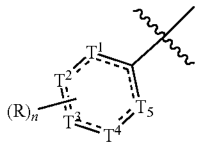

is selected from

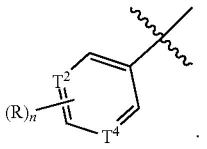

In some embodiments, structural unit

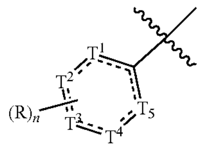

is selected from

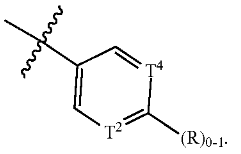

In some embodiments, structural unit

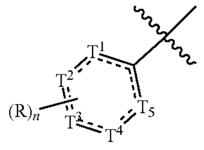

is selected from the group consisting of

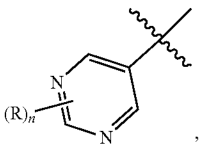 , 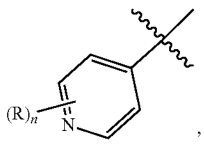 ,

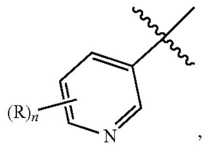 , 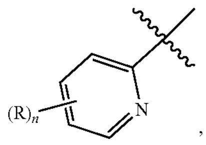 ,

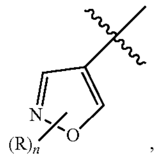 , and 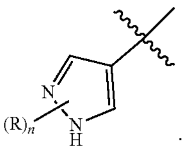 .

In some embodiments, structural unit

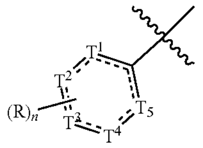

is selected from the group consisting of

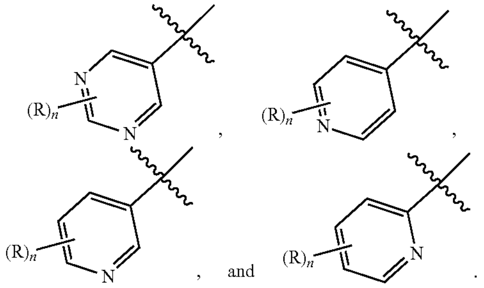

In some embodiments, structural unit

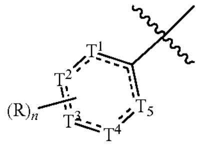

is selected from

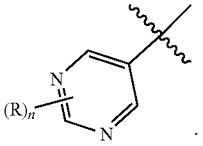

In some embodiments, structural unit

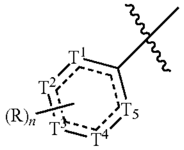

is selected from

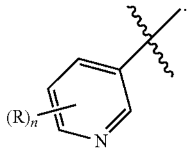

In some embodiments, the present application encompasses the variables defined above and embodiments thereof, as well as any combination thereof.

The heteroatom in the heterocycloalkyl or heteroaromatic ring group described above is selected from the group consisting of nitrogen, oxygen, and sulfur, and the remaining ring atoms are selected from carbon. The heteroatom in the heterocycloalkyl or heteroaromatic ring group described above is selected from the group consisting of nitrogen and oxygen, and the remaining ring atoms are selected from carbon. The heteroatom in the heterocycloalkyl or heteroaromatic ring group described above is selected from nitrogen, and the remaining ring atoms are selected from carbon. In some embodiments, the number of the heteroatom is selected from the group consisting of 1, 2, 3, and 4. In some embodiments, the number of the heteroatom is selected from the group consisting of 1, 2, and 3. In some embodiments, the number of the heteroatom is selected from the group consisting of 1 and 2.

The present application provides compounds, pharmaceutically acceptable salts thereof, or stereoisomers thereof as follows:

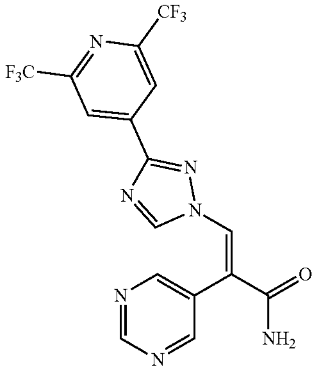

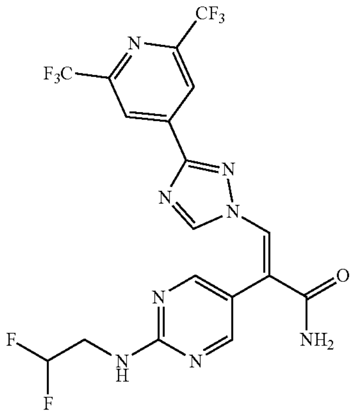

-continued
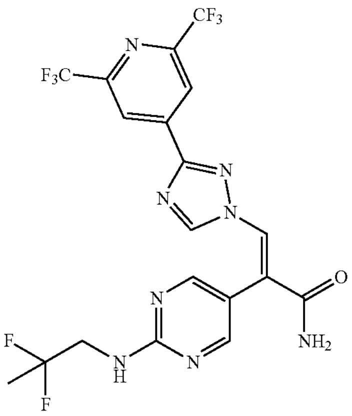
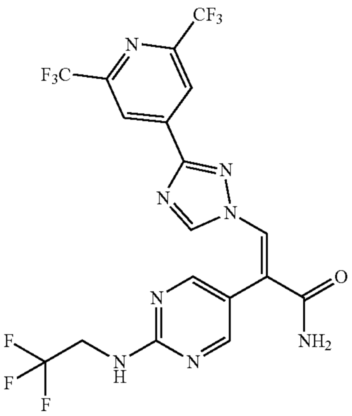
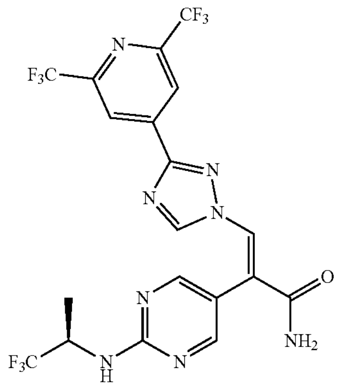
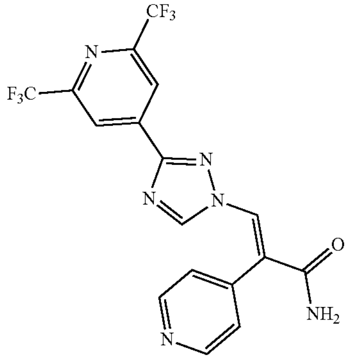
-continued
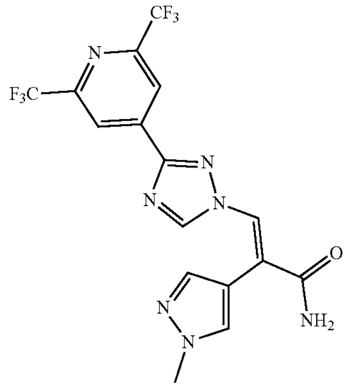
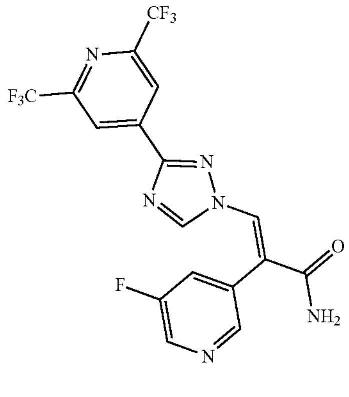
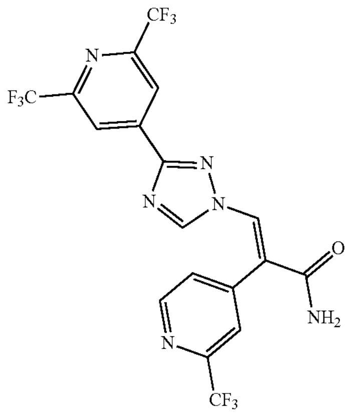
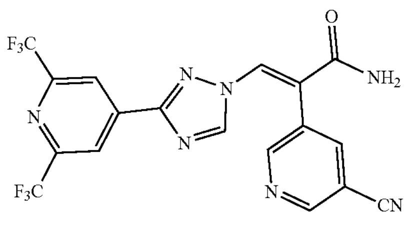

-continued
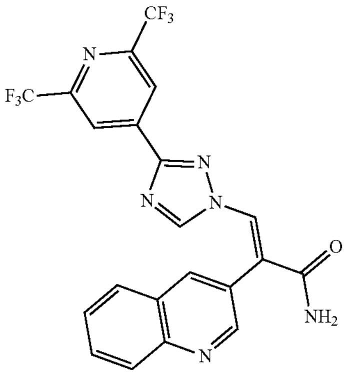
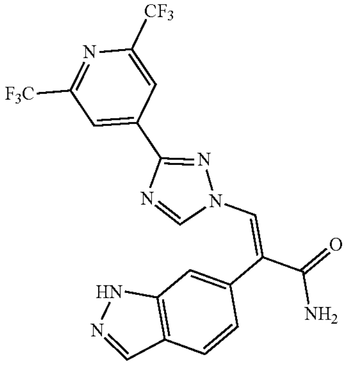
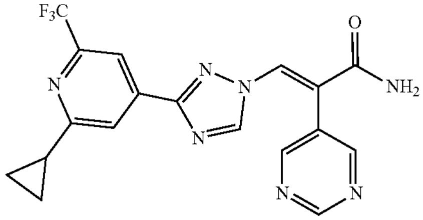
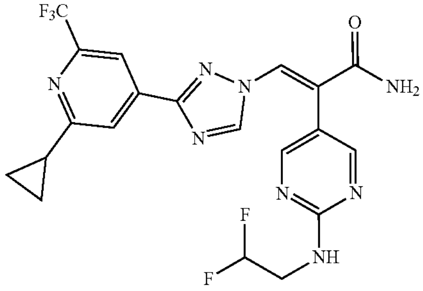
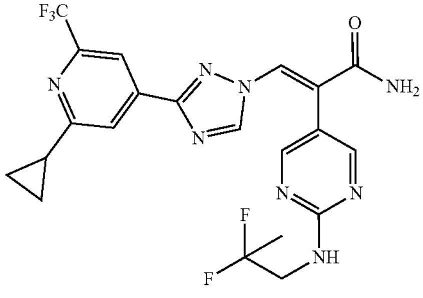
-continued
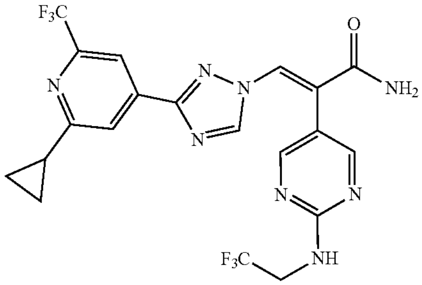
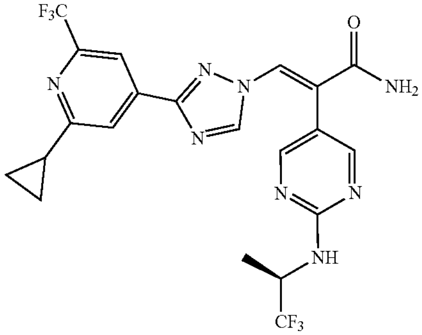
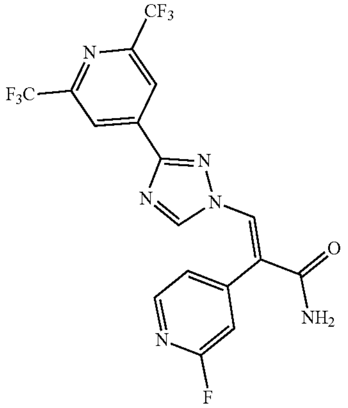
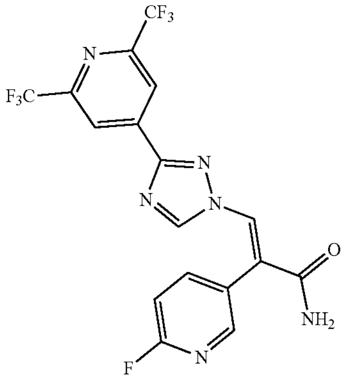

-continued
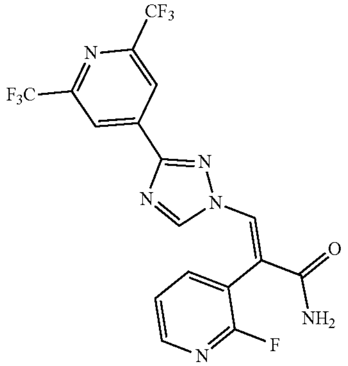
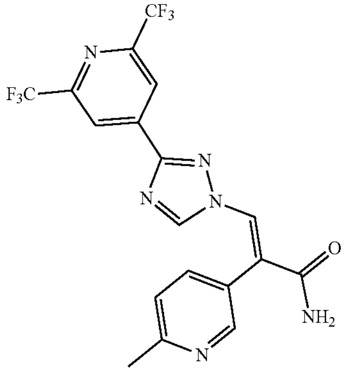
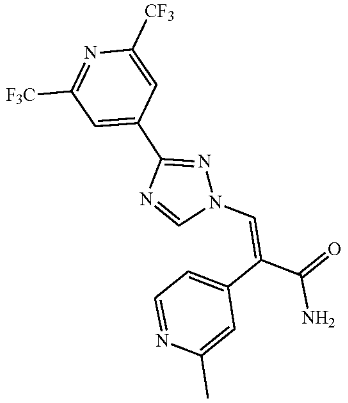
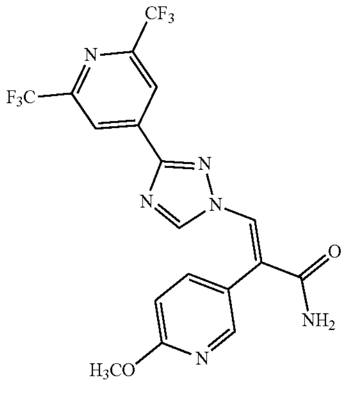
-continued
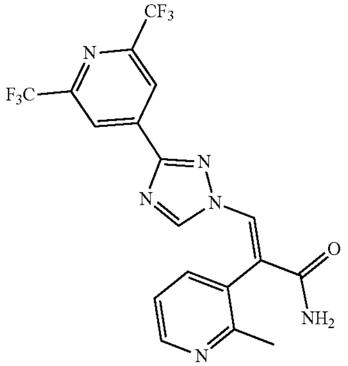
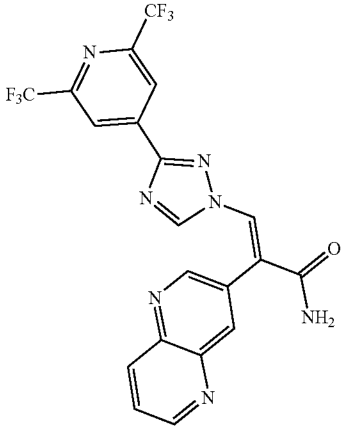
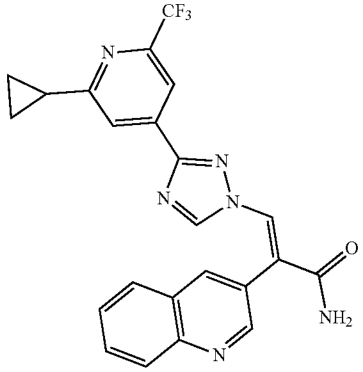
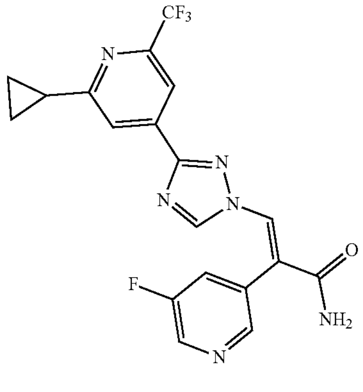

-continued
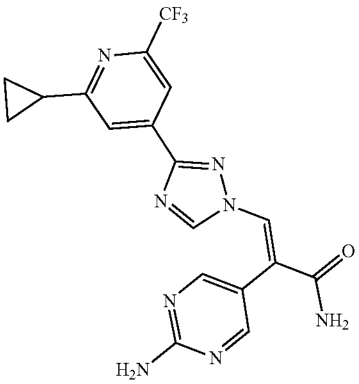
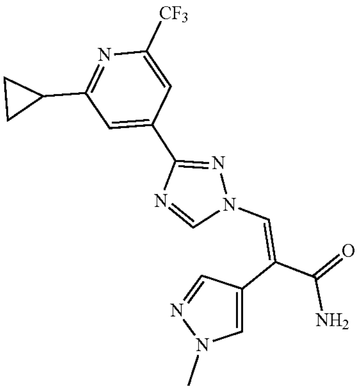
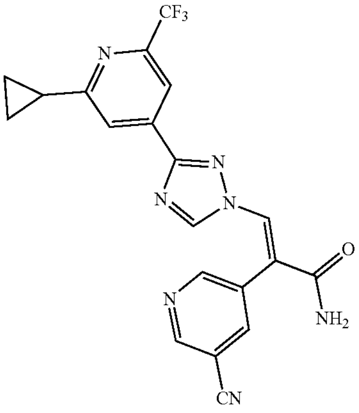
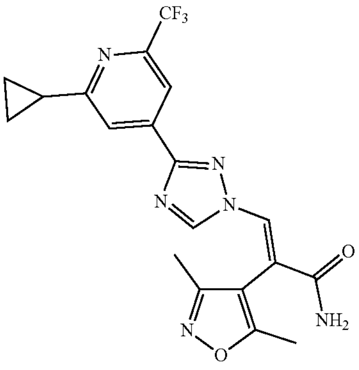
-continued
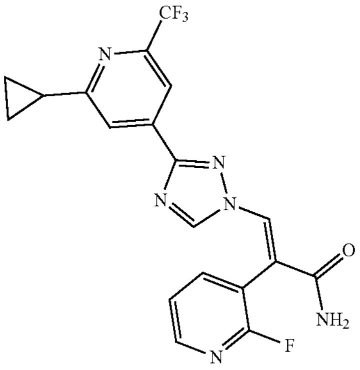
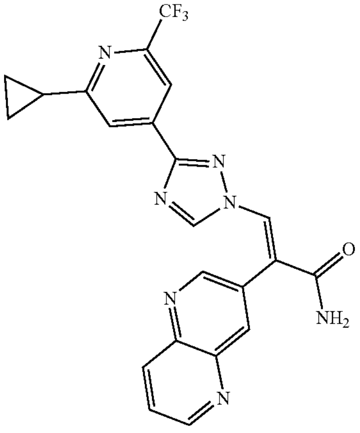
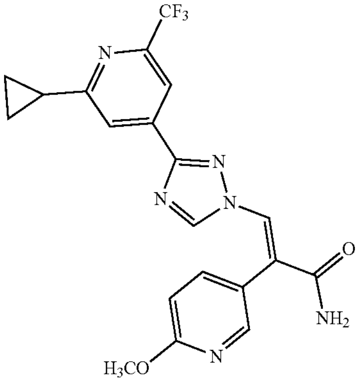
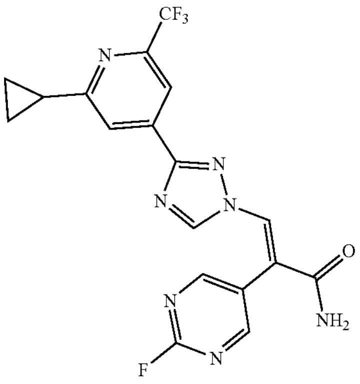

-continued
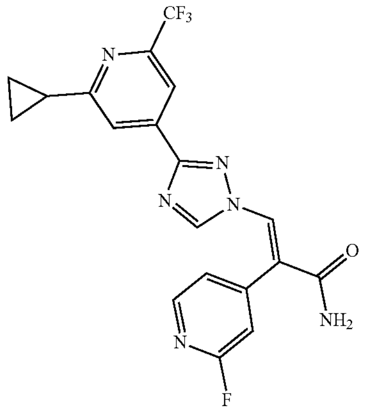
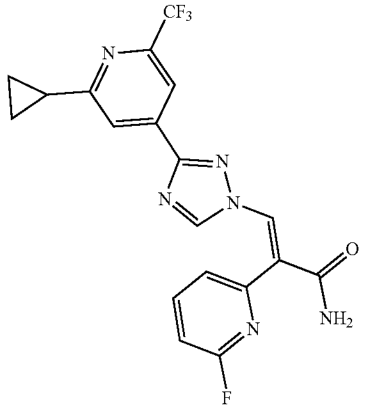
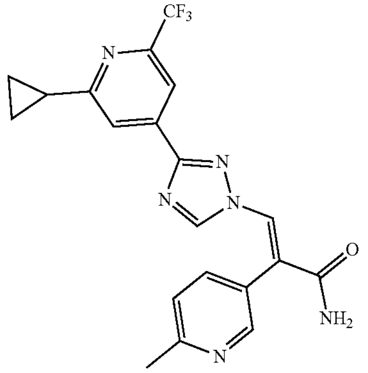
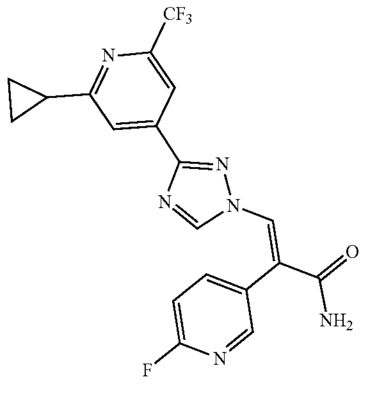
-continued
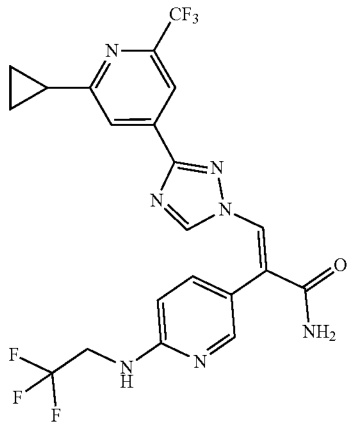
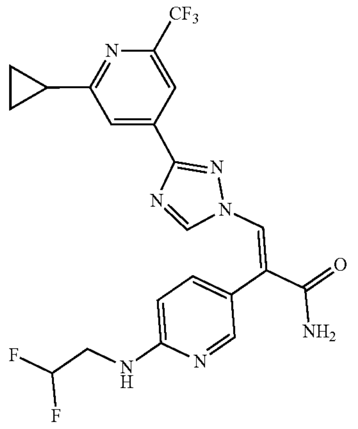
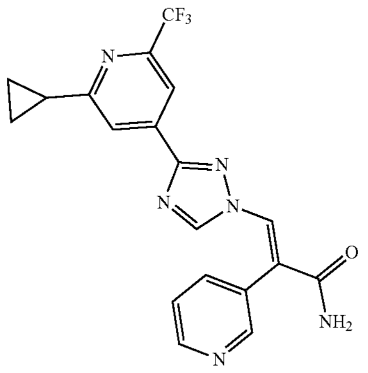
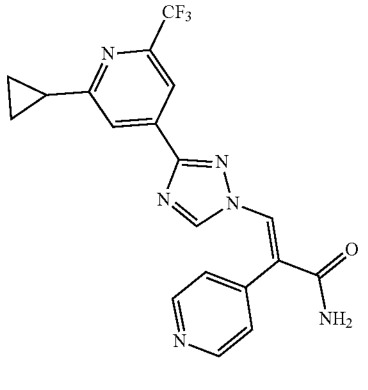

-continued
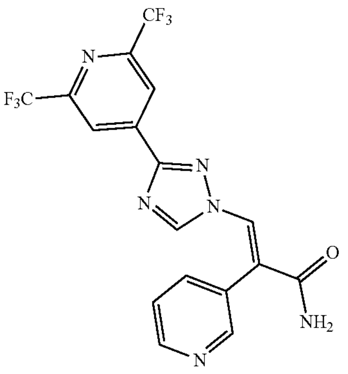
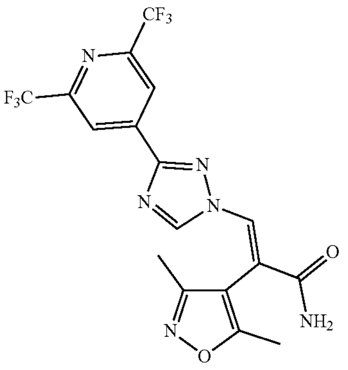
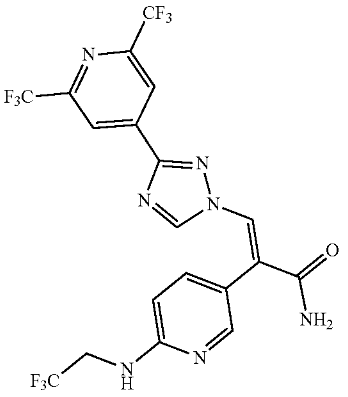
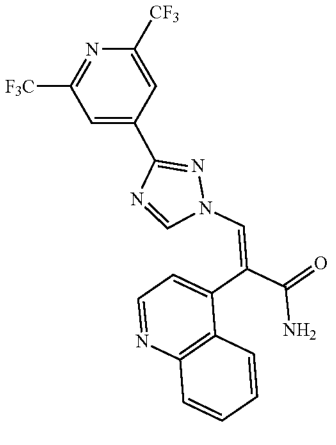
-continued
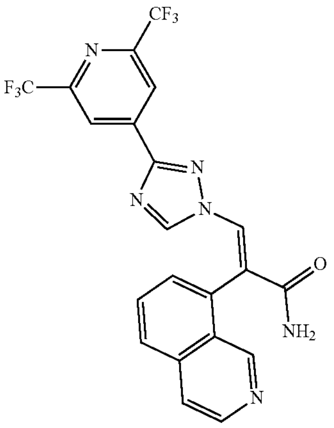
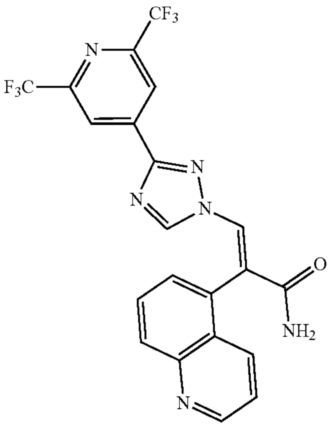
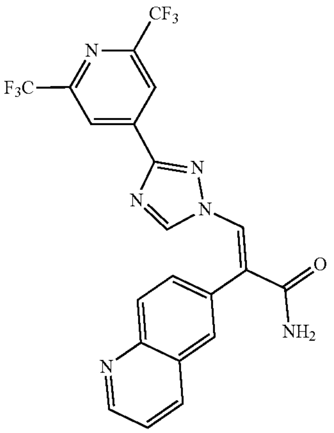
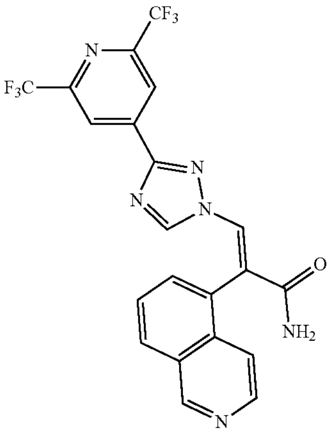

-continued
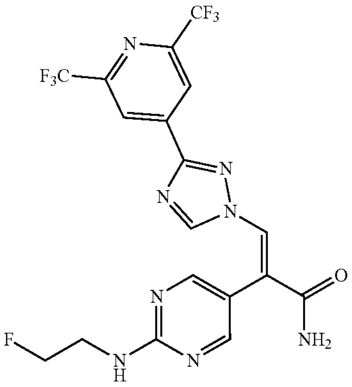
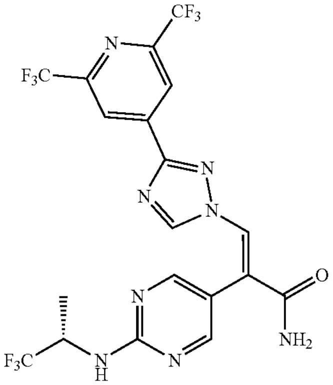
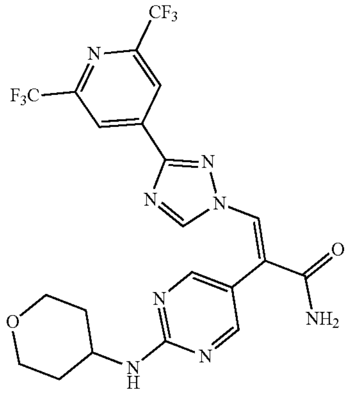
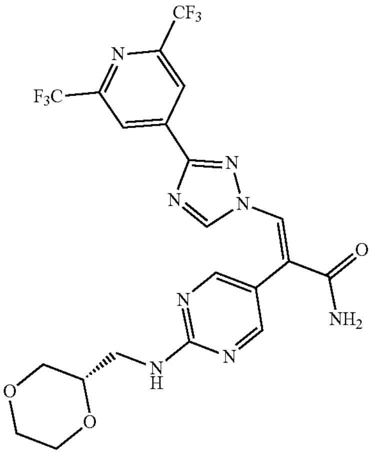
-continued
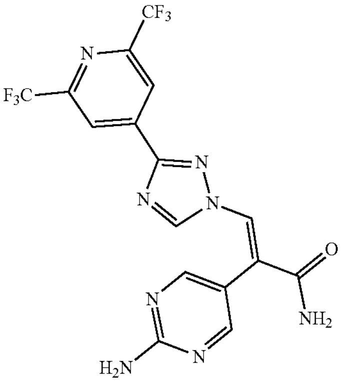
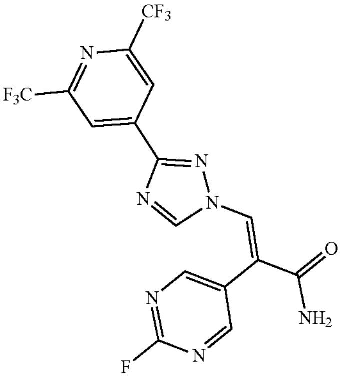
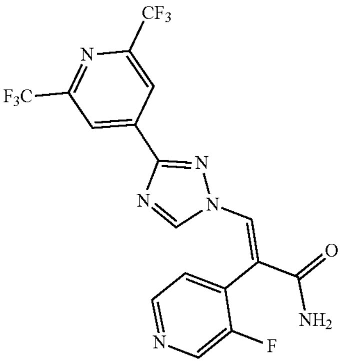
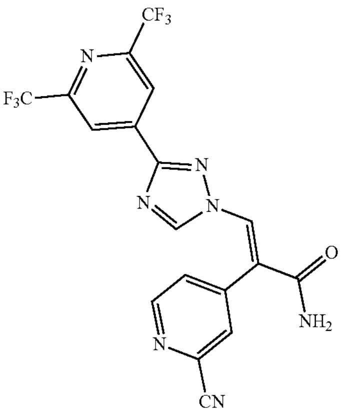

-continued
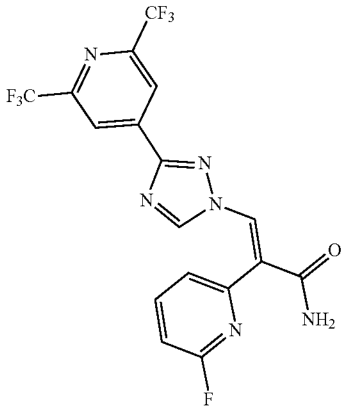
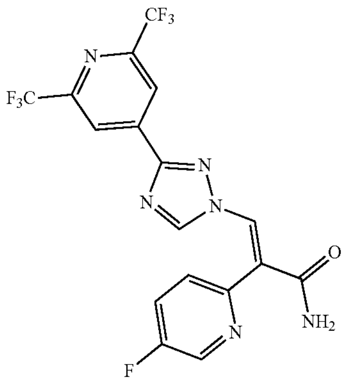
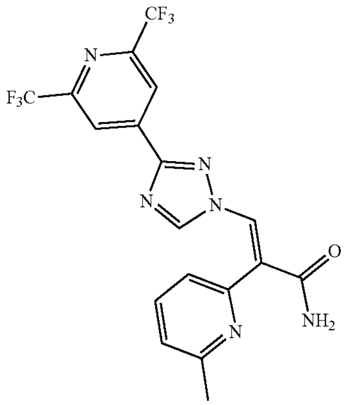
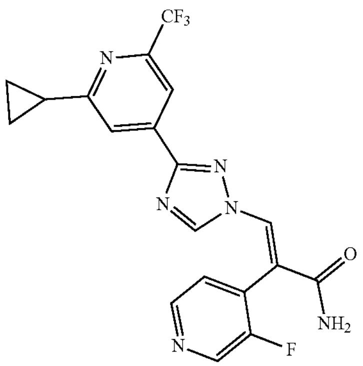
-continued
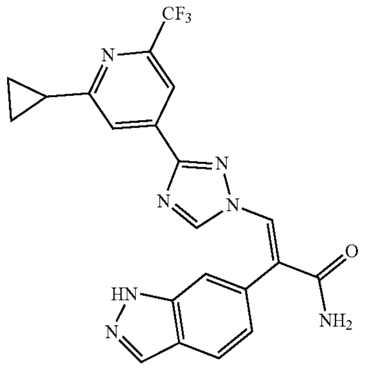
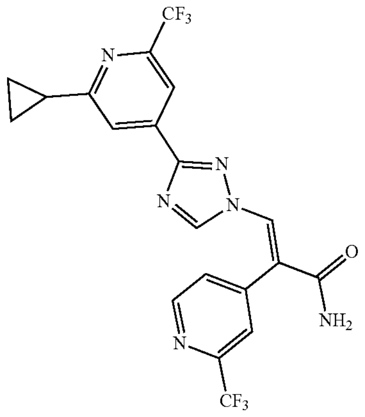
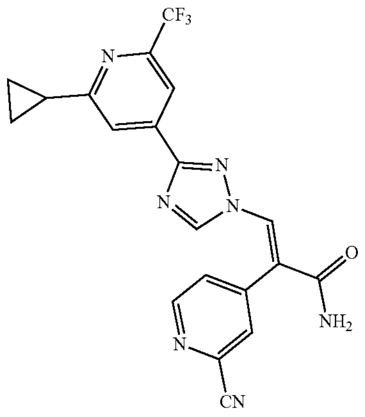
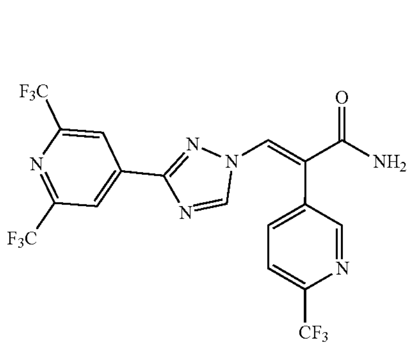

-continued

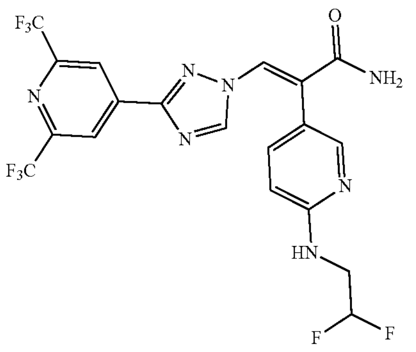

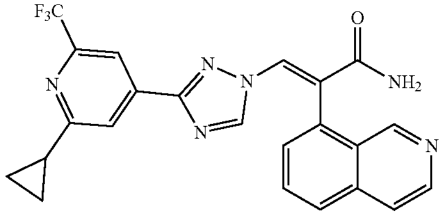

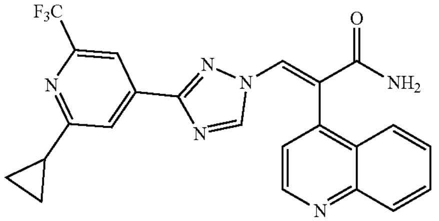

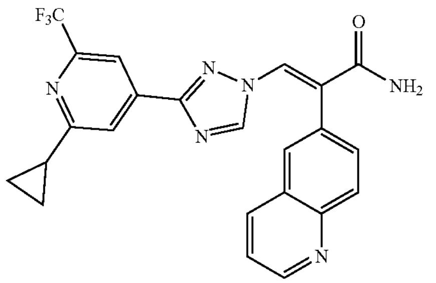

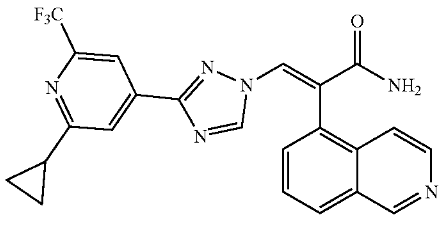

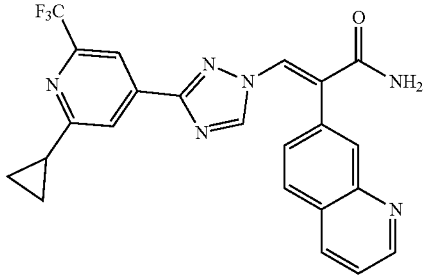

-continued

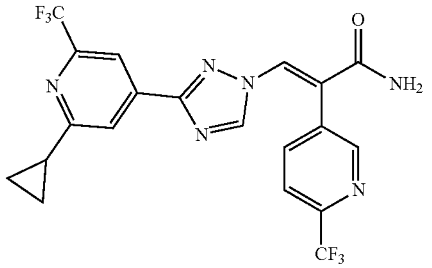

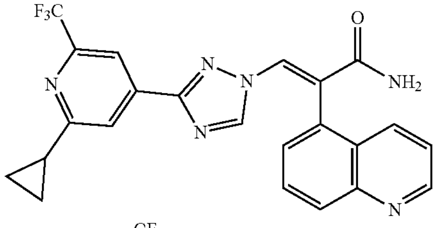

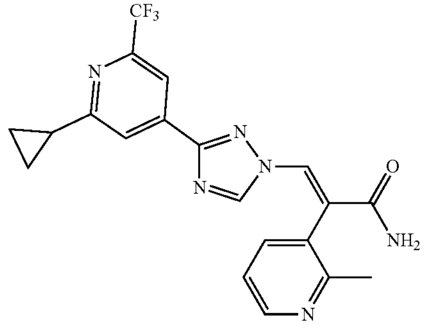

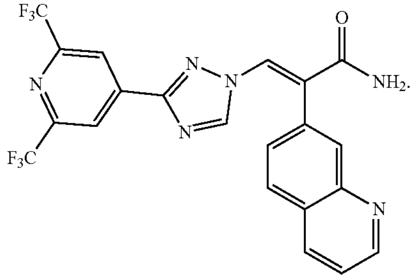

In another aspect, the present application further provides a pharmaceutical composition comprising the compound or the pharmaceutically acceptable salt thereof or the stereoisomer thereof of the present application described above. In some embodiments, the pharmaceutical composition disclosed herein further comprises a pharmaceutically acceptable excipient.

In another aspect, the present application further provides a method for treating various XPO-1-related diseases, comprising administering to a mammal, preferably a human, in need of the treatment a therapeutically effective amount of the compound, the pharmaceutically acceptable salt thereof, or the stereoisomer thereof, or the pharmaceutical composition thereof of the present application described above.

In another aspect, the present application further provides use of the compound or the pharmaceutically acceptable salt thereof or the stereoisomer thereof, or the pharmaceutical composition thereof of the present application described above for preparing a medicament for treating various XPO-1-related diseases.

In another aspect, the present application further provides use of the compound or the pharmaceutically acceptable salt thereof or the stereoisomer thereof, or the pharmaceutical composition thereof of the present application described above for treating various XPO-1-related diseases.

In another aspect, the present application further provides the compound, the pharmaceutically acceptable salt thereof, or the stereoisomer thereof, or the pharmaceutical composition thereof of the present application described above for treating various XPO-1-related diseases.

In some embodiments, the various XPO-1-related diseases are selected from the group consisting of tumors; in some embodiments, the various XPO-1-related diseases are selected from the group consisting of leukemia and lymphoma.

Technical Effects

The compound of the present application has cell proliferation inhibitory activity (e.g., against Jurkat cells and/or OCI-LY10 cells); stable in vitro liver microsome metabolism and good stability in human whole blood; good in vivo pharmacokinetic data (e.g., parameters such as AUC, Cmax, Tmax, or absolute bioavailability), in vivo pharmacodynamic data, and in vivo safety data (parameters such as brain-to-blood ratio).

Definitions

Unless otherwise stated, the following terms used in the present application shall have the following meanings. A certain term, unless otherwise specifically defined, should not be considered ambiguous or unclear, but construed according to its common meaning in the art.

When referring to a trade name, it is intended to refer to its corresponding commercial product or its active ingredient.

When certain structural units or groups in the present application have a covalent bond that is not connected to a specific atom, it means that the covalent bond can be connected to any atom within that structural unit or group, as long as it adheres to the rules of valence bonding.

The term "substituted" means that any one or more hydrogen atoms on a specific atom are substituted with substituents, as long as the valence of the specific atom is normal and the resulting compound is stable. When the substituent is oxo (namely =O), it means that two hydrogen atoms are substituted and oxo is not available on an aromatic group.

The term "optional" or "optionally" means that the subsequently described event or circumstance may, but does not necessarily, occur. The description includes instances where the event or circumstance occurs and instances where it does not. For example, ethyl being "optionally" substituted with halogen means that the ethyl may be unsubstituted ($CH_2CH_3$), monosubstituted (for example, $CH_2CH_2F$), polysubstituted (for example, $CHFCH_2F$, $CH_2CHF_2$, and the like), or fully substituted ($CF_2CF_3$). It will be appreciated by those skilled in the art that for any groups comprising one or more substituents, any substitutions or substituting patterns that may not exist and/or cannot be synthesized spatially are not introduced.

"One or more" used herein refers to an integer ranging from one to ten. For example, "one or more" refers to one, two, three, four, five, six, seven, eight, nine, or ten; or "one or more" refers to one, two, three, four, five, or six; or "one or more" refers to one, two, or three. $C_{m-n}$ used herein means that the moiety has an integer number of carbon atoms in the given range. For example, "$C_{1-6}$" means that the group may have 1 carbon atom, 2 carbon atoms, 3 carbon atoms, 4 carbon atoms, 5 carbon atoms, or 6 carbon atoms. For example, $C_{1-3}$ means that the group may have 1 carbon atom, 2 carbon atoms, or 3 carbon atoms.

When any variable (e.g., R) occurs once or more in the constitution or structure of a compound, the definition of the variable in each case is independent. Therefore, for example, if a group is substituted with 2 R, the definition of each R is independent.

When the number of connecting groups is 0, for example, $-(CH_2)_0-$, it means that the connecting group is a covalent bond.

When one of the variables is selected from a covalent bond, it means that the two groups connected to it are directly linked. For example, in A-L'-Z, where L' represents a covalent bond, it means that the structure is actually A-Z.

When a bond of a substituent is crosslinked to two atoms on a ring, the substituent can be bonded to any atoms on the ring. For example, structural unit

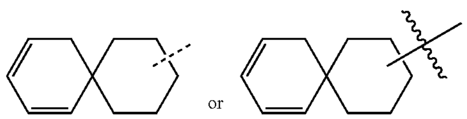

represents that substitution may occur at any one position of cyclohexyl or cyclohexadienyl.

The term "halo-" or "halogen" refers to fluorine, chlorine, bromine, and iodine.

The term "alkyl" refers to hydrocarbyl with a general formula of $C_nH_{2n+1}$. The alkyl may be linear or branched. For example, the term "$C_{1-6}$ alkyl" refers to alkyl containing 1 to 6 carbon atoms (for example, methyl, ethyl, n-propyl, isopropyl, n-butyl, isobutyl, sec-butyl, tert-butyl, n-pentyl, 1-methylbutyl, 2-methylbutyl, 3-methylbutyl, neopentyl, hexyl, 2-methylpentyl, and the like). Likewise, the alkyl moieties (namely alkyl) of alkoxy, alkylamino, dialkylamino, alkylsulfonyl and alkylthio have the same definition as those described above. As another example, the term "$C_{1-3}$ alkyl" refers to alkyl containing 1 to 3 carbon atoms (e.g., methyl, ethyl, propyl, and isopropyl).

The term "alkoxy" refers to —O-alkyl.

The term "cycloalkyl" refers to a carbon ring that is fully saturated and may exist as a monocyclic, bridged cyclic, or spiro cyclic structure. Unless otherwise indicated, the carbon ring is generally a 3- to 10-membered ring (e.g., a 3—, 4-, 5-, 6-, 7-, 8-, 9-, or 10-membered ring). Non-limiting examples of cycloalkyl include, but are not limited to, cyclopropyl, cyclobutyl, cyclopentyl, cyclohexyl, norbornyl (bicyclo[2.2.1]heptyl), bicyclo[2.2.2]octyl, adamantyl, dicyclo[1.1.1]pentan-1-yl, and the like. For example, $C_{34}$ cycloalkyl includes cyclopropyl and cyclobutyl.

The term "heterocycloalkyl" refers to a fully saturated cyclic group that may exist in the form of a monocyclic, bridged cyclic (including fused ring), or spiro cyclic structure. Unless otherwise indicated, the heterocyclyl is generally a 3- to 7-membered ring (e.g., a 3-, 4-, 5-, 6-, or 7-membered ring) containing 1 to 3 heteroatoms (preferably 1 or 2 heteroatoms) independently selected from the group consisting of sulfur, oxygen, and/or nitrogen.

Examples of 3-membered heterocycloalkyl include, but are not limited to, oxiranyl, thiiranyl, and aziranyl. Non-limiting examples of 4-membered heterocycloalkyl include, but are not limited to, azetidinyl, oxetanyl, and thietanyl. Examples of 5-membered heterocycloalkyl include, but are not limited to, tetrahydrofuranyl, tetrahydrothienyl, pyrrolidinyl, isoxazolidinyl, oxazolidinyl, isothiazolidinyl, thiazolidinyl, imidazolidinyl, and tetrahydropyrazolyl. Examples of 6-membered heterocycloalkyl include, but are not limited to, piperidinyl, tetrahydropyranyl, tetrahydrothiapyranyl, morpholinyl, piperazinyl, 1,4-oxathianyl, 1,4-dioxanyl, sulfomorpholinyl, 1,3-dithianyl, and 1,4-dithianyl. Examples of 7-membered heterocycloalkyl include, but are not limited to, azepanyl, oxepanyl, and thiepanyl. Monocyclic heterocycloalkyl having 5 or 6 ring atoms is preferred.

The term "aryl" refers to an all-carbon aromatic monocyclic or fused polycyclic group having a conjugated π-electron system. For example, aryl may have 6-20 carbon atoms, 6-14 carbon atoms, or 6-12 carbon atoms. Non-limiting examples of aryl include, but are not limited to, phenyl, naphthyl, anthryl, 1,2,3,4-tetrahydronaphthalene, and the like.

The term "heteroaryl" or "heteroaromatic ring group" refers to a monocyclic or fused polycyclic system which contains at least one ring atom selected from the group consisting of N, O, and S, with the remaining ring atoms being C, and which has at least one aromatic ring. Preferably, heteroaryl has a single 5- to 8-membered ring (e.g., a 5-, 6-, 7-, or 8-membered ring), or has a plurality of fused rings containing 6 to 14 ring atoms, particularly 6 to 10 ring atoms (e.g., 6-, 7-, 8-, 9-, or 10-membered rings). Non-limiting examples of heteroaryl include, but are not limited to, pyrrolyl, furanyl, thienyl, imidazolyl, oxazolyl, isoxazolyl, pyrazolyl, pyridinyl, pyrimidinyl, pyrazinyl, pyridazinyl, quinolyl, isoquinolyl, tetrazolyl, triazolyl, triazinyl, benzofuranyl, benzothienyl, indolyl, naphthyridinyl, indazolyl, isoindolyl, and the like.

The term "treat" or "treatment" means administering a compound or formulation described herein to ameliorate or eliminate a disease or one or more symptoms associated with the disease, including:

(i) inhibiting a disease or disease state, i.e., arresting its progression; and (ii) alleviating a disease or disease state, i.e., causing its regression.

The term "prevent" or "prevention" means administering a compound or formulation described herein to prevent a disease or one or more symptoms associated with the disease, including preventing the occurrence of the disease or disease state in a mammal, particularly when such a mammal is predisposed to the disease state but has not yet been diagnosed with it.

The term "therapeutically effective amount" refers to an amount of the compound disclosed herein for (i) treating or preventing a specific disease, condition, or disorder; (ii) alleviating, ameliorating, or eliminating one or more symptoms of a specific disease, condition, or disorder, or (iii) preventing or delaying onset of one or more symptoms of a specific disease, condition, or disorder described herein. The amount of the compound disclosed herein composing the "therapeutically effective amount" varies depending on the compound, the disease state and its severity, the administration regimen, and the age of the mammal to be treated, but can be determined routinely by those skilled in the art in accordance with their knowledge and the present disclosure.

The term "pharmaceutically acceptable" is used herein for those compounds, materials, compositions, and/or dosage forms that are, within the scope of sound medical judgment, suitable for use in contact with the tissues of human beings and animals without excessive toxicity, irritation, allergic response, or other problems or complications, and commensurate with a reasonable benefit/risk ratio.

A pharmaceutically acceptable salt, for example, may be a metal salt, an ammonium salt, a salt formed with an organic base, a salt formed with an inorganic acid, a salt formed with an organic acid, a salt formed with a basic or acidic amino acid, and the like.

The term "pharmaceutical composition" refers to a mixture consisting of one or more of the compounds or the salts thereof of the present application and a pharmaceutically acceptable excipient. The pharmaceutical composition is intended to facilitate the administration of the compound of the present application to an organism.

The term "pharmaceutically acceptable excipient" refers to those that do not have a significant irritating effect on an organism and do not impair the biological activity and properties of the active compound. Suitable excipients are well known to those skilled in the art, for example, carbohydrate, wax, water-soluble and/or water-swellable polymers, hydrophilic or hydrophobic material, gelatin, oil, solvent, water, or the like.

The word "comprise" and variations thereof such as "comprises" or "comprising" will be understood in an open, non-exclusive sense, i.e., "including but not limited to".

The compounds and intermediates disclosed herein may also exist in different tautomeric forms, and all such forms are included within the scope of the present application. The term "tautomer" or "tautomeric form" refers to structural isomers of different energies that can interconvert via a low energy barrier. For example, a proton tautomer (also referred to as prototropic tautomer) includes interconversion via proton transfer, such as keto-enol isomerism and imine-enamine isomerization. A specific example of a proton tautomer is an imidazole moiety where a proton can transfer between two ring nitrogens. A valence tautomer includes the interconversion via recombination of some bonding electrons.

The present application also comprises isotopically labeled compounds of the present application which are identical to those recited herein but have one or more atoms replaced by an atom having an atomic mass or mass number different from the atomic mass or mass number generally found in nature. Examples of isotopes that can be incorporated into the compounds of the present application include isotopes of hydrogen, carbon, nitrogen, oxygen, phosphorus, sulfur, fluorine, iodine and chlorine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{123}I$, $^{125}I$ and $^{36}Cl$.

Certain isotopically labeled compounds of the present application (e.g., those labeled with $^{3}H$ and $^{14}C$) can be used to analyze compounds and/or substrate tissue distribution. Tritiated (i.e., $^{3}H$) and carbon-14 (i.e., $^{14}C$) isotopes are particularly preferred for their ease of preparation and detectability. Positron emitting isotopes, such as $^{15}O$, $^{13}N$, $^{11}C$, and $^{18}F$, can be used in positron emission tomography (PET) studies to determine substrate occupancy. Isotopically labeled compounds of the present application can generally be prepared by following procedures analogous to those disclosed in the schemes and/or examples below while substituting a non-isotopically labeled reagent with an isotopically labeled reagent.

Furthermore, substitution with heavier isotopes such as deuterium (i.e., $^{2}H$) may provide certain therapeutic advantages (e.g., increased in vivo half-life or reduced dosage) resulting from greater metabolic stability and hence may be preferred in some circumstances in which deuterium substitution may be partial or complete, wherein partial deuterium substitution refers to substitution of at least one hydrogen with at least one deuterium, and all such forms of the compounds are included within the scope of the present application.

The compound disclosed herein can be asymmetrical, for example, having one or more stereoisomers. Unless otherwise stated, all stereoisomers are included, for example, enantiomers and diastereoisomers. The compound with asymmetrical carbon atoms disclosed herein can be separated in an optically pure form or in a racemic form. The optically pure form can be separated from a racemic mixture or can be synthesized using a chiral raw material or a chiral reagent.

The pharmaceutical composition of the present application can be prepared by combining the compound of the present application with a suitable pharmaceutically acceptable excipient, and can be formulated, for example, into a solid, semisolid, liquid or gaseous formulation such as tablet, pill, capsule, powder, granule, ointment, emulsion, suspension, suppository, injection, inhalant, gel, microsphere, aerosol, and the like.

Typical routes of administration of the compound or the pharmaceutically acceptable salt thereof or the pharmaceutical composition thereof of the present application include, but are not limited to, oral, rectal, local, inhalation, parenteral, sublingual, intravaginal, intranasal, intraocular, intraperitoneal, intramuscular, subcutaneous and intravenous administration.

The pharmaceutical composition of the present application can be manufactured using methods well known in the art, such as conventional mixing, dissolving, granulating, dragee-making, levigating, emulsifying, and lyophilizing.

In some embodiments, the pharmaceutical composition is in an oral form. For oral administration, the pharmaceutical composition can be formulated by mixing the active compounds with pharmaceutically acceptable excipients well known in the art. These excipients enable the compounds of the present application to be formulated into tablets, pills, pastilles, dragees, capsules, liquids, gels, slurries, suspensions, and the like for oral administration to a patient.

A solid oral composition can be prepared by conventional mixing, filling or tableting. For example, it can be obtained by the following method: mixing the active compounds with solid excipients, optionally grinding the resulting mixture, adding additional suitable excipients if desired, and processing the mixture into granules to get the core parts of tablets or dragees. Suitable excipients include, but are not limited to: binders, diluents, disintegrants, lubricants, glidants, sweeteners or flavoring agents, and the like.

The pharmaceutical composition may also be suitable for parenteral administration, such as a sterile solution, a suspension, or a lyophilized product in a suitable unit dosage form.

Therapeutic dosages of the compound of the present application may be determined by, for example, the specific use of a treatment, the route of administration of the compound, the health and condition of a patient, and the judgment of a prescribing physician. The proportion or concentration of the compound disclosed herein in a pharmaceutical composition may not be constant and depends on a variety of factors including dosages, chemical properties (e.g., hydrophobicity), and routes of administration. For example, the compound of the present application may be provided for parenteral administration by a physiological buffered aqueous solution containing about 0.1-10% w/v of the compound. Certain typical dosages range from about 1 μg/kg body weight/day to about 1 g/kg body weight/day. In certain embodiments, the dosage ranges from about 0.01 mg/kg body weight/day to about 100 mg/kg body weight/day. The dosage is likely to depend on such variables as the type and degree of progression of the disease or disorder, the general health condition of a particular patient, the relative biological potency of the compound selected, the excipient formulation, and its route of administration. Effective doses can be extrapolated from dose-response curves derived from in vitro or animal model test systems.

The compounds disclosed herein can be prepared using a variety of synthetic methods well known to those skilled in the art, including the specific embodiments listed below, embodiments formed by combinations thereof with other chemical synthetic methods, and equivalents thereof known to those skilled in the art. The preferred embodiments include, but are not limited to, the examples of the present application.

The chemical reactions of the specific embodiments of the present application are conducted in a proper solvent that must be suitable for the chemical changes in the present application and the reagents and materials required. In order to obtain the compounds of the present application, it is sometimes necessary for those skilled in the art to modify or select a synthesis procedure or a reaction process based on the existing embodiments.

An important consideration in synthetic route planning in the art is the selection of suitable protecting groups for reactive functional groups (e.g., amino in the present application). For example, reference may be made to Greene's Protective Groups in Organic Synthesis (4th Ed.) Hoboken, New Jersey: John Wiley & Sons, Inc.

In some embodiments, the compound disclosed herein may be prepared using the following preparation routes in combination with methods known in the art:

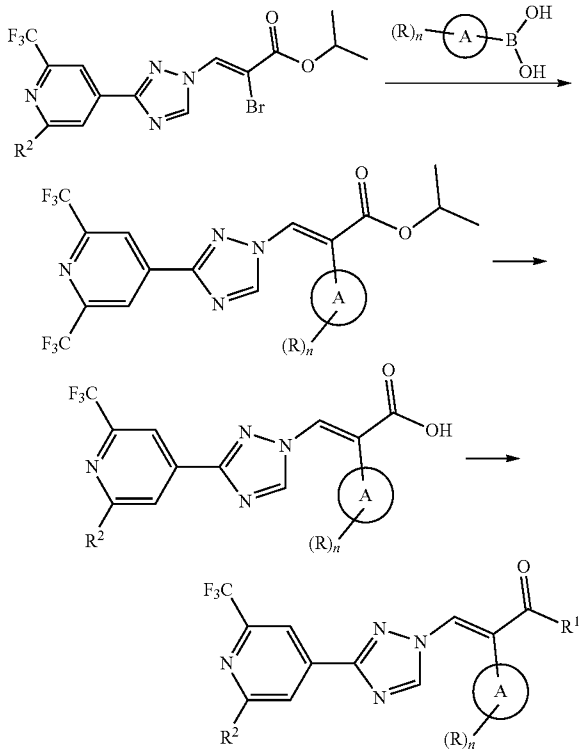

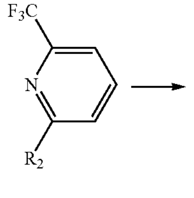

-continued

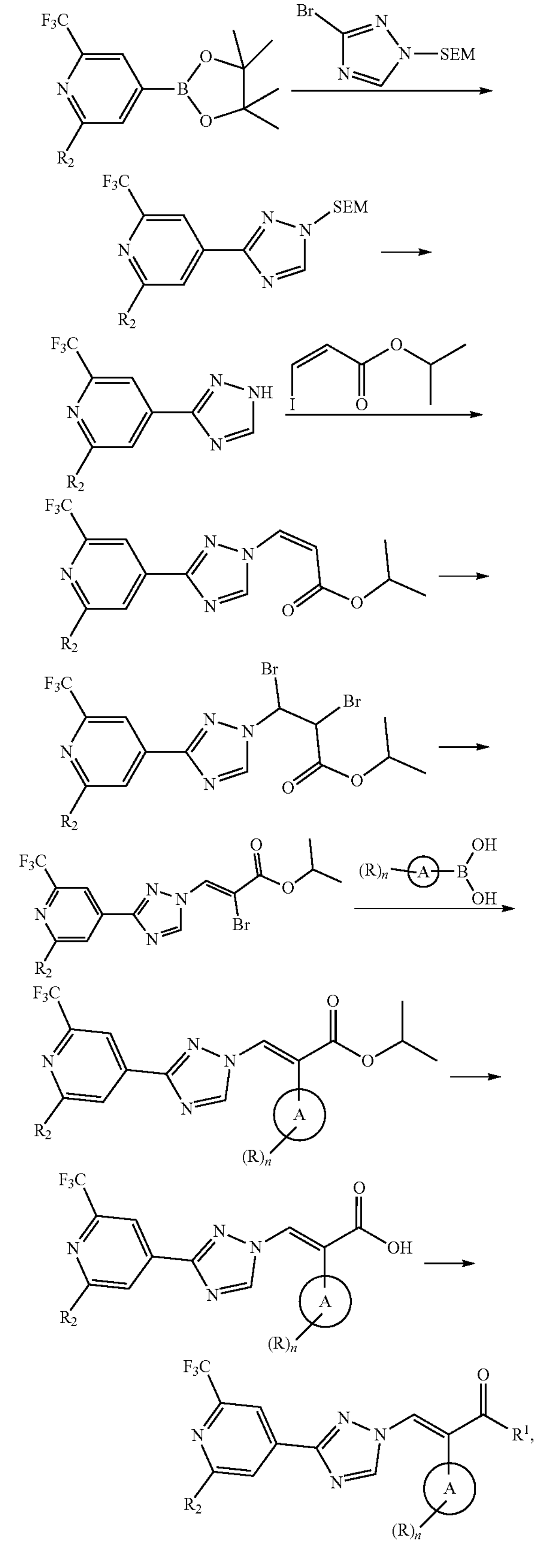

wherein ring A, R, n, $R^2$, and $R^1$ are as defined in the present application.

The following abbreviations are used in this application: $Pd(dppf)Cl_2$ represents [1,1'-bis(diphenylphosphino)ferrocene]palladium dichloride; DMF represents N,N-dimethylformamide; DABCO represents triethylenediamine; THF represents tetrahydrofuran; SEM represents trimethylsilylethoxymethyl.

For clarity, the present application is further described with the following examples, which are, however, not intended to limit the scope of the present application. All reagents used in the present application are commercially available and can be used without further purification.

DETAILED DESCRIPTION

Example 1

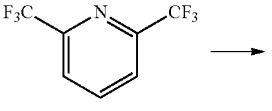

1-1

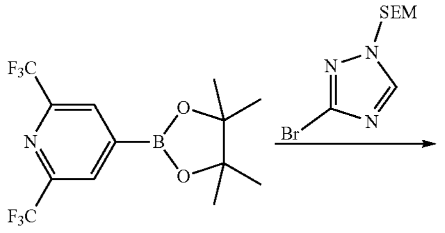

1-2

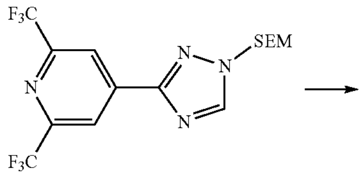

1-3

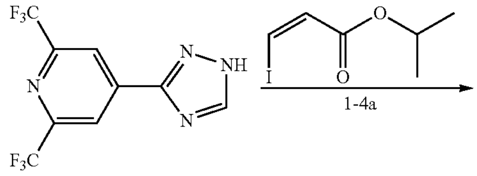

1-4

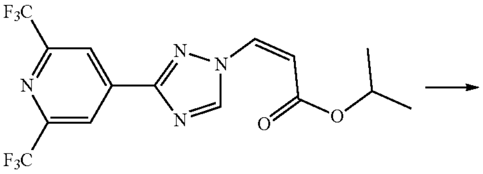

1-5

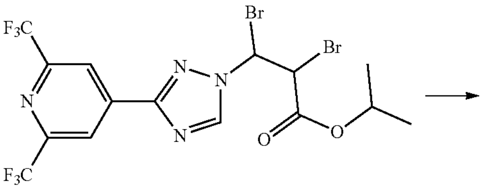

1-6

-continued

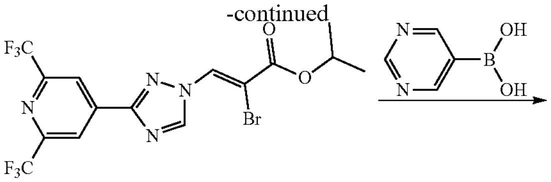

1-7

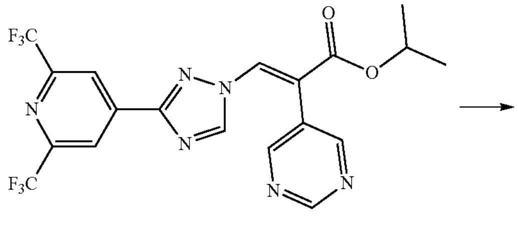

1-8

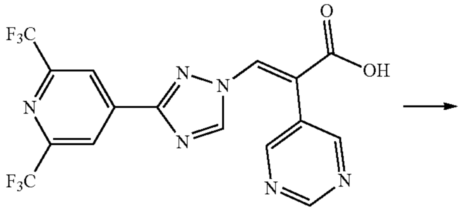

1-9

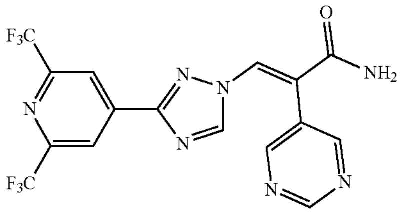

1

(1) Preparation of Compound 1-2

Bis(pinacolato)diboron (2.13 μg), 4,4'-di-tert-butyl-2,2'-bipyridine (18.7 mg), and (1,5-cyclooctadiene)(methoxy) iridium(I) dimer (23.1 mg) were added to cyclohexane (30 mL). Under nitrogen atmosphere, the mixture was stirred for 10 min, and 3,5-bis(trifluoromethyl)pyridine (compound 1-1, 3.0 g) was added. The resulting mixture was stirred at 55° C. under nitrogen atmosphere. After the reaction was completed, the reaction solution was quenched with ice water (20 mL) and extracted with ethyl acetate (30 mL×3). The organic phase was collected, dried over anhydrous sodium sulfate, and filtered, and the filtrate was evaporated to dryness under reduced pressure to give compound 1-2, which was directly used in the next step.

(2) Preparation of Compound 1-3

Compound 1-2 (4.7 g) was added to ethylene glycol dimethyl ether (50 mL), and 3-bromo-1-((2-(trimethylsilyl) ethoxy)methyl)-1H-1,2,4-triazole (3.9 g) and an aqueous solution (10 mL) of potassium carbonate (5.8 g) were added. The mixture was stirred at room temperature under nitrogen atmosphere. After 1 h, tetrakis(triphenylphosphine)palladium (805.8 mg) was added, and the resulting mixture was stirred at 90° C. under nitrogen atmosphere. After the reaction was completed, the reaction solution was quenched with ice water (40 mL) and extracted with ethyl acetate (100 mL). The organic phase was collected and washed with brine (50 mL×2). The organic layer was dried over anhydrous sodium sulfate and filtered, and the filtrate was evaporated to dryness under reduced pressure to give compound 1-3, which was directly used in the next step.

(3) Preparation of Compound 1-4

Compound 1-3 (5.7 g) was dispersed in 4 M HCl/dioxane (50 mL), and the mixture was stirred at 60° C. After the reaction was completed, the reaction solution was slowly poured into an ice saturated sodium bicarbonate solution. The resulting mixture was adjusted to pH=6-7 with sodium bicarbonate and extracted with ethyl acetate (100 mL×3). The organic phase was washed with saturated brine (100 mL), dried over anhydrous sodium sulfate, concentrated under reduced pressure until no liquid flowed out, and purified by column chromatography to give compound 1-4.

(4) Preparation of Compound 1-5 Compound 1-4 (900 mg) was dispersed in DMF (20 mL), and DABCO (716 mg) was added The mixture was stirred at 20-25° C. for 30 min and then cooled to 0-10° C., and compound 1-4a (1.15 g) was added dropwise. After addition, the resulting mixture was stirred at 20-25° C. for 1.5 h. After the reaction was completed, the reaction solution was poured into water (50 mL), and the resulting mixture was extracted with ethyl acetate (50 mL×2). The organic phases were combined, dried over anhydrous sodium sulfate, and purified by column chromatography to give compound 1-5 (750 mg).

(5) Preparation of Compound 1-6

Compound 1-5 (750 mg) was added to dichloromethane (20 mL), and the mixture was cooled to 0° C. Liquid bromine (605 mg) was added dropwise within 15 min. After addition, the mixture was slowly heated to room temperature and stirred for 4 h. After the reaction was completed, the reaction mixture was poured into ice water (30 mL), and the resulting mixture was extracted with dichloromethane (30 mL×3). The organic phases were combined, washed with a saturated sodium bisulfite solution (30 mL), dried over anhydrous sodium sulfate, concentrated under reduced pressure until no liquid flowed out, and purified by column chromatography to give compound 1-6.

(6) Preparation of Compound 1-7

Compound 1-6 (1.05 g) was added to THF (20 mL), and the mixture was cooled to 0° C. Triethylamine (383.5 mg) was added dropwise. After addition, the mixture was slowly heated to room temperature and reacted for 12 h. After the reaction was completed, the reaction solution was diluted with water (20 mL) and extracted with ethyl acetate (30 mL×3). The organic phases were combined, dried over anhydrous sodium sulfate, and purified by column chromatography to give compound 1-7.

(7) Preparation of Compound 1-8

Compound 1-7 (700 mg), 5-pyrimidineboronic acid (220 mg), potassium acetate (435.7 mg), and Pd(dppf)$Cl_2$ (54 mg) were added to dioxane (20 mL) and water (2 mL). The mixture was heated to 90° C. and reacted under nitrogen atmosphere. After the reaction was completed, the reaction solution was diluted with water (20 mL) and extracted with ethyl acetate (30 mL×3). The organic phase was collected, dried over anhydrous sodium sulfate, and filtered, and the filtrate was evaporated to dryness under reduced pressure and purified by column chromatography to give compound 1-8 (200 mg).

(8) Preparation of Compound 1-9

Compound 1-8 (200 mg) was dissolved in tetrahydrofuran (15 mL), a solution of sodium hydroxide (33.9 mg) and water (15 mL) was added dropwise in an ice-water bath, and the mixture was reacted at room temperature overnight. The reaction solution was adjusted to acidity (pH 3-5) with hydrochloric acid, extracted with ethyl acetate (30 mL×3), dried over anhydrous sodium sulfate, and filtered, and the filtrate was evaporated to dryness under reduced pressure to give compound 1-9, which was directly used in the next step.

(9) Preparation of Example 1

Compound 1-9 (182 mg) was added to tetrahydrofuran (15 mL), N-methylmorpholine (85.6 mg) and isobutyl chloroformate (115.5 mg) were added in an ice-water bath, and the mixture was stirred for 30 min. Ammonium hydroxide (88.8 mg) was added dropwise, and the mixture was reacted in an ice-water bath for 10 min. Water was added to quench the reaction, and the resulting mixture was extracted with ethyl acetate (30 mL×3), dried over anhydrous sodium sulfate, concentrated until no liquid flowed out, and purified by preparative liquid chromatography to give Example 1 (13 mg). ESI-MS: m/z=430.26 $[M+H]^+$. $^1H$ NMR (500 MHz, DMSO-$d_6$) δ 9.22 (d, J=9.8 Hz, 2H), 8.74 (s, 2H), 8.45 (s, 1H), 8.07 (s, 2H), 7.68 (s, 1H), 7.44 (s, 1H).

Example 2

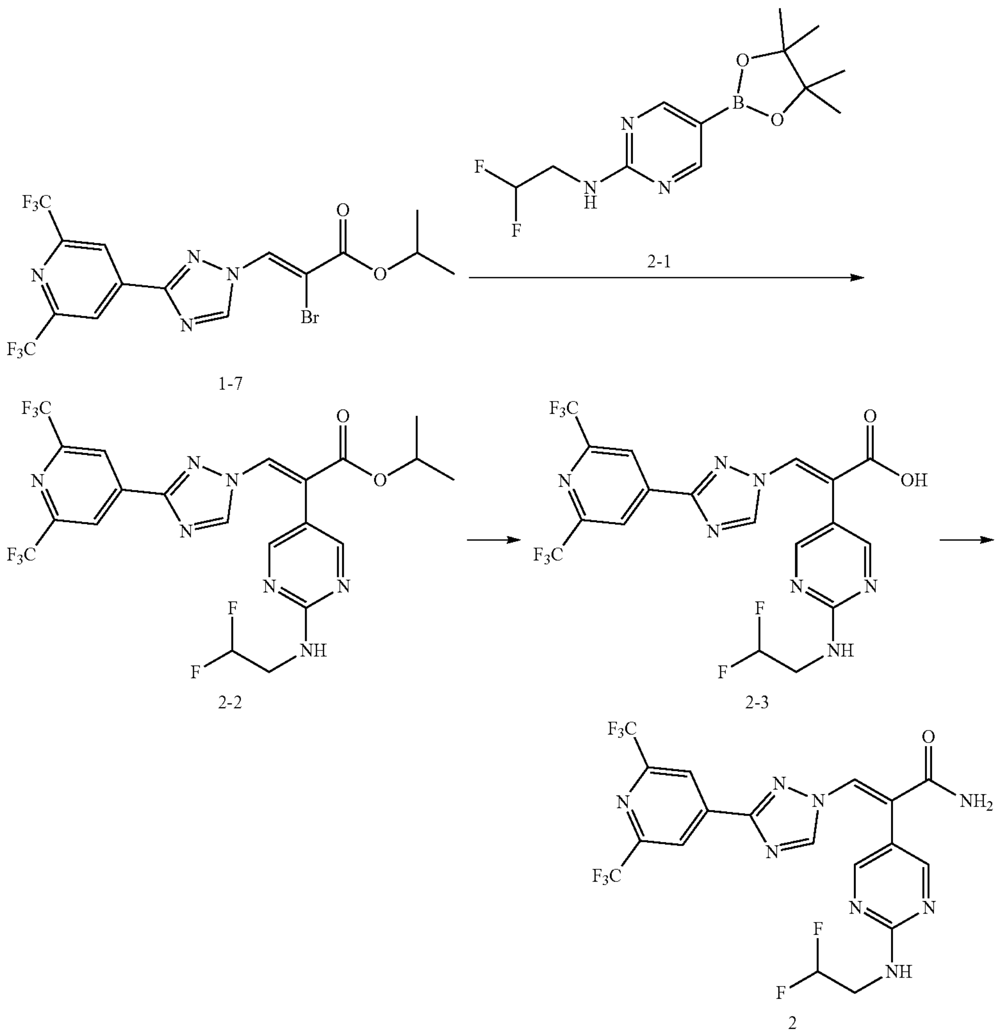

1-7, 2-1, 2-2, 2-3, 2

(1) Preparation of Compound 2-2

Compounds 1-7 (394 mg) and 2-1 (285 mg) were dispersed in 1,4-dioxane (8 mL), and potassium acetate (244 mg), Pd(dppf)$Cl_2$ (29 mg), and water (0.8 mL) were added. The mixture was heated to 90° C. and reacted under nitrogen atmosphere. After the reaction was completed, the reaction solution was concentrated under reduced pressure and purified by column chromatography to give compound 2-2.

(2) Preparation of Compound 2-3

Compound 2-2 (100 mg) was dissolved in tetrahydrofuran (5 mL), a solution of lithium hydroxide hydrate (38.1 mg) and water (5 mL) was added dropwise in an ice-water bath, and the mixture was reacted at room temperature for 2 h. The reaction solution was adjusted to pH 3-5 with hydrochloric acid, extracted with ethyl acetate (20 mL×2), dried over anhydrous sodium sulfate, and filtered, and the filtrate was evaporated to dryness under reduced pressure to give compound 2-3, which was directly used in the next step.

(3) Preparation of Compound 2

Compound 2-3 (91 mg) was dispersed in tetrahydrofuran (5 mL), N-methylmorpholine (36 mg) and isobutyl chloroformate (49 mg) were added in an ice-water bath, and the mixture was stirred for 30 min. Ammonium hydroxide (38 mg) was added dropwise, and the mixture was reacted in an ice-water bath for 10 min. Water was added to quench the reaction, and the resulting mixture was extracted with ethyl acetate (20 mL×2), dried over anhydrous sodium sulfate, concentrated until no liquid flowed out, and purified by preparative liquid chromatography to give compound 2 (41 mg). ESI-MS: m/z=509.32 $[M+H]^+$.

$^1H$ NMR (500 MHz, DMSO-$d_6$) δ 9.14 (s, 1H), 8.25 (d, J=10.4 Hz, 5H), 7.76 (t, J=6.2 Hz, 1H), 7.58 (s, 1H), 7.43 (s, 1H), 6.09 (tt, J=56.5, 4.2 Hz, 1H), 3.74 (dddd, J=19.0, 14.9, 8.2, 5.2 Hz, 2H).

Example 3

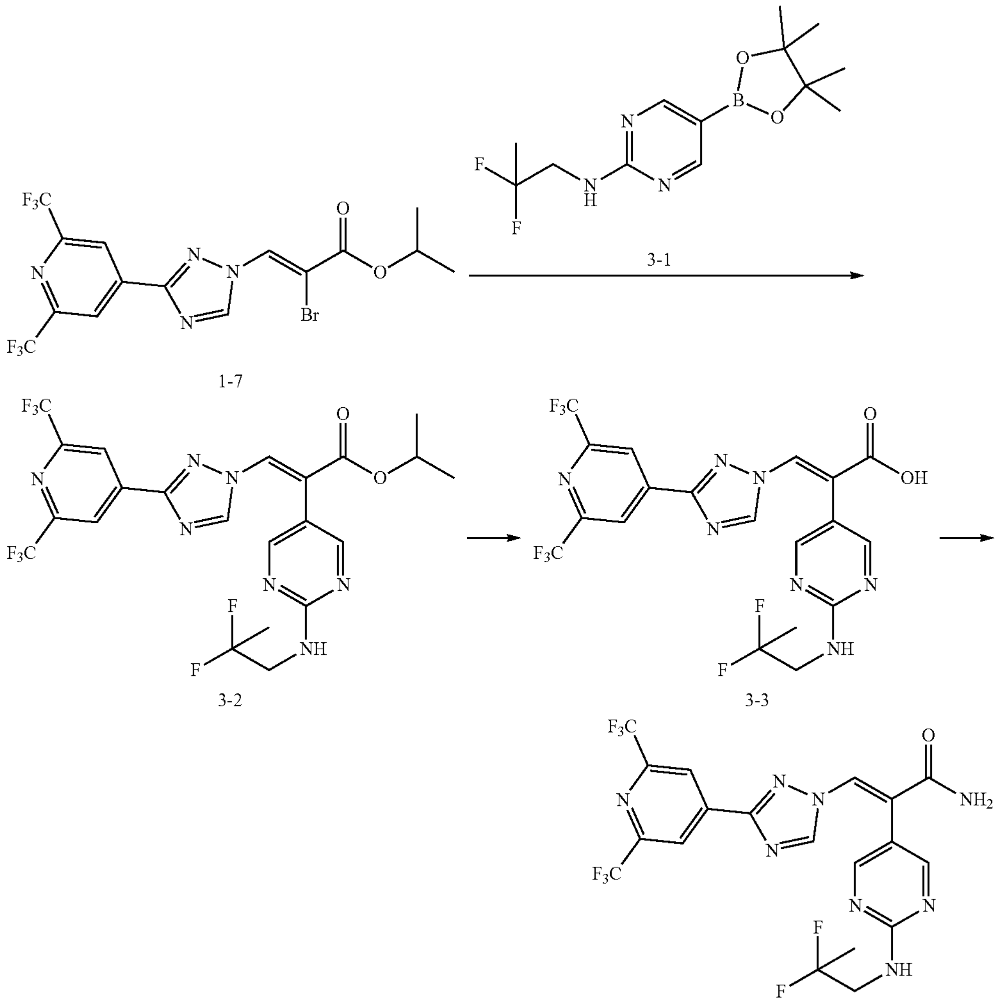

1-7 3-1 3-2 3-3 3

(1) Preparation of Compound 3-2

Compounds 1-7 (394 mg) and 3-1 (299 mg) were dispersed in 1,4-dioxane (8 mL), and potassium acetate (244 mg), Pd(dppf)$Cl_2$ (29 mg), and water (0.8 mL) were added. The mixture was heated to 90° C. and reacted under nitrogen atmosphere. After the reaction was completed, the reaction solution was concentrated under reduced pressure and purified by column chromatography to give compound 3-2.

(2) Preparation of Compound 3-3

Compound 3-2 (360 mg) was dissolved in tetrahydrofuran (5 mL), a solution of lithium hydroxide hydrate (133.6 mg) and water (5 mL) was added dropwise in an ice-water bath, and the mixture was reacted at room temperature for 2 h. The reaction solution was adjusted to pH 3-5 with hydrochloric acid, extracted with ethyl acetate (20 mL×2), dried over anhydrous sodium sulfate, and filtered, and the filtrate was evaporated to dryness under reduced pressure to give compound 3-3, which was directly used in the next step.

(3) Preparation of Compound 3

Compound 3-3 (335 mg) was dispersed in tetrahydrofuran (10 mL), N-methylmorpholine (129 mg) and isobutyl chloroformate (175 mg) were added in an ice-water bath, and the mixture was stirred for 30 min. Ammonium hydroxide (134 mg) was added dropwise, and the mixture was reacted in an ice-water bath for 10 min. Water was added to quench the reaction, and the resulting mixture was extracted with ethyl acetate (20 mL×2), dried over anhydrous sodium sulfate, concentrated until no liquid flowed out, and purified by preparative liquid chromatography to give compound 3 (90 mg). ESI-MS: m/z=523.37 $[M+H]^+$.

$^1H$ NMR (500 MHz, DMSO-$d_6$) δ 9.14 (s, 1H), 8.26 (s, 2H), 8.21 (d, J=5.5 Hz, 3H), 7.76 (t, J=6.6 Hz, 1H), 7.57 (s, 1H), 7.45 (s, 1H), 3.83 (td, J=13.6, 6.6 Hz, 2H), 1.61 (t, J=19.0 Hz, 3H).

Example 4

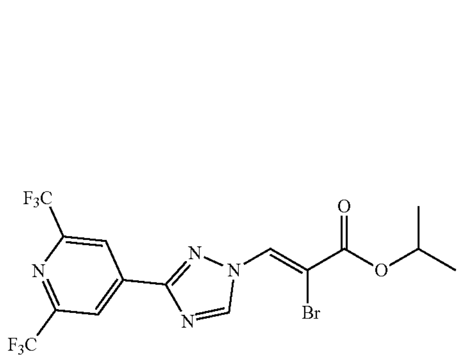

1-7

4-1

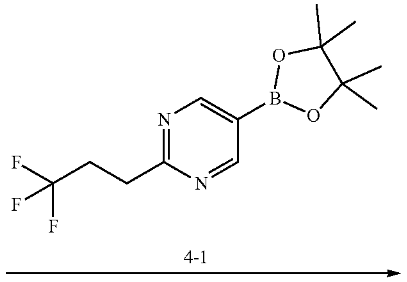

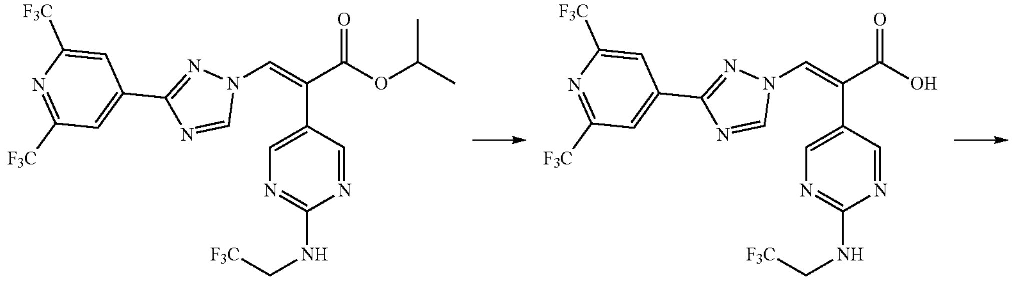

4-2

4-3

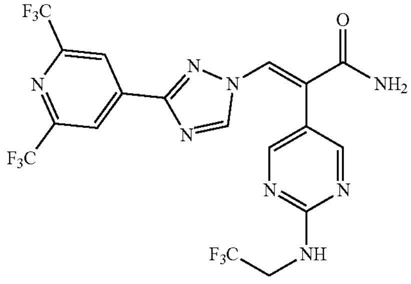

4

(1) Preparation of Compound 4-2

Compounds 1-7 (300 mg) and 4-1 (230 mg) were dispersed in 1,4-dioxane (8 mL), and potassium acetate (186.6 mg), $Pd(dppf)Cl_2$ (46 mg), and water (0.8 mL) were added. The mixture was heated to 90° C. and reacted under nitrogen atmosphere. After the reaction was completed, the reaction solution was concentrated under reduced pressure and purified by column chromatography to give compound 4-2.

(2) Preparation of Compound 4-3

Compound 4-2 (302 mg) was dissolved in tetrahydrofuran (10 mL), a solution of lithium hydroxide hydrate (44.6 mg) and water (10 mL) was added dropwise in an ice-water bath, and the mixture was reacted at room temperature for 3 h. The reaction solution was adjusted to pH 3-5 with hydrochloric acid, extracted with ethyl acetate (20 mL×2), dried over anhydrous sodium sulfate, and filtered, and the filtrate was evaporated to dryness under reduced pressure to give compound 4-3, which was directly used in the next step.

(3) Preparation of Compound 4

Compound 4-3 (280 mg) was dispersed in tetrahydrofuran (15 mL), N-methylmorpholine (107 mg) and isobutyl chloroformate (145 mg) were added in an ice-water bath, and the mixture was stirred for 30 min. Ammonium hydroxide (111 mg) was added dropwise, and the mixture was reacted in an ice-water bath for 10 min. Water was added to quench the reaction, and the resulting mixture was extracted with ethyl acetate (20 mL×2), dried over anhydrous sodium sulfate, concentrated until no liquid flowed out, and purified by preparative liquid chromatography to give compound 4 (30 mg). ESI-MS: m/z=527.17 $[M+H]^+$.

$^1H$ NMR (500 MHz, DMSO-$d_6$) δ 9.16 (s, 1H), 8.24 (d, J=4.6 Hz, 5H), 7.99 (t, J=6.7 Hz, 1H), 7.57 (s, 1H), 7.45 (s, 1H), 4.18 (q, J=8.7, 8.3 Hz, 2H).

Example 5

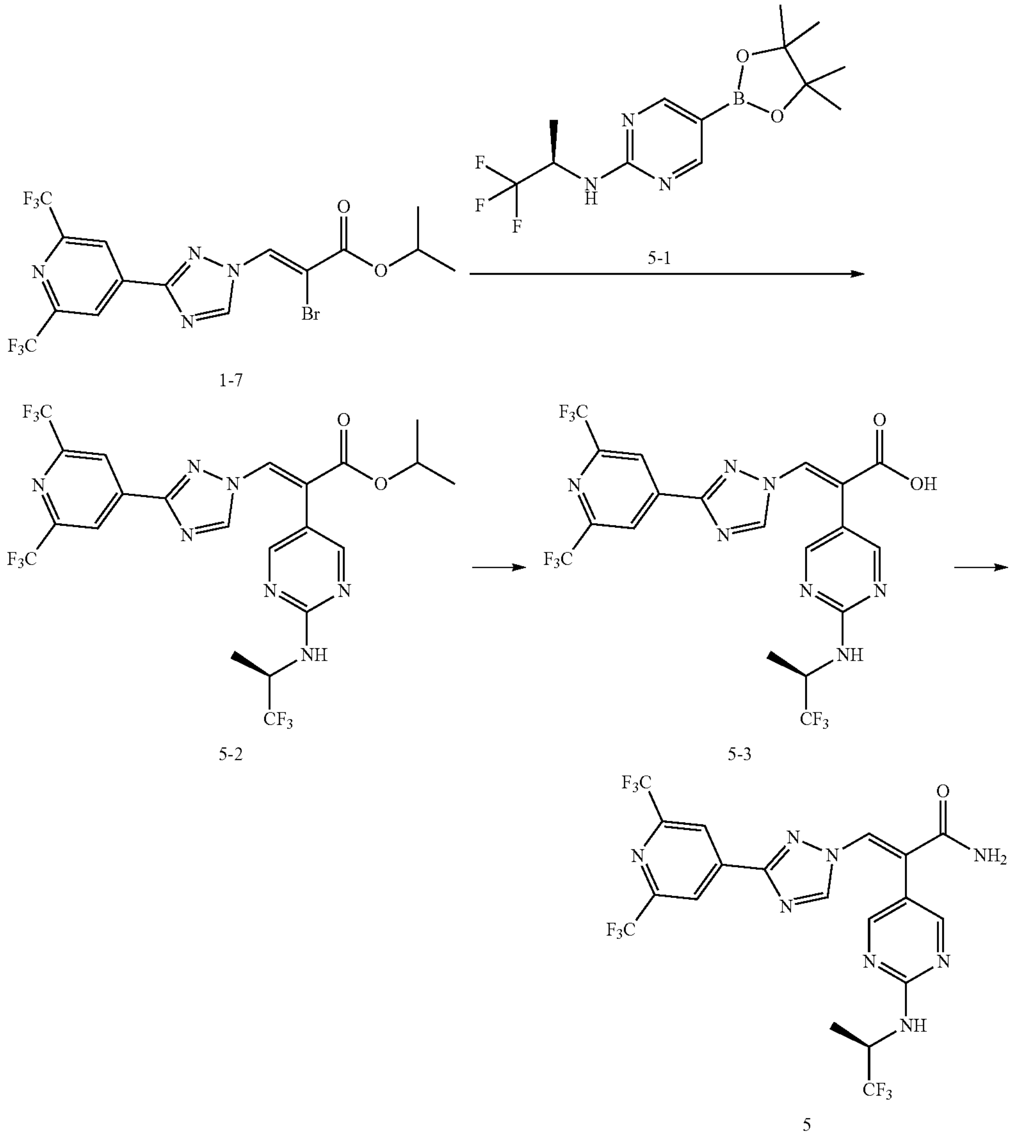

1-7

5-1

5-2

5-3

5

(1) Preparation of Compound 5-2

Compounds 1-7 (300 mg) and 5-1 (241 mg) were dispersed in 1,4-dioxane (8 mL), and potassium acetate (187 mg), Pd(dppf)$Cl_2$ (23 mg), and water (0.8 mL) were added. The mixture was heated to 90° C. and reacted under nitrogen atmosphere. After the reaction was completed, the reaction solution was concentrated under reduced pressure and purified by column chromatography to give compound 5-2.

(2) Preparation of Compound 5-3

Compound 5-2 (200 mg) was dissolved in tetrahydrofuran (10 mL), a solution of lithium hydroxide hydrate (29 mg) and water (10 mL) was added dropwise in an ice-water bath, and the mixture was reacted at 0-10° C. for 3 h. The reaction solution was adjusted to pH 3-5 with hydrochloric acid, extracted with ethyl acetate (20 mL×2), dried over anhydrous sodium sulfate, and filtered, and the filtrate was evaporated to dryness under reduced pressure to give compound 5-3, which was directly used in the next step.

(3) Preparation of Compound 5

Compound 5-3 (185 mg) was dispersed in tetrahydrofuran (15 mL), N-methylmorpholine (69 mg) and isobutyl chloroformate (94 mg) were added in an ice-water bath, and the mixture was stirred for 30 min. Ammonium hydroxide (72 mg) was added dropwise, and the mixture was reacted in an ice-water bath for 10 min. Water was added to quench the reaction, and the resulting mixture was extracted with ethyl acetate (20 mL×2), dried over anhydrous sodium sulfate, concentrated until no liquid flowed out, and purified by preparative liquid chromatography to give compound 5 (50 mg). ESI-MS: m/z=541.25 $[M+H]^+$.

$^1$H NMR (500 MHz, DMSO-$d_6$) δ 9.17 (d, J=3.5 Hz, 1H), 8.25 (q, J=3.8 Hz, 5H), 7.96 (dd, J=9.3, 3.2 Hz, 1H), 7.58 (s, 1H), 7.47 (s, 1H), 5.02-4.86 (m, 1H), 1.36 (dd, J=7.3, 3.2 Hz, 3H).

Example 6

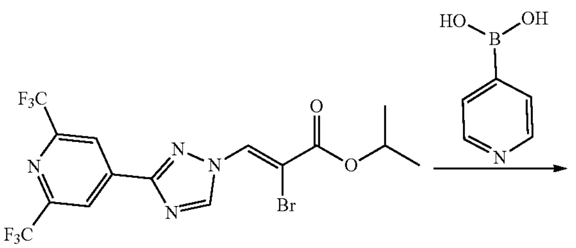

1-7

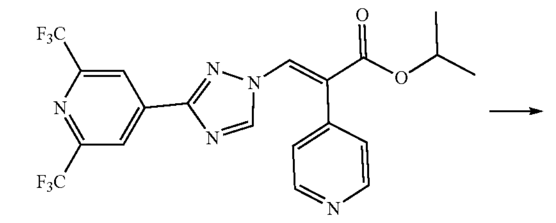

6-1

-continued

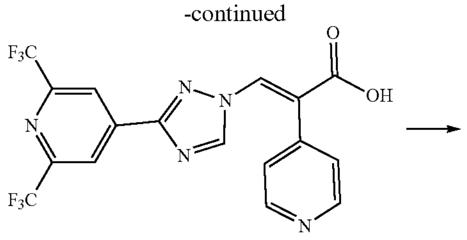

6-2

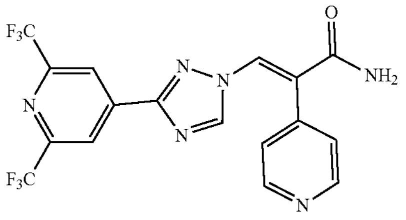

6

(1) Preparation of Compound 6-1

Compound 1-7 (200 mg) and pyridine-4-boronic acid (62.35 mg) were dispersed in 1,4-dioxane (10 mL), and potassium acetate (124.4 mg), Pd(dppf)$Cl_2$ (15.5 mg), and water (1 mL) were added. The mixture was heated to 90° C. and reacted under nitrogen atmosphere. After the reaction was completed, the reaction solution was concentrated under reduced pressure and purified by column chromatography to give compound 6-1.

(2) Preparation of Compound 6-2

Compound 6-1 (150 mg) was dissolved in tetrahydrofuran (10 mL), a solution of lithium hydroxide hydrate (67.14 mg) and water (10 mL) was added dropwise in an ice-water bath, and the mixture was reacted at room temperature for 3 h. The reaction solution was adjusted to pH 3-5 with hydrochloric acid, extracted with ethyl acetate (20 mL×2), dried over anhydrous sodium sulfate, and filtered, and the filtrate was evaporated to dryness under reduced pressure to give compound 6-2, which was directly used in the next step.

(3) Preparation of Compound 6

Compound 6-2 (137.4 mg) was dispersed in tetrahydrofuran (10 mL), N-methylmorpholine (64.74 mg) and isobutyl chloroformate (87.41 mg) were added in an ice-water bath, and the mixture was stirred for 30 min. Ammonium hydroxide (67.2 mg) was added dropwise, and the mixture was reacted in an ice-water bath for 10 min. Water was added to quench the reaction, and the resulting mixture was extracted with ethyl acetate (20 mL×2), dried over anhydrous sodium sulfate, concentrated until no liquid flowed out, and purified by preparative liquid chromatography to give compound 6 (10 mg). ESI-MS: m/z=429.19 $[M+H]^+$.

$^1$H NMR (500 MHz, DMSO-$d_6$) δ 9.02 (s, 1H), 8.65 (d, J=5.0 Hz, 2H), 8.26 (s, 1H), 8.10 (s, 2H), 7.66 (s, 1H), 7.32 (d, J=5.0 Hz, 2H), 7.23 (s, 1H).

Example 7

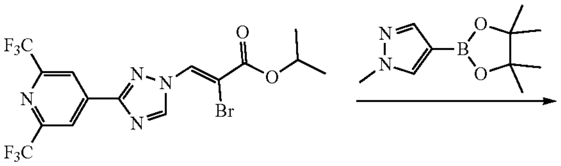

1-7

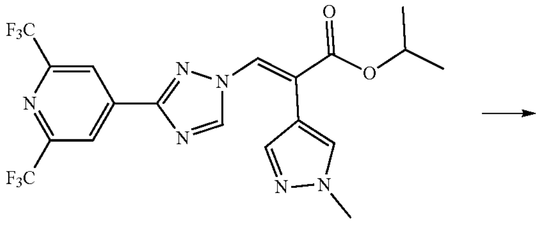

7-1

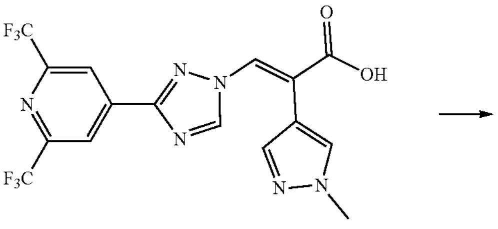

7-2

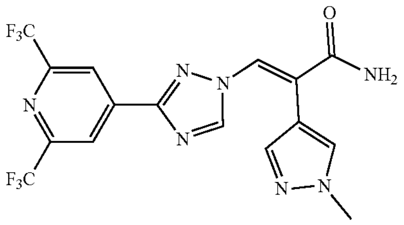

7

(1) Preparation of Compound 7-1

Compound 1-7 (300 mg) and 1-methylpyrazole-4-boronic acid pinacol ester (158.3 mg) were dispersed in 1,4-dioxane (8 mL), and potassium acetate (186.6 mg), Pd(dppf)$Cl_2$ (46 mg), and water (0.8 mL) were added. The mixture was heated to 90° C. and reacted under nitrogen atmosphere. After the reaction was completed, the reaction solution was concentrated under reduced pressure to give compound 7-1, which was directly used in the next step.

(2) Preparation of Compound 7-2

Compound 7-1 (298 mg) was dissolved in tetrahydrofuran (10 mL), a solution of lithium hydroxide hydrate (52.87 mg) and water (10 mL) was added dropwise in an ice-water bath, and the mixture was reacted at room temperature for 3 h. The reaction solution was adjusted to pH 3-5 with hydrochloric acid, extracted with ethyl acetate (20 mL×2), dried over anhydrous sodium sulfate, and filtered, and the filtrate was evaporated to dryness under reduced pressure to give compound 7-2, which was directly used in the next step.

(3) Preparation of Compound 7

Compound 7-2 (270 mg) was dispersed in tetrahydrofuran (15 mL), N-methylmorpholine (127.45 mg) and isobutyl chloroformate (154.41 mg) were added in an ice-water bath, and the mixture was stirred for 30 min. Ammonium hydroxide (132.3 mg) was added dropwise, and the mixture was reacted in an ice-water bath for 10 min. Water was added to quench the reaction, and the resulting mixture was extracted with ethyl acetate (20 mL×2), dried over anhydrous sodium sulfate, concentrated until no liquid flowed out, and purified by preparative liquid chromatography to give compound 7 (77 mg). ESI-MS: m/z=432.18 $[M+H]^+$.

$^1H$ NMR (500 MHz, DMSO-$d_6$) δ 8.87 (s, 1H), 8.48 (s, 2H), 7.84 (s, 1H), 7.73 (s, 1H), 7.58 (s, 1H), 7.54 (s, 1H), 7.26 (d, J=0.9 Hz, 1H), 3.85 (s, 3H).

Example 8

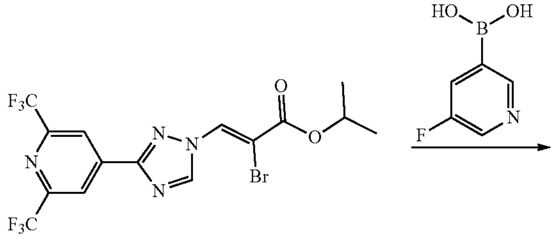

1-7

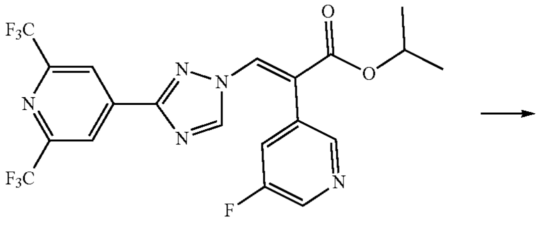

8-1

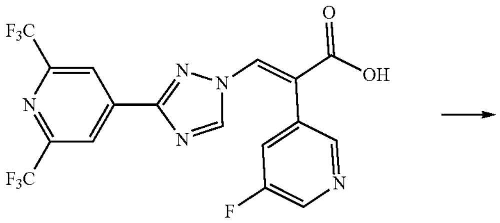

8-2

-continued

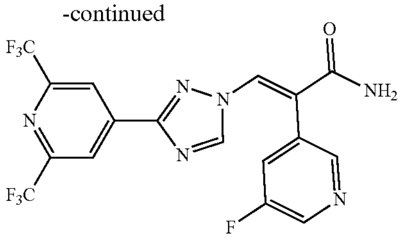

8

(1) Preparation of Compound 8-1

Compound 1-7 (200 mg) and 5-fluoro-3-pyridineboronic acid (75.03 mg) were dispersed in 1,4-dioxane (10 mL), and potassium acetate (124.4 mg), Pd(dppf)$Cl_2$ (15.5 mg), and water (1 mL) were added. The mixture was heated to 90° C. and reacted under nitrogen atmosphere. After the reaction was completed, the reaction solution was concentrated under reduced pressure and purified by column chromatography to give compound 8-1.

(2) Preparation of Compound 8-2

Compound 8-1 (150 mg) was dissolved in tetrahydrofuran (10 mL), a solution of lithium hydroxide hydrate (65.1 mg) and water (10 mL) was added dropwise in an ice-water bath, and the mixture was reacted at room temperature for 3 h. The reaction solution was adjusted to pH 3-5 with hydrochloric acid, extracted with ethyl acetate (20 mL×2), dried over anhydrous sodium sulfate, and filtered, and the filtrate was evaporated to dryness under reduced pressure to give compound 8-2, which was directly used in the next step.

(3) Preparation of Compound 8

Compound 8-2 (138.65 mg) was dispersed in tetrahydrofuran (10 mL), N-methylmorpholine (62.71 mg) and isobutyl chloroformate (84.68 mg) were added in an ice-water bath, and the mixture was stirred for 30 min. Ammonium hydroxide (65.1 mg) was added dropwise, and the mixture was reacted in an ice-water bath for 10 min. Water was added to quench the reaction, and the resulting mixture was extracted with ethyl acetate (20 mL×2), dried over anhydrous sodium sulfate, concentrated until no liquid flowed out, and purified by preparative liquid chromatography to give compound 8 (43 mg). ESI-MS: m/z=447.14 $[M+H]^+$.

$^1H$ NMR (500 MHz, DMSO-$d_6$) δ 9.15 (s, 1H), 8.63 (d, J=2.8 Hz, 1H), 8.39 (s, 1H), 8.34 (d, J=1.8 Hz, 1H), 8.09 (s, 2H), 7.76 (dt, J=10.0, 2.2 Hz, 1H), 7.67 (s, 1H), 7.28 (s, 1H).

Example 9

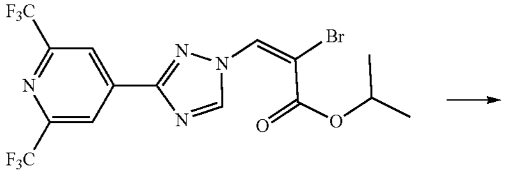

1-7

-continued

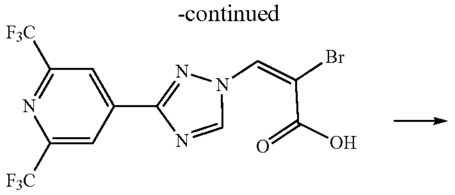

9-1

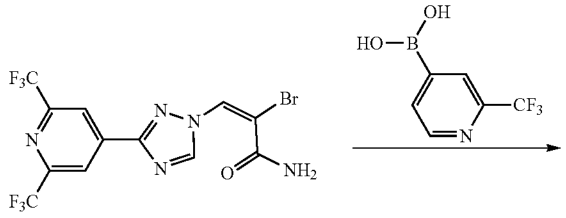

9-2

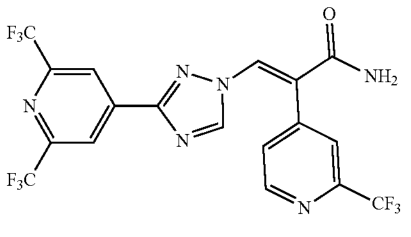

9

(1) Preparation of Compound 9-1

Compound 1-7 (500 mg) was dissolved in tetrahydrofuran (12 mL), a solution of sodium hydroxide (84.5 mg) and water (12 mL) was added dropwise in an ice-water bath, and the mixture was reacted at room temperature overnight. The reaction solution was adjusted to pH 3-5 with hydrochloric acid, extracted with ethyl acetate (30 mL×2), dried over anhydrous sodium sulfate, and filtered, and the filtrate was evaporated to dryness under reduced pressure to give compound 9-1, which was directly used in the next step.

(2) Preparation of Compound 9-2

Compound 9-1 (455 mg) was dispersed in tetrahydrofuran (15 mL), N-methylmorpholine (213.7 mg) and isobutyl chloroformate (288.6 mg) were added in an ice-water bath, and the mixture was stirred for 30 min. Ammonium hydroxide (222 mg) was added dropwise, and the mixture was reacted in an ice-water bath for 10 min. Water was added to quench the reaction, and the resulting mixture was extracted with ethyl acetate (20 mL×2), dried over anhydrous sodium sulfate, and concentrated until no liquid flowed out to give compound 9-2. ESI-MS: m/z=430.04/432.06 $[M+H]^+$.

(3) Preparation of Compound 9

Compound 9-2 (180 mg) and 4-boronic acid-2-trifluoromethylpyridine (95.9 mg) were dispersed in 1,4-dioxane (6 mL), and potassium acetate (123 mg), Pd(dppf)$Cl_2$ (15.3 mg), and water (0.6 mL) were added. The mixture was heated to 90° C. and reacted under nitrogen atmosphere. After the reaction was completed, the reaction solution was concentrated under reduced pressure and purified by preparative liquid chromatography to give compound 9 (18 mg). ESI-MS: m/z=497.09 $[M+H]^+$.

$^{1}H$ NMR (500 MHz, DMSO-$d_6$) δ 9.21 (s, 1H), 8.83 (d, J=4.9 Hz, 1H), 8.39 (s, 1H), 7.99 (s, 2H), 7.89 (s, 1H), 7.69 (s, 1H), 7.62 (d, J=4.9 Hz, 1H), 7.29 (s, 1H).

Example 10

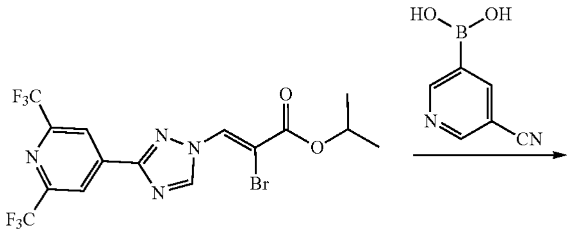

1-7

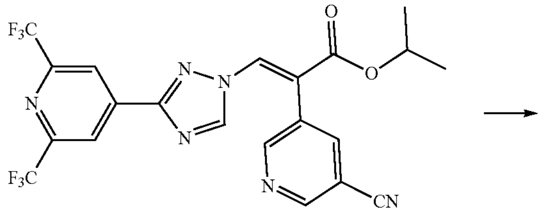

10-1

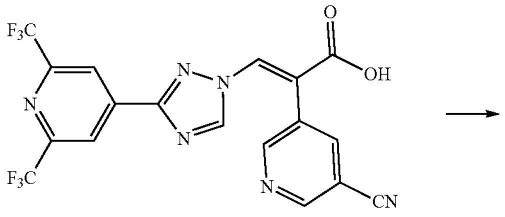

10-2

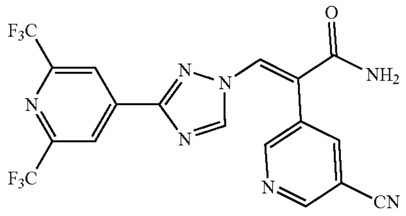

10

(1) Preparation of Compound 10-1

Compound 1-7 (200 mg) and 5-cyano-3-pyridinylboronic acid (75.03 mg) were dispersed in 1,4-dioxane (10 mL), and potassium acetate (124.4 mg), Pd(dppf)$Cl_2$ (15.5 mg), and water (1 mL) were added. The mixture was heated to 90° C. and reacted under nitrogen atmosphere. After the reaction was completed, the reaction solution was concentrated under reduced pressure and purified by column chromatography to give compound 10-1.

(2) Preparation of Compound 10-2

Compound 10-1 (173 mg) was dissolved in tetrahydrofuran (10 mL), a solution of lithium hydroxide hydrate (73.12 mg) and water (10 mL) was added dropwise in an ice-water bath, and the mixture was reacted at room temperature for 3 h. The reaction solution was adjusted to pH 3-5 with hydrochloric acid, extracted with ethyl acetate (20 mL×2), dried over anhydrous sodium sulfate, and filtered, and the filtrate was evaporated to dryness under reduced pressure to give compound 10-2, which was directly used in the next step.

(3) Preparation of Compound 10

Compound 10-2 (159 mg) was dispersed in tetrahydrofuran (10 mL), N-methylmorpholine (70.8 mg) and isobutyl chloroformate (95.6 mg) were added in an ice-water bath, and the mixture was stirred for 30 min. Ammonium hydroxide (73.5 mg) was added dropwise, and the mixture was reacted in an ice-water bath for 10 min. Water was added to quench the reaction, and the resulting mixture was extracted with ethyl acetate (20 mL×2), dried over anhydrous sodium sulfate, concentrated until no liquid flowed out, and purified by preparative liquid chromatography to give compound 10 (23 mg). ESI-MS: m/z=454.20 $[M+H]^+$.

$^{1}H$ NMR (500 MHz, DMSO-$d_6$) δ 9.21 (s, 1H), 9.09 (d, J=2.0 Hz, 1H), 8.76 (d, J=2.1 Hz, 1H), 8.45 (s, 1H), 8.36 (t, J=2.1 Hz, 1H), 8.05 (s, 2H), 7.70 (s, 1H), 7.30 (s, 1H).

Example 11

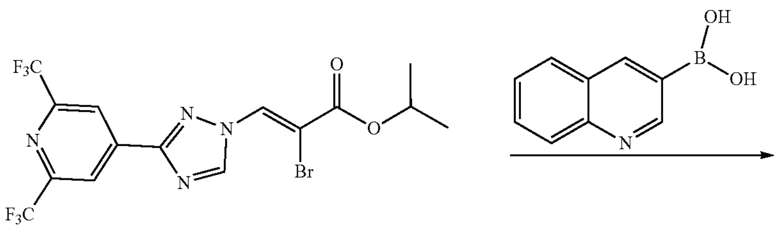

1-7

-continued

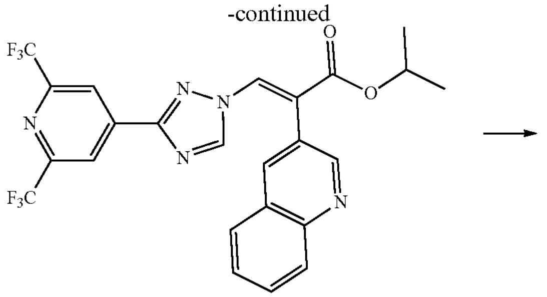

11-1

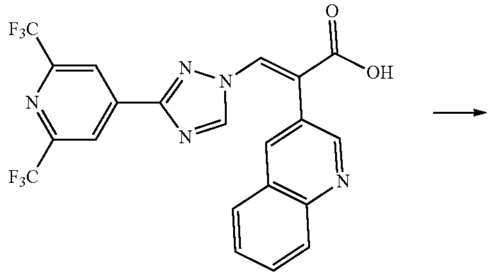

11-2

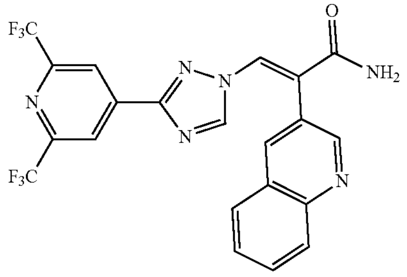

11

(1) Preparation of Compound 11-1

Compound 1-7 (300 mg) and 3-quinolineboronic acid (131.61 mg) were dispersed in 1,4-dioxane (8 mL), and potassium acetate (186.6 mg), Pd(dppf)$Cl_2$ (46 mg), and water (0.8 mL) were added. The mixture was heated to 90° C. and reacted under nitrogen atmosphere. After the reaction was completed, the reaction solution was concentrated under reduced pressure to give compound 11-1, which was directly used in the next step.

(2) Preparation of Compound 11-2

Compound 11-1 (328 mg) was dissolved in tetrahydrofuran (10 mL), a solution of lithium hydroxide hydrate (52.87 mg) and water (10 mL) was added dropwise in an ice-water bath, and the mixture was reacted at room temperature for 3 h. The reaction solution was adjusted to pH 3-5 with hydrochloric acid, extracted with ethyl acetate (20 mL×2), dried over anhydrous sodium sulfate, and filtered, and the filtrate was evaporated to dryness under reduced pressure to give compound 11-2, which was directly used in the next step.

(3) Preparation of Compound 11

Compound 11-2 (301 mg) was dispersed in tetrahydrofuran (15 mL), N-methylmorpholine (127.45 mg) and isobutyl chloroformate (154.41 mg) were added in an ice-water bath, and the mixture was stirred for 30 min. Ammonium hydroxide (132.3 mg) was added dropwise, and the mixture was reacted in an ice-water bath for 10 min. Water was added to quench the reaction, and the resulting mixture was extracted with ethyl acetate (20 mL×2), dried over anhydrous sodium sulfate, concentrated until no liquid flowed out, and purified by preparative liquid chromatography to give compound 11 (30 mg); ESI-MS: m/z=479.31 $[M+H]^+$.

$^1H$ NMR (500 MHz, DMSO-$d_6$) δ 9.17 (s, 1H), 8.76 (d, J=2.2 Hz, 1H), 8.43 (s, 1H), 8.30 (d, J=2.2 Hz, 1H), 8.08 (d, J=8.4 Hz, 1H), 8.01 (dd, J=8.1, 1.4 Hz, 1H), 7.88 (s, 2H), 7.84 (ddd, J=8.5, 6.9, 1.5 Hz, 1H), 7.70-7.62 (m, 2H), 7.36 (s, 1H).

Example 12

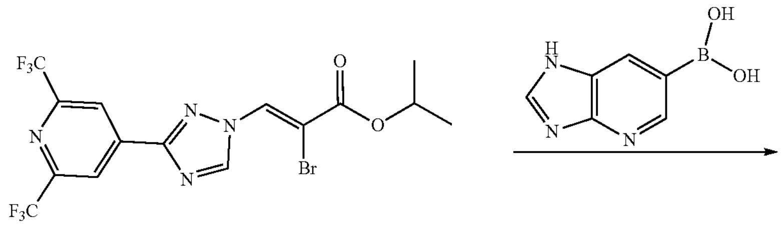

1-7

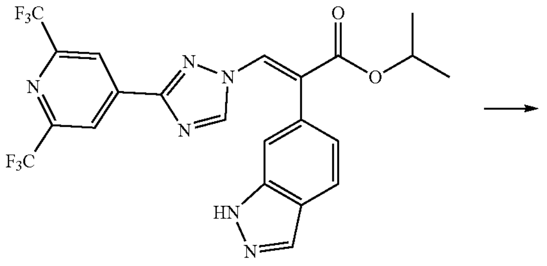

12-1

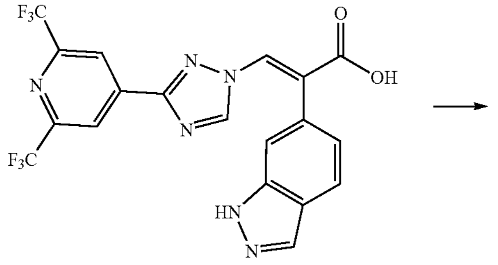

12-2

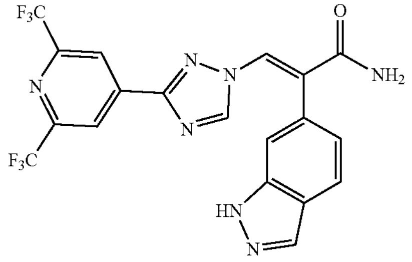

12

(1) Preparation of Compound 12-1

Compound 1-7 (300 mg) and indazole-6-boronic acid (123.22 mg) were dispersed in 1,4-dioxane (8 mL), and potassium acetate (186.6 mg), Pd(dppf)$Cl_2$ (46 mg), and water (0.8 mL) were added. The mixture was heated to 90° C. and reacted under nitrogen atmosphere. After the reaction was completed, the reaction solution was concentrated under reduced pressure to give compound 12-1, which was directly used in the next step.

(2) Preparation of Compound 12-2

Compound 12-1 (321 mg) was dissolved in tetrahydrofuran (10 mL), a solution of lithium hydroxide hydrate (52.87 mg) and water (10 mL) was added dropwise in an ice-water bath, and the mixture was reacted at room temperature for 3 h. The reaction solution was adjusted to pH 3-5 with hydrochloric acid, extracted with ethyl acetate (20 mL×2), dried over anhydrous sodium sulfate, and filtered, and the filtrate was evaporated to dryness under reduced pressure to give compound 12-2, which was directly used in the next step.

(3) Preparation of Compound 12

Compound 12-2 (295 mg) was dispersed in tetrahydrofuran (15 mL), N-methylmorpholine (127.45 mg) and isobutyl chloroformate (154.41 mg) were added in an ice-water bath, and the mixture was stirred for 30 min. Ammonium hydroxide (132.3 mg) was added dropwise, and the mixture was reacted in an ice-water bath for 10 min. Water was added to quench the reaction, and the resulting mixture was extracted with ethyl acetate (20 mL×2), dried over anhydrous sodium sulfate, concentrated until no liquid flowed out, and purified by preparative liquid chromatography to give compound 12 (40 mg). ESI-MS: m/z=468.22 $[M+H]^+$.

$^1$H NMR (500 MHz, DMSO-$d_6$) δ 13.11 (s, 1H), 8.63 (s, 1H), 8.19 (s, 1H), 8.13 (t, J=1.3 Hz, 1H), 8.09 (s, 2H), 7.82 (d, J=8.2 Hz, 1H), 7.62 (s, 1H), 7.47-7.43 (m, 1H), 7.11 (s, 1H), 6.95 (dd, J=8.3, 1.4 Hz, 1H).

Example 13

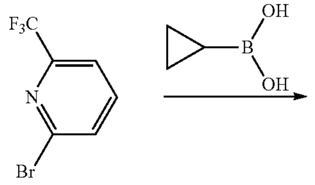

13-1

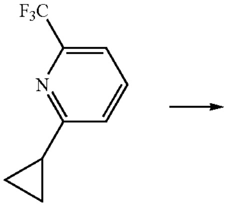

13-2

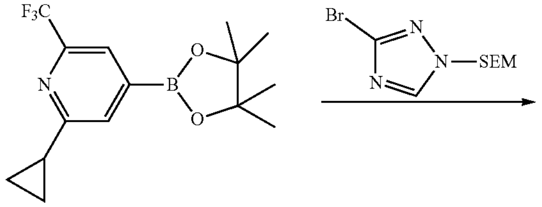

13-3

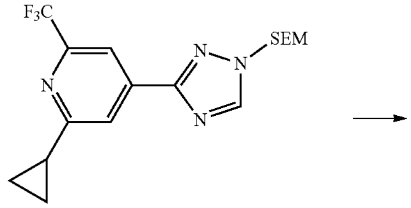

13-4

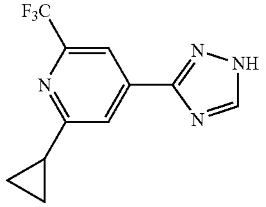

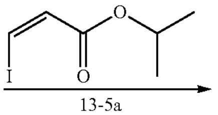

13-5a 13-5

-continued

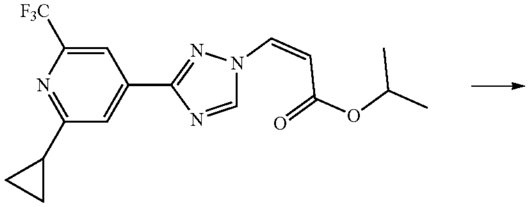

13-6

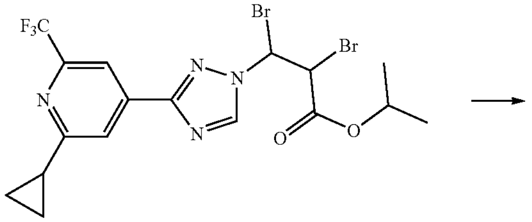

13-7

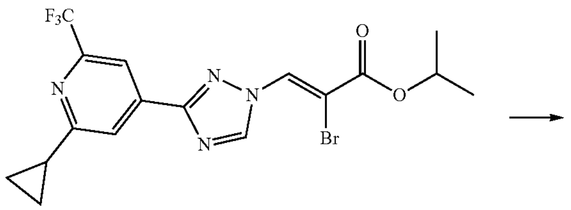

13-8

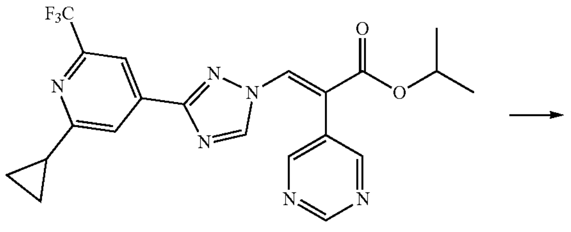

13-9

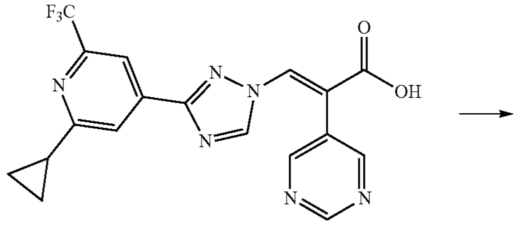

13-10

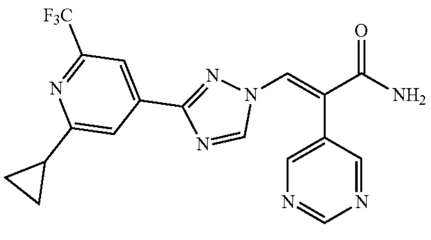

13

(1) Preparation of Compound 13-2

Compound 13-1 (15 g), cyclopropylboronic acid (11.4 g), potassium carbonate (27.5 g), and Pd(dppf)$Cl_2$ (2.4 g) were dispersed in dioxane (150 mL) and water (15 mL). The mixture was heated to 90° C. and reacted under nitrogen atmosphere. After the reaction was completed, the reaction solution was diluted with water (1000 mL) and extracted with ethyl acetate (100 mL×3). The organic phase was collected, dried over anhydrous sodium sulfate, and filtered, and the filtrate was evaporated to dryness under reduced pressure and purified by column chromatography to give compound 13-2.

(2) Preparation of Compound 13-3

Bis(pinacolato)diboron (6.51 μg), 4,4'-di-tert-butyl-2,2'-bipyridine (76.16 mg), and (1,5-cyclooctadiene)(methoxy) iridium(I) dimer (70.82 mg) were dispersed in cyclohexane (80 mL). The mixture was stirred for 10 min under nitrogen atmosphere, and compound 13-2 (8.0 g) was added. The resulting mixture was stirred at 55° C. under nitrogen atmosphere. After the reaction was completed, the reaction solution was quenched with ice water (80 mL) and extracted with ethyl acetate (80 mL×3). The organic phase was collected, dried over anhydrous sodium sulfate, and filtered, and the filtrate was evaporated to dryness under reduced pressure to give compound 13-3, which was directly used in the next step.

(3) Preparation of Compound 13-4

Compound 13-3 (10.7 g) was dispersed in ethylene glycol dimethyl ether (80 mL), and 3-bromo-1-((2-(trimethylsilyl) ethoxy)methyl)-1H-1,2,4-triazole (10.5 g) and an aqueous solution (16 mL) of potassium carbonate (14.18 g) were added. The mixture was stirred at room temperature under nitrogen atmosphere. After 1 h, tetrakis(triphenylphosphine) palladium (1.97 g) was added, and the resulting mixture was stirred at 90° C. under nitrogen atmosphere. After the reaction was completed, the reaction solution was quenched with ice water (60 mL) and extracted with ethyl acetate (100 mL×3).

The organic phase was collected and washed with brine (60 mL×2). The organic layer was dried over anhydrous sodium sulfate and filtered, and the filtrate was evaporated to dryness under reduced pressure to give compound 13-4, which was directly used in the next step.

(4) Preparation of Compound 13-5

Compound 13-4 (6.0 g) was dispersed in a solution of hydrogen chloride in 1,4-dioxane (4.0 M, 50 mL), and the mixture was stirred at 60° C. until the reaction was completed. The reaction solution was slowly poured into an ice saturated sodium bicarbonate solution. The resulting mixture was adjusted to pH=7-8 with sodium bicarbonate and extracted with ethyl acetate (100 mL×3). The organic phase was washed with saturated brine (100 mL), dried over anhydrous sodium sulfate, concentrated under reduced pressure until no liquid flowed out, and purified by column chromatography to give compound 13-5.

(5) Preparation of Compound 13-6

Compound 13-5 (4 g) was dispersed in DMF (20 mL) and dioxane (20 mL), and DABCO (3.5 g) was added. The mixture was stirred at 20-25° C. for 30 min and then cooled to 0-10° C., and compound 13-5a (5.6 g) was added dropwise. After addition, the resulting mixture was stirred at 20-25° C. for 1.5 h. After the reaction was completed, the reaction solution was poured into water (100 mL), and the resulting mixture was extracted with ethyl acetate (100 mL×2). The organic phases were combined, dried over anhydrous sodium sulfate, and purified by column chromatography to give compound 13-6 (3.0 g).

(6) Preparation of Compound 13-7

Compound 13-6 (3 g) was dispersed in dichloromethane (30 mL), and the mixture was cooled to 0° C. Liquid bromine (2.6 g) was added dropwise within 15 min. After addition, the mixture was slowly heated to room temperature and stirred for 6 h. After the reaction was completed, the reaction mixture was poured into ice water (40 mL), and the resulting mixture was extracted with dichloromethane (40 mL×3). The organic phases were combined, washed with a saturated sodium bisulfite solution (30 mL), dried over anhydrous sodium sulfate, concentrated under reduced pressure until no liquid flowed out, and purified by column chromatography to give compound 13-7.

(7) Preparation of Compound 13-8

Compound 13-7 (4.3 g) was dispersed in tetrahydrofuran (40 mL), and the mixture was cooled to 0° C. Triethylamine (1.65 g) was added dropwise. After addition, the mixture was slowly heated to room temperature and reacted for 6 h. After the reaction was completed, the reaction solution was diluted with water (40 mL) and extracted with ethyl acetate (40 mL×3). The organic phases were combined, dried over anhydrous sodium sulfate, and purified by column chromatography to give compound 13-8 (2 g).

(8) Preparation of Compound 13-9

Compound 13-8 (300 mg), 5-pyrimidineboronic acid (100 mg), potassium acetate (198 mg), and Pd(dppf)$Cl_2$ (24.6 mg) were dispersed in dioxane (8 mL) and water (0.8 mL). The mixture was heated to 90° C. and reacted under nitrogen atmosphere. After the reaction was completed, the reaction solution was diluted with water (15 mL) and extracted with ethyl acetate (20 mL×3). The organic phase was collected, dried over anhydrous sodium sulfate, and filtered, and the filtrate was evaporated to dryness under reduced pressure and purified by column chromatography to give compound 13-9 (200 mg).

(9) Preparation of Compound 13-10

Compound 13-9 (200 mg) was dissolved in tetrahydrofuran (8 mL), a solution of sodium hydroxide (36 mg) and water (8 mL) was added dropwise in an ice-water bath, and the mixture was reacted at room temperature overnight. The reaction solution was adjusted to pH 3-5 with hydrochloric acid, extracted with ethyl acetate (20 mL×3), dried over anhydrous sodium sulfate, and filtered, and the filtrate was evaporated to dryness under reduced pressure to give compound 13-10, which was directly used in the next step.

(10) Preparation of Compound 13

Compound 13-10 (181 mg) was dispersed in tetrahydrofuran (10 mL), N-methylmorpholine (91 mg) and isobutyl chloroformate (123 mg) were added in an ice-water bath, and the mixture was stirred for 30 min. Ammonium hydroxide (95 mg) was added dropwise, and the mixture was reacted in an ice-water bath for 10 min. Water was added to quench the reaction, and the resulting mixture was extracted with ethyl acetate (20 mL×3), dried over anhydrous sodium sulfate, concentrated until no liquid flowed out, and purified by preparative liquid chromatography to give compound 13 (57 mg). ESI-MS: m/z=402.27 $[M+H]^+$.

$^1$H NMR (500 MHz, DMSO-$d_6$) δ 9.24 (s, 1H), 9.13 (s, 1H), 8.73 (s, 2H), 8.42 (s, 1H), 7.69 (s, 1H), 7.65 (s, 1H), 7.49 (s, 1H), 7.41 (s, 1H), 2.28 (tt, J=8.3, 4.7 Hz, 1H), 1.10 (dq, J=6.6, 3.8 Hz, 2H), 0.99-0.91 (m, 2H).

Example 14

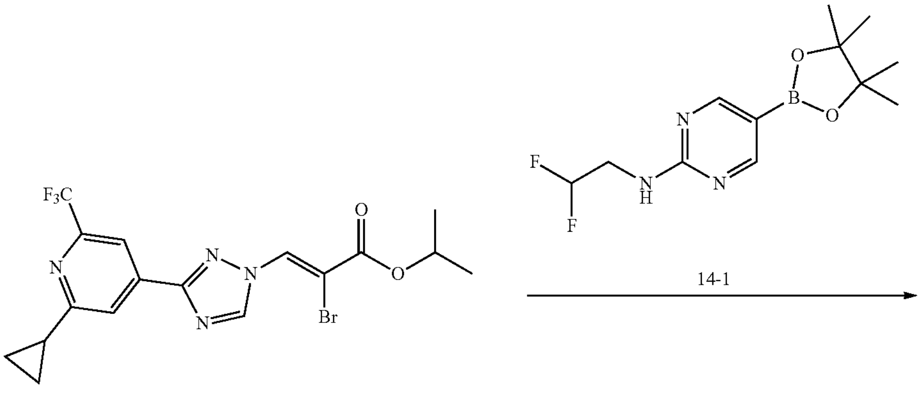

13-8

14-1

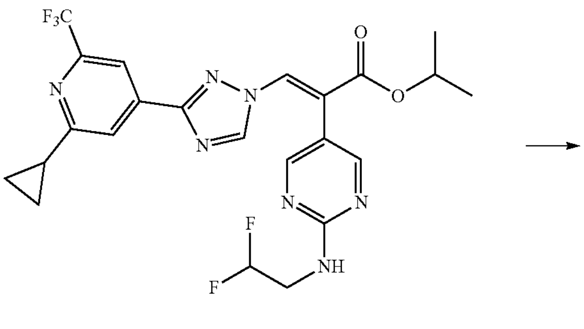

14-2

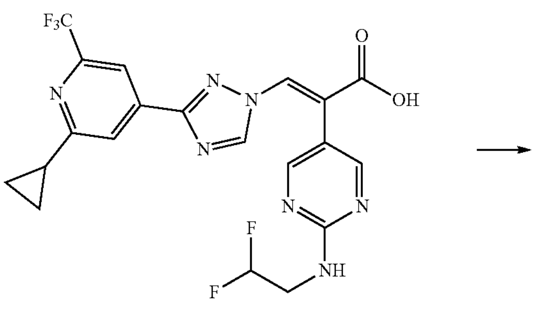

14-3

-continued

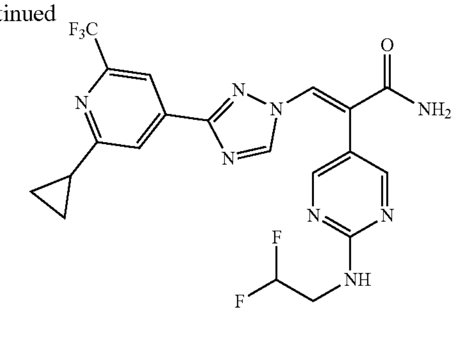

14

(1) Preparation of Compound 14-2

Compounds 13-8 (300 mg) and 14-1 (228 mg) were dispersed in 1,4-dioxane (15 mL), and potassium acetate (196 mg), Pd(dppf)$Cl_2$ (22 mg), and water (1.5 mL) were added. The mixture was heated to 90° C. and reacted under nitrogen atmosphere. After the reaction was completed, the reaction solution was concentrated under reduced pressure and purified by column chromatography to give compound 14-2.

(2) Preparation of Compound 14-3

Compound 14-2 (100 mg) was dissolved in tetrahydrofuran (5 mL), a solution of lithium hydroxide hydrate (40.1 mg) and water (5 mL) was added dropwise in an ice-water bath, and the mixture was reacted at room temperature for 2 h. The reaction solution was adjusted to pH 3-5 with hydrochloric acid, extracted with ethyl acetate (20 mL×2), dried over anhydrous sodium sulfate, and filtered, and the filtrate was evaporated to dryness under reduced pressure to give compound 14-3, which was directly used in the next step.

(3) Preparation of Compound 14

Compound 14-3 (60 mg) was dispersed in tetrahydrofuran (5 mL), N-methylmorpholine (26 mg) and isobutyl chloroformate (35 mg) were added in an ice-water bath, and the mixture was stirred for 30 min. Ammonium hydroxide (27 mg) was added dropwise, and the mixture was reacted in an ice-water bath for 10 min. Water was added to quench the reaction, and the resulting mixture was extracted with ethyl acetate (20 mL×2), dried over anhydrous sodium sulfate, concentrated until no liquid flowed out, and purified by preparative liquid chromatography to give compound 14 (10 mg). ESI-MS: m/z=481.3 $[M+H]^+$.

$^1H$ NMR (500 MHz, DMSO-$d_6$) δ 9.05 (s, 1H), 8.21 (s, 3H), 7.84 (d, J=1.3 Hz, 1H), 7.76 (t, J=6.2 Hz, 1H), 7.71 (d, J=1.3 Hz, 1H), 7.55 (s, 1H), 7.40 (s, 1H), 6.10 (tt, J=56.5, 4.2 Hz, 1H), 3.74 (tdd, J=15.0, 6.2, 4.1 Hz, 2H), 2.30 (tt, J=8.1, 4.7 Hz, 1H), 1.08 (dt, J=8.1, 3.2 Hz, 2H), 0.99-0.95 (m, 2H).

Example 15

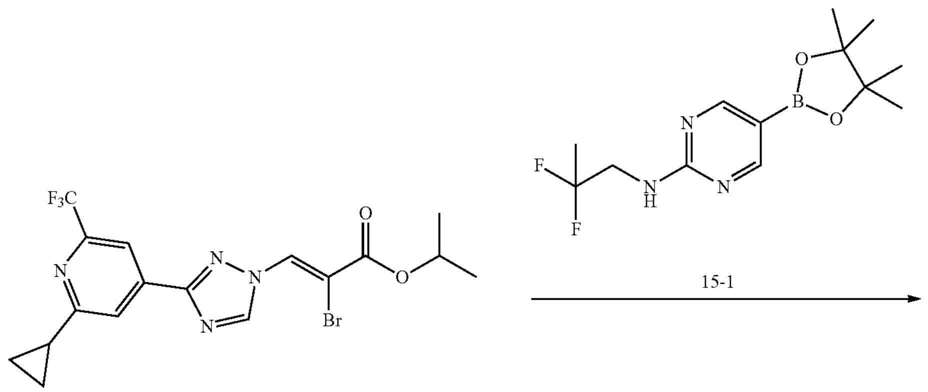

13-8

-continued

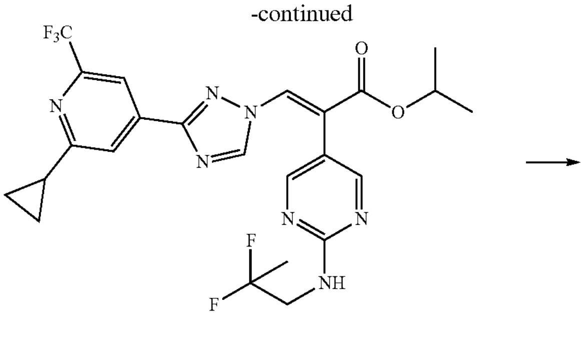

15-2

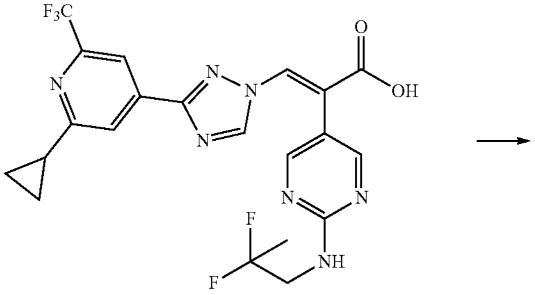

15-3

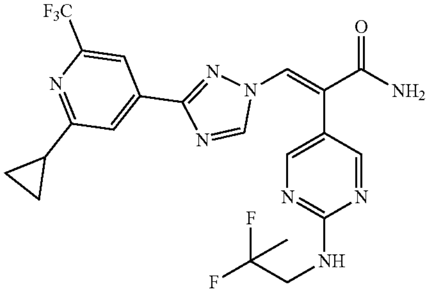

15

(1) Preparation of Compound 15-2

Compounds 13-8 (371 mg) and 15-1 (299 mg) were dispersed in 1,4-dioxane (55 mL), and potassium acetate (244 mg), Pd(dppf)$Cl_2$ (30 mg), and water (1.5 mL) were added. The mixture was heated to 90° C. and reacted under nitrogen atmosphere. After the reaction was completed, the reaction solution was concentrated under reduced pressure and purified by column chromatography to give compound 15-2.

(2) Preparation of Compound 15-3

Compound 15-2 (340 mg) was dissolved in tetrahydrofuran (5 mL), a solution of lithium hydroxide hydrate (132.7 mg) and water (5 mL) was added dropwise in an ice-water bath, and the mixture was reacted at room temperature for 2 h. The reaction solution was adjusted to pH 3-5 with hydrochloric acid, extracted with ethyl acetate (20 mL×2), dried over anhydrous sodium sulfate, and filtered, and the filtrate was evaporated to dryness under reduced pressure to give compound 15-3, which was directly used in the next step.

(3) Preparation of Compound 15

Compound 15-3 (312 mg) was dispersed in tetrahydrofuran (5 mL), N-methylmorpholine (127 mg) and isobutyl chloroformate (172 mg) were added in an ice-water bath, and the mixture was stirred for 30 min. Ammonium hydroxide (132 mg) was added dropwise, and the mixture was reacted in an ice-water bath for 10 min. Water was added to quench the reaction, and the resulting mixture was extracted with ethyl acetate (20 mL×2), dried over anhydrous sodium sulfate, concentrated until no liquid flowed out, and purified by preparative liquid chromatography to give compound 15 (70 mg). ESI-MS: m/z=495.39 $[M+H]^+$.

$^1H$ NMR (500 MHz, DMSO-$d_6$) δ 9.05 (s, 1H), 8.20 (d, J=3.2 Hz, 3H), 7.84 (d, J=1.2 Hz, 1H), 7.77 (t, J=6.6 Hz, 1H), 7.73 (d, J=1.3 Hz, 1H), 7.54 (s, 1H), 7.42 (s, 1H), 3.83 (td, J=13.6, 6.6 Hz, 2H), 2.29 (tt, J=8.3, 4.7 Hz, 1H), 1.61 (t, J=19.0 Hz, 3H), 1.08 (dt, J=8.0, 3.2 Hz, 2H), 1.00-0.94 (m, 2H).

Example 16
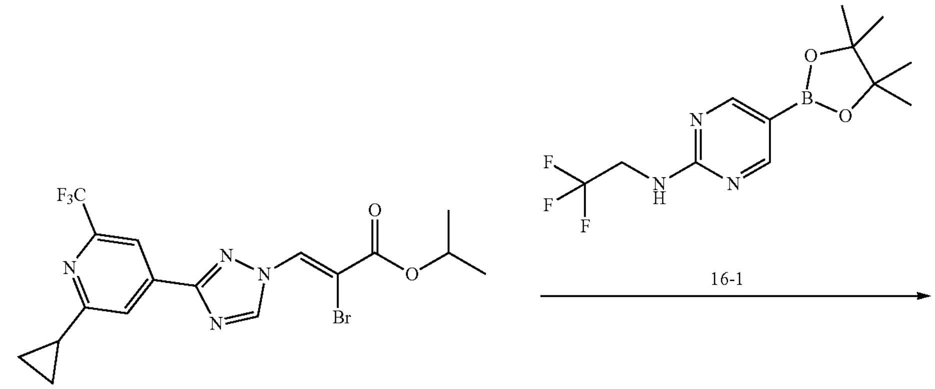
13-8
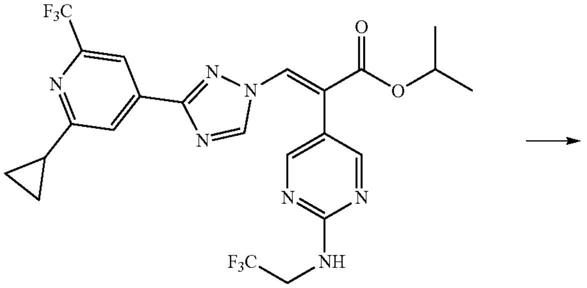
16-2
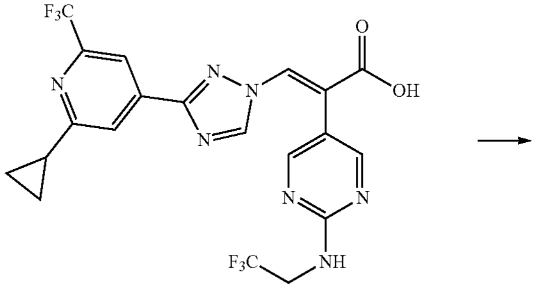
16-3
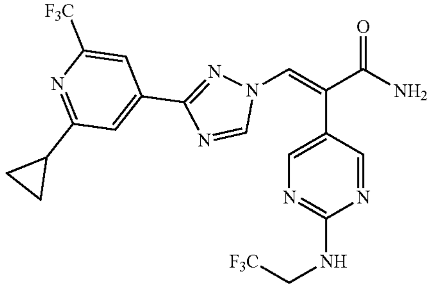
16

(1) Preparation of Compound 16-2

Compounds 13-8 (400 mg) and 16-1 (327 mg) were dispersed in 1,4-dioxane (15 mL), and potassium acetate (264 mg), Pd(dppf)$Cl_2$ (65.7 mg), and water (1.5 mL) were added. The mixture was heated to 90° C. and reacted under nitrogen atmosphere. After the reaction was completed, the reaction solution was concentrated under reduced pressure and purified by column chromatography to give compound 16-2.

(2) Preparation of Compound 16-3

Compound 16-2 (300 mg) was dissolved in tetrahydrofuran (10 mL), a solution of lithium hydroxide hydrate (46.5 mg) and water (10 mL) was added dropwise in an ice-water bath, and the mixture was reacted at room temperature for 3 h. The reaction solution was adjusted to pH 3-5 with hydrochloric acid, extracted with ethyl acetate (20 mL×2), dried over anhydrous sodium sulfate, and filtered, and the filtrate was evaporated to dryness under reduced pressure to give compound 16-3, which was directly used in the next step.

(3) Preparation of Compound 16

Compound 16-3 (276 mg) was dispersed in tetrahydrofuran (15 mL), N-methylmorpholine (112 mg) and isobutyl chloroformate (151 mg) were added in an ice-water bath, and the mixture was stirred for 30 min. Ammonium hydroxide (116 mg) was added dropwise, and the mixture was reacted in an ice-water bath for 10 min. Water was added to quench the reaction, and the resulting mixture was extracted with ethyl acetate (20 mL×2), dried over anhydrous sodium sulfate, concentrated until no liquid flowed out, and purified by preparative liquid chromatography to give compound 16 (58.4 mg). ESI-MS: m/z=499.28 $[M+H]^+$.

$^1H$ NMR (500 MHz, DMSO-$d_6$) δ 9.07 (s, 1H), 8.23 (d, J=6.1 Hz, 3H), 8.00 (t, J=6.7 Hz, 1H), 7.83 (d, J=1.3 Hz, 1H), 7.70 (d, J=1.3 Hz, 1H), 7.55 (s, 1H), 7.42 (s, 1H), 4.18 (qd, J=9.5, 6.6 Hz, 2H), 2.28 (tt, J=8.1, 4.7 Hz, 1H), 1.08 (dt, J=8.0, 3.2 Hz, 2H), 0.99-0.94 (m, 2H).

Example 17

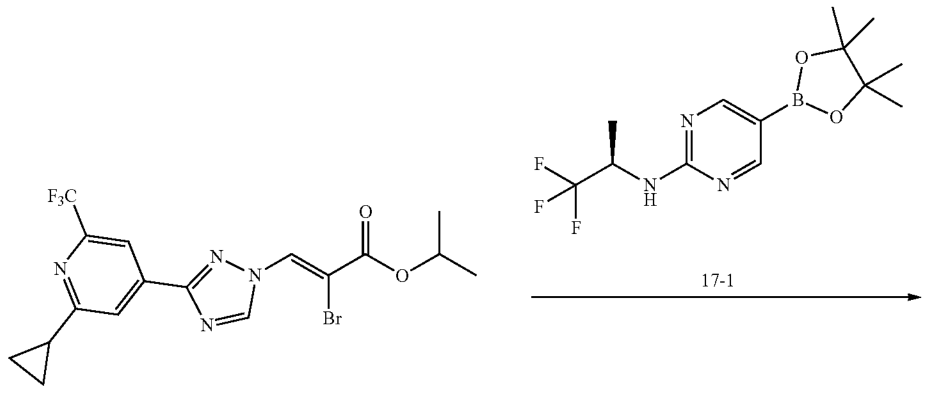

13-8

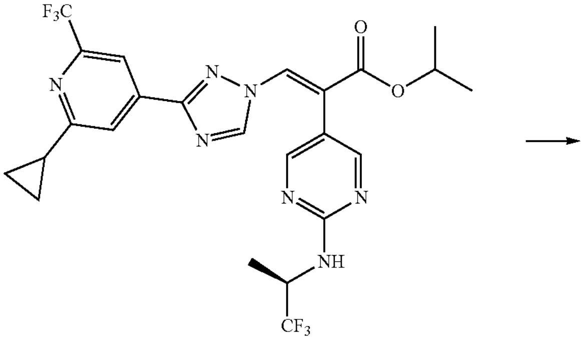

17-2

-continued

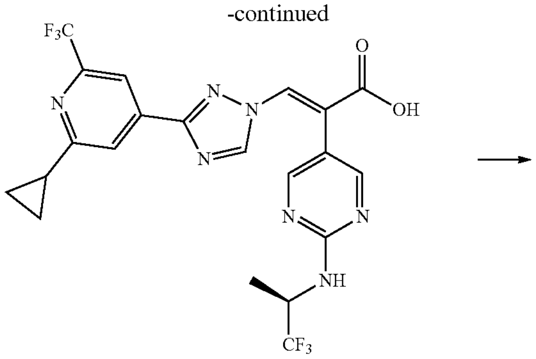

17-3

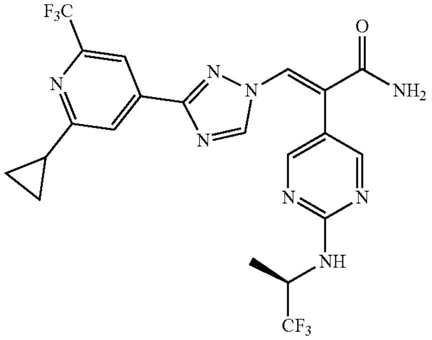

17

(1) Preparation of Compound 17-2

Compounds 13-8 (400 mg) and 17-1 (342 mg) were dispersed in 1,4-dioxane (15 mL), and potassium acetate (264 mg), Pd(dppf)$Cl_2$ (65.7 mg), and water (1.5 mL) were added. The mixture was heated to 90° C. and reacted under nitrogen atmosphere. After the reaction was completed, the reaction solution was concentrated under reduced pressure and purified by column chromatography to give compound 17-2.

(2) Preparation of Compound 17-3

Compound 17-2 (400 mg) was dissolved in tetrahydrofuran (10 mL), and a solution of lithium hydroxide hydrate (91 mg) and water (10 mL) was added dropwise in an ice-water bath. The temperature was controlled at 0-10° C., and the mixture was reacted for 3 h. The reaction solution was adjusted to pH 3-5 with hydrochloric acid, extracted with ethyl acetate (20 mL×2), dried over anhydrous sodium sulfate, and filtered, and the filtrate was evaporated to dryness under reduced pressure to give compound 17-3, which was directly used in the next step.

(3) Preparation of Compound 17

Compound 17-3 (370 mg) was dispersed in tetrahydrofuran (15 mL), N-methylmorpholine (146 mg) and isobutyl chloroformate (197 mg) were added in an ice-water bath, and the mixture was stirred for 30 min. Ammonium hydroxide (151 mg) was added dropwise, and the mixture was reacted in an ice-water bath for 10 min. Water was added to quench the reaction, and the resulting mixture was extracted with ethyl acetate (20 mL×2), dried over anhydrous sodium sulfate, concentrated until no liquid flowed out, and purified by preparative liquid chromatography to give compound 17 (49 mg). ESI-MS: m/z=513.33 $[M+H]^+$.

$^1H$ NMR (500 MHz, DMSO-$d_6$) δ 9.07 (s, 1H), 8.23 (d, J=7.2 Hz, 3H), 7.96 (d, J=9.1 Hz, 1H), 7.85 (s, 1H), 7.71 (d, J=1.3 Hz, 1H), 7.54 (s, 1H), 7.43 (s, 1H), 4.95 (h, J=7.2 Hz, 1H), 2.29 (tt, J=8.3, 4.7 Hz, 1H), 1.35 (d, J=7.0 Hz, 3H), 1.07 (dt, J=8.3, 3.1 Hz, 2H), 0.98 (dq, J=7.0, 3.4 Hz, 2H).

Example 18

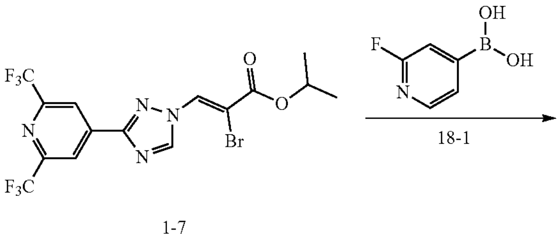

1-7

-continued

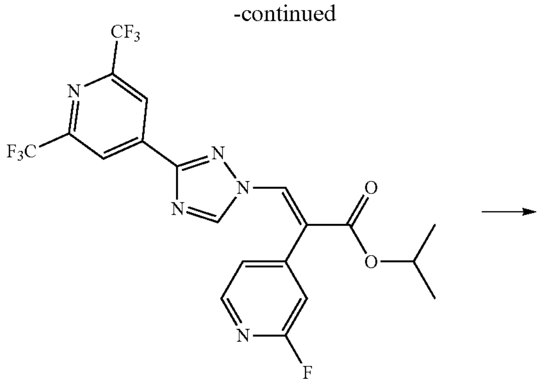

18-2

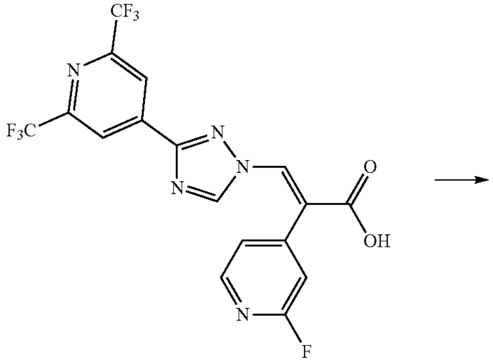

18-3

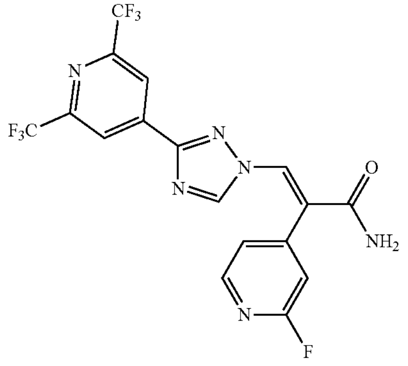

18

(1) Preparation of Compound 18-2

Compound 1-7 (300 mg) and 2-fluoropyridine-4-boronic acid (18-1, 107 mg) were dispersed in 1,4-dioxane (8 mL), and potassium acetate (186.6 mg), Pd(dppf)$Cl_2$ (23.2 mg), and water (0.8 mL) were added. The mixture was heated to 90° C. and reacted under nitrogen atmosphere. After the starting materials were consumed completely as detected by TLC, the reaction solution was concentrated under reduced pressure and purified by column chromatography to give compound 18-2.

(2) Preparation of Compound 18-3

Compound 18-2 (240 mg) was dissolved in tetrahydrofuran (10 mL), a solution of lithium hydroxide hydrate (61.7 mg) and water (10 mL) was added dropwise in an ice-water bath, and the mixture was reacted at 0-5° C. for 2 h. The reaction solution was adjusted to pH 6-7 with hydrochloric acid, extracted with ethyl acetate, dried over anhydrous sodium sulfate, and filtered, and the filtrate was evaporated to dryness under reduced pressure to give compound 18-3, which was directly used in the next step.

(3) Preparation of Compound 18

Compound 18-3 (219 mg) was dispersed in tetrahydrofuran (15 mL), N-methylmorpholine (99 mg) and isobutyl chloroformate (133.8 mg) were added in an ice-water bath, and the mixture was stirred for 30 min. Ammonium hydroxide (102.9 mg) was added dropwise, and the mixture was reacted in an ice-water bath for 10 min. Water was added to quench the reaction, and the resulting mixture was extracted with ethyl acetate, dried over anhydrous sodium sulfate, concentrated until no liquid flowed out, and purified by preparative liquid chromatography to give compound 18 (57 mg). ESI-MS: m/z=447.17 $[M+H]^+$.

$^1H$ NMR (500 MHz, DMSO-$d_6$) δ 9.13 (s, 1H), 8.34 (s, 1H), 8.30 (d, J=5.1 Hz, 1H), 8.09 (s, 2H), 7.68 (s, 1H), 7.26 (dt, J=5.1, 1.7 Hz, 1H), 7.21 (s, 1H), 7.19 (d, J=1.6 Hz, 1H).

Example 19

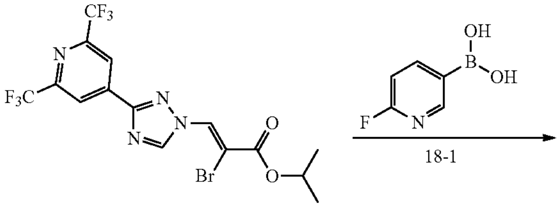

1-7

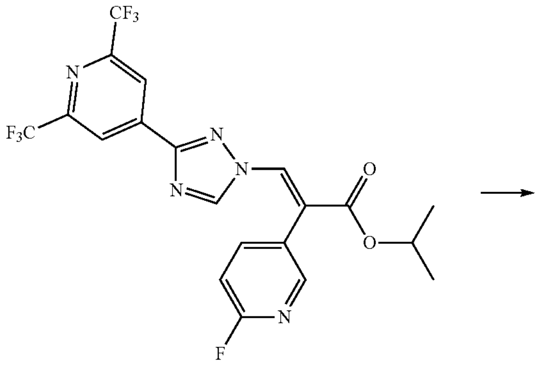

19-2

-continued

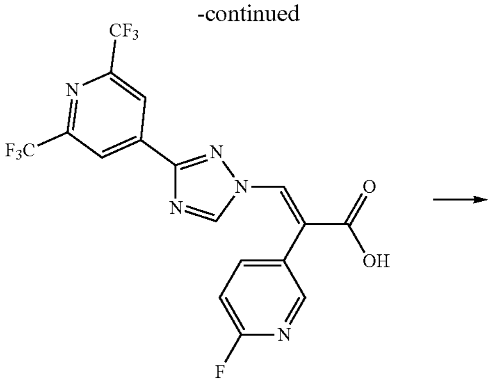

19-3

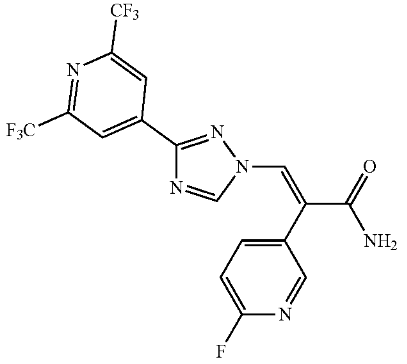

19

(1) Preparation of Compound 19-2

Compound 1-7 (200 mg) and 2-fluoropyridine-5-boronic acid (19-1, 71.5 mg) were dispersed in 1,4-dioxane (10 mL), and potassium acetate (124.4 mg), $Pd(dppf)Cl_2$ (15.5 mg), and water (1 mL) were added. The mixture was heated to 90° C. and reacted under nitrogen atmosphere. After the starting materials were consumed completely as detected by TLC, the reaction solution was concentrated under reduced pressure and purified by column chromatography to give compound 19-2.

(2) Preparation of Compound 19-3

Compound 19-2 (205 mg) was dissolved in tetrahydrofuran (10 mL), a solution of lithium hydroxide hydrate (35.4 mg) and water (10 mL) was added dropwise in an ice-water bath, and the mixture was reacted at room temperature for 3 h. The reaction solution was adjusted to pH 6-7 with hydrochloric acid, extracted with ethyl acetate, dried over anhydrous sodium sulfate, and filtered, and the filtrate was evaporated to dryness under reduced pressure to give compound 19-3, which was directly used in the next step.

(3) Preparation of Compound 19

Compound 19-3 (137.4 mg) was dispersed in tetrahydrofuran (10 mL), N-methylmorpholine (64.74 mg) and isobutyl chloroformate (87.41 mg) were added in an ice-water bath, and the mixture was stirred for 30 min. Ammonium hydroxide (67.2 mg) was added dropwise, and the mixture was reacted in an ice-water bath for 10 min. Water was added to quench the reaction, and the resulting mixture was extracted with ethyl acetate, dried over anhydrous sodium sulfate, concentrated until no liquid flowed out, and purified by preparative liquid chromatography to give compound 19 (70 mg). ESI-MS: m/z=447.15 $[M+H]^+$.

$^1H$ NMR (500 MHz, DMSO-$d_6$) δ 9.14 (s, 1H), 8.37 (s, 1H), 8.14 (d, J=2.4 Hz, 1H), 8.11 (s, 2H), 7.89 (td, J=8.1, 2.5 Hz, 1H), 7.64 (s, 1H), 7.27 (dd, J=8.4, 2.7 Hz, 2H).

Example 20

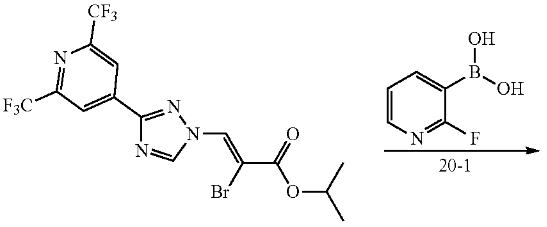

1-7

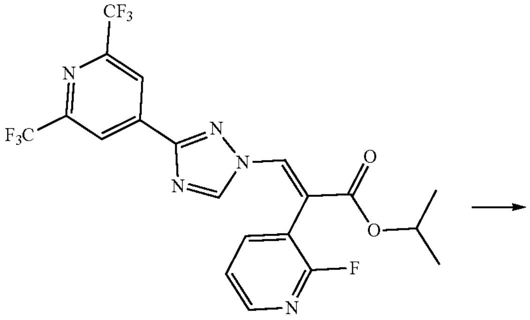

20-2

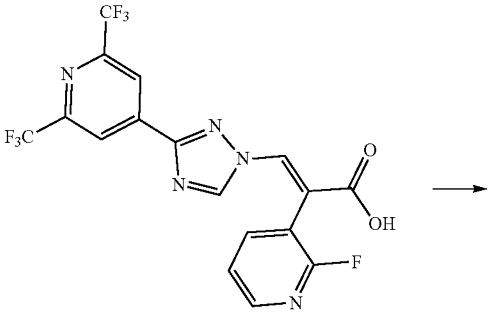

20-3

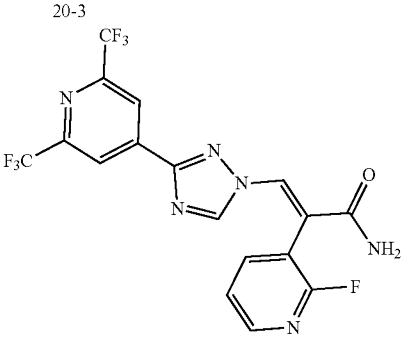

20

(1) Preparation of Compound 20-2

Compound 1-7 (200 mg) and 2-fluoropyridine-3-boronic acid (20-1, 71.5 mg) were dispersed in 1,4-dioxane (10 mL), and potassium acetate (124.4 mg), $Pd(dppf)Cl_2$ (15.5 mg), and water (1 mL) were added. The mixture was heated to 90° C. and reacted under nitrogen atmosphere. After the starting materials were consumed completely as detected by TLC, the reaction solution was concentrated under reduced pressure and purified by column chromatography to give compound 20-2.

(2) Preparation of Compound 20-3

Compound 20-2 (205 mg) was dissolved in tetrahydrofuran (10 mL), a solution of lithium hydroxide hydrate (35.4 mg) and water (10 mL) was added dropwise in an ice-water bath, and the mixture was reacted at room temperature for 3 h. The reaction solution was adjusted to pH 6-7 with hydrochloric acid, extracted with ethyl acetate, dried over anhydrous sodium sulfate, and filtered, and the filtrate was evaporated to dryness under reduced pressure to give compound 20-3, which was directly used in the next step.

(3) Preparation of Compound 20

Compound 20-3 (137.4 mg) was dispersed in tetrahydrofuran (10 mL), N-methylmorpholine (64.74 mg) and isobutyl chloroformate (87.41 mg) were added in an ice-water bath, and the mixture was stirred for 30 min. Ammonium hydroxide (67.2 mg) was added dropwise, and the mixture was reacted in an ice-water bath for 10 min. Water was added to quench the reaction, and the resulting mixture was extracted with ethyl acetate, dried over anhydrous sodium sulfate, concentrated until no liquid flowed out, and purified by preparative liquid chromatography to give compound 20 (15 mg). ESI-MS: m/z=447.16 $[M+H]^+$.

Example 21

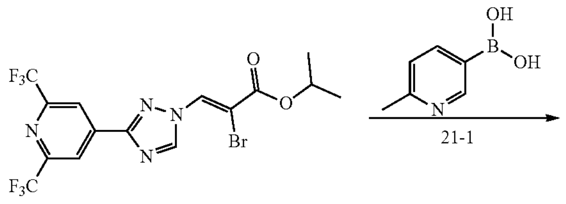

21-1

1-7

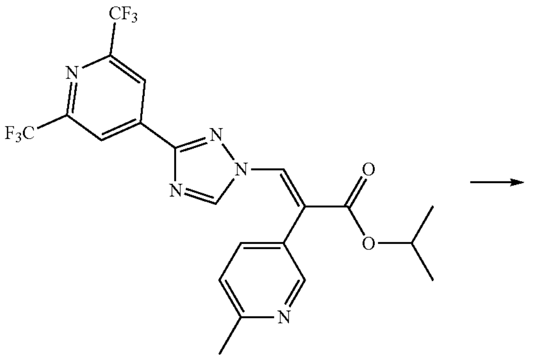

21-2

-continued

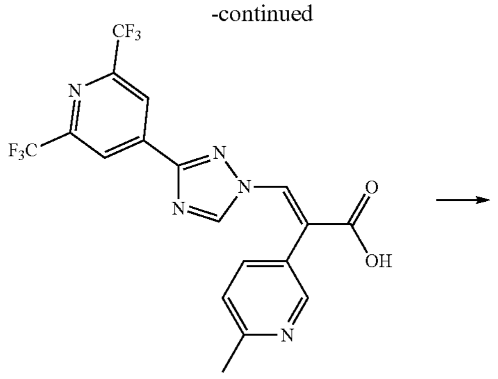

21-3

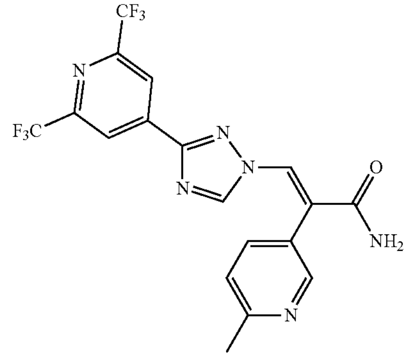

21

(1) Preparation of Compound 21-2

Compound 1-7 (300 mg) and 6-methylpyridine-3-boronic acid (21-1, 104 mg) were dispersed in 1,4-dioxane (8 mL), and potassium acetate (186.6 mg), $Pd(dppf)Cl_2$ (23.2 mg), and water (0.8 mL) were added. The mixture was heated to 90° C. and reacted under nitrogen atmosphere. After the starting materials were consumed completely as detected by TLC, the reaction solution was concentrated under reduced pressure and purified by column chromatography to give compound 21-2.

(2) Preparation of Compound 21-3

Compound 21-2 (120 mg) was dissolved in tetrahydrofuran (10 mL), a solution of lithium hydroxide hydrate (20.7 mg) and water (10 mL) was added dropwise in an ice-water bath, and the mixture was reacted at 0-5° C. for 2 h. The reaction solution was adjusted to pH 6-7 with hydrochloric acid, extracted with ethyl acetate, dried over anhydrous sodium sulfate, and filtered, and the filtrate was evaporated to dryness under reduced pressure to give compound 21-3, which was directly used in the next step.

(3) Preparation of Compound 21

Compound 21-3 (109 mg) was dispersed in tetrahydrofuran (15 mL), N-methylmorpholine (50 mg) and isobutyl chloroformate (67.5 mg) were added in an ice-water bath, and the mixture was stirred for 30 min. Ammonium hydroxide (51.9 mg) was added dropwise, and the mixture was reacted in an ice-water bath for 10 min. Water was added to quench the reaction, and the resulting mixture was extracted with ethyl acetate, dried over anhydrous sodium sulfate, concentrated until no liquid flowed out, and purified by preparative liquid chromatography to give compound 21 (42 mg). ESI-MS: m/z=443.17 $[M+H]^+$.

$^1H$ NMR (500 MHz, DMSO-$d_6$) δ 9.05 (s, 1H), 8.32 (d, J=2.1 Hz, 1H), 8.29 (s, 1H), 8.11 (s, 2H), 7.61 (s, 1H), 7.57 (dd, J=7.9, 2.3 Hz, 1H), 7.34 (d, J=7.9 Hz, 1H), 7.23 (s, 1H), 2.54 (s, 3H).

Example 22

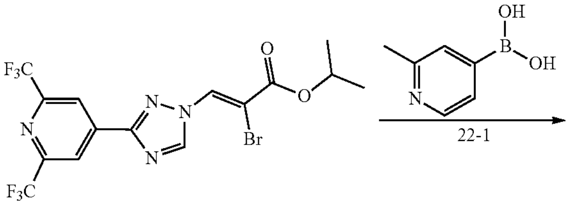

22-1

1-7

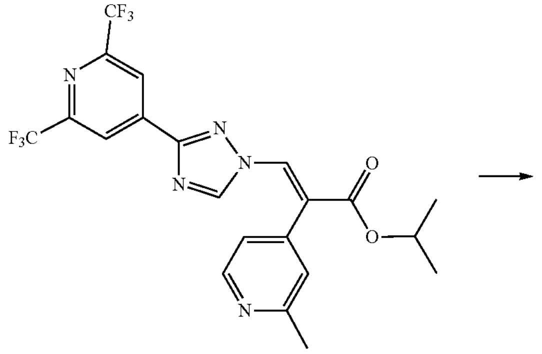

22-2

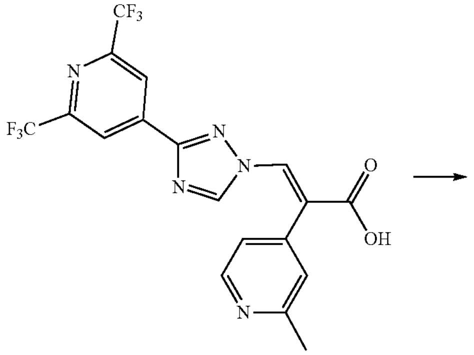

22-3

-continued

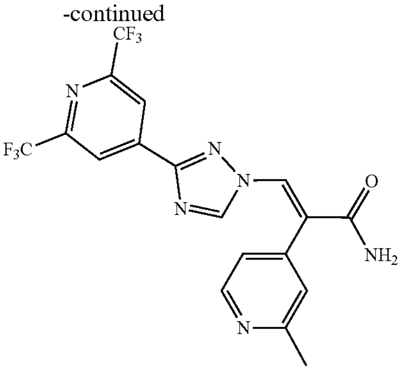

22

(1) Preparation of Compound 22-2

Compound 1-7 (300 mg) and 2-methylpyridine-4-boronic acid (22-1, 104 mg) were dispersed in 1,4-dioxane (8 mL), and potassium acetate (186.6 mg), Pd(dppf)$Cl_2$ (23.2 mg), and water (0.8 mL) were added. The mixture was heated to 90° C. and reacted under nitrogen atmosphere. After the starting materials were consumed completely as detected by TLC, the reaction solution was concentrated under reduced pressure and purified by column chromatography to give compound 22-2.

(2) Preparation of Compound 22-3

Compound 22-2 (170 mg) was dissolved in tetrahydrofuran (10 mL), a solution of lithium hydroxide hydrate (29 mg) and water (10 mL) was added dropwise in an ice-water bath, and the mixture was reacted at 0-5° C. for 2 h. The reaction solution was adjusted to pH 6-7 with hydrochloric acid, extracted with ethyl acetate, dried over anhydrous sodium sulfate, and filtered, and the filtrate was evaporated to dryness under reduced pressure to give compound 22-3, which was directly used in the next step.

(3) Preparation of Compound 22

Compound 22-3 (155 mg) was dispersed in tetrahydrofuran (15 mL), N-methylmorpholine (70.8 mg) and isobutyl chloroformate (95.6 mg) were added in an ice-water bath, and the mixture was stirred for 30 min. Ammonium hydroxide (73.5 mg) was added dropwise, and the mixture was reacted in an ice-water bath for 10 min. Water was added to quench the reaction, and the resulting mixture was extracted with ethyl acetate, dried over anhydrous sodium sulfate, concentrated until no liquid flowed out, and purified by preparative liquid chromatography to give compound 22 (57 mg). ESI-MS: m/z=443.16 $[M+H]^+$.

$^1H$ NMR (500 MHz, DMSO-$d_6$) δ 8.99 (s, 1H), 8.49 (dd, J=5.0, 0.8 Hz, 1H), 8.23 (s, 1H), 8.12 (s, 2H), 7.64 (s, 1H), 7.21-7.19 (m, 1H), 7.17 (s, 1H), 7.06 (dd, J=5.1, 1.6 Hz, 1H), 2.49 (s, 3H).

Example 23
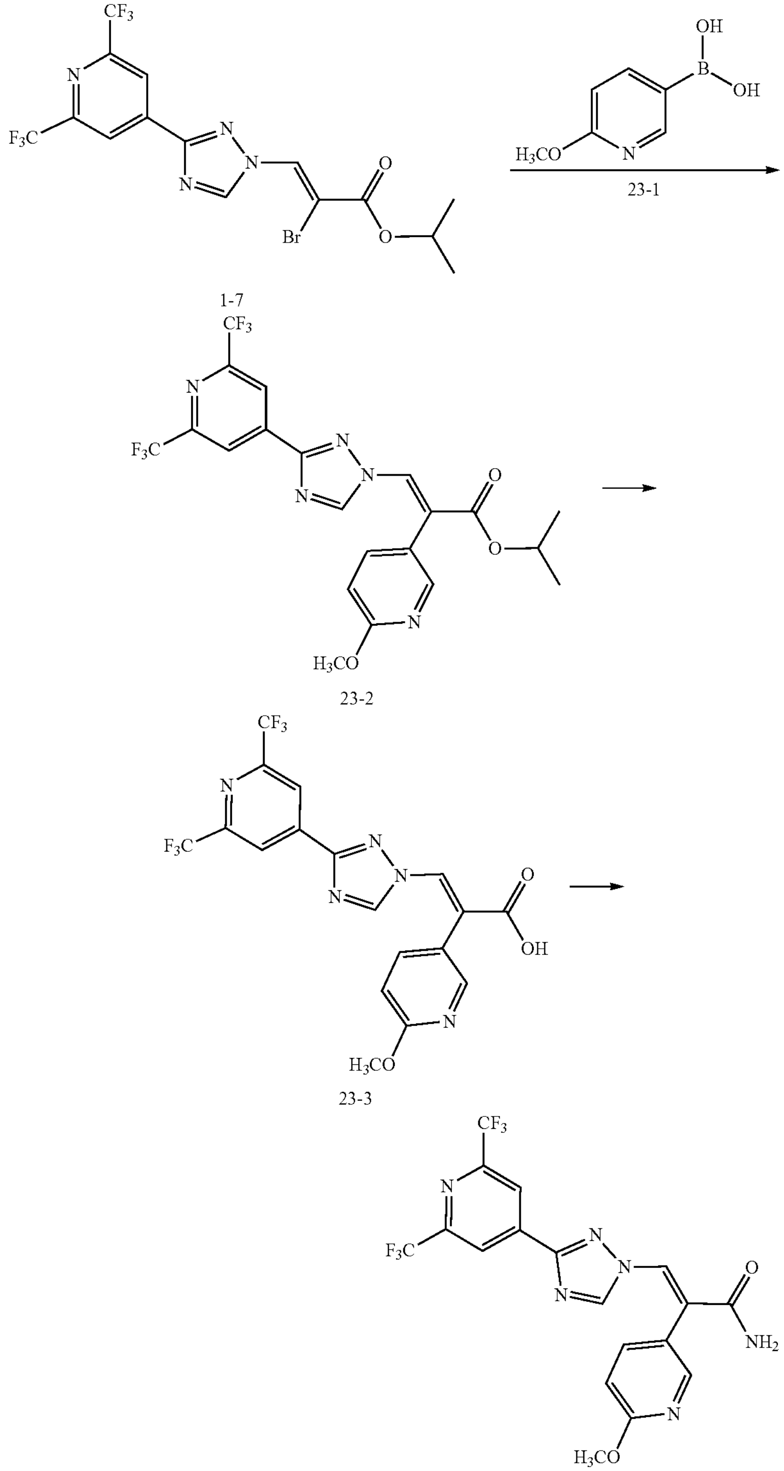
1-7
23-2
23-3
23
(1) Preparation of Compound 23-2
Compound 1-7 (300 mg) and 6-methoxy-3-pyridineboronic acid (23-1, 116.23 mg) were dispersed in 1,4-dioxane (10 mL), and potassium acetate (186.7 mg), Pd(dppf)$Cl_2$ (23.2 mg), and water (1 mL) were added. The mixture was heated to 90° C. and reacted under nitrogen atmosphere. After the starting materials were consumed completely as detected by TLC, the reaction solution was concentrated under reduced pressure and purified by column chromatography to give compound 23-2.

(2) Preparation of Compound 23-3

Compound 23-2 (306 mg) was dissolved in tetrahydrofuran (10 mL), a solution of lithium hydroxide hydrate (53.2 mg) and water (10 mL) was added dropwise in an ice-water bath, and the mixture was reacted at room temperature for 3 h. The reaction solution was adjusted to pH 6-7 with hydrochloric acid, extracted with ethyl acetate, dried over anhydrous sodium sulfate, and filtered, and the filtrate was evaporated to dryness under reduced pressure to give compound 23-3, which was directly used in the next step.

(3) Preparation of Compound 23

Compound 23-3 (289 mg) was dispersed in tetrahydrofuran (10 mL), N-methylmorpholine (128.3 mg) and isobutyl chloroformate (173.2 mg) were added in an ice-water bath, and the mixture was stirred for 30 min. Ammonium hydroxide (133.1 mg) was added dropwise, and the mixture was reacted in an ice-water bath for 10 min. Water was added to quench the reaction, and the resulting mixture was extracted with ethyl acetate, dried over anhydrous sodium sulfate, concentrated until no liquid flowed out, and purified by preparative liquid chromatography to give compound 23 (100 mg). ESI-MS: m/z=459.22 $[M+H]^+$.

$^1H$ NMR (500 MHz, DMSO-$d_6$) δ 9.04 (s, 1H), 8.25 (s, 1H), 8.17 (s, 2H), 8.07-8.04 (m, 1H), 7.58 (dd, J=8.5, 2.5 Hz, 2H), 7.23 (s, 1H), 6.90 (dd, J=8.6, 0.7 Hz, 1H), 3.91 (s, 3H).

Example 24

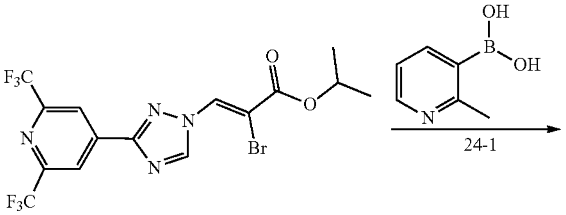

24-1

1-7

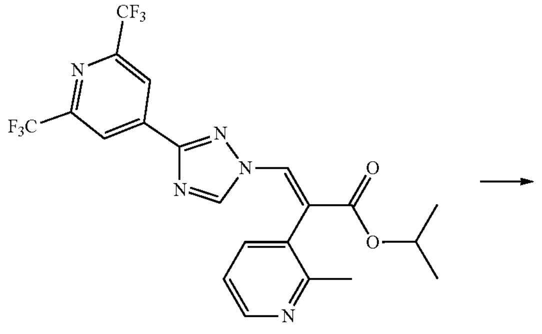

24-2

-continued

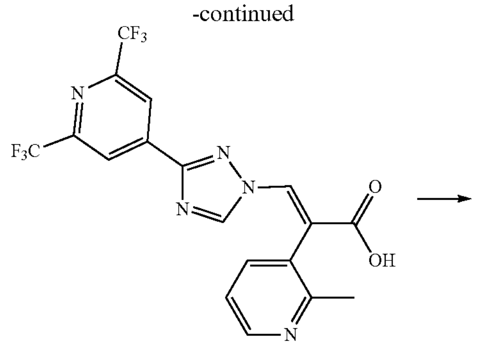

24-3

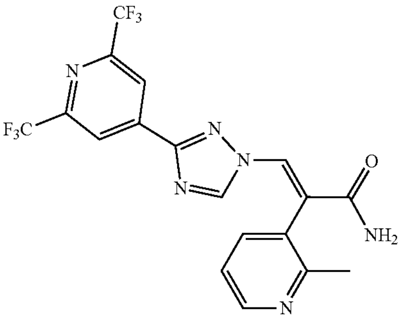

24

(1) Preparation of Compound 24-2

Compound 1-7 (300 mg) and 2-methylpyridine-3-boronic acid (24-1, 104 mg) were dispersed in 1,4-dioxane (8 mL), and potassium acetate (186.6 mg), $Pd(dppf)Cl_2$ (23.2 mg), and water (0.8 mL) were added. The mixture was heated to 90° C. and reacted under nitrogen atmosphere. After the starting materials were consumed completely as detected by TLC, the reaction solution was concentrated under reduced pressure and purified by column chromatography to give compound 24-2.

(1) Preparation of Compound 24-3

Compound 24-2 (150 mg) was dissolved in tetrahydrofuran (10 mL), a solution of lithium hydroxide hydrate (38.9 mg) and water (10 mL) was added dropwise in an ice-water bath, and the mixture was reacted at 0-25° C. for 2 h. The reaction solution was adjusted to pH 6-7 with hydrochloric acid, extracted with ethyl acetate, dried over anhydrous sodium sulfate, and filtered, and the filtrate was evaporated to dryness under reduced pressure to give compound 24-3, which was directly used in the next step.

(3) Preparation of Compound 24

Compound 24-3 (137 mg) was dispersed in tetrahydrofuran (15 mL), N-methylmorpholine (62.5 mg) and isobutyl chloroformate (84.4 mg) were added in an ice-water bath, and the mixture was stirred for 30 min. Ammonium hydroxide (64.9 mg) was added dropwise, and the mixture was reacted in an ice-water bath for 10 min. Water was added to quench the reaction, and the resulting mixture was extracted with ethyl acetate, dried over anhydrous sodium sulfate, concentrated until no liquid flowed out, and purified by preparative liquid chromatography to give compound 24 (82 mg). ESI-MS: m/z=443.28 $[M+H]^+$.

$^1$H NMR (500 MHz, DMSO-$d_6$) δ 9.07 (s, 1H), 8.51 (dd, J=4.9, 1.7 Hz, 1H), 8.34 (s, 1H), 8.05 (s, 2H), 7.59 (s, 1H), 7.51 (dd, J=7.6, 1.7 Hz, 1H), 7.29 (dd, J=7.6, 4.9 Hz, 1H), 7.18 (s, 1H), 2.28 (s, 3H).
Example 25
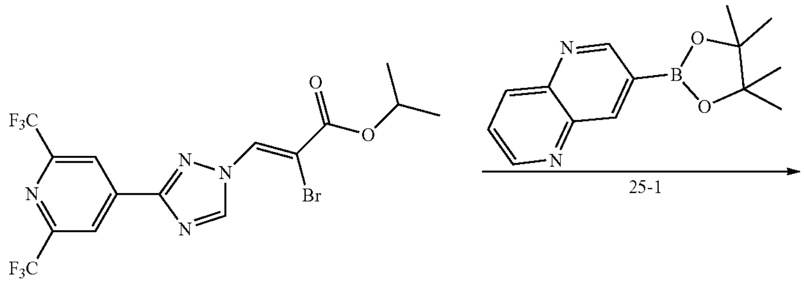
25-1
1-7
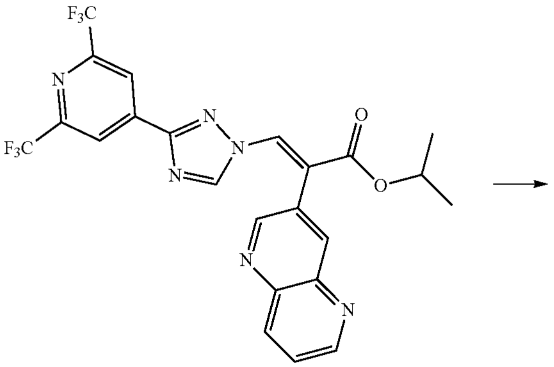
25-2
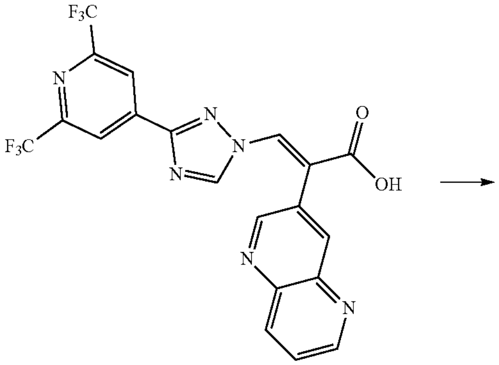
25-3
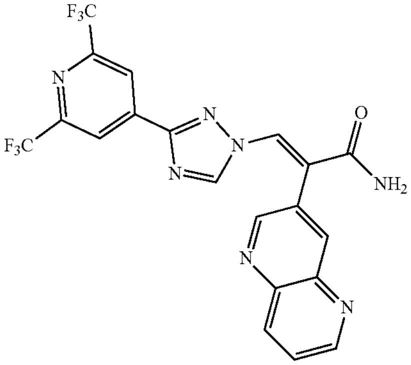
25

(1) Preparation of Compound 25-2

Compounds 1-7 (300 mg) and 25-1 (195 mg) were dispersed in 1,4-dioxane (8 mL), and potassium acetate (186.6 mg), Pd(dppf)$Cl_2$ (46 mg), and water (0.8 mL) were added. The mixture was heated to 90° C. and reacted under nitrogen atmosphere. After the starting materials were consumed completely as detected by TLC, the reaction solution was concentrated under reduced pressure to give compound 25-2.

(2) Preparation of Compound 25-3

Compound 25-2 (240 mg) was dissolved in tetrahydrofuran (10 mL), a solution of lithium hydroxide hydrate (57.8 mg) and water (10 mL) was added dropwise in an ice-water bath, and the mixture was reacted at room temperature for 3 h. The reaction solution was adjusted to pH 6-7 with hydrochloric acid, extracted with ethyl acetate, dried over anhydrous sodium sulfate, and filtered, and the filtrate was evaporated to dryness under reduced pressure to give compound 25-3, which was directly used in the next step.

(3) Preparation of Compound 25

Compound 25-3 (220 mg) was dispersed in tetrahydrofuran (15 mL), N-methylmorpholine (93 mg) and isobutyl chloroformate (125 mg) were added in an ice-water bath, and the mixture was stirred for 30 min. Ammonium hydroxide (96 mg) was added dropwise, and the mixture was reacted in an ice-water bath for 10 min. Water was added to quench the reaction, and the resulting mixture was extracted with ethyl acetate, dried over anhydrous sodium sulfate, concentrated until no liquid flowed out, and purified by preparative liquid chromatography to give compound 25 (86 mg). ESI-MS: m/z=480.24 $[M+H]^+$.

$^1H$ NMR (500 MHz, DMSO-$d_6$) δ 9.22 (s, 1H), 9.04 (dd, J=4.2, 1.7 Hz, 1H), 8.89 (d, J=2.1 Hz, 1H), 8.53-8.45 (m, 2H), 8.34 (d, J=2.1 Hz, 1H), 7.88 (dd, J=8.5, 4.2 Hz, 1H), 7.82 (s, 2H), 7.70 (s, 1H), 7.38 (s, 1H).

Example 26

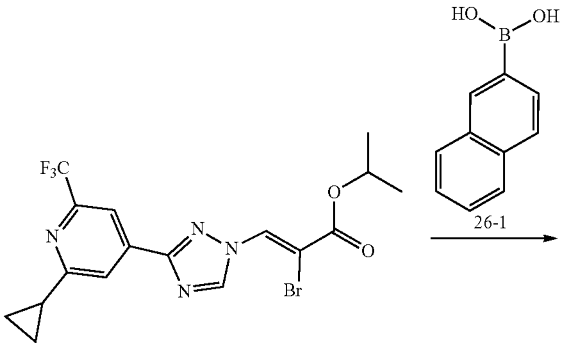

13-8

-continued

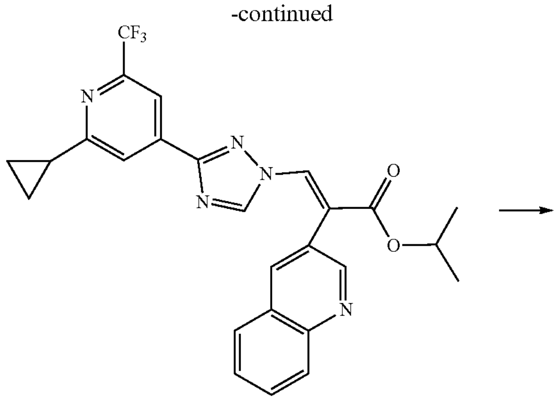

26-2

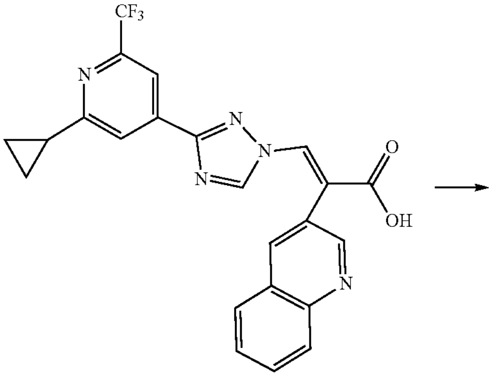

26-3

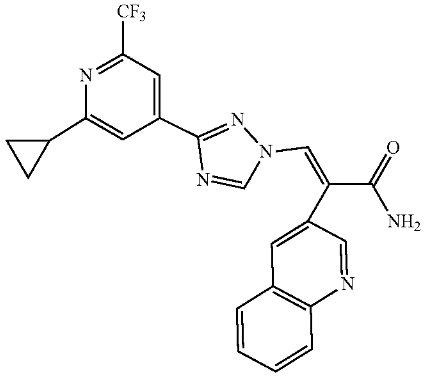

26

(1) Preparation of Compound 26-2

Compound 13-8 (200 mg) and 3-quinolineboronic acid (26-1, 76.6 mg) were dispersed in 1,4-dioxane (5 mL), and potassium acetate (132.5 mg), Pd(dppf)$Cl_2$ (14.6 mg), and water (0.5 mL) were added. The mixture was heated to 90° C. and reacted under nitrogen atmosphere. After the starting materials were consumed completely as detected by TLC, the reaction solution was concentrated under reduced pressure and purified by column chromatography to give compound 26-2.

(2) Preparation of Compound 26-3

Compound 26-2 (120 mg) was dissolved in tetrahydrofuran (4 mL), a solution of lithium hydroxide hydrate (30.6 mg) and water (4 mL) was added dropwise in an ice-water bath, and the mixture was reacted at room temperature for 4 h. The reaction solution was adjusted to pH 6-7 with hydrochloric acid, extracted with ethyl acetate, dried over anhydrous sodium sulfate, and filtered, and the filtrate was evaporated to dryness under reduced pressure to give compound 26-3, which was directly used in the next step.

(3) Preparation of Compound 26

Compound 26-3 (100 mg) was dispersed in tetrahydrofuran (5 mL), N-methylmorpholine (44.5 mg) and isobutyl chloroformate (60.1 mg) were added in an ice-water bath, and the mixture was stirred for 30 min. Ammonium hydroxide (46.2 mg) was added dropwise, and the mixture was reacted in an ice-water bath for 10 min. Water was added to quench the reaction, and the resulting mixture was extracted with ethyl acetate, dried over anhydrous sodium sulfate, concentrated until no liquid flowed out, and purified by preparative liquid chromatography to give compound 26 (40 mg); ESI-MS: m/z=451.20 $[M+H]^+$.

$^1$H NMR (500 MHz, DMSO-$d_6$) δ 9.07 (s, 1H), 8.74 (d, J=2.2 Hz, 1H), 8.40 (s, 1H), 8.29 (d, J=2.2 Hz, 1H), 8.09 (dd, J=8.4, 1.1 Hz, 1H), 8.01 (dd, J=8.1, 1.5 Hz, 1H), 7.82 (ddd, J=8.5, 6.9, 1.5 Hz, 1H), 7.64 (ddd, J=8.1, 6.9, 1.2 Hz, 2H), 7.48 (d, J=1.4 Hz, 1H), 7.33 (s, 1H), 7.29 (d, J=1.3 Hz, 1H), 2.07 (tt, J=8.1, 4.7 Hz, 1H), 1.06-0.97 (m, 2H), 0.83-0.75 (m, 2H).

Example 27

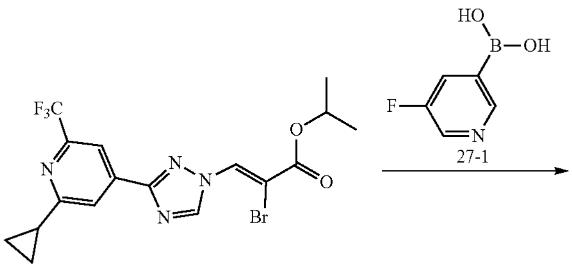

13-8

27-1

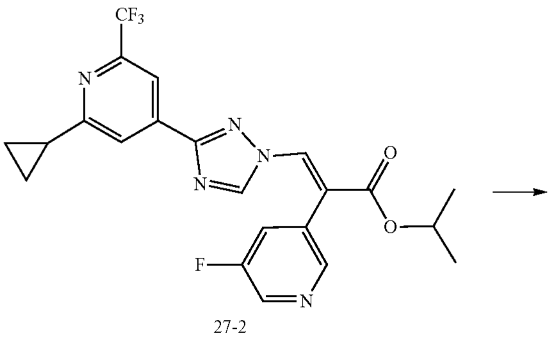

27-2

-continued

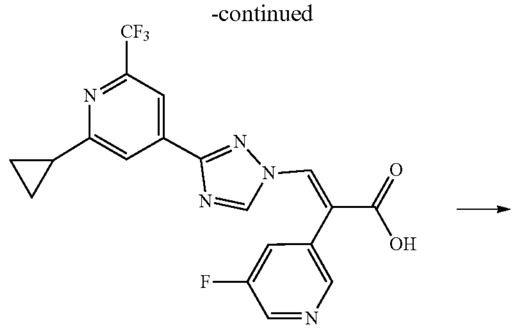

27-3

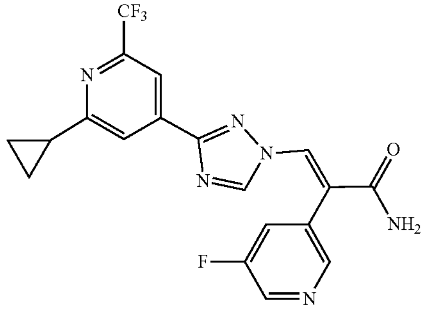

27

(1) Preparation of Compound 27-2

Compound 13-8 (200 mg) and 5-fluoro-3-pyridineboronic acid (27-1, 76.1 mg) were dispersed in 1,4-dioxane (5 mL), and potassium acetate (132.5 mg), Pd(dppf)$Cl_2$ (14.6 mg), and water (0.5 mL) were added. The mixture was heated to 90° C. and reacted under nitrogen atmosphere. After the starting materials were consumed completely as detected by TLC, the reaction solution was concentrated under reduced pressure and purified by column chromatography to give compound 27-2.

(2) Preparation of Compound 27-3

Compound 27-2 (120 mg) was dissolved in tetrahydrofuran (4 mL), a solution of lithium hydroxide hydrate (32.8 mg) and water (4 mL) was added dropwise in an ice-water bath, and the mixture was reacted at room temperature for 4 h. The reaction solution was adjusted to pH 6-7 with hydrochloric acid, extracted with ethyl acetate, dried over anhydrous sodium sulfate, and filtered, and the filtrate was evaporated to dryness under reduced pressure to give compound 27-3, which was directly used in the next step.

(3) Preparation of Compound 27

Compound 27-3 (100 mg) was dispersed in tetrahydrofuran (5 mL), N-methylmorpholine (48.6 mg) and isobutyl chloroformate (65.6 mg) were added in an ice-water bath, and the mixture was stirred for 30 min. Ammonium hydroxide (50.4 mg) was added dropwise, and the mixture was reacted in an ice-water bath for 10 min. Water was added to quench the reaction, and the resulting mixture was extracted with ethyl acetate, dried over anhydrous sodium sulfate, concentrated until no liquid flowed out, and purified by preparative liquid chromatography to give compound 27 (40 mg). ESI-MS: m/z=419.22 $[M+H]^+$.

$^1$H NMR (500 MHz, DMSO-$d_6$) δ 9.05 (s, 1H), 8.63 (d, J=2.8 Hz, 1H), 8.34 (d, J=19.3 Hz, 2H), 7.79-7.69 (m, 2H), 7.64 (s, 1H), 7.51 (s, 1H), 7.25 (s, 1H), 2.28 (tt, J=8.4, 4.7 Hz, 1H), 1.10 (dd, J=8.0, 3.0 Hz, 2H), 0.93 (dd, J=4.7, 2.6 Hz, 2H).

Example 28

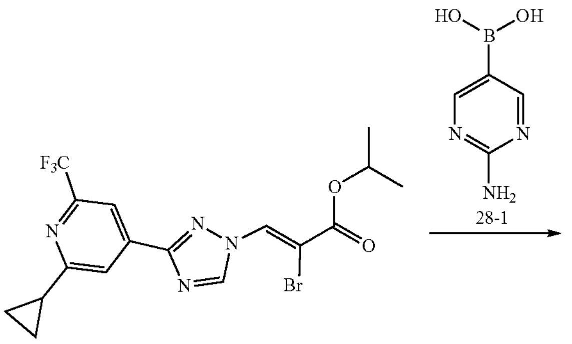

13-8

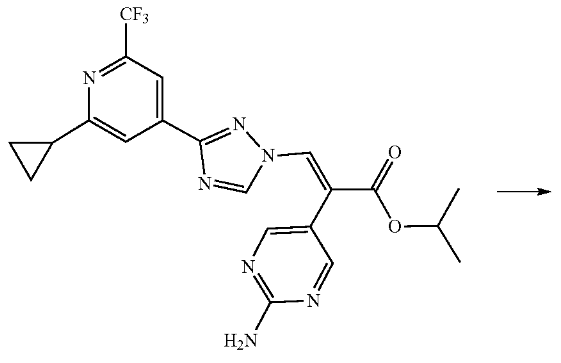

28-2

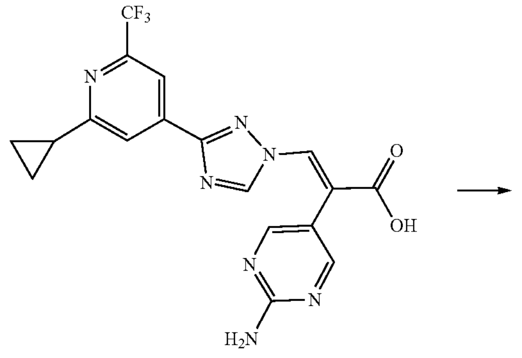

28-3

-continued

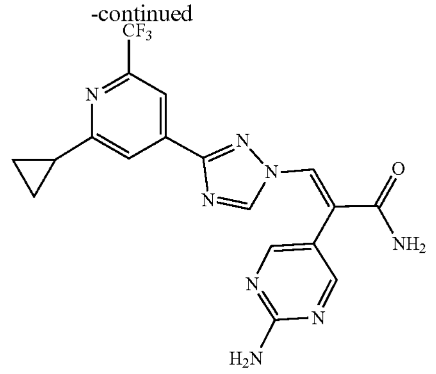

28

(1) Preparation of Compound 28-2

Compound 13-8 (200 mg) and 2-aminopyrimidine-5-boronic acid (28-1, 75 mg) were dispersed in 1,4-dioxane (5 mL), and potassium acetate (132.5 mg), Pd(dppf)$Cl_2$ (14.6 mg), and water (0.5 mL) were added. The mixture was heated to 90° C. and reacted under nitrogen atmosphere. After the starting materials were consumed completely as detected by TLC, the reaction solution was concentrated under reduced pressure and purified by column chromatography to give compound 28-2.

(2) Preparation of Compound 28-3

Compound 28-2 (102 mg) was dissolved in tetrahydrofuran (4 mL), a solution of lithium hydroxide hydrate (27.7 mg) and water (4 mL) was added dropwise in an ice-water bath, and the mixture was reacted at room temperature for 4 h. The reaction solution was adjusted to pH 6-7 with hydrochloric acid, extracted with ethyl acetate, dried over anhydrous sodium sulfate, and filtered, and the filtrate was evaporated to dryness under reduced pressure to give compound 28-3, which was directly used in the next step.

(3) Preparation of Compound 28

Compound 28-3 (100 mg) was dispersed in tetrahydrofuran (5 mL), N-methylmorpholine (48.6 mg) and isobutyl chloroformate (65.6 mg) were added in an ice-water bath, and the mixture was stirred for 30 min. Ammonium hydroxide (50.4 mg) was added dropwise, and the mixture was reacted in an ice-water bath for 10 min. Water was added to quench the reaction, and the resulting mixture was extracted with ethyl acetate, dried over anhydrous sodium sulfate, concentrated until no liquid flowed out, and purified by preparative liquid chromatography to give compound 28 (45 mg); ESI-MS: m/z=417.22 $[M+H]^+$.

$^1$H NMR (500 MHz, DMSO-$d_6$) δ 9.00 (s, 1H), 8.15 (s, 1H), 8.08 (s, 2H), 7.85 (d, J=1.2 Hz, 1H), 7.78 (d, J=1.3 Hz, 1H), 7.53 (s, 1H), 7.41 (s, 1H), 6.84 (s, 2H), 2.36-2.28 (m, 1H), 1.09 (dt, J=8.0, 3.2 Hz, 2H), 0.98 (dq, J=6.9, 3.9 Hz, 2H).

Example 29

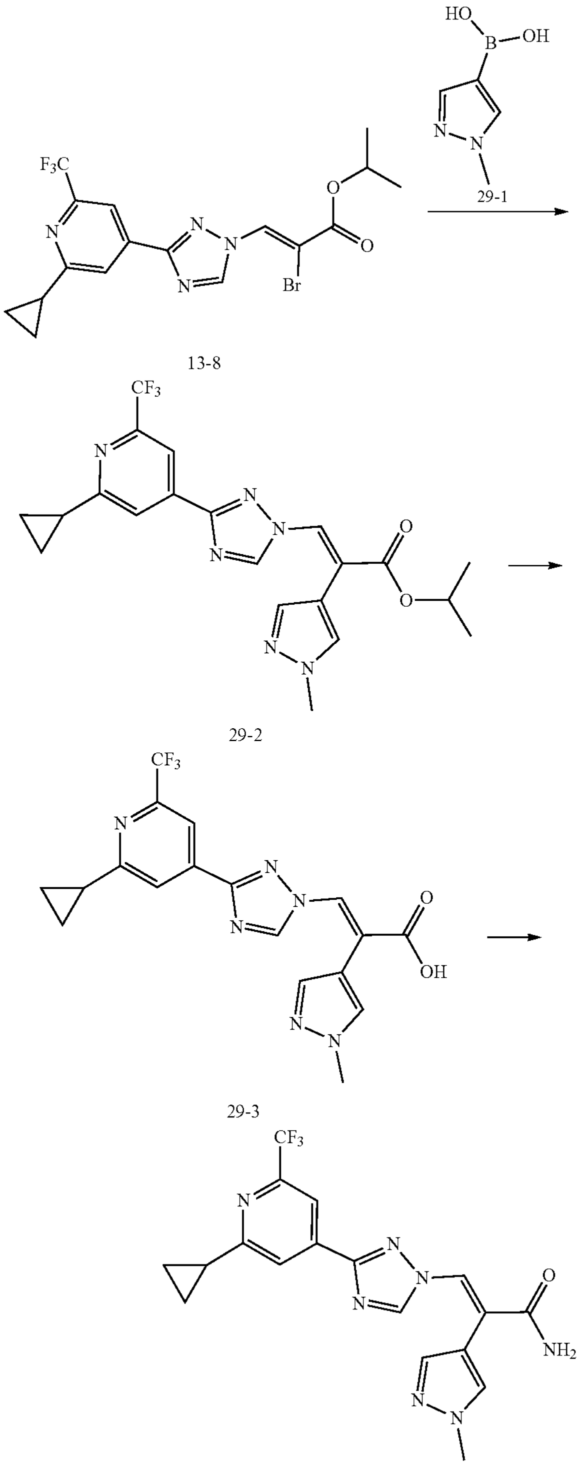

13-8, 29-1, 29-2, 29-3, 29

(1) Preparation of Compound 29-2

Compound 13-8 (200 mg) and 1-methyl-1H-pyrazole-4-boronic acid (29-1, 68 mg) were dispersed in 1,4-dioxane (5 mL), and potassium acetate (132.5 mg), Pd(dppf)$Cl_2$ (14.6 mg), and water (0.5 mL) were added. The mixture was heated to 90° C. and reacted under nitrogen atmosphere. After the starting materials were consumed completely as detected by TLC, the reaction solution was concentrated under reduced pressure and purified by column chromatography to give compound 29-2.

(2) Preparation of Compound 29-3

Compound 29-2 (100 mg) was dissolved in tetrahydrofuran (4 mL), a solution of lithium hydroxide hydrate (27.7 mg) and water (4 mL) was added dropwise in an ice-water bath, and the mixture was reacted at room temperature for 4 h. The reaction solution was adjusted to pH 6-7 with hydrochloric acid, extracted with ethyl acetate, dried over anhydrous sodium sulfate, and filtered, and the filtrate was evaporated to dryness under reduced pressure to give compound 29-3, which was directly used in the next step.

(3) Preparation of Compound 29

Compound 29-3 (88.96 mg) was dispersed in tetrahydrofuran (5 mL), N-methylmorpholine (44.5 mg) and isobutyl chloroformate (60.09 mg) were added in an ice-water bath, and the mixture was stirred for 30 min. Ammonium hydroxide (46.2 mg) was added dropwise, and the mixture was reacted in an ice-water bath for 10 min. Water was added to quench the reaction, and the resulting mixture was extracted with ethyl acetate, dried over anhydrous sodium sulfate, concentrated until no liquid flowed out, and purified by preparative liquid chromatography to give compound 29 (30 mg). ESI-MS: m/z=404.24 $[M+H]^+$.

$^1H$ NMR (500 MHz, DMSO-$d_6$) δ 8.75 (s, 1H), 8.08-8.03 (m, 1H), 7.94 (d, J=1.3 Hz, 1H), 7.82 (s, 1H), 7.72 (s, 1H), 7.55 (s, 1H), 7.49 (s, 1H), 7.25 (s, 1H), 3.85 (s, 3H), 2.37 (tt, J=8.1, 4.7 Hz, 1H), 1.10 (dt, J=8.1, 3.2 Hz, 2H), 1.00 (dq, J=7.0, 4.3, 3.9 Hz, 2H).

Example 30

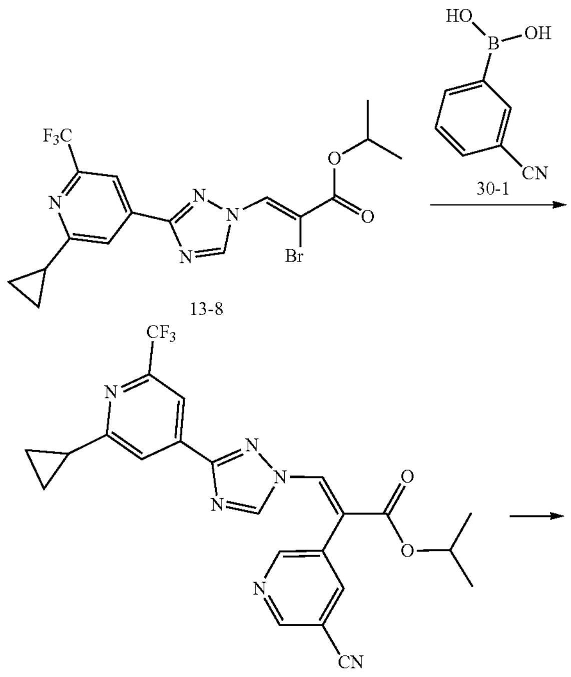

13-8, 30-1, 30-2

-continued

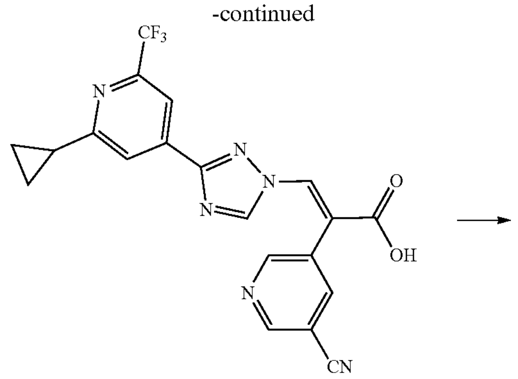

30-3

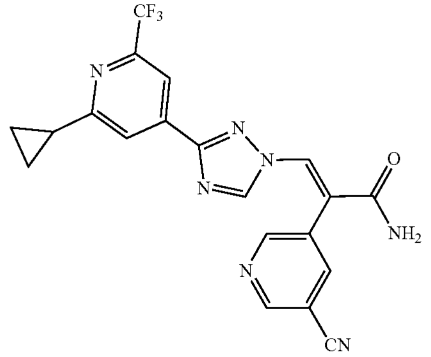

30

(1) Preparation of Compound 30-2

Compound 13-8 (200 mg) and 5-cyano-pyridine-3-boronic acid (30-1, 79.8 mg) were dispersed in 1,4-dioxane (5 mL), and potassium acetate (132.5 mg), Pd(dppf)$Cl_2$ (14.6 mg), and water (0.5 mL) were added. The mixture was heated to 90° C. and reacted under nitrogen atmosphere. After the starting materials were consumed completely as detected by TLC, the reaction solution was concentrated under reduced pressure and purified by column chromatography to give compound 30-2.

(2) Preparation of Compound 30-3

Compound 30-2 (150 mg) was dissolved in tetrahydrofuran (4 mL), a solution of lithium hydroxide hydrate (40.28 mg) and water (4 mL) was added dropwise in an ice-water bath, and the mixture was reacted at room temperature for 4 h. The reaction solution was adjusted to pH 6-7 with hydrochloric acid, extracted with ethyl acetate, dried over anhydrous sodium sulfate, and filtered, and the filtrate was evaporated to dryness under reduced pressure to give compound 30-3, which was directly used in the next step.

(3) Preparation of Compound 30

Compound 30-3 (136.44 mg) was dispersed in tetrahydrofuran (5 mL), N-methylmorpholine (64.74 mg) and isobutyl chloroformate (87.4 mg) were added in an ice-water bath, and the mixture was stirred for 30 min. Ammonium hydroxide (67.2 mg) was added dropwise, and the mixture was reacted in an ice-water bath for 10 min. Water was added to quench the reaction, and the resulting mixture was extracted with ethyl acetate, dried over anhydrous sodium sulfate, concentrated until no liquid flowed out, and purified by preparative liquid chromatography to give compound 30 (45 mg). ESI-MS: m/z=426.21 $[M+H]^+$.

$^1$H NMR (500 MHz, DMSO-$d_6$) δ 9.12 (s, 1H), 9.09 (d, J=2.0 Hz, 1H), 8.75 (d, J=2.1 Hz, 1H), 8.42 (s, 1H), 8.35 (t, J=2.1 Hz, 1H), 7.70 (d, J=1.3 Hz, 1H), 7.66 (s, 1H), 7.45 (d, J=1.3 Hz, 1H), 7.28 (s, 1H), 2.29 (tt, J=8.1, 4.7 Hz, 1H), 1.10 (dt, J=8.1, 3.3 Hz, 2H), 0.97-0.89 (m, 2H).

Example 31

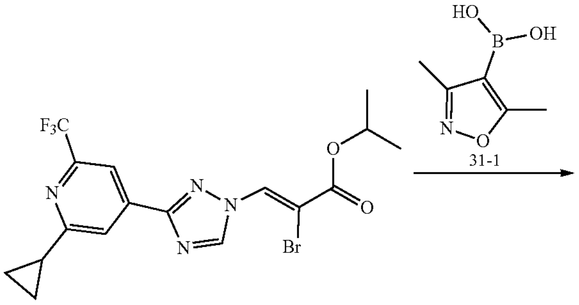

13-8

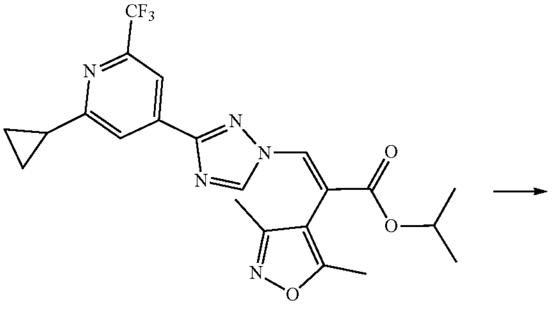

31-2

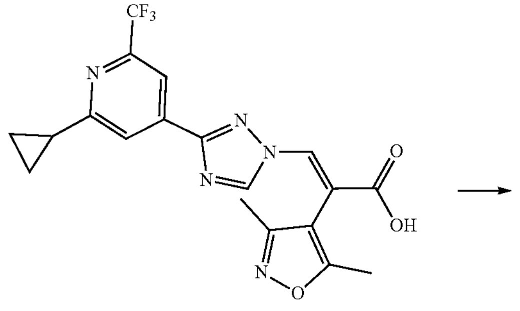

31-3

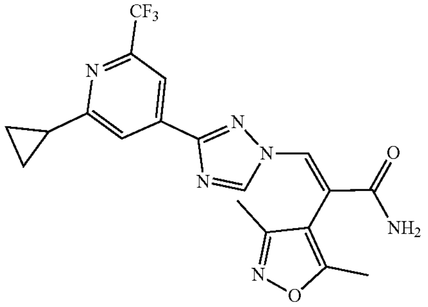

31

(1) Preparation of Compound 31-2

Compound 13-8 (200 mg) and 3,5-dimethylisoxazole-4-boronic acid (31-1, 76.1 mg) were dispersed in 1,4-dioxane (5 mL), and potassium carbonate (186.6 mg), Pd(dppf)$Cl_2$ (14.6 mg), and water (0.5 mL) were added. The mixture was heated to 90° C. and reacted under nitrogen atmosphere. After the starting materials were consumed completely as detected by TLC, the reaction solution was concentrated under reduced pressure and purified by column chromatography to give compound 31-2.

(2) Preparation of Compound 31-3

Compound 31-2 (150 mg) was dissolved in tetrahydrofuran (4 mL), a solution of lithium hydroxide hydrate (41.54 mg) and water (4 mL) was added dropwise in an ice-water bath, and the mixture was reacted at room temperature for 4 h. The reaction solution was adjusted to pH 6-7 with hydrochloric acid, extracted with ethyl acetate, dried over anhydrous sodium sulfate, and filtered, and the filtrate was evaporated to dryness under reduced pressure to give compound 31-3, which was directly used in the next step.

(3) Preparation of Compound 31

Compound 31-3 (134 mg) was dispersed in tetrahydrofuran (5 mL), N-methylmorpholine (64.74 mg) and isobutyl chloroformate (87.4 mg) were added in an ice-water bath, and the mixture was stirred for 30 min. Ammonium hydroxide (67.2 mg) was added dropwise, and the mixture was reacted in an ice-water bath for 10 min. Water was added to quench the reaction, and the resulting mixture was extracted with ethyl acetate, dried over anhydrous sodium sulfate, concentrated until no liquid flowed out, and purified by preparative liquid chromatography to give compound 31 (30 mg). ESI-MS: m/z=419.23 $[M+H]^+$.

$^{1}$H NMR (500 MHz, DMSO-$d_6$) δ 9.07 (s, 1H), 8.38 (s, 1H), 7.86 (d, J=1.3 Hz, 1H), 7.78 (d, J=1.3 Hz, 1H), 7.52 (s, 1H), 7.37 (s, 1H), 2.31 (tt, J=8.1, 4.7 Hz, 1H), 2.17 (s, 3H), 1.96 (s, 3H), 1.14-1.08 (m, 2H), 1.01-0.95 (m, 2H).

Example 32

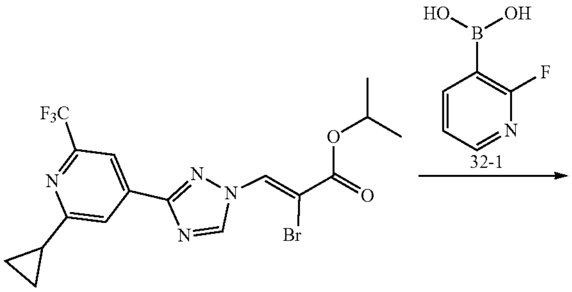

32-1

13-8

-continued

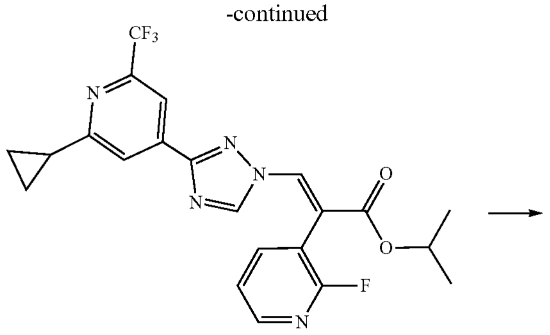

32-2

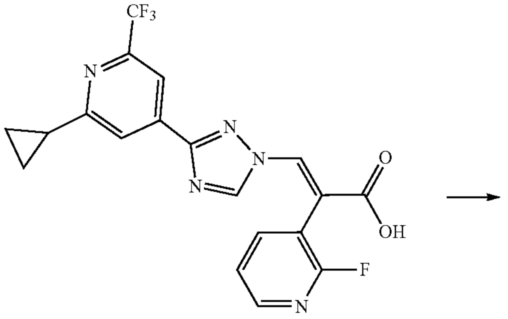

32-3

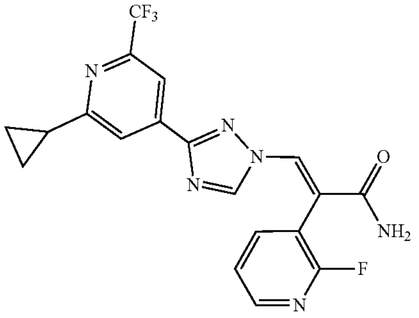

32

(1) Preparation of Compound 32-2

Compound 13-8 (200 mg) and 2-fluoro-pyridine-3-boronic acid (32-1, 76.1 mg) were dispersed in 1,4-dioxane (5 mL), and potassium carbonate (186.6 mg), Pd(dppf)$Cl_2$ (14.6 mg), and water (0.5 mL) were added. The mixture was heated to 90° C. and reacted under nitrogen atmosphere. After the starting materials were consumed completely as detected by TLC, the reaction solution was concentrated under reduced pressure and purified by column chromatography to give compound 32-2.

(2) Preparation of Compound 32-3

Compound 32-2 (70 mg) was dissolved in tetrahydrofuran (4 mL), a solution of lithium hydroxide hydrate (18.9 mg) and water (4 mL) was added dropwise in an ice-water bath, and the mixture was reacted at room temperature for 4 h. The reaction solution was adjusted to pH 6-7 with hydrochloric acid, extracted with ethyl acetate, dried over anhydrous sodium sulfate, and filtered, and the filtrate was evaporated to dryness under reduced pressure to give compound 32-3, which was directly used in the next step.

(3) Preparation of Compound 32

Compound 32-3 (50 mg) was dispersed in tetrahydrofuran (5 mL), N-methylmorpholine (24.3 mg) and isobutyl chloroformate (32.7 mg) were added in an ice-water bath, and the mixture was stirred for 30 min. Ammonium hydroxide (25.2 mg) was added dropwise, and the mixture was reacted in an ice-water bath for 10 min. Water was added to quench the reaction, and the resulting mixture was extracted with ethyl acetate, dried over anhydrous sodium sulfate, concentrated until no liquid flowed out, and purified by preparative liquid chromatography to give compound 32 (10 mg). ESI-MS: m/z=419.21 [M+H]$^{1}$H NMR (500 MHz, DMSO-$d_6$) δ 9.13 (s, 1H), 8.39 (s, 1H), 8.32 (dd, J=5.0, 1.9 Hz, 1H), 7.86 (ddd, J=9.5, 7.3, 1.9 Hz, 1H), 7.69 (d, J=1.3 Hz, 1H), 7.59 (s, 1H), 7.50 (d, J=1.3 Hz, 1H), 7.44 (ddd, J=7.1, 4.9, 1.9 Hz, 1H), 7.40 (s, 1H), 2.27 (tt, J=8.2, 4.7 Hz, 1H), 1.10 (dt, J=8.1, 3.3 Hz, 2H), 0.97-0.90 (m, 2H).

Example 33

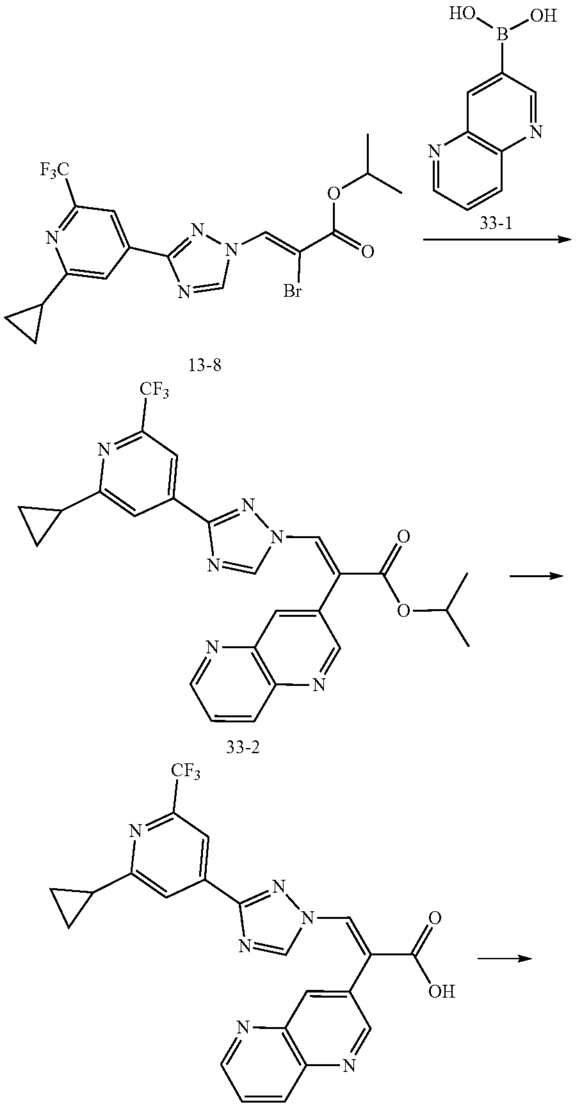

33-1

13-8

33-2

33-3

-continued

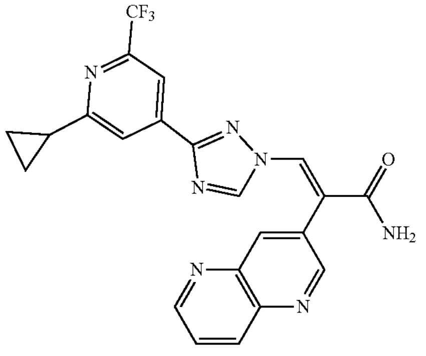

33

(1) Preparation of Compound 33-2

Compound 13-8 (200 mg) and [1,5]naphthyridine-3-boronic acid (33-1, 138.3 mg) were dispersed in 1,4-dioxane (5 mL), and potassium acetate (132.5 mg), Pd(dppf)$Cl_2$ (14.6 mg), and water (0.5 mL) were added. The mixture was heated to 90° C. and reacted under nitrogen atmosphere. After the starting materials were consumed completely as detected by TLC, the reaction solution was concentrated under reduced pressure and purified by column chromatography to give compound 33-2.

(2) Preparation of Compound 33-3

Compound 33-2 (160 mg) was dissolved in tetrahydrofuran (4 mL), a solution of lithium hydroxide hydrate (40.28 mg) and water (4 mL) was added dropwise in an ice-water bath, and the mixture was reacted at room temperature for 4 h. The reaction solution was adjusted to pH 6-7 with hydrochloric acid, extracted with ethyl acetate, dried over anhydrous sodium sulfate, and filtered, and the filtrate was evaporated to dryness under reduced pressure to give compound 33-3, which was directly used in the next step.

(3) Preparation of Compound 33

Compound 33-3 (144.7 mg) was dispersed in tetrahydrofuran (5 mL), N-methylmorpholine (64.74 mg) and isobutyl chloroformate (87.4 mg) were added in an ice-water bath, and the mixture was stirred for 30 min. Ammonium hydroxide (67.2 mg) was added dropwise, and the mixture was reacted in an ice-water bath for 10 min. Water was added to quench the reaction, and the resulting mixture was extracted with ethyl acetate, dried over anhydrous sodium sulfate, concentrated until no liquid flowed out, and purified by preparative liquid chromatography to give compound 33 (20 mg). ESI-MS: m/z=452.21 $[M+H]^+$.

$^{1}$H NMR (500 MHz, DMSO-$d_6$) δ 9.12 (s, 1H), 9.03 (dd, J=4.2, 1.7 Hz, 1H), 8.87 (d, J=2.2 Hz, 1H), 8.51 (d, J=8.5 Hz, 1H), 8.46 (s, 1H), 8.31 (d, J=2.2 Hz, 1H), 7.86 (dd, J=8.5, 4.2 Hz, 1H), 7.65 (s, 1H), 7.51 (s, 1H), 7.34 (s, 1H), 7.20-7.14 (m, 1H), 2.10 (tt, J=8.4, 4.7 Hz, 1H), 1.01 (dt, J=6.4, 3.3 Hz, 2H), 0.79 (dq, J=6.9, 4.0 Hz, 2H).

Example 34

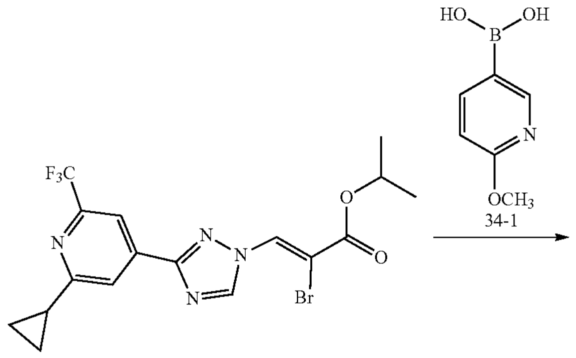

34-1

13-8

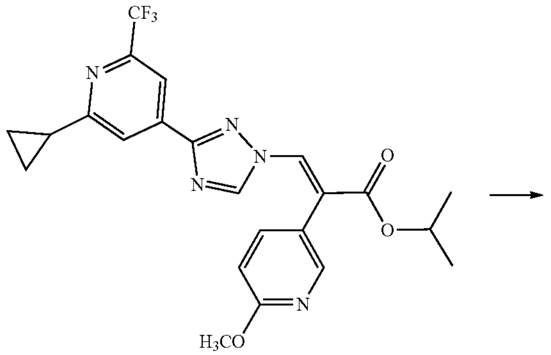

34-2

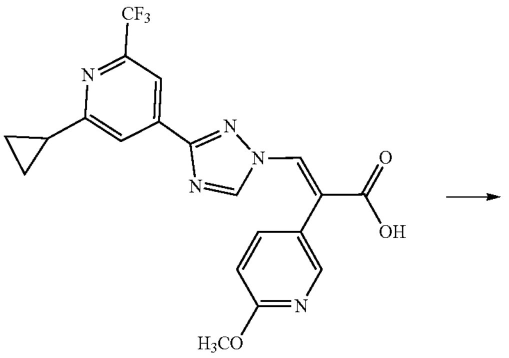

34-3

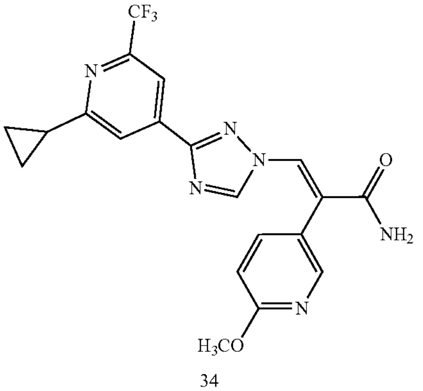

34

(1) Preparation of Compound 34-2

Compound 13-8 (200 mg) and 2-methoxypyridine-5-boronic acid (34-1, 82.6 mg) were dispersed in 1,4-dioxane (5 mL), and potassium acetate (132.5 mg), Pd(dppf)$Cl_2$ (14.6 mg), and water (0.5 mL) were added. The mixture was heated to 90° C. and reacted under nitrogen atmosphere. After the starting materials were consumed completely as detected by TLC, the reaction solution was concentrated under reduced pressure and purified by column chromatography to give compound 34-2.

(2) Preparation of Compound 34-3

Compound 34-2 (180 mg) was dissolved in tetrahydrofuran (4 mL), a solution of lithium hydroxide hydrate (47.9 mg) and water (4 mL) was added dropwise in an ice-water bath, and the mixture was reacted at room temperature for 4 h. The reaction solution was adjusted to pH 6-7 with hydrochloric acid, extracted with ethyl acetate, dried over anhydrous sodium sulfate, and filtered, and the filtrate was evaporated to dryness under reduced pressure to give compound 34-3, which was directly used in the next step.

(3) Preparation of Compound 34

Compound 34-3 (163.9 mg) was dispersed in tetrahydrofuran (5 mL), N-methylmorpholine (76.8 mg) and isobutyl chloroformate (103.8 mg) were added in an ice-water bath, and the mixture was stirred for 30 min. Ammonium hydroxide (79.8 mg) was added dropwise, and the mixture was reacted in an ice-water bath for 10 min. Water was added to quench the reaction, and the resulting mixture was extracted with ethyl acetate, dried over anhydrous sodium sulfate, concentrated until no liquid flowed out, and purified by preparative liquid chromatography to give compound 34 (80 mg). ESI-MS: m/z=431.19 $[M+H]^+$.

$^1$H NMR (500 MHz, DMSO-$d_6$) δ 8.91 (s, 1H), 8.21 (s, 1H), 8.04 (d, J=2.4 Hz, 1H), 7.81 (d, J=1.3 Hz, 1H), 7.61 (d, J=1.3 Hz, 1H), 7.58 (d, J=2.4 Hz, 1H), 7.56 (d, J=2.5 Hz, 1H), 7.55 (s, 1H), 7.20 (s, 1H), 6.89 (d, J=8.5 Hz, 1H), 3.91 (s, 3H), 2.29 (tt, J=8.1, 4.8 Hz, 1H), 1.12-1.05 (m, 2H), 0.98-0.93 (m, 2H).

Example 35

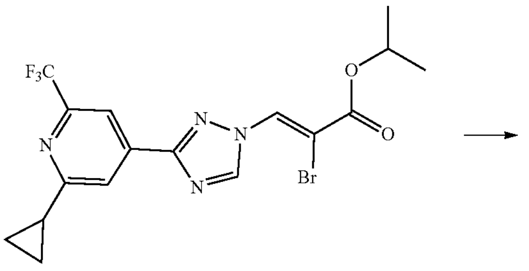

13-8

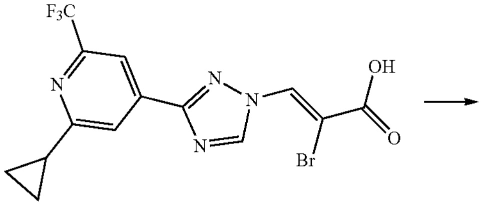

35-1

-continued

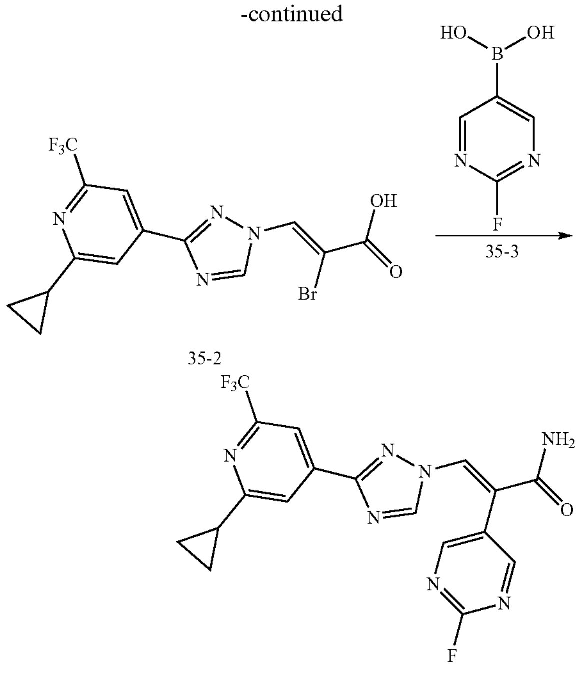

35-2

35-3

35

(1) Preparation of Compound 35-1

Compound 13-8 (200 mg) was dissolved in tetrahydrofuran (4 mL), a solution of lithium hydroxide hydrate (56.65 mg) and water (4 mL) was added dropwise in an ice-water bath, and the mixture was reacted at room temperature for 4 h. The reaction solution was adjusted to pH 6-7 with hydrochloric acid, extracted with ethyl acetate, dried over anhydrous sodium sulfate, and filtered, and the filtrate was evaporated to dryness under reduced pressure to give compound 35-1, which was directly used in the next step.

(2) Preparation of Compound 35-2

Compound 35-1 (181.4 mg) was dispersed in tetrahydrofuran (5 mL), N-methylmorpholine (91.04 mg) and isobutyl chloroformate (122.9 mg) were added in an ice-water bath, and the mixture was stirred for 30 min. Ammonium hydroxide (94.5 mg) was added dropwise, and the mixture was reacted in an ice-water bath for 10 min. Water was added to quench the reaction, and the resulting mixture was extracted with ethyl acetate, dried over anhydrous sodium sulfate, and concentrated until no liquid flowed out to give compound 35-2, which was directly used in the next step.

(2) Preparation of Compound 35

Compound 35-2 (200 mg) and 2-fluoro-pyrimidine-5-boronic acid (35-3, 134.4 mg) were dispersed in 1,4-dioxane (5 mL), and potassium acetate (147.21 mg), Pd(dppf)$Cl_2$ (18.3 mg), and water (0.5 mL) were added. The mixture was heated to 90° C. and reacted under nitrogen atmosphere. After the starting materials were consumed completely as detected by TLC, the reaction solution was concentrated under reduced pressure and purified by preparative liquid chromatography to give compound 35 (30 mg). ESI-MS: m/z=420.19 $[M+H]^+$.

$^1$H NMR (500 MHz, DMSO-$d_6$) δ 9.18 (s, 1H), 8.74 (s, 2H), 8.47 (s, 1H), 7.74 (s, 1H), 7.66 (s, 1H), 7.49 (s, 1H), 7.35 (s, 1H), 2.28 (tt, J=8.4, 4.7 Hz, 1H), 1.11 (dq, J=6.7, 3.9 Hz, 2H), 1.00-0.89 (m, 2H).

Example 36

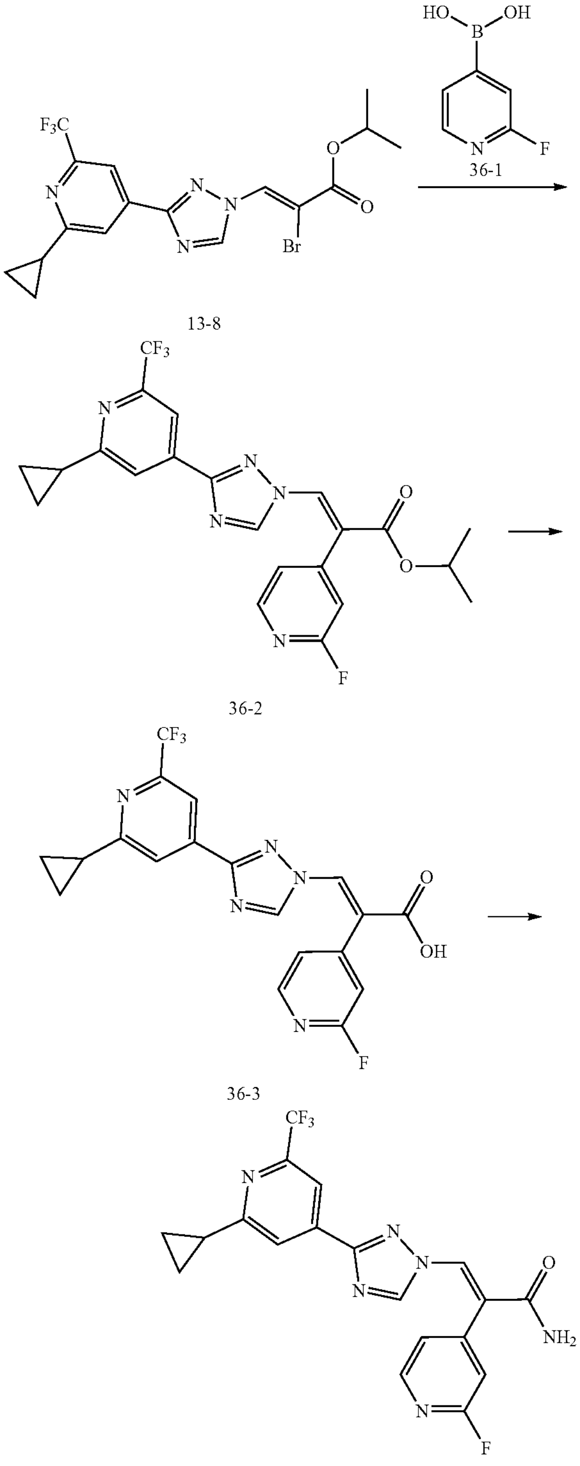

13-8

36-1

36-2

36-3

36

(1) Preparation of Compound 36-2

Compound 13-8 (200 mg) and 2-fluoro-pyridine-4-boronic acid (36-1, 76.09 mg) were dispersed in 1,4-dioxane (5 mL), and potassium acetate (132.5 mg), $Pd(dppf)Cl_2$ (14.6 mg), and water (0.5 mL) were added. The mixture was heated to 90° C. and reacted under nitrogen atmosphere. After the starting materials were consumed completely as detected by TLC, the reaction solution was concentrated under reduced pressure and purified by column chromatography to give compound 36-2.

(2) Preparation of Compound 36-3

Compound 36-2 (150 mg) was dissolved in tetrahydrofuran (4 mL), a solution of lithium hydroxide hydrate (40.3 mg) and water (4 mL) was added dropwise in an ice-water bath, and the mixture was reacted at room temperature for 4 h. The reaction solution was adjusted to pH 6-7 with hydrochloric acid, extracted with ethyl acetate, dried over anhydrous sodium sulfate, and filtered, and the filtrate was evaporated to dryness under reduced pressure to give compound 36-3, which was directly used in the next step.

(3) Preparation of Compound 36

Compound 36-3 (100 mg) was dispersed in tetrahydrofuran (5 mL), N-methylmorpholine (48.5 mg) and isobutyl chloroformate (65.5 mg) were added in an ice-water bath, and the mixture was stirred for 30 min. Ammonium hydroxide (50.4 mg) was added dropwise, and the mixture was reacted in an ice-water bath for 10 min. Water was added to quench the reaction, and the resulting mixture was extracted with ethyl acetate, dried over anhydrous sodium sulfate, concentrated until no liquid flowed out, and purified by preparative liquid chromatography to give compound 36 (30 mg). ESI-MS: m/z=419.19 $[M+H]^+$.

$^1H$ NMR (500 MHz, DMSO-$d_6$) δ 9.03 (s, 1H), 8.29 (d, J=5.3 Hz, 2H), 7.68 (s, 1H), 7.63 (s, 1H), 7.53 (s, 1H), 7.25 (d, J=5.0 Hz, 1H), 7.18 (d, J=6.6 Hz, 2H), 2.26 (tt, J=8.3, 4.7 Hz, 1H), 1.10 (dq, J=6.8, 3.9 Hz, 2H), 0.94 (dq, J=6.7, 4.0 Hz, 2H).

Example 37

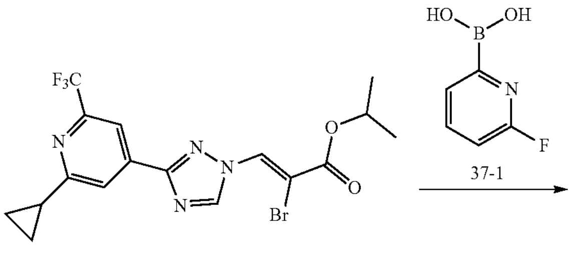

37-1

13-8

-continued

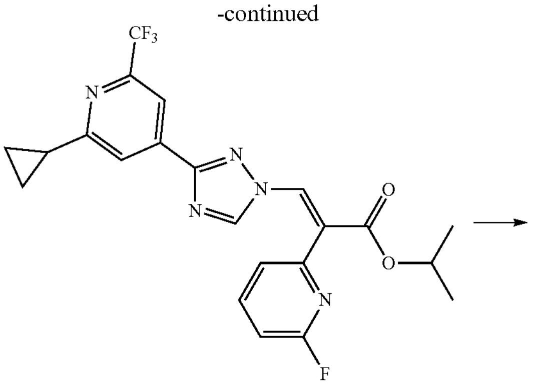

37-2

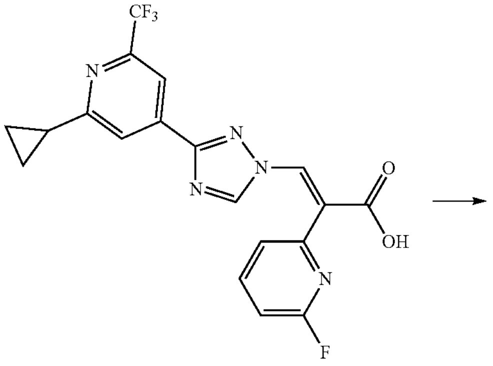

37-3

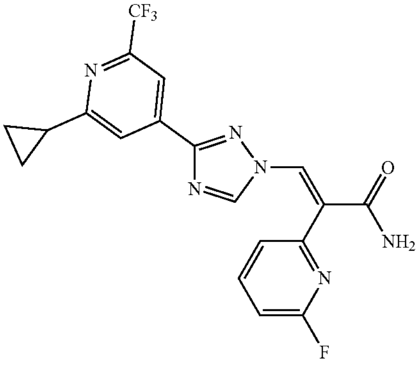

37

(1) Preparation of Compound 37-2

Compound 13-8 (200 mg) and 6-fluoro-pyridine-2-boronic acid (37-1, 76.09 mg) were dispersed in 1,4-dioxane (5 mL), and potassium acetate (132.5 mg), $Pd(dppf)Cl_2$ (14.6 mg), and water (0.5 mL) were added. The mixture was heated to 90° C. and reacted under nitrogen atmosphere. After the starting materials were consumed completely as detected by TLC, the reaction solution was concentrated under reduced pressure and purified by column chromatography to give compound 37-2.

(2) Preparation of Compound 37-3

Compound 37-2 (170 mg) was dissolved in tetrahydrofuran (4 mL), a solution of lithium hydroxide hydrate (46.4 mg) and water (4 mL) was added dropwise in an ice-water bath, and the mixture was reacted at room temperature for 4 h. The reaction solution was adjusted to pH 6-7 with hydrochloric acid, extracted with ethyl acetate, dried over anhydrous sodium sulfate, and filtered, and the filtrate was evaporated to dryness under reduced pressure to give compound 37-3, which was directly used in the next step.

(3) Preparation of Compound 37

Compound 37-3 (155.2 mg) was dispersed in tetrahydrofuran (5 mL), N-methylmorpholine (74.8 mg) and isobutyl chloroformate (101.1 mg) were added in an ice-water bath, and the mixture was stirred for 30 min. Ammonium hydroxide (77.7 mg) was added dropwise, and the mixture was reacted in an ice-water bath for 10 min. Water was added to quench the reaction, and the resulting mixture was extracted with ethyl acetate, dried over anhydrous sodium sulfate, concentrated until no liquid flowed out, and purified by preparative liquid chromatography to give compound 37 (40 mg). ESI-MS: m/z=419.19 $[M+H]^+$.

$^1$H NMR (500 MHz, DMSO-$d_6$) δ 9.01 (d, J=1.4 Hz, 1H), 8.27 (d, J=1.4 Hz, 1H), 8.05 (q, J=8.1 Hz, 1H), 7.73 (s, 1H), 7.60 (s, 1H), 7.51 (d, J=1.4 Hz, 1H), 7.34 (dd, J=7.4, 2.3 Hz, 1H), 7.23 (dd, J=8.5, 2.3 Hz, 2H), 2.29 (tt, J=8.4, 4.7 Hz, 1H), 1.09 (dq, J=6.5, 3.8 Hz, 2H), 0.94 (dt, J=5.0, 3.3 Hz, 2H).

Example 38

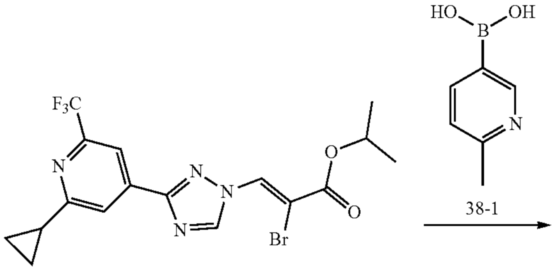

13-8

38-1

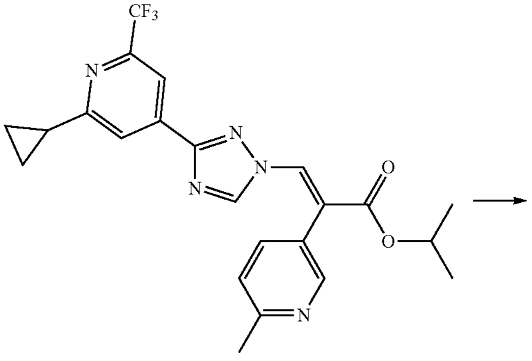

38-2

-continued

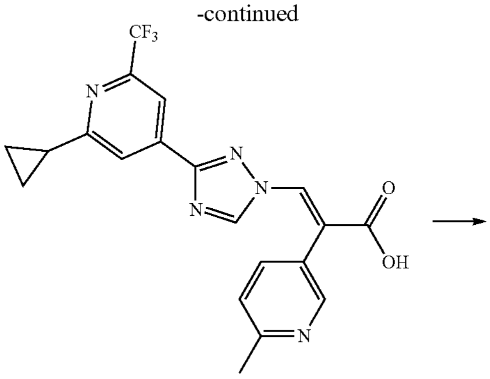

38-3

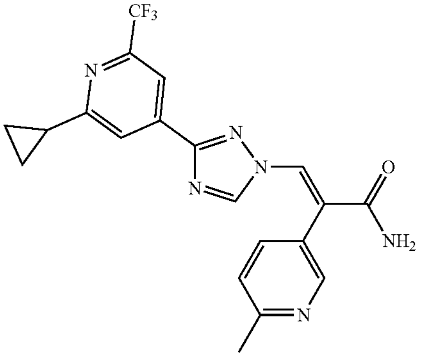

38

(1) Preparation of Compound 38-2

Compound 13-8 (200 mg) and 2-methyl-pyridine-5-boronic acid (38-1, 73.95 mg) were dispersed in 1,4-dioxane (5 mL), and potassium acetate (132.5 mg), Pd(dppf)$Cl_2$ (14.6 mg), and water (0.5 mL) were added. The mixture was heated to 90° C. and reacted under nitrogen atmosphere. After the starting materials were consumed completely as detected by TLC, the reaction solution was concentrated under reduced pressure and purified by column chromatography to give compound 38-2.

(2) Preparation of Compound 38-3

Compound 38-2 (105 mg) was dissolved in tetrahydrofuran (4 mL), a solution of lithium hydroxide hydrate (28.95 mg) and water (4 mL) was added dropwise in an ice-water bath, and the mixture was reacted at room temperature for 4 h. The reaction solution was adjusted to pH 6-7 with hydrochloric acid, extracted with ethyl acetate, dried over anhydrous sodium sulfate, and filtered, and the filtrate was evaporated to dryness under reduced pressure to give compound 38-3, which was directly used in the next step.

(3) Preparation of Compound 38

Compound 38-3 (95.5 mg) was dispersed in tetrahydrofuran (5 mL), N-methylmorpholine (46.5 mg) and isobutyl chloroformate (62.8 mg) were added in an ice-water bath, and the mixture was stirred for 30 min. Ammonium hydroxide (48.3 mg) was added dropwise, and the mixture was reacted in an ice-water bath for 10 min. Water was added to quench the reaction, and the resulting mixture was extracted with ethyl acetate, dried over anhydrous sodium sulfate, concentrated until no liquid flowed out, and purified by preparative liquid chromatography to give compound 38 (30 mg). ESI-MS: m/z=415.24 $[M+H]^+$.

$^1H$ NMR (500 MHz, DMSO-$d_6$) δ 8.93 (s, 1H), 8.30 (d, J=2.3 Hz, 1H), 8.24 (s, 1H), 7.78 (s, 1H), 7.56 (dd, J=8.0, 2.4 Hz, 2H), 7.53 (d, J=1.3 Hz, 1H), 7.33 (d, J=7.9 Hz, 1H), 7.20 (s, 1H), 2.54 (s, 3H), 2.29 (tt, J=8.3, 4.7 Hz, 1H), 1.09 (dt, J=8.1, 3.3 Hz, 2H), 1.00-0.89 (m, 2H).

Example 39

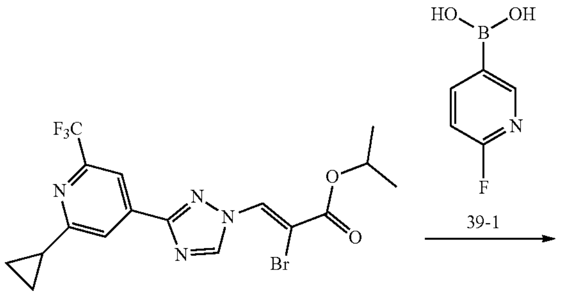

13-8

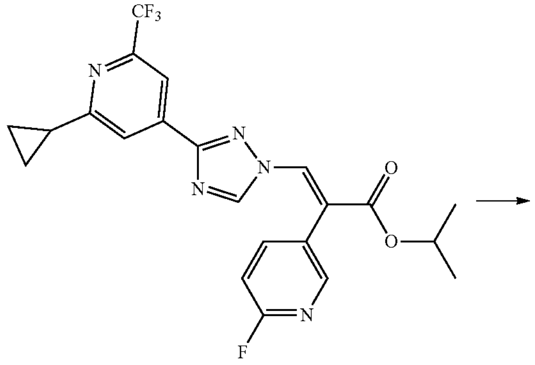

39-2

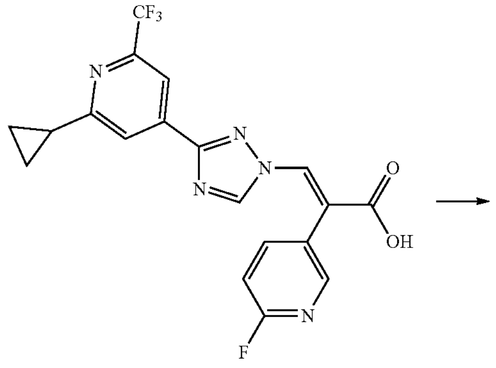

39-3

-continued

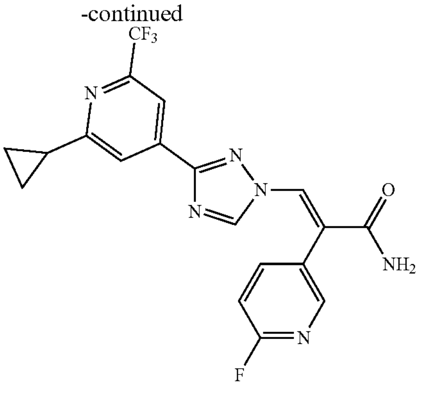

39

(1) Preparation of Compound 39-2

Compound 13-8 (200 mg) and 2-fluoro-pyridine-5-boronic acid (39-1, 76.09 mg) were dispersed in 1,4-dioxane (5 mL), and potassium acetate (132.5 mg), Pd(dppf)$Cl_2$ (14.6 mg), and water (0.5 mL) were added. The mixture was heated to 90° C. and reacted under nitrogen atmosphere. After the starting materials were consumed completely as detected by TLC, the reaction solution was concentrated under reduced pressure and purified by column chromatography to give compound 39-2.

(2) Preparation of Compound 39-3

Compound 39-2 (180 mg) was dissolved in tetrahydrofuran (4 mL), a solution of lithium hydroxide hydrate (49.1 mg) and water (4 mL) was added dropwise in an ice-water bath, and the mixture was reacted at room temperature for 4 h. The reaction solution was adjusted to pH 6-7 with hydrochloric acid, extracted with ethyl acetate, dried over anhydrous sodium sulfate, and filtered, and the filtrate was evaporated to dryness under reduced pressure to give compound 39-3, which was directly used in the next step.

(3) Preparation of Compound 39

Compound 39-3 (163 mg) was dispersed in tetrahydrofuran (5 mL), N-methylmorpholine (78.9 mg) and isobutyl chloroformate (106.5 mg) were added in an ice-water bath, and the mixture was stirred for 30 min. Ammonium hydroxide (81.9 mg) was added dropwise, and the mixture was reacted in an ice-water bath for 10 min. Water was added to quench the reaction, and the resulting mixture was extracted with ethyl acetate, dried over anhydrous sodium sulfate, concentrated until no liquid flowed out, and purified by preparative liquid chromatography to give compound 39 (40 mg). ESI-MS: m/z=419.20 $[M+H]^+$.

$^1H$ NMR (500 MHz, DMSO-$d_6$) δ 9.04 (s, 1H), 8.33 (s, 1H), 8.13 (d, J=2.4 Hz, 1H), 7.88 (td, J=8.2, 2.5 Hz, 1H), 7.75 (d, J=1.2 Hz, 1H), 7.61 (s, 1H), 7.52 (d, J=1.3 Hz, 1H), 7.27 (dd, J=8.4, 2.7 Hz, 1H), 7.24 (s, 1H), 2.28 (tt, J=8.0, 4.7 Hz, 1H), 1.09 (dt, J=8.0, 3.3 Hz, 2H), 0.99-0.89 (m, 2H).

Example 40

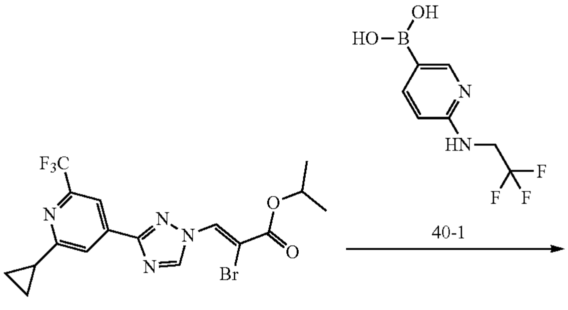

13-8

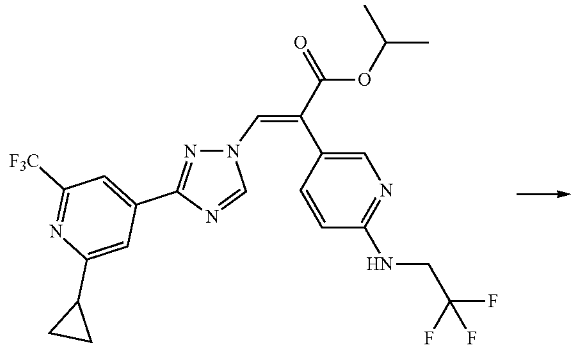

40-2

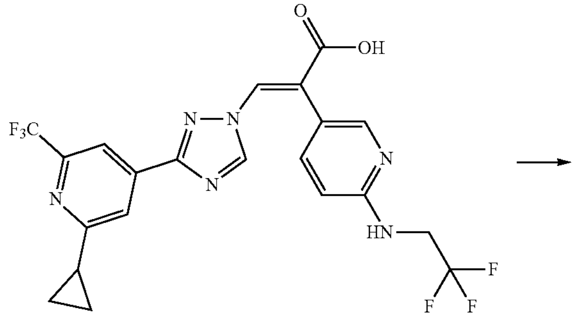

40-3

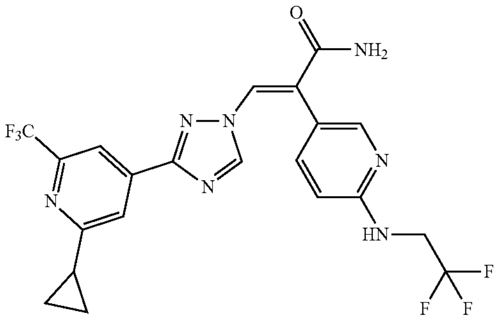

40

(1) Preparation of Compound 40-2

Compound 13-8 (200 mg, 0.45 mmol, 1.0 eq) and 2-trifluoroethylaminopyridine-5-boronic acid (40-1, 118.08 mg) were dispersed in 1,4-dioxane (5 mL), and potassium acetate (132.5 mg), Pd(dppf)$Cl_2$ (14.6 mg), and water (0.5 mL) were added. The mixture was heated to 90° C. and reacted under nitrogen atmosphere. After the starting materials were consumed completely as detected by TLC, the reaction solution was concentrated under reduced pressure and purified by column chromatography to give compound 40-2.

(2) Preparation of Compound 40-3

Compound 40-2 (130 mg) was dissolved in tetrahydrofuran (4 mL), a solution of lithium hydroxide hydrate (30.3 mg) and water (4 mL) was added dropwise in an ice-water bath, and the mixture was reacted at room temperature for 4 h. The reaction solution was adjusted to pH 6-7 with hydrochloric acid, extracted with ethyl acetate, dried over anhydrous sodium sulfate, and filtered, and the filtrate was evaporated to dryness under reduced pressure to give compound 40-3, which was directly used in the next step.

(3) Preparation of Compound 40

Compound 40-3 (119.6 mg) was dispersed in tetrahydrofuran (5 mL), N-methylmorpholine (48.6 mg) and isobutyl chloroformate (65.6 mg) were added in an ice-water bath, and the mixture was stirred for 30 min. Ammonium hydroxide (50.4 mg) was added dropwise, and the mixture was reacted in an ice-water bath for 10 min. Water was added to quench the reaction, and the resulting mixture was extracted with ethyl acetate, dried over anhydrous sodium sulfate, concentrated until no liquid flowed out, and purified by preparative liquid chromatography to give compound 40 (50 mg). ESI-MS: m/z=498.29 $[M+H]^+$.

$^1H$ NMR (500 MHz, DMSO-$d_6$) δ 8.78 (s, 1H), 8.05 (s, 1H), 7.88 (d, J=2.0 Hz, 2H), 7.75 (d, J=1.3 Hz, 1H), 7.56-7.49 (m, 1H), 7.39 (t, J=6.6 Hz, 1H), 7.32 (dd, J=8.5, 2.4 Hz, 1H), 7.24 (s, 1H), 6.69 (d, J=8.5 Hz, 1H), 4.19 (qd, J=9.7, 6.5 Hz, 2H), 2.30 (tt, J=8.2, 4.7 Hz, 1H), 1.08 (dt, J=8.0, 3.2 Hz, 2H), 1.02-0.91 (m, 2H).

Example 41

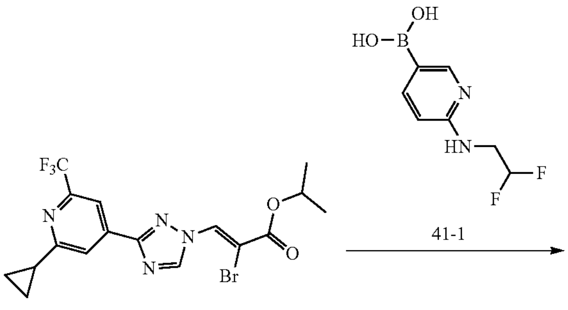

13-8

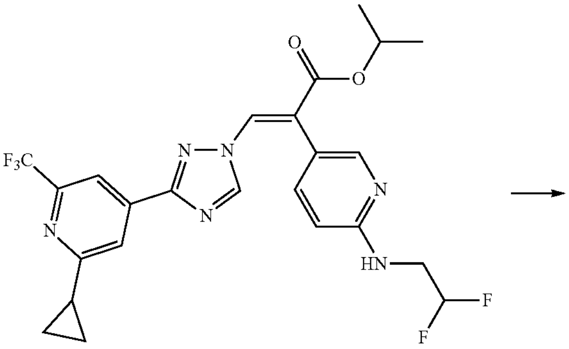

41-2

-continued

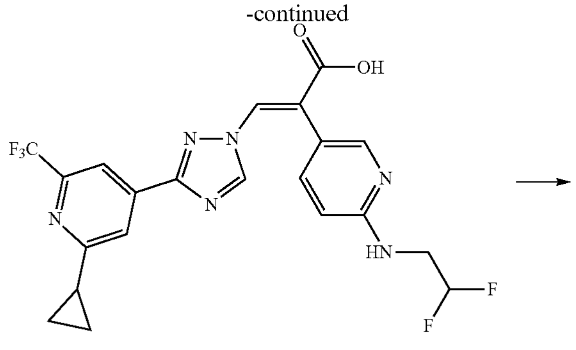

41-3

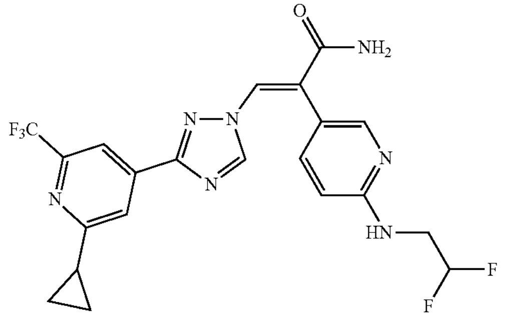

41

(1) Preparation of Compound 41-2

Compound 13-8 (200 mg) and 6-(2,2-difluoroethylamino) pyridine-3-boronic acid (41-1, 108.86 mg) were dispersed in 1,4-dioxane (5 mL), and potassium acetate (132.5 mg), $Pd(dppf)Cl_2$ (14.6 mg), and water (0.5 mL) were added. The mixture was heated to 90° C. and reacted under nitrogen atmosphere. After the starting materials were consumed completely as detected by TLC, the reaction solution was concentrated under reduced pressure and purified by column chromatography to give compound 41-2.

(2) Preparation of Compound 41-3

Compound 41-2 (120 mg) was dissolved in tetrahydrofuran (4 mL), a solution of lithium hydroxide hydrate (28.9 mg) and water (4 mL) was added dropwise in an ice-water bath, and the mixture was reacted at room temperature for 4 h. The reaction solution was adjusted to pH 6-7 with hydrochloric acid, extracted with ethyl acetate, dried over anhydrous sodium sulfate, and filtered, and the filtrate was evaporated to dryness under reduced pressure to give compound 41-3, which was directly used in the next step.

(3) Preparation of Compound 41

Compound 41-3 (110.5 mg) was dispersed in tetrahydrofuran (5 mL), N-methylmorpholine (46.5 mg) and isobutyl chloroformate (62.8 mg) were added in an ice-water bath, and the mixture was stirred for 30 min. Ammonium hydroxide (48.3 mg) was added dropwise, and the mixture was reacted in an ice-water bath for 10 min. Water was added to quench the reaction, and the resulting mixture was extracted with ethyl acetate, dried over anhydrous sodium sulfate, concentrated until no liquid flowed out, and purified by preparative liquid chromatography to give compound 41 (40 mg). ESI-MS: m/z=480.31 $[M+H]^+$.

$^1H$ NMR (500 MHz, DMSO-$d_6$) δ 8.74 (s, 1H), 8.03 (s, 1H), 7.90 (d, J=1.3 Hz, 1H), 7.87 (d, J=2.4 Hz, 1H), 7.77 (d, J=1.2 Hz, 1H), 7.53 (s, 1H), 7.27 (dd, J=8.6, 2.4 Hz, 1H), 7.25-7.18 (m, 2H), 6.64 (d, J=8.6 Hz, 1H), 6.09 (tt, J=56.6, 4.1 Hz, 1H), 3.73 (tdd, J=15.4, 6.1, 4.1 Hz, 2H), 2.31 (tt, J=8.1, 4.7 Hz, 1H), 1.08 (dt, J=8.0, 3.2 Hz, 2H), 1.00-0.94 (m, 2H).

Example 42

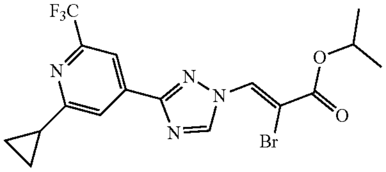

13-8

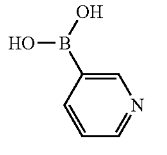

42-1

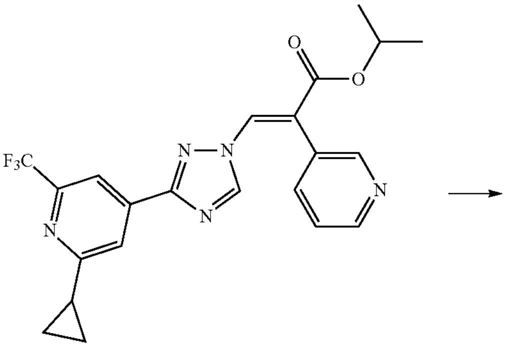

42-2

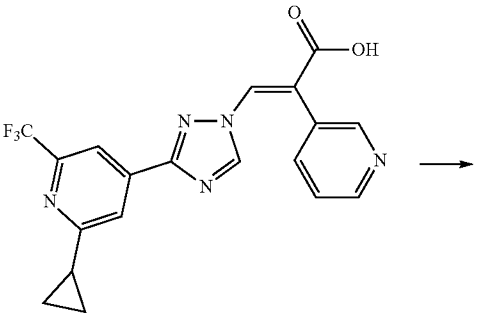

42-3

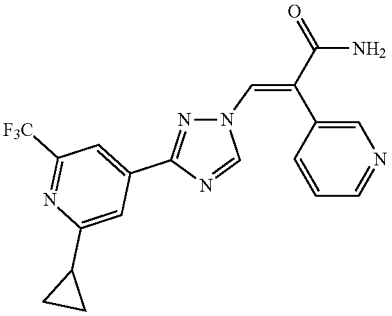

42

(1) Preparation of Compound 42-2

Compound 13-8 (200 mg) and pyridine-3-boronic acid (42-1, 66.37 mg) were dispersed in 1,4-dioxane (5 mL), and potassium acetate (132.5 mg), Pd(dppf)$Cl_2$ (14.6 mg), and water (0.5 mL) were added. The mixture was heated to 90° C. and reacted under nitrogen atmosphere. After the starting materials were consumed completely as detected by TLC, the reaction solution was concentrated under reduced pressure and purified by column chromatography to give compound 42-2.

(2) Preparation of Compound 42-3

Compound 42-2 (85 mg) was dissolved in tetrahydrofuran (4 mL), a solution of lithium hydroxide hydrate (24.1 mg) and water (4 mL) was added dropwise in an ice-water bath, and the mixture was reacted at room temperature for 4 h. The reaction solution was adjusted to pH 6-7 with hydrochloric acid, extracted with ethyl acetate, dried over anhydrous sodium sulfate, and filtered, and the filtrate was evaporated to dryness under reduced pressure to give compound 42-3, which was directly used in the next step.

(3) Preparation of Compound 42

Compound 42-3 (76.28 mg) was dispersed in tetrahydrofuran (5 mL), N-methylmorpholine (38.4 mg) and isobutyl chloroformate (51.9 mg) were added in an ice-water bath, and the mixture was stirred for 30 min. Ammonium hydroxide (39.9 mg) was added dropwise, and the mixture was reacted in an ice-water bath for 10 min. Water was added to quench the reaction, and the resulting mixture was extracted with ethyl acetate, dried over anhydrous sodium sulfate, concentrated until no liquid flowed out, and purified by preparative liquid chromatography to give compound 42 (20 mg). ESI-MS: m/z=401.32 $[M+H]^+$.

Example 43

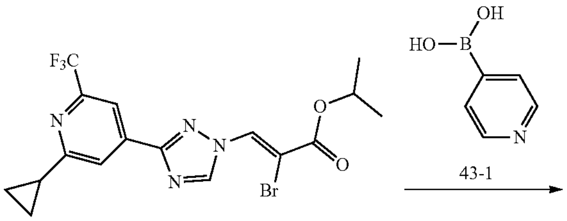

13-8

43-1

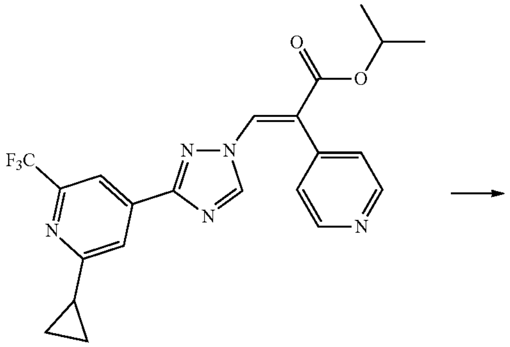

43-2

-continued

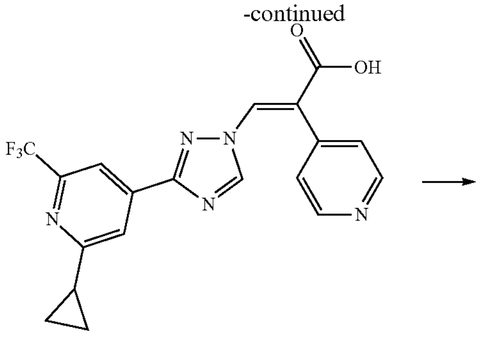

43-3

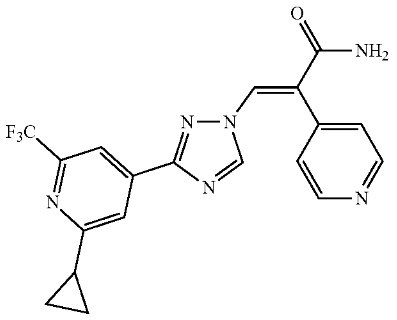

43

(1) Preparation of Compound 43-2

Compound 13-8 (200 mg) and 4-pyridineboronic acid (43-1, 66.37 mg) were dispersed in 1,4-dioxane (5 mL), and potassium acetate (132.5 mg), Pd(dppf)$Cl_2$ (14.6 mg), and water (0.5 mL) were added. The mixture was heated to 90° C. and reacted under nitrogen atmosphere. After the starting materials were consumed completely as detected by TLC, the reaction solution was concentrated under reduced pressure and purified by column chromatography to give compound 43-2.

(2) Preparation of Compound 43-3

Compound 43-2 (120 mg) was dissolved in tetrahydrofuran (4 mL), a solution of lithium hydroxide hydrate (34.06 mg) and water (4 mL) was added dropwise in an ice-water bath, and the mixture was reacted at room temperature for 4 h. The reaction solution was adjusted to pH 6-7 with hydrochloric acid, extracted with ethyl acetate, dried over anhydrous sodium sulfate, and filtered, and the filtrate was evaporated to dryness under reduced pressure to give compound 43-3, which was directly used in the next step.

(3) Preparation of Compound 43

Compound 43-3 (108.4 mg) was dispersed in tetrahydrofuran (5 mL), N-methylmorpholine (54.6 mg) and isobutyl chloroformate (73.7 mg) were added in an ice-water bath, and the mixture was stirred for 30 min. Ammonium hydroxide (56.7 mg) was added dropwise, and the mixture was reacted in an ice-water bath for 10 min. Water was added to quench the reaction, and the resulting mixture was extracted with ethyl acetate, dried over anhydrous sodium sulfate, concentrated until no liquid flowed out, and purified by preparative liquid chromatography to give compound 43 (60 mg). ESI-MS: m/z=401.24 $[M+H]^+$.

Example 44

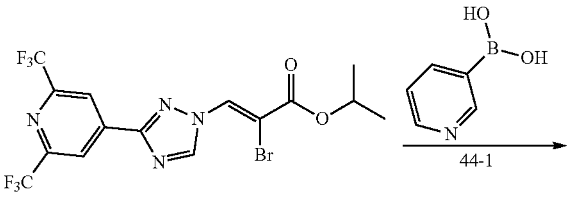

1-7

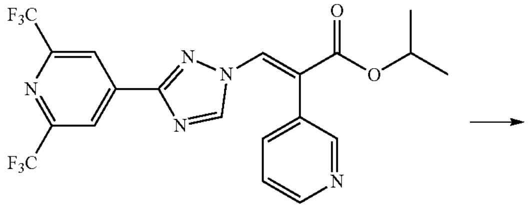

44-2

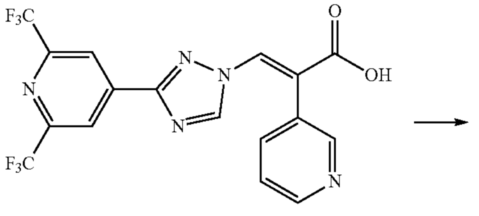

44-3

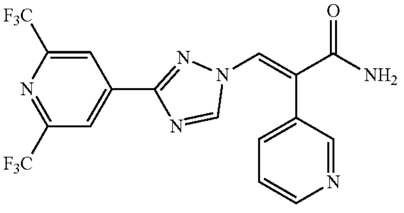

44

(1) Preparation of Compound 44-2

Compound 1-7 (200 mg) and pyridine-3-boronic acid (44-1, 62.4 mg) were dispersed in 1,4-dioxane (8 mL), and potassium carbonate (175 mg), Pd(dppf)$Cl_2$ (15.5 mg), and water (0.8 mL) were added. The mixture was heated to 90° C. and reacted under nitrogen atmosphere. After the starting materials were consumed completely as detected by TLC, the reaction solution was concentrated under reduced pressure and purified by column chromatography to give compound 44-2.

(2) Preparation of Compound 44-3

Compound 44-2 (100 mg) was dissolved in tetrahydrofuran (5 mL), a solution of lithium hydroxide hydrate (290 mg) and water (5 mL) was added dropwise in an ice-water bath, and the mixture was reacted at room temperature for 2 h. The reaction solution was adjusted to pH 6-7 with hydrochloric acid, extracted with ethyl acetate, dried over anhydrous sodium sulfate, and filtered, and the filtrate was evaporated to dryness under reduced pressure to give compound 44-3, which was directly used in the next step.

(3) Preparation of Compound 44

Compound 44-3 (91 mg) was dispersed in tetrahydrofuran (10 mL), N-methylmorpholine (42.9 mg) and isobutyl chloroformate (58 mg) were added in an ice-water bath, and the mixture was stirred for 30 min. Ammonium hydroxide (44.5 mg) was added dropwise, and the mixture was reacted in an ice-water bath for 10 min. Water was added to quench the reaction, and the resulting mixture was extracted with ethyl acetate, dried over anhydrous sodium sulfate, concentrated until no liquid flowed out, and purified by preparative liquid chromatography to give compound 44 (60 mg). ESI-MS: m/z=429.29 $[M+H]^+$.

$^1H$ NMR (500 MHz, DMSO-$d_6$) δ 9.05 (s, 1H), 8.62 (d, J=4.9 Hz, 1H), 8.46 (d, J=2.2 Hz, 1H), 8.31 (s, 1H), 8.10 (s, 2H), 7.70 (dt, J=7.9, 1.9 Hz, 1H), 7.64 (s, 1H), 7.48 (dd, J=7.8, 4.8 Hz, 1H), 7.28 (s, 1H).

Example 45

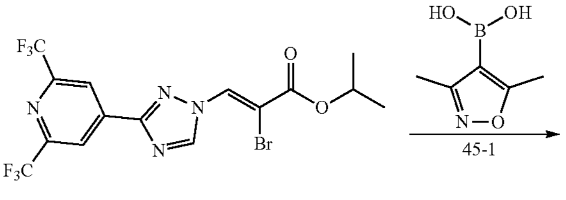

1-7

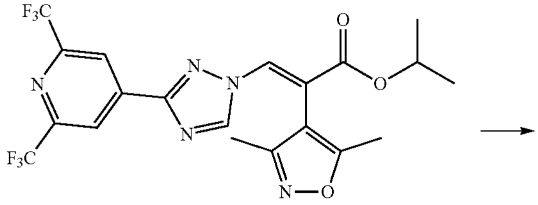

45-2

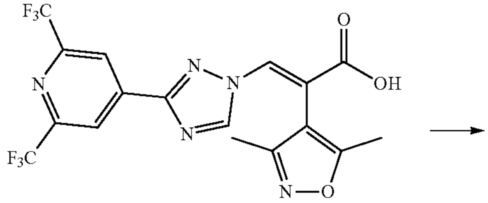

45-3

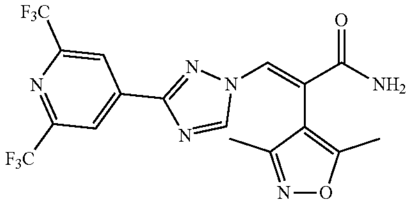

45

(1) Preparation of Compound 45-2

Compound 1-7 (200 mg) and 3,5-dimethylisoxazole-4-boronic acid (45-1, 71.6 mg) were dispersed in 1,4-dioxane (8 mL), and potassium carbonate (175 mg), Pd(dppf)$Cl_2$ (15.5 mg), and water (0.8 mL) were added. The mixture was heated to 90° C. and reacted under nitrogen atmosphere.

After the starting materials were consumed completely as detected by TLC, the reaction solution was concentrated under reduced pressure and purified by column chromatography to give compound 45-2.

(2) Preparation of Compound 45-3

Compound 45-2 (159 mg) was dissolved in tetrahydrofuran (10 mL), a solution of lithium hydroxide hydrate (44.7 mg) and water (10 mL) was added dropwise in an ice-water bath, and the mixture was reacted at room temperature for 2 h. The reaction solution was adjusted to pH 6-7 with hydrochloric acid, extracted with ethyl acetate, dried over anhydrous sodium sulfate, and filtered, and the filtrate was evaporated to dryness under reduced pressure to give compound 45-3, which was directly used in the next step.

(3) Preparation of Compound 45

Compound 45-3 (145 mg) was dispersed in tetrahydrofuran (10 mL), N-methylmorpholine (65.7 mg) and isobutyl chloroformate (88.7 mg) were added in an ice-water bath, and the mixture was stirred for 30 min. Ammonium hydroxide (68 mg) was added dropwise, and the mixture was reacted in an ice-water bath for 10 min. Water was added to quench the reaction, and the resulting mixture was extracted with ethyl acetate, dried over anhydrous sodium sulfate, concentrated until no liquid flowed out, and purified by preparative liquid chromatography to give compound 45 (66 mg). ESI-MS: m/z=447.29 $[M+H]^+$.

$^1H$ NMR (500 MHz, DMSO-$d_6$) δ 9.16 (s, 1H), 8.41 (s, 1H), 8.31 (s, 2H), 7.57 (s, 1H), 7.42 (s, 1H), 2.18 (s, 3H), 1.97 (s, 3H).

Example 46

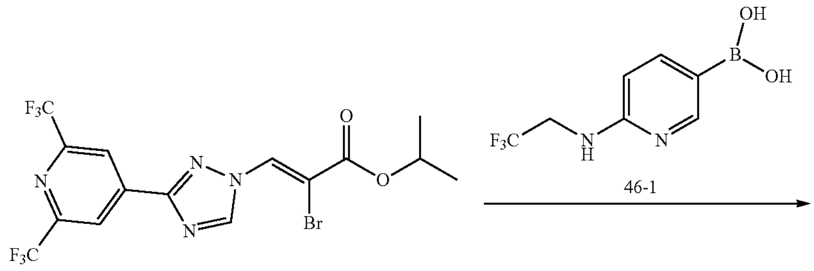

1-7

46-1

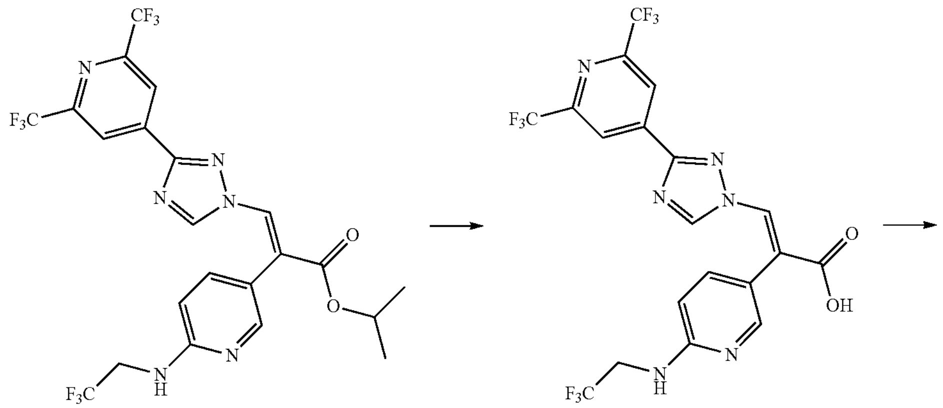

46-2

46-3

-continued

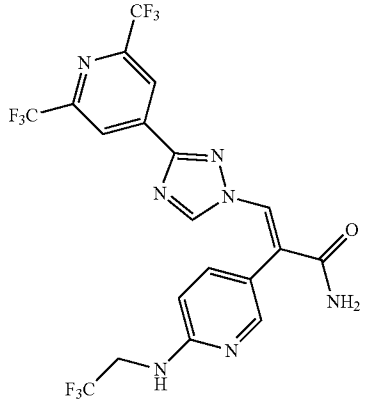

46

(1) Preparation of Compound 46-2

Compound 1-7 (250 mg) and 6-(2,2,2-trifluoroethylamino)pyridine-3-boronic acid (46-1, 140 mg) were dispersed in 1,4-dioxane (8 mL), and potassium carbonate (219 mg), $Pd(dppf)Cl_2$ (19.3 mg), and water (0.8 mL) were added. The mixture was heated to 90° C. and reacted under nitrogen atmosphere. After the starting materials were consumed completely as detected by TLC, the reaction solution was concentrated under reduced pressure and purified by column chromatography to give compound 46-2.

(2) Preparation of Compound 46-3

Compound 46-2 (220 mg) was dissolved in tetrahydrofuran (10 mL), a solution of lithium hydroxide hydrate (48.7 mg) and water (10 mL) was added dropwise in an ice-water bath, and the mixture was reacted at room temperature for 2 h. The reaction solution was adjusted to pH 6-7 with hydrochloric acid, extracted with ethyl acetate, dried over anhydrous sodium sulfate, and filtered, and the filtrate was evaporated to dryness under reduced pressure to give compound 46-3, which was directly used in the next step.

(3) Preparation of Compound 46

Compound 46-3 (203 mg) was dispersed in tetrahydrofuran (10 mL), N-methylmorpholine (78 mg) and isobutyl chloroformate (106 mg) were added in an ice-water bath, and the mixture was stirred for 30 min. Ammonium hydroxide (81 mg) was added dropwise, and the mixture was reacted in an ice-water bath for 10 min. Water was added to quench the reaction, and the resulting mixture was extracted with ethyl acetate, dried over anhydrous sodium sulfate, concentrated until no liquid flowed out, and purified by preparative liquid chromatography to give compound 46 (30 mg). ESI-MS: m/z=526.33 $[M+H]^+$.

$^1H$ NMR (500 MHz, DMSO-$d_6$) δ 8.91 (s, 1H), 8.28 (s, 2H), 8.08 (s, 1H), 7.89 (d, J=2.3 Hz, 1H), 7.55 (s, 1H), 7.40 (t, J=6.5 Hz, 1H), 7.33 (dd, J=8.6, 2.4 Hz, 1H), 7.27 (s, 1H), 6.68 (d, J=8.6 Hz, 1H), 4.18 (qd, J=9.7, 6.4 Hz, 2H).

Example 47

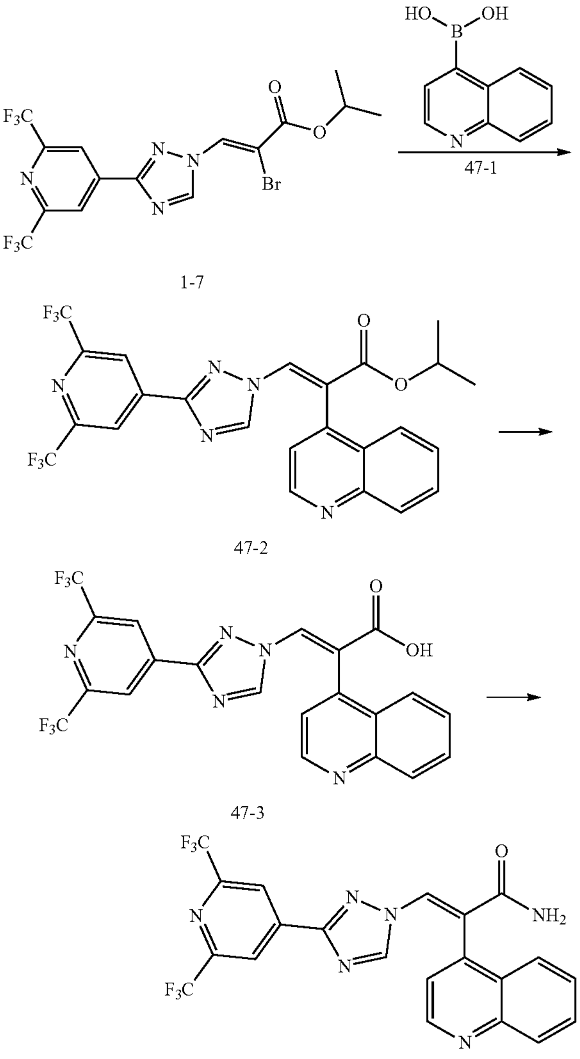

1-7

47-1

47-2

47-3

47

(1) Preparation of Compound 47-2

Compound 1-7 (200 mg) and 4-quinolineboronic acid (47-1, 87.7 mg) were dispersed in 1,4-dioxane (8 mL), and potassium acetate (124 mg), Pd(dppf)$Cl_2$ (15.5 mg), and water (0.8 mL) were added. The mixture was heated to 90° C. and reacted under nitrogen atmosphere. After the starting materials were consumed completely as detected by TLC, the reaction solution was concentrated under reduced pressure and purified by column chromatography to give compound 47-2.

(2) Preparation of Compound 47-3

Compound 47-2 (200 mg) was dissolved in tetrahydrofuran (10 mL), a solution of lithium hydroxide hydrate (48 mg) and water (10 mL) was added dropwise in an ice-water bath, and the mixture was reacted at room temperature for 2 h. The reaction solution was adjusted to pH 6-7 with hydrochloric acid, extracted with ethyl acetate, dried over anhydrous sodium sulfate, and filtered, and the filtrate was evaporated to dryness under reduced pressure to give compound 47-3, which was directly used in the next step.

(3) Preparation of Compound 47

Compound 47-3 (184 mg) was dispersed in tetrahydrofuran (10 mL), N-methylmorpholine (77.7 mg) and isobutyl chloroformate (105 mg) were added in an ice-water bath, and the mixture was stirred for 30 min. Ammonium hydroxide (80 mg) was added dropwise, and the mixture was reacted in an ice-water bath for 10 min. Water was added to quench the reaction, and the resulting mixture was extracted with ethyl acetate, dried over anhydrous sodium sulfate, concentrated until no liquid flowed out, and purified by preparative liquid chromatography to give compound 47 (90 mg). ESI-MS: m/z=479.22 $[M+H]^+$.

$^1$H NMR (500 MHz, DMSO-$d_6$) δ 9.10 (s, 1H), 8.95 (d, J=4.4 Hz, 1H), 8.57 (s, 1H), 8.12 (d, J=8.4 Hz, 1H), 7.77 (dd, J=8.4, 1.4 Hz, 1H), 7.74 (ddd, J=8.3, 6.8, 1.4 Hz, 1H), 7.63 (s, 1H), 7.61 (s, 2H), 7.52 (ddd, J=8.2, 6.8, 1.2 Hz, 1H), 7.42 (d, J=4.4 Hz, 1H), 7.22 (s, 1H).

Example 48

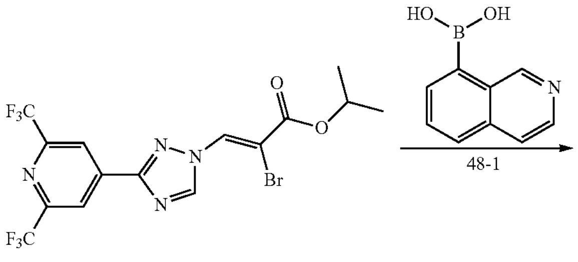

48-1

1-7

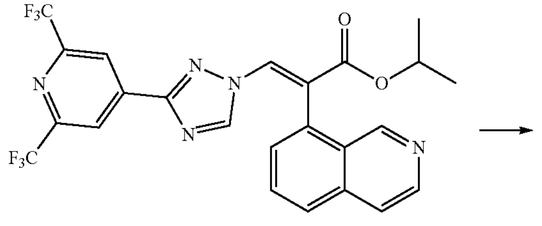

48-2

-continued

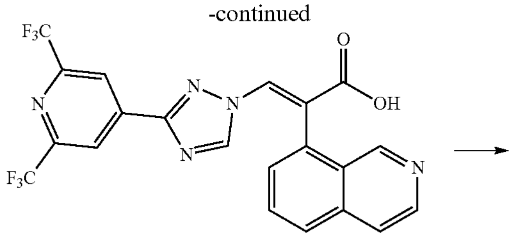

48-3

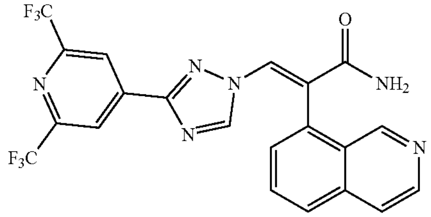

48

(1) Preparation of Compound 48-2

Compound 1-7 (200 mg) and 8-isoquinolineboronic acid (48-1, 87.7 mg) were dispersed in 1,4-dioxane (8 mL), and potassium acetate (124 mg), Pd(dppf)$Cl_2$ (15.5 mg), and water (0.8 mL) were added. The mixture was heated to 90° C. and reacted under nitrogen atmosphere. After the starting materials were consumed completely as detected by TLC, the reaction solution was concentrated under reduced pressure and purified by column chromatography to give compound 48-2.

(2) Preparation of Compound 48-3

Compound 48-2 (170 mg) was dissolved in tetrahydrofuran (10 mL), a solution of lithium hydroxide hydrate (41 mg) and water (10 mL) was added dropwise in an ice-water bath, and the mixture was reacted at room temperature for 2 h. The reaction solution was adjusted to pH 6-7 with hydrochloric acid, extracted with ethyl acetate, dried over anhydrous sodium sulfate, and filtered, and the filtrate was evaporated to dryness under reduced pressure to give compound 48-3, which was directly used in the next step.

(3) Preparation of Compound 48

Compound 48-3 (156 mg) was dispersed in tetrahydrofuran (10 mL), N-methylmorpholine (66 mg) and isobutyl chloroformate (89 mg) were added in an ice-water bath, and the mixture was stirred for 30 min. Ammonium hydroxide (68 mg) was added dropwise, and the mixture was reacted in an ice-water bath for 10 min. Water was added to quench the reaction, and the resulting mixture was extracted with ethyl acetate, dried over anhydrous sodium sulfate, concentrated until no liquid flowed out, and purified by preparative liquid chromatography to give compound 48 (45 mg). ESI-MS: m/z=479.24 $[M+H]^+$.

$^1$H NMR (500 MHz, DMSO-$d_6$) δ 9.10 (d, J=43.7 Hz, 2H), 8.54 (d, J=37.6 Hz, 2H), 8.08 (d, J=8.1 Hz, 1H), 7.99-7.81 (m, 2H), 7.66 (s, 3H), 7.55 (d, J=7.0 Hz, 1H), 7.28 (s, 1H).

Example 49

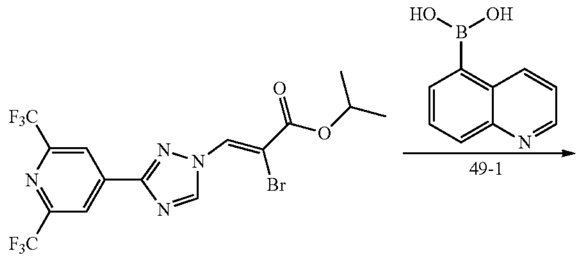
49-1

1-7

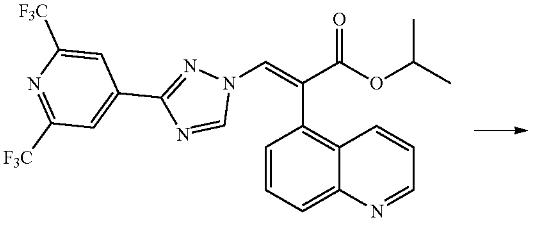

49-2

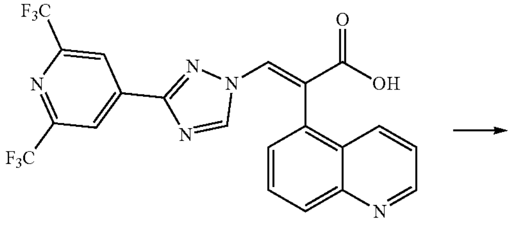

49-3

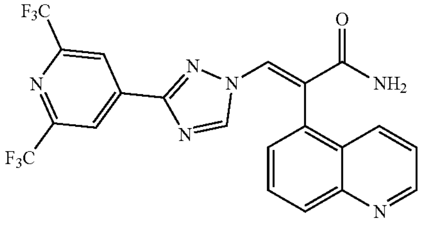

49

(1) Preparation of Compound 49-2

Compound 1-7 (200 mg) and 5-quinolineboronic acid (49-1, 87.7 mg) were dispersed in 1,4-dioxane (8 mL), and potassium carbonate (175 mg), Pd(dppf)$Cl_2$ (15.5 mg), and water (0.8 mL) were added. The mixture was heated to 90° C. and reacted under nitrogen atmosphere. After the starting materials were consumed completely as detected by TLC, the reaction solution was concentrated under reduced pressure and purified by column chromatography to give compound 49-2.

(2) Preparation of Compound 49-3

Compound 49-2 (200 mg) was dissolved in tetrahydrofuran (10 mL), a solution of lithium hydroxide hydrate (48 mg) and water (10 mL) was added dropwise in an ice-water bath, and the mixture was reacted at room temperature for 2 h. The reaction solution was adjusted to pH 6-7 with hydrochloric acid, extracted with ethyl acetate, dried over anhydrous sodium sulfate, and filtered, and the filtrate was evaporated to dryness under reduced pressure to give compound 49-3, which was directly used in the next step.

(3) Preparation of Compound 49

Compound 49-3 (184 mg) was dispersed in tetrahydrofuran (10 mL), N-methylmorpholine (77.7 mg) and isobutyl chloroformate (105 mg) were added in an ice-water bath, and the mixture was stirred for 30 min. Ammonium hydroxide (80 mg) was added dropwise, and the mixture was reacted in an ice-water bath for 10 min. Water was added to quench the reaction, and the resulting mixture was extracted with ethyl acetate, dried over anhydrous sodium sulfate, concentrated until no liquid flowed out, and purified by preparative liquid chromatography to give compound 49 (62 mg). ESI-MS: m/z=479.25 $[M+H]^+$.

$^1H$ NMR (500 MHz, DMSO-$d_6$) δ 8.98 (s, 1H), 8.93 (d, J=4.4 Hz, 1H), 8.56 (s, 1H), 8.18 (dd, J=18.0, 8.5 Hz, 2H), 7.88 (t, J=7.8 Hz, 1H), 7.72 (s, 2H), 7.63 (s, 1H), 7.59-7.43 (m, 2H), 7.15 (s, 1H).

Example 50

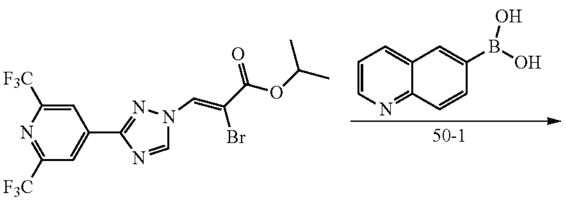
50-1

1-7

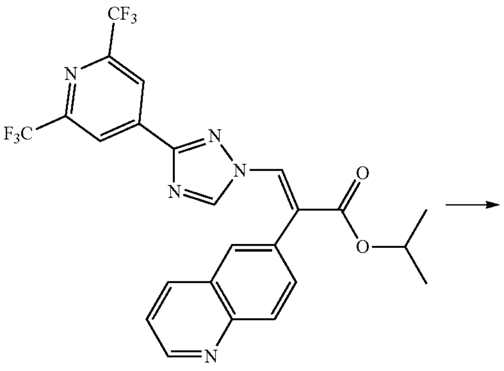

50-2

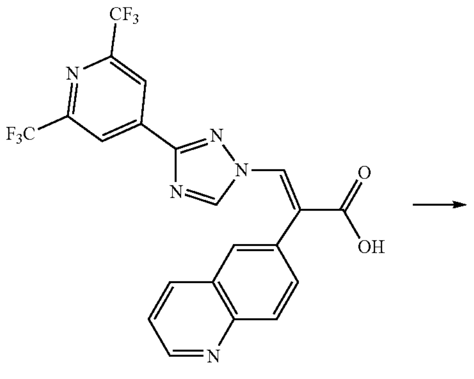

50-3

-continued

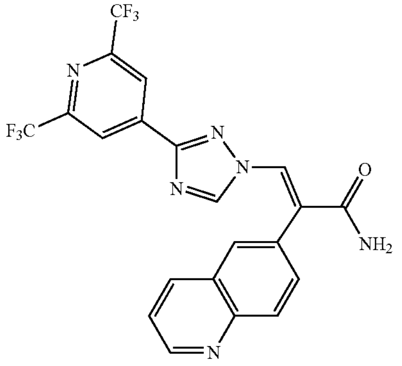

50

(1) Preparation of Compound 50-2

Compound 1-7 (200 mg) and 6-quinolineboronic acid (50-1, 87.7 mg) were dispersed in 1,4-dioxane (8 mL), and potassium carbonate (175 mg), Pd(dppf)$Cl_2$ (15.5 mg), and water (0.8 mL) were added. The mixture was heated to 90° C. and reacted under nitrogen atmosphere. After the starting materials were consumed completely as detected by TLC, the reaction solution was concentrated under reduced pressure and purified by column chromatography to give compound 50-2.

(2) Preparation of Compound 50-3

Compound 50-2 (150 mg) was dissolved in tetrahydrofuran (10 mL), a solution of lithium hydroxide hydrate (36 mg) and water (10 mL) was added dropwise in an ice-water bath, and the mixture was reacted at room temperature for 2 h. The reaction solution was adjusted to pH 6-7 with hydrochloric acid, extracted with ethyl acetate, dried over anhydrous sodium sulfate, and filtered, and the filtrate was evaporated to dryness under reduced pressure to give compound 50-3, which was directly used in the next step.

(3) Preparation of Compound 50

Compound 50-3 (138 mg) was dispersed in tetrahydrofuran (10 mL), N-methylmorpholine (58 mg) and isobutyl chloroformate (78.7 mg) were added in an ice-water bath, and the mixture was stirred for 30 min. Ammonium hydroxide (60.5 mg) was added dropwise, and the mixture was reacted in an ice-water bath for 10 min. Water was added to quench the reaction, and the resulting mixture was extracted with ethyl acetate, dried over anhydrous sodium sulfate, concentrated until no liquid flowed out, and purified by preparative liquid chromatography to give compound 50 (87 mg). ESI-MS: m/z=479.22 $[M+H]^+$.

$^1H$ NMR (500 MHz, DMSO-$d_6$) δ 9.00 (dd, J=4.3, 1.7 Hz, 1H), 8.95 (s, 1H), 8.45 (dd, J=8.4, 1.8 Hz, 1H), 8.32 (s, 1H), 8.09 (d, J=8.6 Hz, 1H), 7.98 (d, J=1.9 Hz, 1H), 7.92 (s, 2H), 7.67 (s, 1H), 7.65-7.62 (m, 1H), 7.62-7.58 (m, 1H), 7.19 (s, 1H).

Example 51

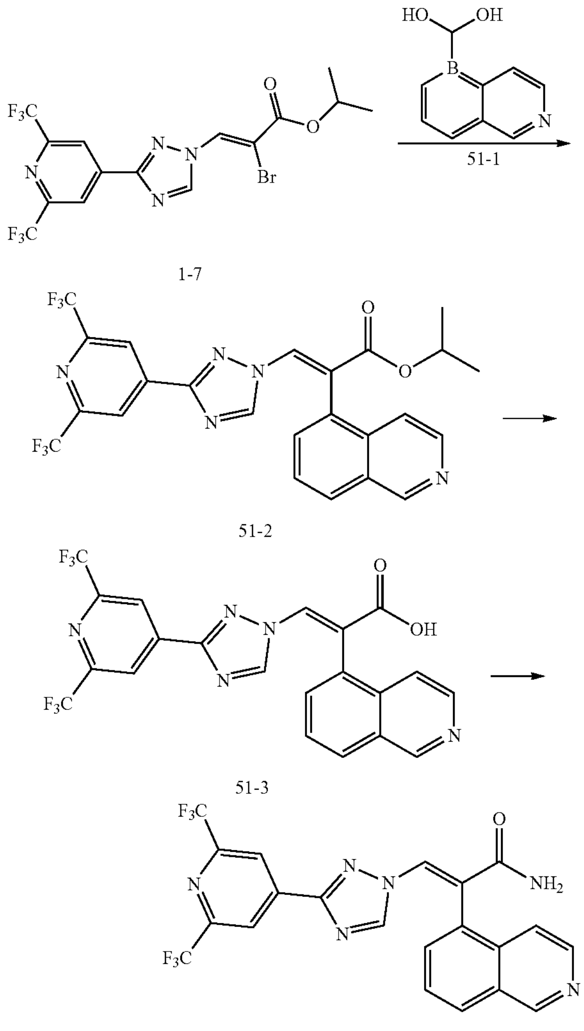

1-7

51-1

51-2

51-3

51

(1) Preparation of Compound 51-2

Compound 1-7 (200 mg) and 5-quinolineboronic acid (51-1, 87.7 mg) were dispersed in 1,4-dioxane (8 mL), and potassium carbonate (175 mg), Pd(dppf)$Cl_2$ (15.5 mg), and water (0.8 mL) were added. The mixture was heated to 90° C. and reacted under nitrogen atmosphere. After the starting materials were consumed completely as detected by TLC, the reaction solution was concentrated under reduced pressure and purified by column chromatography to give compound 51-2.

(2) Preparation of Compound 51-3

Compound 51-2 (200 mg) was dissolved in tetrahydrofuran (10 mL), a solution of lithium hydroxide hydrate (48 mg) and water (10 mL) was added dropwise in an ice-water bath, and the mixture was reacted at room temperature for 2 h. The reaction solution was adjusted to pH 6-7 with hydrochloric acid, extracted with ethyl acetate, dried over anhydrous sodium sulfate, and filtered, and the filtrate was evaporated to dryness under reduced pressure to give compound 51-3, which was directly used in the next step.

(3) Preparation of Compound 51

Compound 51-3 (184 mg) was dispersed in tetrahydrofuran (10 mL), N-methylmorpholine (77.7 mg) and isobutyl chloroformate (105 mg) were added in an ice-water bath, and the mixture was stirred for 30 min. Ammonium hydroxide (80 mg) was added dropwise, and the mixture was reacted in an ice-water bath for 10 min. Water was added to quench the reaction, and the resulting mixture was extracted with ethyl acetate, dried over anhydrous sodium sulfate, concentrated until no liquid flowed out, and purified by preparative liquid chromatography to give compound 51 (29 mg). ESI-MS: m/z=479.23 $[M+H]^+$.

$^1$H NMR (500 MHz, DMSO-$d_6$) δ 9.39 (s, 1H), 9.02 (s, 1H), 8.56 (s, 1H), 8.42 (d, J=5.8 Hz, 1H), 8.24 (d, J=8.2 Hz, 1H), 7.90-7.49 (m, 6H), 7.16 (s, 1H).

Example 52

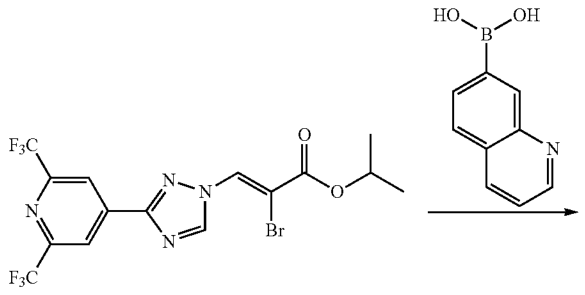

1-7

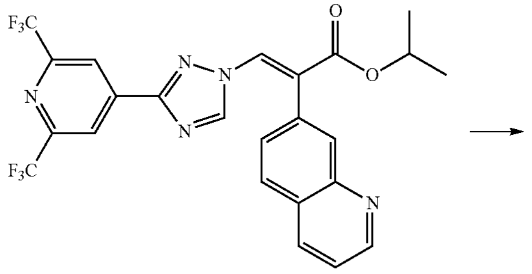

52-1

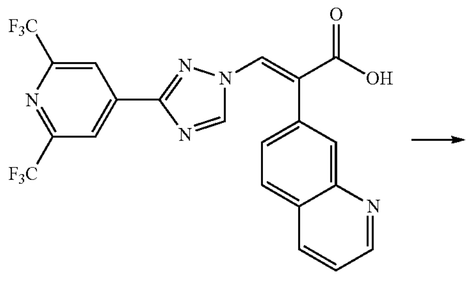

52-2

-continued

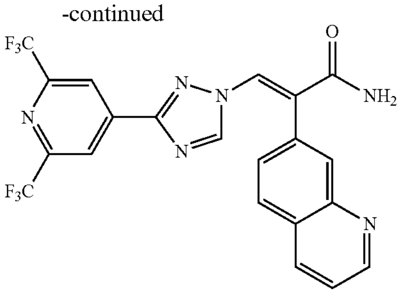

52

(1) Preparation of Compound 52-1

Compound 1-7 (300 mg) and 5-quinolineboronic acid (131.6 mg) were dispersed in 1,4-dioxane (8 mL), and potassium carbonate (263 mg), Pd(dppf)$Cl_2$ (23.2 mg), and water (0.8 mL) were added. The mixture was heated to 90° C. and reacted under nitrogen atmosphere. After the reaction was completed, the reaction solution was concentrated under reduced pressure and purified by column chromatography to give compound 52-1.

(2) Preparation of Compound 52-2

Compound 52-1 (200 mg) was dissolved in tetrahydrofuran (10 mL), a solution of lithium hydroxide hydrate (48 mg) and water (10 mL) was added dropwise in an ice-water bath, and the mixture was reacted at room temperature for 2 h. The reaction solution was adjusted to pH 6-7 with hydrochloric acid, extracted with ethyl acetate (20 mL×2), dried over anhydrous sodium sulfate, and filtered, and the filtrate was evaporated to dryness under reduced pressure to give compound 52-2, which was directly used in the next step.

(3) Preparation of Compound 52

Compound 52-2 (184 mg) was dispersed in tetrahydrofuran (10 mL), N-methylmorpholine (77.7 mg) and isobutyl chloroformate (105 mg) were added in an ice-water bath, and the mixture was stirred for 30 min. Ammonium hydroxide (80 mg) was added dropwise, and the mixture was reacted in an ice-water bath for 10 min. Water was added to quench the reaction, and the resulting mixture was extracted with ethyl acetate (20 mL×2), dried over anhydrous sodium sulfate, concentrated until no liquid flowed out, and purified by preparative liquid chromatography to give compound 52 (90 mg in total). ESI-MS: m/z=479.14 $[M+H]^+$.

$^1$H NMR (500 MHz, DMSO-$d_6$) δ 8.96 (s, 1H), 8.92 (dd, J=4.2, 1.7 Hz, 1H), 8.44 (dd, J=8.5, 1.8 Hz, 1H), 8.31 (s, 1H), 8.04 (d, J=8.4 Hz, 1H), 7.94 (d, J=1.6 Hz, 1H), 7.91 (s, 2H), 7.65 (s, 1H), 7.61 (dd, J=8.3, 4.2 Hz, 1H), 7.47 (dd, J=8.3, 1.7 Hz, 1H), 7.19 (s, 1H).

Example 53

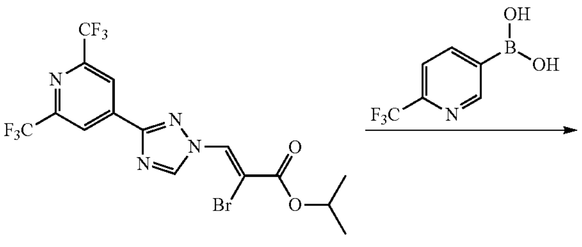

1-7

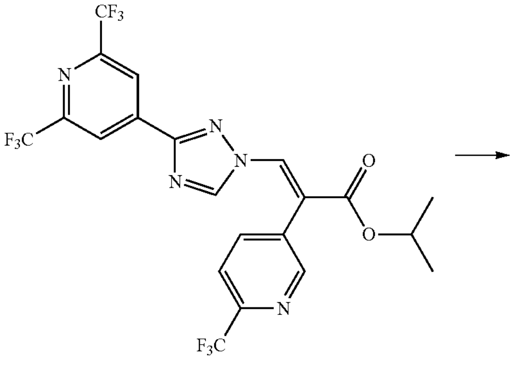

53-1

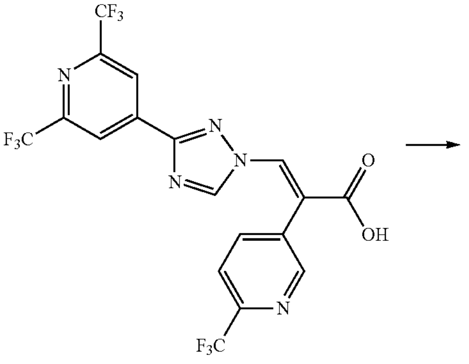

53-2

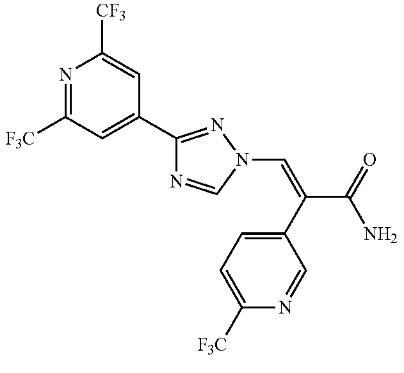

53

(1) Preparation of Compound 53-1

Compound 1-7 (300 mg) and 6-trifluoromethyl-3-pyridineboronic acid (145 mg) were dispersed in 1,4-dioxane (8 mL), and potassium carbonate (138.2 mg), Pd(dppf)$Cl_2$ (23.2 mg), and water (0.8 mL) were added. The mixture was heated to 90° C. and reacted under nitrogen atmosphere. After the reaction was completed, the reaction solution was concentrated under reduced pressure and purified by column chromatography to give compound 53-1.

(2) Preparation of Compound 53-2

Compound 53-1 (300 mg) was dissolved in tetrahydrofuran (10 mL), a solution of lithium hydroxide hydrate (70 mg) and water (10 mL) was added dropwise in an ice-water bath, and the mixture was reacted at room temperature for 3 h. The reaction solution was adjusted to pH 6-7 with hydrochloric acid, extracted with ethyl acetate (20 mL×2), dried over anhydrous sodium sulfate, and filtered, and the filtrate was evaporated to dryness under reduced pressure to give compound 53-2, which was directly used in the next step.

(3) Preparation of Compound 53

Compound 53-2 (276 mg) was dispersed in tetrahydrofuran (10 mL), N-methylmorpholine (112 mg) and isobutyl chloroformate (152 mg) were added in an ice-water bath, and the mixture was stirred for 30 min. Ammonium hydroxide (117 mg) was added dropwise, and the mixture was reacted in an ice-water bath for 10 min. Water was added to quench the reaction, and the resulting mixture was extracted with ethyl acetate (20 mL×2), dried over anhydrous sodium sulfate, concentrated until no liquid flowed out, and purified by preparative liquid chromatography to give compound 53 (150 mg in total). ESI-MS: m/z=497.05 $[M+H]^+$.

$^1$H NMR (500 MHz, DMSO-$d_6$) δ 9.22 (s, 1H), 8.68 (d, J=2.0 Hz, 1H), 8.44 (s, 1H), 8.01 (d, J=4.4 Hz, 3H), 7.98 (d, J=8.0 Hz, 1H), 7.67 (s, 1H), 7.33 (s, 1H).

Example 54

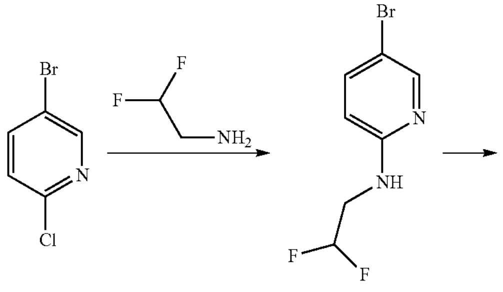

54-1

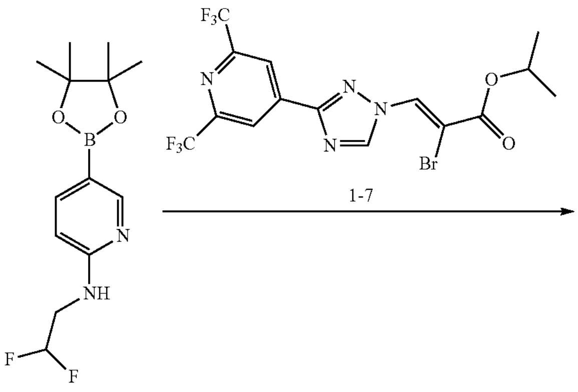

54-2

-continued

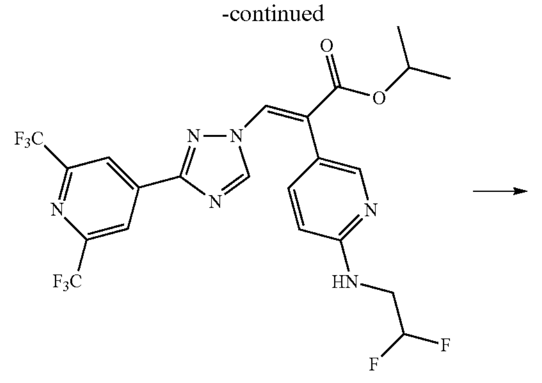

54-3

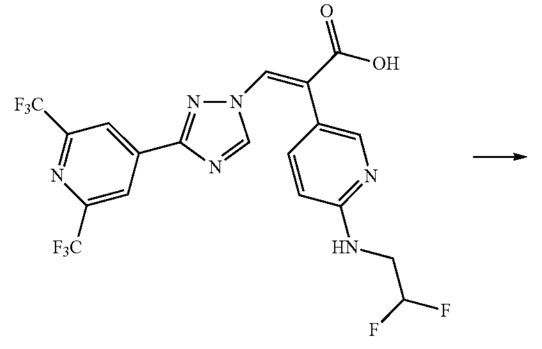

54-4

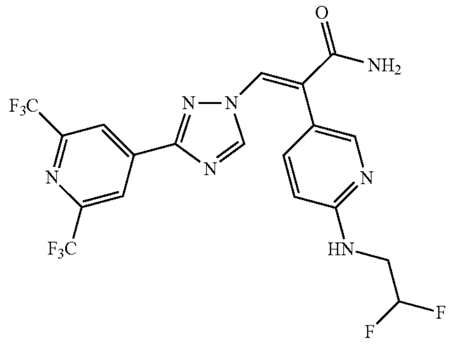

54

(1) Preparation of Compound 54-1

Compounds 5-bromo-2-chloropyridine (2.4 g) and 2,2-difluoroethylamine (1.76 g) were dispersed in 1,4-dioxane (30 mL), and bis(dibenzylideneacetone)palladium (420 mg), 1,1'-bis(di-tert-butylphosphino)ferrocene (710 mg), and potassium tert-butoxide (5.6 g) were added. The mixture was heated to 90° C. and reacted under nitrogen atmosphere. After the reaction was completed, the reaction solution was concentrated under reduced pressure and purified by column chromatography to give compound 54-1.

(2) Preparation of Compound 54-2

Compound 54-1 (200 mg) was dispersed in 1,4-dioxane (10 mL), and bis(pinacolato)diboron (236 mg), potassium acetate (331 mg), and Pd(dppf)$Cl_2$ (62 mg) were added. The mixture was reacted at 90° C. for 3 h under nitrogen atmosphere. The reaction solution was diluted with water (10 mL), extracted with ethyl acetate (20 mL×2), dried over anhydrous sodium sulfate, and concentrated until no liquid flowed out to give compound 54-2.

(3) Preparation of Compound 54-3

Compounds 1-7 (332 mg) and 54-2 (240 mg) were dispersed in 1,4-dioxane (10 mL), and potassium acetate (207 mg), Pd(dppf)$Cl_2$ (25.7 mg), and water (1 mL) were added. The mixture was heated to 90° C. and reacted under nitrogen atmosphere. After the reaction was completed, the reaction solution was concentrated under reduced pressure and purified by column chromatography to give compound 54-3.

(4) Preparation of Compound 54-4

Compound 54-3 (180 mg) was dissolved in tetrahydrofuran (8 mL), a solution of lithium hydroxide hydrate (41 mg) and water (8 mL) was added dropwise in an ice-water bath, and the mixture was reacted at room temperature for 4 h. The reaction solution was adjusted to pH 6-7 with hydrochloric acid, extracted with ethyl acetate (20 mL×2), dried over anhydrous sodium sulfate, and filtered, and the filtrate was evaporated to dryness under reduced pressure to give compound 54-4, which was directly used in the next step.

(5) Preparation of Compound 54

Compound 54-4 (166 mg) was dispersed in tetrahydrofuran (10 mL), N-methylmorpholine (66 mg) and isobutyl chloroformate (89 mg) were added in an ice-water bath, and the mixture was stirred for 30 min. Ammonium hydroxide (69 mg) was added dropwise, and the mixture was reacted in an ice-water bath for 10 min. Water was added to quench the reaction, and the resulting mixture was extracted with ethyl acetate (20 mL×2), dried over anhydrous sodium sulfate, concentrated until no liquid flowed out, and purified by preparative liquid chromatography to give compound 54 (73 mg). ESI-MS: m/z=508.16 $[M+H]^+$.

$^1H$ NMR (500 MHz, DMSO-$d_6$) δ 8.87 (s, 1H), 8.31 (s, 2H), 8.06 (s, 1H), 7.88 (d, J=2.4 Hz, 1H), 7.55 (s, 1H), 7.31-7.19 (m, 3H), 6.64 (dd, J=8.6, 0.8 Hz, 1H), 6.08 (tt, J=56.6, 4.1 Hz, 1H), 3.73 (tdd, J=15.4, 6.1, 4.2 Hz, 2H).

Example 55

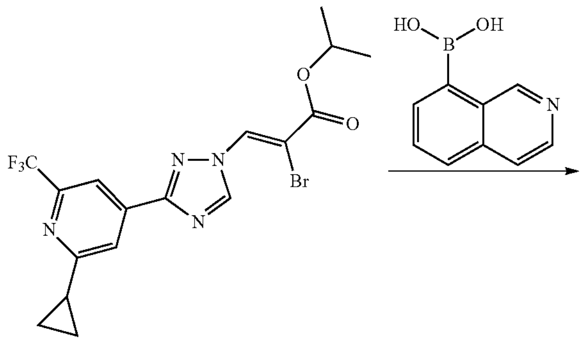

13-8

-continued

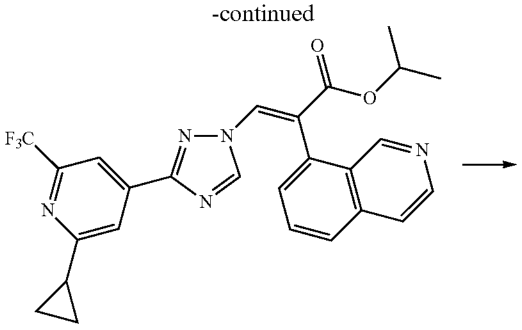

55-1

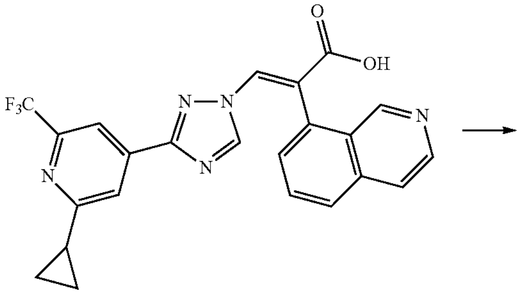

55-2

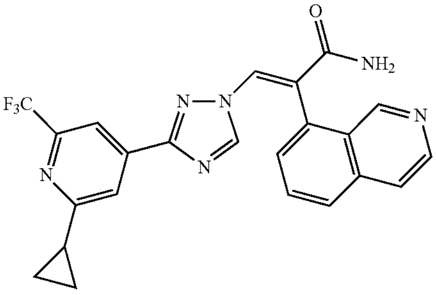

55

(1) Preparation of Compound 55-1

Compound 13-8 (200 mg) and isoquinoline-8-boronic acid (93.4 mg) were dispersed in 1,4-dioxane (5 mL), and potassium carbonate (186.57 mg), Pd(dppf)$Cl_2$ (14.6 mg), and water (0.5 mL) were added. The mixture was heated to 90° C. and reacted under nitrogen atmosphere. After the reaction was completed, the reaction solution was concentrated under reduced pressure and purified by column chromatography to give compound 55-1.

(2) Preparation of Compound 55-2

Compound 55-1 (170 mg) was dissolved in tetrahydrofuran (4 mL), a solution of lithium hydroxide hydrate (43.4 mg) and water (4 mL) was added dropwise in an ice-water bath, and the mixture was reacted at room temperature for 4 h. The reaction solution was adjusted to pH 6-7 with hydrochloric acid, extracted with ethyl acetate (20 mL×2), dried over anhydrous sodium sulfate, and filtered, and the filtrate was evaporated to dryness under reduced pressure to give compound 55-2, which was directly used in the next step.

(3) Preparation of Compound 55

Compound 55-2 (171.5 mg) was dispersed in tetrahydrofuran (5 mL), N-methylmorpholine (76.8 mg) and isobutyl chloroformate (103.8 mg) were added in an ice-water bath, and the mixture was stirred for 30 min. Ammonium hydroxide (79.8 mg) was added dropwise, and the mixture was reacted in an ice-water bath for 10 min. Water was added to quench the reaction, and the resulting mixture was extracted with ethyl acetate (20 mL×2), dried over anhydrous sodium sulfate, concentrated until no liquid flowed out, and purified by preparative liquid chromatography to give compound 55 (30 mg). ESI-MS: m/z=451.23 $[M+H]^+$.

$^1$H NMR (500 MHz, DMSO-$d_6$) δ 9.12 (s, 1H), 8.93 (s, 1H), 8.51 (d, J=12.6 Hz, 2H), 8.07 (d, J=8.2 Hz, 1H), 8.01-7.76 (m, 2H), 7.71-7.47 (m, 2H), 7.38 (s, 1H), 7.22 (s, 1H), 7.03 (s, 1H), 2.18 (s, 1H), 1.05 (d, J=8.3 Hz, 2H), 0.84 (s, 2H).

Example 56

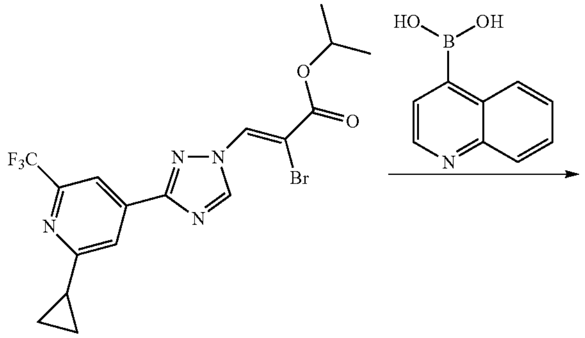

13-8

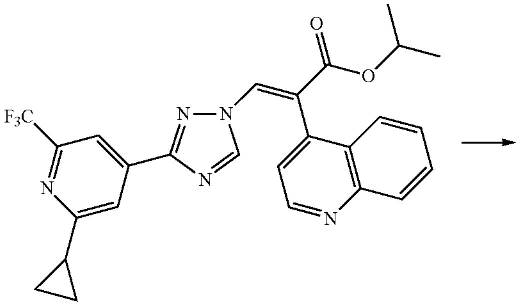

56-1

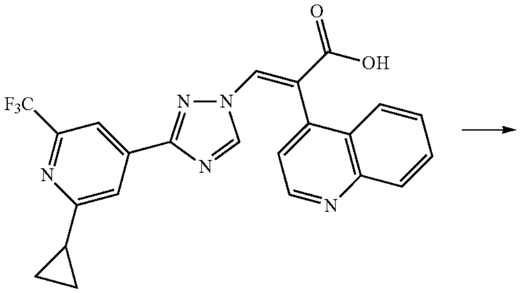

56-2

-continued

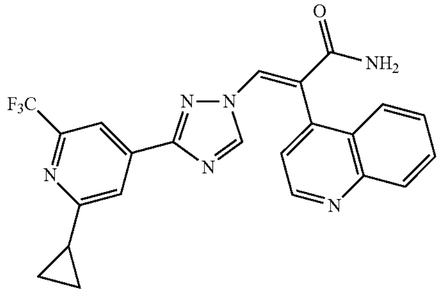

56

(1) Preparation of Compound 56-1

Compound 13-8 (200 mg) and quinoline-4-boronic acid (93.4 mg) were dispersed in 1,4-dioxane (5 mL), and potassium carbonate (186.57 mg), Pd(dppf)$Cl_2$ (14.6 mg), and water (0.5 mL) were added. The mixture was heated to 90° C. and reacted under nitrogen atmosphere. After the reaction was completed, the reaction solution was concentrated under reduced pressure and purified by column chromatography to give compound 56-1.

(2) Preparation of Compound 56-2

Compound 56-1 (160 mg) was dissolved in tetrahydrofuran (4 mL), a solution of lithium hydroxide hydrate (40.8 mg) and water (4 mL) was added dropwise in an ice-water bath, and the mixture was reacted at room temperature for 4 h. The reaction solution was adjusted to pH 6-7 with hydrochloric acid, extracted with ethyl acetate (20 mL×2), dried over anhydrous sodium sulfate, and filtered, and the filtrate was evaporated to dryness under reduced pressure to give compound 56-2, which was directly used in the next step.

(3) Preparation of Compound 56

Compound 56-2 (144.4 mg) was dispersed in tetrahydrofuran (5 mL), N-methylmorpholine (64.7 mg) and isobutyl chloroformate (87.4 mg) were added in an ice-water bath, and the mixture was stirred for 30 min. Ammonium hydroxide (67.2 mg) was added dropwise, and the mixture was reacted in an ice-water bath for 10 min. Water was added to quench the reaction, and the resulting mixture was extracted with ethyl acetate (20 mL×2), dried over anhydrous sodium sulfate, concentrated until no liquid flowed out, and purified by preparative liquid chromatography to give compound 56 (60 mg). ESI-MS: m/z=451.26 $[M+H]^+$.

$^1$H NMR (500 MHz, DMSO-$d_6$) δ 9.00 (s, 1H), 8.95 (d, J=4.3 Hz, 1H), 8.54 (s, 1H), 8.13 (d, J=8.4 Hz, 1H), 7.82-7.70 (m, 2H), 7.59 (s, 1H), 7.52 (t, J=7.6 Hz, 1H), 7.42 (d, J=4.3 Hz, 1H), 7.23 (s, 1H), 7.18 (s, 1H), 7.05 (s, 1H), 2.14 (tt, J=8.3, 4.7 Hz, 1H), 1.06 (dd, J=8.1, 3.0 Hz, 2H), 0.90-0.75 (m, 2H).

Example 57

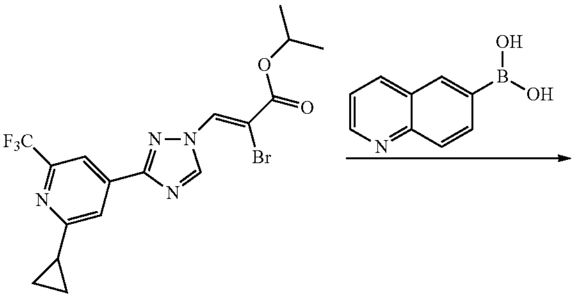

13-8

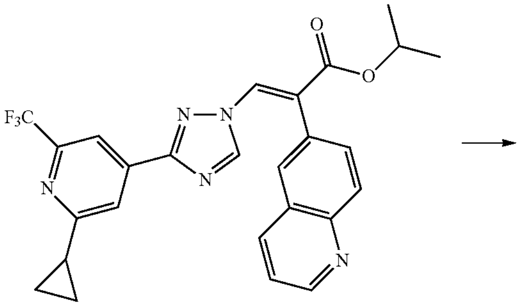

57-1

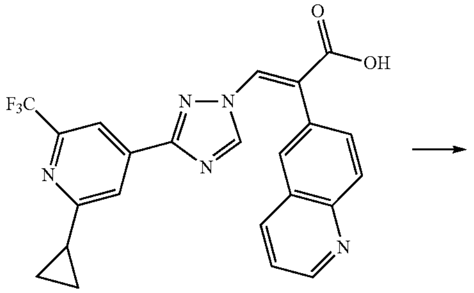

57-2

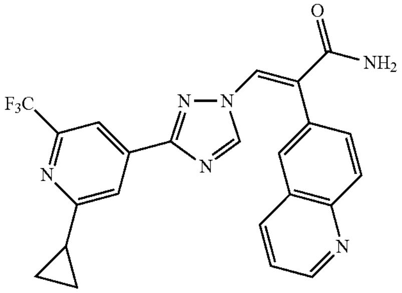

57

(1) Preparation of Compound 57-1

Compound 13-8 (200 mg) and quinoline-6-boronic acid (93.4 mg) were dispersed in 1,4-dioxane (5 mL), and potassium carbonate (186.57 mg), Pd(dppf)$Cl_2$ (14.6 mg), and water (0.5 mL) were added. The mixture was heated to 90° C. and reacted under nitrogen atmosphere. After the reaction was completed, the reaction solution was concentrated under reduced pressure and purified by column chromatography to give compound 57-1.

(2) Preparation of Compound 57-2

Compound 57-1 (150 mg) was dissolved in tetrahydrofuran (4 mL), a solution of lithium hydroxide hydrate (38.3 mg) and water (4 mL) was added dropwise in an ice-water bath, and the mixture was reacted at room temperature for 4 h. The reaction solution was adjusted to pH 6-7 with hydrochloric acid, extracted with ethyl acetate (20 mL×2), dried over anhydrous sodium sulfate, and filtered, and the filtrate was evaporated to dryness under reduced pressure to give compound 57-2, which was directly used in the next step.

(3) Preparation of Compound 57

Compound 57-2 (135.4 mg) was dispersed in tetrahydrofuran (5 mL), N-methylmorpholine (60.7 mg) and isobutyl chloroformate (81.9 mg) were added in an ice-water bath, and the mixture was stirred for 30 min. Ammonium hydroxide (63 mg) was added dropwise, and the mixture was reacted in an ice-water bath for 10 min. Water was added to quench the reaction, and the resulting mixture was extracted with ethyl acetate (20 mL×2), dried over anhydrous sodium sulfate, concentrated until no liquid flowed out, and purified by preparative liquid chromatography to give compound 57 (30 mg). ESI-MS: m/z=451.21 $[M+H]^+$.

$^1H$ NMR (500 MHz, DMSO-$d_6$) δ 8.96 (dd, J=4.2, 1.7 Hz, 1H), 8.81 (s, 1H), 8.39 (dd, J=8.6, 1.8 Hz, 1H), 8.27 (s, 1H), 8.07 (d, J=8.6 Hz, 1H), 7.93 (d, J=1.9 Hz, 1H), 7.65-7.53 (m, 4H), 7.37 (d, J=1.3 Hz, 1H), 7.15 (s, 1H), 2.10 (ddd, J=8.2, 6.5, 4.1 Hz, 1H), 1.03-0.98 (m, 2H), 0.82-0.77 (m, 2H).

Example 58

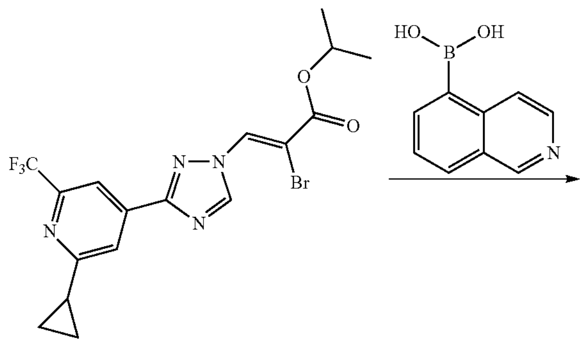

13-8

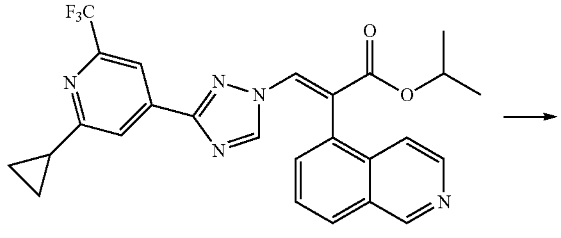

58-1

-continued

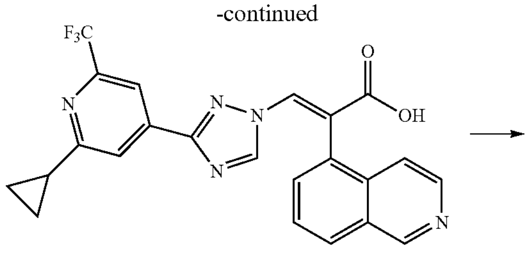

58-2

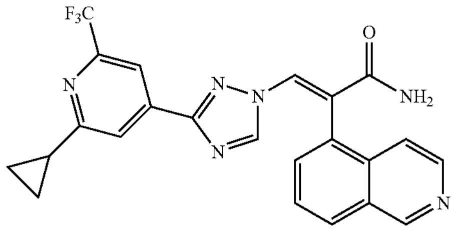

58

(1) Preparation of Compound 58-1

Compound 13-8 (200 mg) and isoquinoline-5-boronic acid (93.4 mg) were dispersed in 1,4-dioxane (5 mL), and potassium carbonate (186.57 mg), Pd(dppf)$Cl_2$ (14.6 mg), and water (0.5 mL) were added. The mixture was heated to 90° C. and reacted under nitrogen atmosphere. After the reaction was completed, the reaction solution was concentrated under reduced pressure and purified by column chromatography to give compound 58-1.

(2) Preparation of Compound 58-2

Compound 58-1 (160 mg) was dissolved in tetrahydrofuran (4 mL), a solution of lithium hydroxide hydrate (40.8 mg) and water (4 mL) was added dropwise in an ice-water bath, and the mixture was reacted at room temperature for 4 h. The reaction solution was adjusted to pH 6-7 with hydrochloric acid, extracted with ethyl acetate (20 mL×2), dried over anhydrous sodium sulfate, and filtered, and the filtrate was evaporated to dryness under reduced pressure to give compound 58-2, which was directly used in the next step.

(3) Preparation of Compound 58

Compound 58-2 (144.4 mg) was dispersed in tetrahydrofuran (5 mL), N-methylmorpholine (64.7 mg) and isobutyl chloroformate (87.4 mg) were added in an ice-water bath, and the mixture was stirred for 30 min. Ammonium hydroxide (67.2 mg) was added dropwise, and the mixture was reacted in an ice-water bath for 10 min. Water was added to quench the reaction, and the resulting mixture was extracted with ethyl acetate (20 mL×2), dried over anhydrous sodium sulfate, concentrated until no liquid flowed out, and purified by preparative liquid chromatography to give compound 58 (40 mg). ESI-MS: m/z=451.20 $[M+H]^+$.

$^1H$ NMR (500 MHz, DMSO-$d_6$) δ 9.39 (s, 1H), 8.89 (s, 1H), 8.51 (s, 1H), 8.41 (d, J=5.9 Hz, 1H), 8.23 (d, J=8.2 Hz, 1H), 7.76 (dd, J=8.2, 7.1 Hz, 1H), 7.66 (dd, J=7.0, 1.2 Hz, 1H), 7.56 (s, 1H), 7.54 (d, J=5.9 Hz, 1H), 7.37 (d, J=1.2 Hz,

1H), 7.11 (s, 1H), 7.04 (d, J=1.2 Hz, 1H), 2.18 (tt, J=8.1, 4.7 Hz, 1H), 1.05 (dd, J=8.2, 2.9 Hz, 2H), 0.85 (d, J=7.0 Hz, 2H).

Example 59

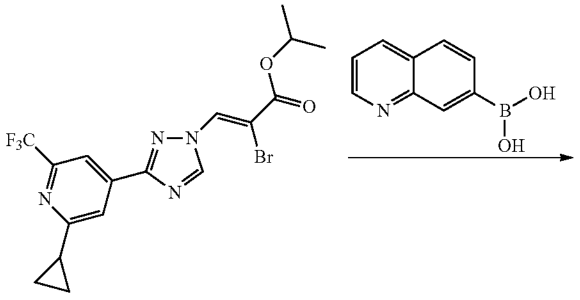

13-8

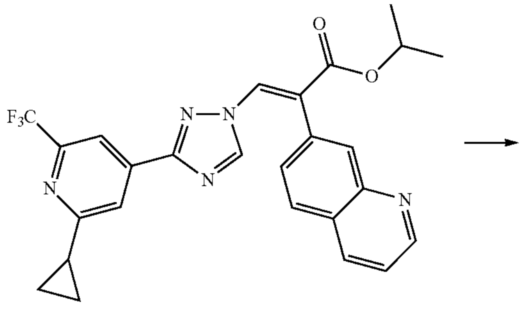

59-1

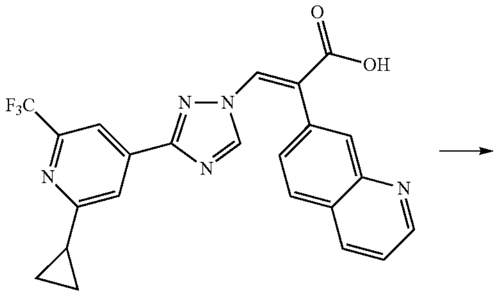

59-2

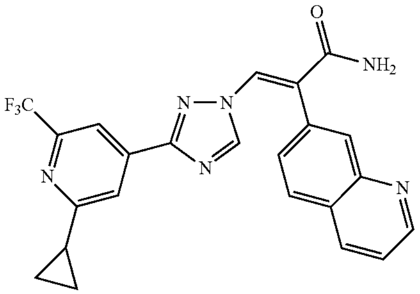

59

(1) Preparation of Compound 59-1

Compound 13-8 (200 mg) and quinoline-7-boronic acid (93.4 mg) were dispersed in 1,4-dioxane (5 mL), and potassium carbonate (186.57 mg), Pd(dppf)$Cl_2$ (14.6 mg), and water (0.5 mL) were added. The mixture was heated to 90° C. and reacted under nitrogen atmosphere. After the reaction was completed, the reaction solution was concentrated under reduced pressure and purified by column chromatography to give compound 59-1.

(2) Preparation of Compound 59-2

Compound 59-1 (145 mg) was dissolved in tetrahydrofuran (4 mL), a solution of lithium hydroxide hydrate (37 mg) and water (4 mL) was added dropwise in an ice-water bath, and the mixture was reacted at room temperature for 4 h. The reaction solution was adjusted to pH 6-7 with hydrochloric acid, extracted with ethyl acetate (20 mL×2), dried over anhydrous sodium sulfate, and filtered, and the filtrate was evaporated to dryness under reduced pressure to give compound 59-2, which was directly used in the next step.

(3) Preparation of Compound 59

Compound 59-2 (135.4 mg) was dispersed in tetrahydrofuran (5 mL), N-methylmorpholine (60.6 mg) and isobutyl chloroformate (81.9 mg) were added in an ice-water bath, and the mixture was stirred for 30 min. Ammonium hydroxide (63 mg) was added dropwise, and the mixture was reacted in an ice-water bath for 10 min. Water was added to quench the reaction, and the resulting mixture was extracted with ethyl acetate (20 mL×2), dried over anhydrous sodium sulfate, concentrated until no liquid flowed out, and purified by preparative liquid chromatography to give compound 59 (40 mg). ESI-MS: m/z=451.22 $[M+H]^+$.

$^1$H NMR (500 MHz, DMSO-$d_6$) δ 8.93 (dd, J=4.2, 1.8 Hz, 1H), 8.83 (s, 1H), 8.44 (dd, J=8.4, 1.8 Hz, 1H), 8.27 (s, 1H), 8.04 (d, J=8.4 Hz, 1H), 7.93 (d, J=1.6 Hz, 1H), 7.66-7.55 (m, 3H), 7.46 (dd, J=8.4, 1.7 Hz, 1H), 7.32 (d, J=1.3 Hz, 1H), 7.17 (s, 1H), 2.12 (tt, J=8.4, 4.7 Hz, 1H), 1.01 (dt, J=8.1, 3.3 Hz, 2H), 0.83-0.77 (m, 2H).

Example 60

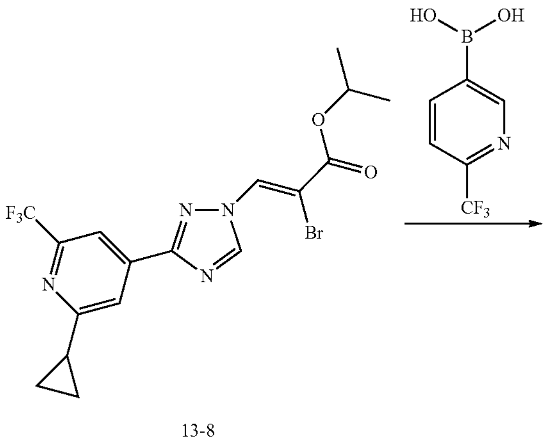

13-8

-continued

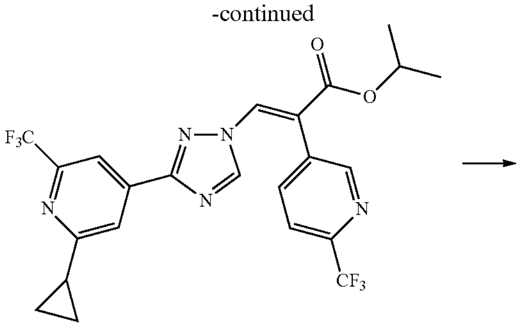

60-1

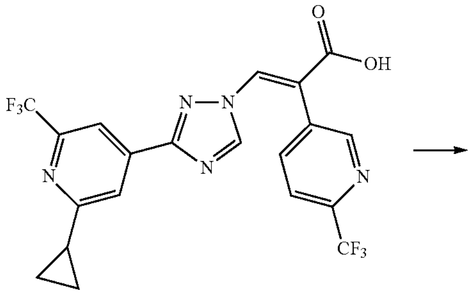

60-2

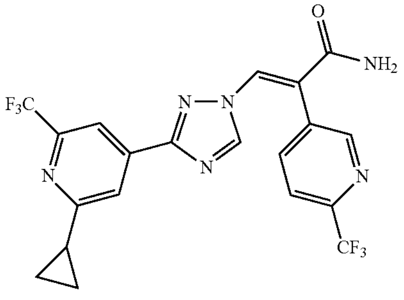

60

(1) Preparation of Compound 60-1

Compound 13-8 (200 mg) and 6-trifluoromethylpyridine-3-boronic acid (103.1 mg) were dispersed in 1,4-dioxane (5 mL), and potassium carbonate (186.57 mg), Pd(dppf)$Cl_2$ (14.6 mg), and water (0.5 mL) were added. The mixture was heated to 90° C. and reacted under nitrogen atmosphere. After the reaction was completed, the reaction solution was concentrated under reduced pressure and purified by column chromatography to give compound 60-1.

(2) Preparation of Compound 60-2

Compound 60-1 (130 mg) was dissolved in tetrahydrofuran (4 mL), a solution of lithium hydroxide hydrate (32 mg) and water (4 mL) was added dropwise in an ice-water bath, and the mixture was reacted at room temperature for 4 h. The reaction solution was adjusted to pH 6-7 with hydrochloric acid, extracted with ethyl acetate (20 mL×2), dried over anhydrous sodium sulfate, and filtered, and the filtrate was evaporated to dryness under reduced pressure to give compound 60-2, which was directly used in the next step.

(3) Preparation of Compound 60

Compound 60-2 (117.3 mg) was dispersed in tetrahydrofuran (5 mL), N-methylmorpholine (50.6 mg) and isobutyl chloroformate (68.3 mg) were added in an ice-water bath, and the mixture was stirred for 30 min. Ammonium hydroxide (52.5 mg) was added dropwise, and the mixture was reacted in an ice-water bath for 10 min. Water was added to quench the reaction, and the resulting mixture was extracted with ethyl acetate (20 mL×2), dried over anhydrous sodium sulfate, concentrated until no liquid flowed out, and purified by preparative liquid chromatography to give compound 60 (45 mg). ESI-MS: m/z=469.19 $[M+H]^+$.

$^1$H NMR (500 MHz, DMSO-$d_6$) δ 9.13 (s, 1H), 8.66 (d, J=2.0 Hz, 1H), 8.41 (s, 1H), 8.04-7.94 (m, 2H), 7.74 (s, 1H), 7.64 (s, 1H), 7.38 (s, 1H), 7.30 (s, 1H), 2.24 (tt, J=8.3, 4.7 Hz, 1H), 1.06 (dt, J=8.0, 3.3 Hz, 2H), 0.99-0.86 (m, 2H).

Example 61

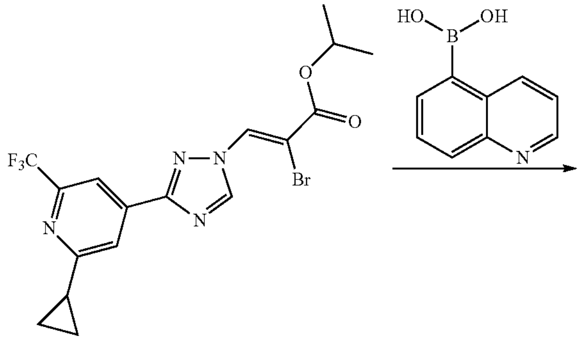

13-8

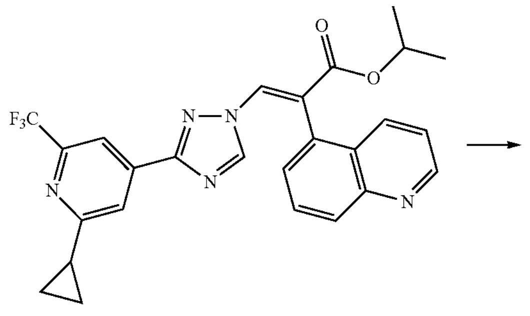

61-1

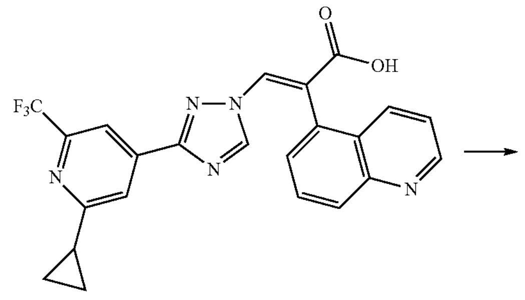

61-2

-continued

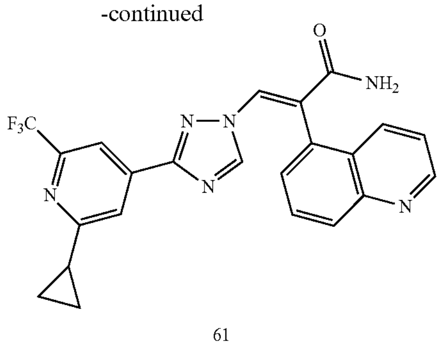

61

(1) Preparation of Compound 61-1

Compound 13-8 (200 mg) and quinoline-5-boronic acid (93.4 mg) were dispersed in 1,4-dioxane (5 mL), and potassium carbonate (186.57 mg), Pd(dppf)$Cl_2$ (14.6 mg), and water (0.5 mL) were added. The mixture was heated to 90° C. and reacted under nitrogen atmosphere. After the reaction was completed, the reaction solution was concentrated under reduced pressure and purified by column chromatography to give compound 61-1.

(2) Preparation of Compound 61-2

Compound 61-1 (220 mg) was dissolved in tetrahydrofuran (4 mL), a solution of lithium hydroxide hydrate (56.6 mg) and water (4 mL) was added dropwise in an ice-water bath, and the mixture was reacted at room temperature for 4 h. The reaction solution was adjusted to pH 6-7 with hydrochloric acid, extracted with ethyl acetate (20 mL×2), dried over anhydrous sodium sulfate, and filtered, and the filtrate was evaporated to dryness under reduced pressure to give compound 61-2, which was directly used in the next step.

(3) Preparation of Compound 61

Compound 61-2 (203.1 mg) was dispersed in tetrahydrofuran (5 mL), N-methylmorpholine (91 mg) and isobutyl chloroformate (123 mg) were added in an ice-water bath, and the mixture was stirred for 30 min. Ammonium hydroxide (94 mg) was added dropwise, and the mixture was reacted in an ice-water bath for 10 min. Water was added to quench the reaction, and the resulting mixture was extracted with ethyl acetate (20 mL×2), dried over anhydrous sodium sulfate, concentrated until no liquid flowed out, and purified by preparative liquid chromatography to give compound 61 (70 mg). ESI-MS: m/z=451.21 $[M+H]^+$.

$^1H$ NMR (500 MHz, DMSO-$d_6$) δ 8.89 (dd, J=4.1, 1.7 Hz, 1H), 8.83 (s, 1H), 8.51 (s, 1H), 8.18-8.08 (m, 2H), 7.84 (dd, J=8.5, 7.1 Hz, 1H), 7.57 (s, 1H), 7.50 (dd, J=7.0, 1.2 Hz, 1H), 7.45 (dd, J=8.5, 4.1 Hz, 1H), 7.32 (d, J=1.3 Hz, 1H), 7.17 (d, J=1.4 Hz, 1H), 7.09 (s, 1H), 2.16 (tt, J=8.0, 4.7 Hz, 1H), 1.06 (dd, J=8.2, 2.8 Hz, 2H), 0.85 (q, J=4.2 Hz, 2H).

Example 62

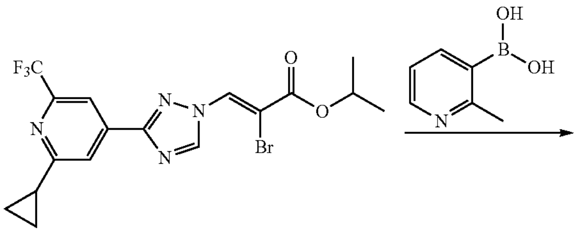

13.8

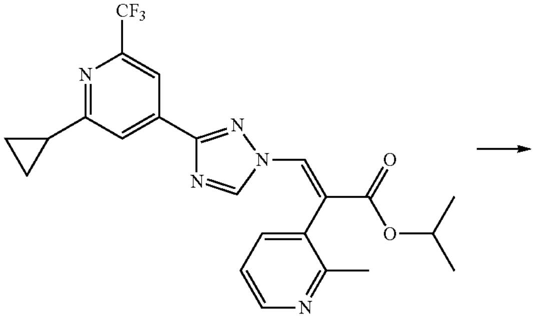

62-1.

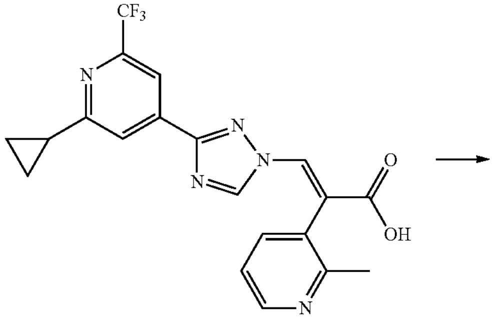

62-2

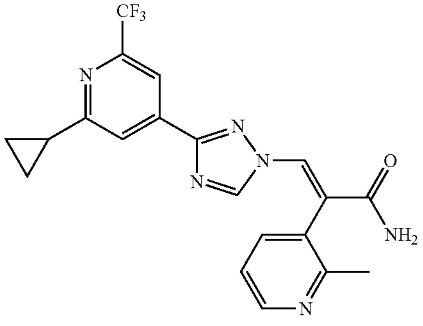

62

(1) Preparation of Compound 62-1

Compound 13-8 (200 mg) and 2-methylpyridine-3-boronic acid (73.95 mg) were dispersed in 1,4-dioxane (5 mL), and potassium carbonate (186.6 mg), Pd(dppf)$Cl_2$ (14.6 mg), and water (0.5 mL) were added. The mixture was heated to 90° C. and reacted under nitrogen atmosphere. After the reaction was completed, the reaction solution was concentrated under reduced pressure and purified by column chromatography to give compound 62-1.

(2) Preparation of Compound 62-2

Compound 62-1 (140 mg) was dissolved in tetrahydrofuran (5 mL), a solution of lithium hydroxide hydrate (38.5 mg) and water (5 mL) was added dropwise in an ice-water bath, and the mixture was reacted at room temperature for 2 h. The reaction solution was adjusted to pH 6-7 with hydrochloric acid, extracted with ethyl acetate (20 mL×2), dried over anhydrous sodium sulfate, and filtered, and the filtrate was evaporated to dryness under reduced pressure to give compound 62-2, which was directly used in the next step.

(3) Preparation of Compound 62

Compound 62-2 (124.6 mg) was dispersed in tetrahydrofuran (5 mL), N-methylmorpholine (60.7 mg) and isobutyl chloroformate (81.9 mg) were added in an ice-water bath, and the mixture was stirred for 30 min. Ammonium hydroxide (63 mg) was added dropwise, and the mixture was reacted in an ice-water bath for 10 min. Water was added to quench the reaction, and the resulting mixture was extracted with ethyl acetate (20 mL×2), dried over anhydrous sodium sulfate, concentrated until no liquid flowed out, and purified by preparative liquid chromatography to give compound 62 (72 mg). ESI-MS: m/z=415.27 $[M+H]^+$.

$^1H$ NMR (500 MHz, DMSO-$d_6$) δ 8.95 (s, 1H), 8.52 (dd, J=4.9, 1.8 Hz, 1H), 8.31 (s, 1H), 7.66 (d, J=1.3 Hz, 1H), 7.57-7.52 (m, 1H), 7.50 (dt, J=4.4, 2.4 Hz, 2H), 7.29 (dd, J=7.6, 4.9 Hz, 1H), 7.14 (s, 1H), 2.28 (s, 3H), 2.27-2.23 (m, 1H), 1.09 (dt, J=8.3, 3.2 Hz, 2H), 0.96-0.90 (m, 2H).

Test Example 1. Inhibitory Activity on In Vitro Cell Proliferation 1.1 Assay for inhibitory activity on Jurkat cell proliferation Jurkat cells in a good growth state were collected into a centrifuge tube, adjusted to a cell density of $5\times10^4$ cells/mL, and seeded in a 96-well plate (100 μL/well). The cells were incubated overnight in a cell incubator. Compounds were added using a nanoliter pipettor such that the final concentrations of the compounds were 1000 nM-0.46 nM (the addition was performed in duplicate). Meanwhile, a control was set. After another 72 h of incubation in the cell incubator, the assay reagent CCK-8 (manufacturer: Dojindo Laboratories, Beijing; 10 L/well) was added. After 2 h of incubation in the cell incubator, absorbance was measured at 450 nm on an Envision microplate reader. A four-parameter analysis was performed, a dose-response curve was fit, and $IC_{50}$ was calculated. 1.2 Assay for inhibitory activity on OCI-LY10 cell proliferation OCI-LY10 cells in a good growth state were collected into a centrifuge tube, adjusted to a cell density of $9\times10^4$ cells/mL, and seeded in a 96-well plate (100 μL/well). The cells were incubated overnight in a cell incubator. Compounds were added using a nanoliter pipettor such that the final concentrations of the compounds were 1000 nM-0.46 nM (the addition was performed in duplicate). Meanwhile, a control was set. After another 72 h of incubation in the cell incubator, the assay reagent CCK-8 (manufacturer: Dojindo Laboratories, Beijing; 10 L/well) was added. After 2 h of incubation in the cell incubator, absorbance was measured at 450 nm on an Envision microplate reader. A four-parameter analysis was performed, a dose-response curve was fit, and $IC_{50}$ was calculated. 1.3 Assay for inhibitory activity on RPMI-8226 cell proliferation RPMI-8226 cells in a good growth state were collected into a centrifuge tube. The cell density was adjusted, and the cells were seeded in a 96-well plate and incubated overnight in a cell incubator. Compounds were added using a nanoliter pipettor, and a control was set. The plate was placed in the cell incubator for further incubation, and the assay reagent was added. After the cells were incubated in the cell incubator for a period of time, absorbance was measured on an Envision microplate reader. A four-parameter analysis was performed, a dose-response curve was fit, and $IC_{50}$ was calculated.

The specific results are shown in Table 1. For the inhibitory activity on Jurkat cell proliferation, A represents $IC_{50}$<20 nM; For the inhibitory activity on OCI-LY10 cell proliferation, + represents $IC_{50}$<40 nM.

TABLE 1

Activity assay results for compounds

| Compound No. | Inhibitory activity on Jurkat cell proliferation ($IC_{50}$, nM) | Inhibitory activity on OCI-LY10 cell proliferation ($IC_{50}$, nM) |
|---|---|---|
| 1 | A | + |
| 2 | A | + |
| 3 | A | + |
| 4 | A | + |
| 5 | A | + |
| 10 | A | + |
| 11 | A | + |
| 13 | A | + |
| 14 | A | + |
| 15 | A | + |
| 16 | A | + |
| 17 | A | + |
| 25 | A | + |
| 26 | A | + |
| 30 | A | + |
| 32 | A | + |
| 33 | A | + |
| 36 | A | + |
| 37 | A | + |
| 38 | A | + |
| 39 | A | + |
| 40 | A | + |
| 41 | A | + |
| 43 | A | + |
| 46 | A | + |
| 53 | A | + |
| 54 | A | + |
| 57 | A | + |
| 59 | A | + |
| 60 | A | + |

The compounds of the present application showed good results in the in vitro cell proliferation inhibitory activity assay.

Test Example 2. In Vitro Liver Microsomal Stability

Liver microsome incubation samples were prepared by mixing a PBS buffer (pH=7.4), a liver microsome solution (0.5 mg/mL), a test compound, and an NADPH+$MgCl_2$ solution, and incubated at 37° C. and 300 rpm for 1 h. Zero-hour samples were prepared by mixing a PBS buffer (pH=7.4), a liver microsome solution (0.5 mg/mL), and a test compound. An acetonitrile solution containing an internal standard was added to the samples, and supernatants were prepared by protein precipitation, diluted, and then assayed by LC/MS/MS.

The assay results are shown in Table 2.

TABLE 2

| In vitro metabolic stability of related compounds in liver microsomes of various species | | |
|---|---|---|
| Compound No. | Mouse liver microsome | Human liver microsome |
| | Residuals at 60 min (%) | |
| 1 | 97.97% | 101.38% |
| 2 | 87.82% | 92.23% |
| 3 | 94.26% | 95.65% |
| 4 | 93.27% | 100.33% |
| 5 | 99.03% | 97.64% |
| 8 | 98.98% | 101.7% |
| 10 | 93.99% | 95.75% |
| 11 | 89.63% | 86.18% |
| 13 | 91.15% | 93.23% |
| 14 | 83.14% | 80.48% |
| 15 | 88.38% | 87.55% |
| 16 | 90.60% | 88.75% |
| 17 | 95.11% | 93.92% |
| 21 | 99.28% | 94.26% |
| 25 | 94.66% | 110.48% |
| 26 | 90.27% | 96.64% |
| 27 | 94.24% | 102.54% |
| 30 | 89.94% | 98.75% |
| 32 | 95.08% | 100.32% |
| 33 | 98.21% | 104.79% |
| 34 | 87.79% | 101.21% |
| 38 | 83.25% | 102.40% |
| 39 | 89.18% | 106.91% |

The compounds of the present application showed good properties in the liver microsomal stability assay.

Test Example 3. In Vivo Pharmacokinetics 3.1 Mouse pharmacokinetics

ICR mice weighing 18-22 g were randomized into groups of 9 mice per group after 3-5 days of acclimatization and then administered intragastrically at a dose of 3 mg/kg.

Plasma samples to be tested were prepared by taking blood from the orbit at time points of 15 min, 30 min, 1 h, 2 h, 4 h, 6 h, 8 h, 10 h, and 24 h.

20 μL of each plasma sample to be tested and a standard curve sample were taken, and an acetonitrile solution containing an internal standard was added. A supernatant was obtained by protein precipitation, diluted, and then assayed by LC/MS/MS.

Pharmacokinetic parameters were fitted using a non-compartmental model. The assay results are shown in Table 3.

The compounds of the present application showed good properties in the pharmacokinetic assay, including but not limited to, good bioavailability, AUC, and the like.

3.2 Mouse Brain Distribution

ICR mice weighing 20-26 g were randomized into groups of 3 mice per group after 3-5 days of acclimatization and then administered intragastrically at a dose of 5 mg/kg.

Plasma samples to be tested were prepared by taking blood from the orbit at a time point of 3 h. Meanwhile, brain tissue at each time point was collected, and the homogenate was weighed.

20 μL of each plasma to be tested and tissue homogenate sample and a standard curve sample were taken, and an acetonitrile solution was added. A supernatant was obtained by protein precipitation, diluted, and then assayed by LC/MS/MS. The brain-to-blood ratio was calculated.

The brain-to-blood ratios of the compounds of the present application were less than 1, showing a low brain uptake amount.

Test Example 4. In Vivo Pharmacodynamics

Efficacy evaluation in OCI-LY10 human diffuse large B-cell lymphoma NOD-SCID mouse subcutaneous xenograft tumor model (1) SPF female NOD-SCID mice (source: Jiangsu Huachuang Xinnuo Pharmaceutical Technology Co., Ltd.) were inoculated subcutaneously at the right side armpit with OCI-LY10 human diffuse large B-cell lymphoma cells at $1\times10^7$ cells/mouse. When the mean tumor volume reached about 200 $mm^3$, the animals were divided into a control group (vehicle control group) and treatment groups (compound groups).

The administration dose included 1 mg/kg, 2 mg/kg, and 4 mg/kg, and the administration frequency was once daily. The day of grouping was defined as day 0, and intragastric administration was started on day 0 for 21 consecutive days.

Alternatively, the administration dose was 4 mg/kg, and the administration frequency was 5 times per week. The day of grouping was defined as day 0, and intragastric administration was started on day 0 five times per week for two consecutive weeks.

The tumor volume was measured once every 3 days, and meanwhile, the mice were weighed and the data were recorded; the general behavior of the mice was observed and recorded every day. After the experiment was completed, the tumors were removed, weighed, and photographed.

TABLE 3

| | Mice administered by single intravenous injection 1 mpk | | | | Mice administered intragastrically 3 mpk | | | | | |
|---|---|---|---|---|---|---|---|---|---|---|
| Compound No. | AUC (0-24) (h * ng/mL) | AUC (0-∞) h * ng/mL | t½ (h) | CL (L/h/kg) | AUC (0-24) (h * ng/mL) | AUC (0-∞) (h * ng/mL) | Tmax(h) | t½ (h) | Cmax (ng/mL) | Absolute bioavailability F (%) |
| 2 | 874 | 879 | 1.26 | 1.14 | 2726 | 2731 | 3.0 | 2.57 | 483 | 103.93% |
| 3 | 1544 | 1574 | 1.66 | 0.635 | 5277 | 5296 | 3.0 | 2.80 | 681 | 113.9% |
| 15 | 1619 | 1629 | 1.34 | 0.614 | 4604 | 4654 | 3.0 | 3.48 | 599 | 94.77% |
| 21 | 1629 | 1633 | 3.02 | 0.61 | 4754 | 4759 | 1.0 | 2.35 | 871 | 97.31% |
| 38 | 1037 | 1044 | 1.41 | 0.958 | 3485 | 3804 | 1.0 | 2.55 | 874 | 112.06% |

The detection index and the calculation formula are as follows:

Tumor volume TV ($mm^3$)=½×(a×$b^2$), wherein a is the long diameter of the tumor, and b is the short diameter of the tumor;

Relative tumor volume RTV=$TV_t/TV_0$, wherein $TV_0$ is the tumor volume on day 0, and $TV_t$ is the tumor volume at each measurement;

Relative tumor proliferation rate T/C (%)=($T_{RT}V/C_{RT}V$)×100%, wherein $T_{RT}V$ is $R_{TV}$ of the treatment group, and $C_{RT}V$ is RTV of the vehicle control group;

Tumor growth inhibition rate TGI (%)=(1−TW/$TW_0$)×100%; wherein TW is the tumor weight of the treatment group, and $TW_0$ is the tumor weight of the vehicle control group;

Weight change rate WCR (%)=($Wt_t$−$Wt_0$)/$Wt_0$×100%, wherein $Wt_0$ is the body weight of the mouse on day 0, and $Wt_t$ is the body weight of the mouse at each measurement.

The specific assay results are shown in Table 4 and Table 5.

TABLE 4

Effect on OCI-LY10 cell (NOD-SCID) mouse subcutaneous xenograft tumor

| Compound | Dose | Day 21 of assay TV($mm^3$) (mean ± SD) | RTV (mean ± SD) | T/C(%) | Day 23 of assay Weight change rate (%) (mean ± SD) | TGI(%) |
|---|---|---|---|---|---|---|
| Control group | N/A | 2260 ± 850 | 10.8 ± 4.3 | — | 9.9 ± 4.7 | — |
| Compound 21 | 2 mg/kg | 520 ± 178 | 2.4 ± 0.4 | 22.2% | −2.0 ± 6.5 | 89.3%* |
| Compound 25 | 4 mg/kg | 360 ± 105 | 1.8 ± 0.6 | 16.7% | 1.7 ± 5.3 | 91.1%* |

Note:
comparison with the control group, where
*denotes $p < 0.05$ and
**denotes $p < 0.01$.

TABLE 5

Effect on OCI-LY10 cell (NOD-SCID) mouse subcutaneous xenograft tumor

| Group | Dose | Day 18 of assay TV ($mm^3$) (mean ± SD) | RTV (mean ± SD) | T/C (%) | Day 21 of assay Weight change rate (%) (mean ± SD) | TGI (%) |
|---|---|---|---|---|---|---|
| Control group | N/A | 1525 ± 586 | 7.8 ± 3.5 | — | 7.9 ± 1.0 | — |
| Compound 11 | 4 mg/kg | 326 ± 52 | 1.7 ± 0.2 | 21.8% | 0.6 ± 8.1 | 89.7%** |

Note:
comparison with the control group, where
**denotes $p < 0.01$.

The compounds of the present application had no significant toxicity in the assay, and the results showed that the compounds had good tumor growth inhibition rates.

The invention claimed is:

1. A compound of formula I, a pharmaceutically acceptable salt thereof, or a stereoisomer thereof:

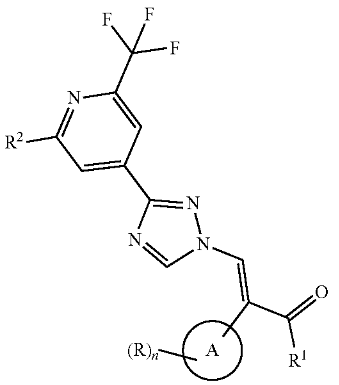

I wherein, $R^1$ is selected from the group consisting of —$NH_2$, $C_{1-6}$ alkyl-O—, $C_{1-6}$ alkyl-NH—, and ($C_{1-6}$ alkyl)$_2$N—;

ring A is selected from the group consisting of a $C_{6-10}$ aromatic ring group and a 5- to 10-membered heteroaromatic ring group;

R is selected from the group consisting of halogen, CN, OH, $NH_2$, $C_{1-6}$ alkyl, $C_{1-6}$ alkyl-O—, $C_{1-6}$ alkyl-S—, $C_{1-6}$ haloalkyl-O—, $C_{1-6}$ haloalkyl-S—, $C_{1-6}$ haloalkyl, $C_{1-6}$ alkyl substituted with 3- to 10-membered heterocycloalkyl, $R^a$NH—, and ($R^a$)$_2$N—;

$R^a$ is selected from the group consisting of $C_{1-6}$ alkyl, $C_{3-10}$ cycloalkyl, and 3- to 10-membered heterocycloalkyl, and $R^a$ is optionally substituted with one or more groups selected from the group consisting of halogen, CN, OH, $NH_2$, $C_{1-6}$ alkyl, $C_{1-6}$ alkyl-O—, and 5- to 6-membered heterocycloalkyl;

n is selected from the group consisting of 0, 1, 2, 3, and 4;

$R^2$ is selected from the group consisting of cyclopropyl and trifluoromethyl.

2. The compound of formula I, the pharmaceutically acceptable salt thereof, or the stereoisomer thereof according to claim 1, wherein $R^1$ is selected from the group consisting of —$NH_2$, $C_{1-4}$ alkyl-O—, $C_{1-4}$ alkyl-NH—, and ($C_{1-4}$ alkyl)$_2$N—;

alternatively, $R^1$ is selected from the group consisting of —$NH_2$, $C_{1-3}$ alkyl-O—, $C_{1-3}$ alkyl-NH—, and ($C_{1-3}$ alkyl)$_2$N—;

alternatively, $R^1$ is selected from the group consisting of —$NH_2$, isopropyl-O—, and methyl-NH—;

alternatively, $R^1$ is selected from the group consisting of —$NH_2$ and isopropyl-O.

3. The compound of formula I, the pharmaceutically acceptable salt thereof, or the stereoisomer thereof according to claim 1, wherein ring A is selected from the group consisting of phenyl and a 5- to 10-membered heteroaromatic ring group;

alternatively, ring A is selected from the group consisting of 5-, 6-, 7-, 8-, 9-, and 10-membered heteroaromatic ring groups;

alternatively, ring A is selected from the group consisting of 5- to 6-membered and 9- to 10-membered heteroaromatic ring groups;

alternatively, ring A is selected from a 10-membered heteroaromatic ring group;

alternatively, ring A is selected from the group consisting of 5- to 6-membered heteroaromatic ring groups;

alternatively, ring A is selected from the group consisting of pyrimidinyl, pyridinyl, pyrazolyl, isoxazolyl, oxazolyl, quinolyl, indazolyl, pyridazinyl, thiazolyl, furanyl, pyranyl, thienyl, pyrrolyl, pyrazinyl, isothiazolyl, oxazolyl, indolyl, naphthyridinyl, isoquinolyl, quinazolinyl, and benzofuranyl;

alternatively, ring A is selected from the group consisting of pyrimidinyl, pyridinyl, pyrazolyl, isoxazolyl, quinolyl, indazolyl, naphthyridinyl, and isoquinolyl;

alternatively, ring A is selected from the group consisting of pyrimidinyl and pyridinyl;

alternatively, ring A is selected from pyrimidinyl;

alternatively, ring A is selected from pyridinyl;

alternatively, ring A is selected from the group consisting of pyrazolyl and isoxazolyl;

alternatively, ring A is selected from the group consisting of quinolyl, indazolyl, naphthyridinyl, and isoquinolyl;

alternatively, ring A is selected from the group consisting of

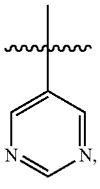 , 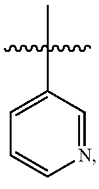 , 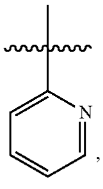 , 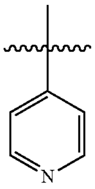 , 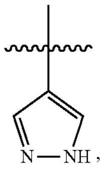 ,

-continued

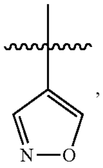 , 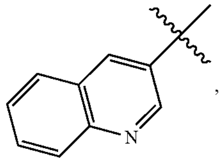 , 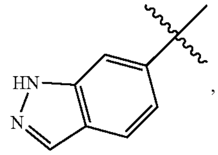 ,

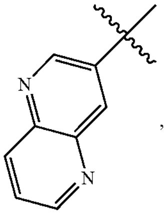 , 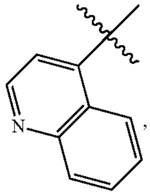 , 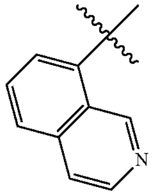 ,

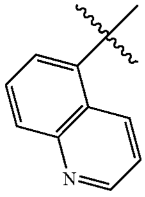 , 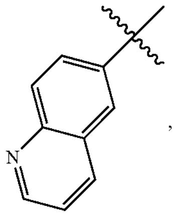 , 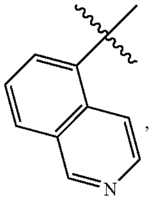 , and

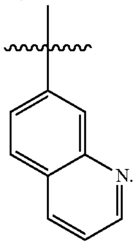.

4. The compound of formula I, the pharmaceutically acceptable salt thereof, or the stereoisomer thereof according to claim 1, wherein R is selected from the group consisting of halogen, CN, OH, $NH_2$, $C_{1-4}$ alkyl, $C_{1-4}$ alkyl-O—, $C_{1-4}$ alkyl-S—, $C_{1-4}$ haloalkyl-O—, $C_{1-4}$ haloalkyl-S—, $C_{1-4}$ haloalkyl, $R^a$NH—, and ($R^a$)$_2$N—;

alternatively, R is selected from the group consisting of halogen, CN, OH, $NH_2$, $C_{1-3}$ alkyl, $C_{1-3}$ alkyl-O—, $C_{1-3}$ alkyl-S—, $C_{1-3}$ haloalkyl-O—, $C_{1-3}$ haloalkyl-S—, $C_{1-3}$ haloalkyl, $R^a$NH—, and ($R^a$)$_2$N—;

alternatively, R is selected from the group consisting of fluorine, chlorine, CN, OH, $NH_2$, $C_{1-3}$ alkyl, $C_{1-3}$ alkyl-O—, $C_{1-3}$ haloalkyl, and $R^a$NH—;

alternatively, R is selected from the group consisting of fluorine, CN, $NH_2$, methyl, methoxy, trifluoromethyl, and $R^a$NH.

5. The compound of formula I, the pharmaceutically acceptable salt thereof, or the stereoisomer thereof according to claim 1, wherein $R^a$ is selected from the group consisting of $C_{1-4}$ alkyl, $C_{3-6}$ cycloalkyl, and 3- to 6-membered heterocycloalkyl, and $R^a$ is optionally substituted with one or more groups selected from the group consisting of halogen, CN, OH, $NH_2$, and 5- to 6-membered heterocycloalkyl;

alternatively, $R^a$ is selected from the group consisting of $C_{1-3}$ alkyl, $C_{5-6}$ cycloalkyl, and 5- to 6-membered heterocycloalkyl, and $R^a$ is optionally substituted with one or more groups selected from the group consisting of halogen, CN, OH, $NH_2$, and 5- to 6-membered heterocycloalkyl;

alternatively, $R^a$ is selected from the group consisting of $C_{1-3}$ alkyl and 5- to 6-membered heterocycloalkyl, and $R^a$ is optionally substituted with one or more groups selected from the group consisting of halogen, CN, OH, $NH_2$, and 5- to 6-membered heterocycloalkyl;

alternatively, $R^a$ is selected from the group consisting of $C_{1-3}$ alkyl and 6-membered heterocycloalkyl, and $R^a$ is optionally substituted with one or more groups selected from the group consisting of fluorine, chlorine, bromine, CN, OH, $NH_2$, and 6-membered heterocycloalkyl;

alternatively, $R^a$ is selected from the group consisting of methyl, ethyl, propyl, and tetrahydropyranyl, and $R^a$ is optionally substituted with one or more fluorine or dioxane.

6. The compound of formula I, the pharmaceutically acceptable salt thereof, or the stereoisomer thereof according to claim 1, wherein n is selected from the group consisting of 0, 1, 2, and 3;

alternatively, n is selected from the group consisting of 0, 1, and 2;

alternatively, n is selected from the group consisting of 0 and 1.

7. The compound of formula I, the pharmaceutically acceptable salt thereof, or the stereoisomer thereof according to claim 1, wherein $R^2$ is selected from cyclopropyl.

8. The compound of formula I, the pharmaceutically acceptable salt thereof, or the stereoisomer thereof according to claim 1, wherein structural unit

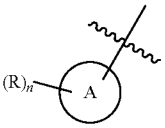

is selected from the group consisting of

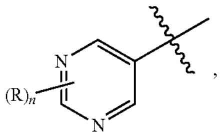,
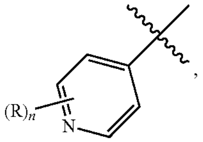,
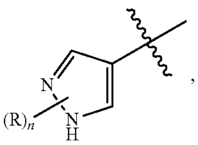,
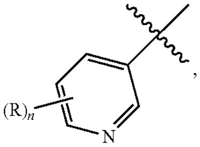,
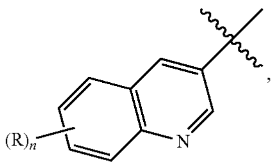,
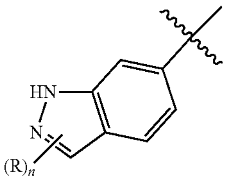,
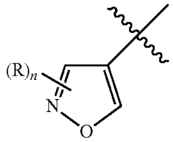,
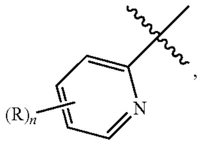, -continued

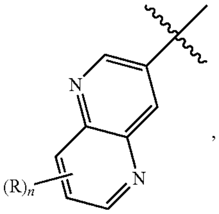,
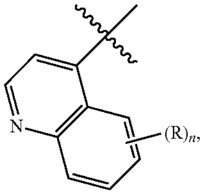,
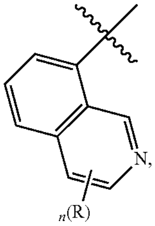
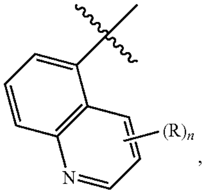,
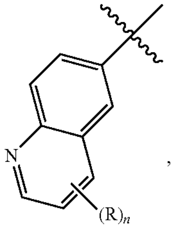,
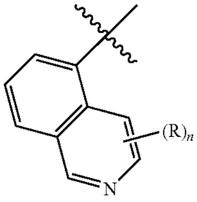, and
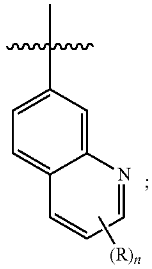;

alternatively, structural unit

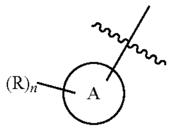

is selected from the group consisting of

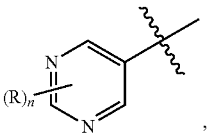,
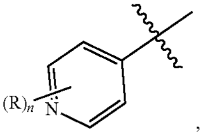,
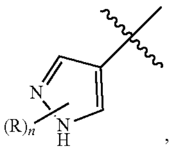,
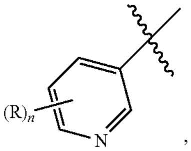,
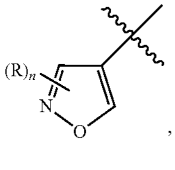, and
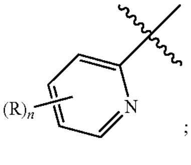;

alternatively, structural unit

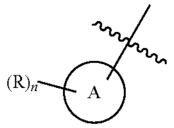

is selected from the group consisting of

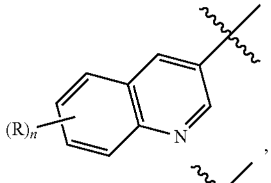 , 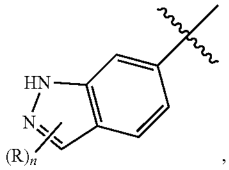 , 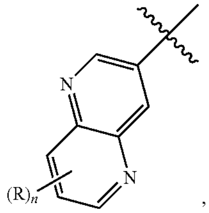 , 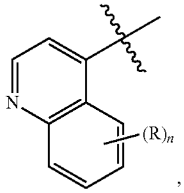 , 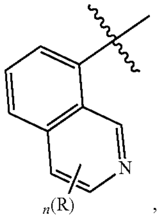 , 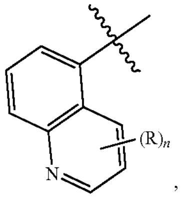 , 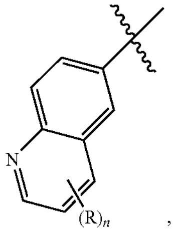 , 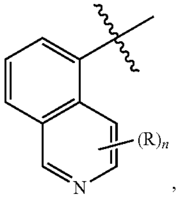 , and 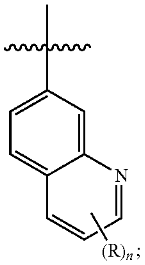 ;

alternatively, structural unit

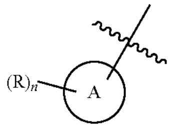

is selected from

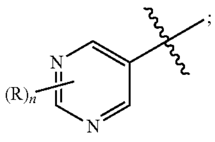 ;

alternatively, structural unit

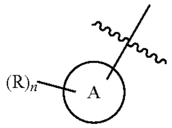

is selected from

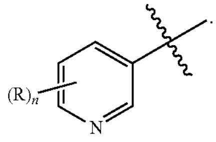 .

9. The compound of formula I, the pharmaceutically acceptable salt thereof, or the stereoisomer thereof according to claim 1, wherein structural unit

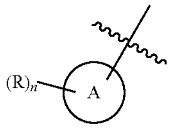

is selected from the group consisting of

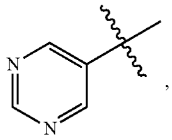 , 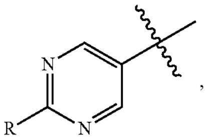 , 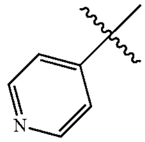 , 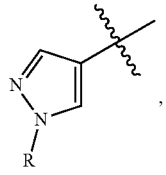 , 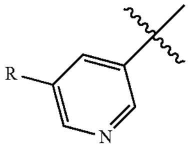 , 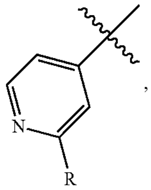 , 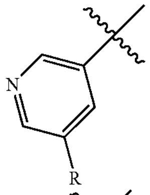 , 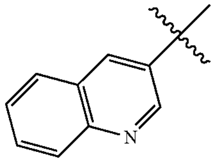 , 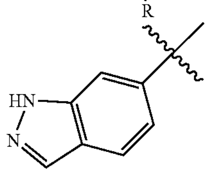 , 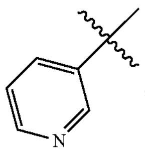 , 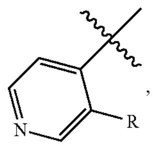 , 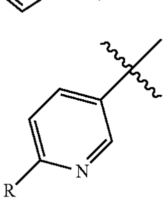 , 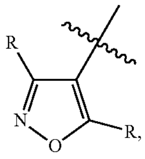 , 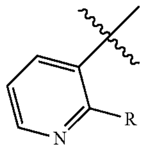 , -continued
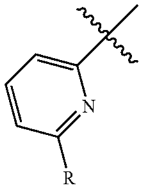, 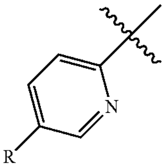, 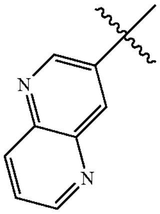,
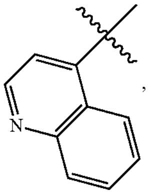, 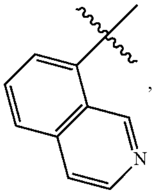, 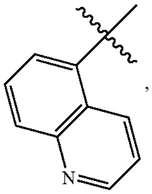,
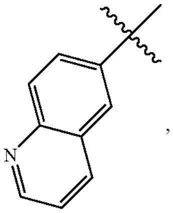, 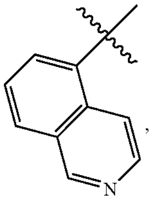, and 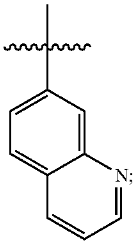;
optionally, structural unit
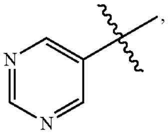,
is selected from the group consisting of
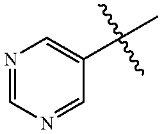, 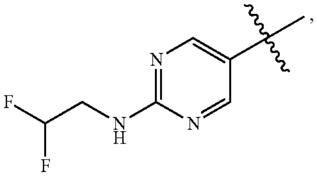,
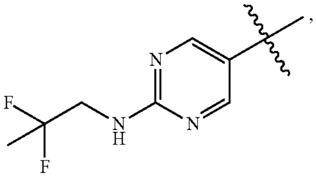,
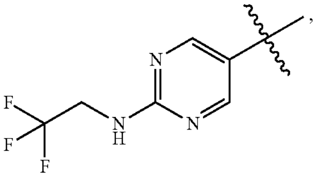,
-continued
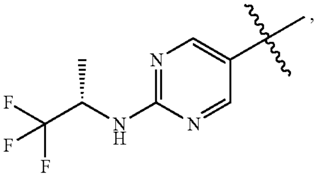,
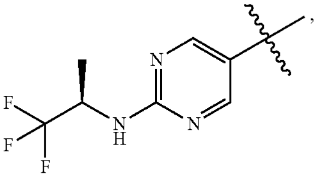,
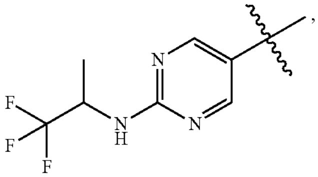, 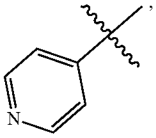,
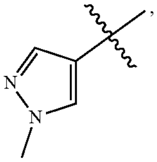, 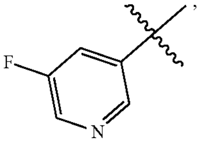, 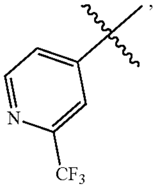,
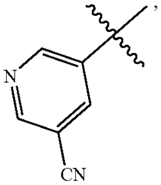, 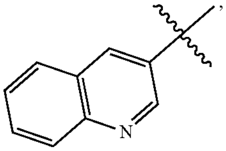,
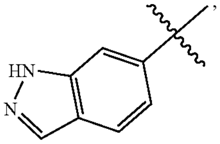, 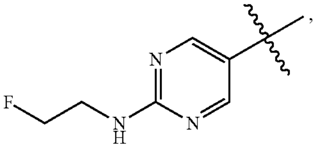,
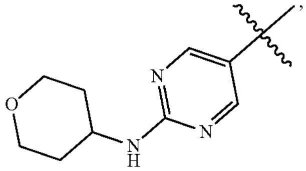,
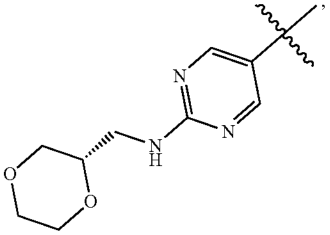, -continued
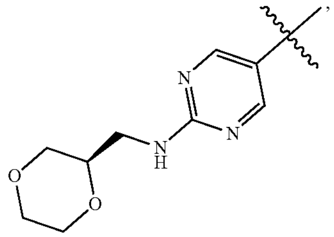
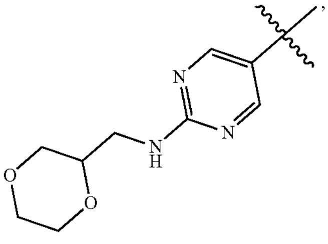
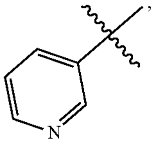
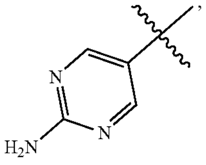
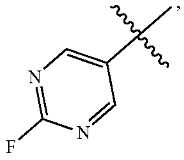
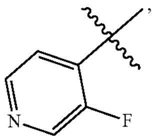
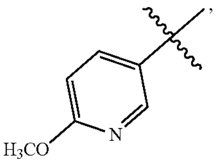
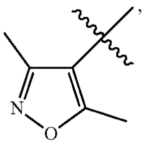
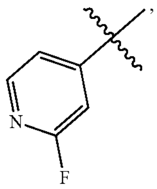
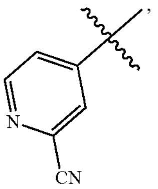
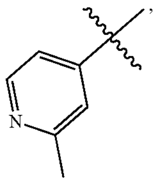
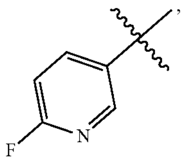
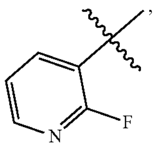
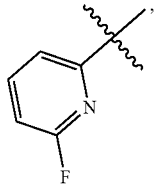
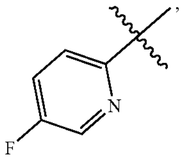
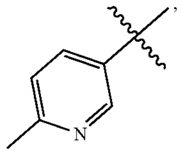
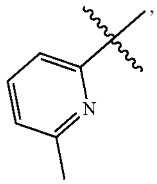
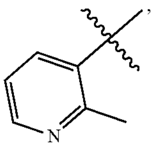
-continued
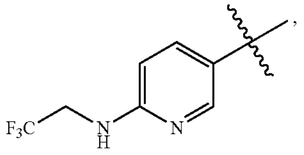
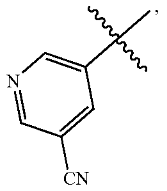
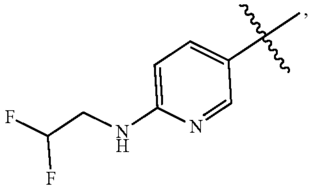
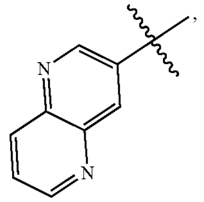
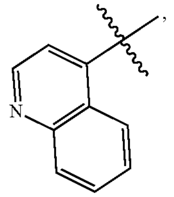
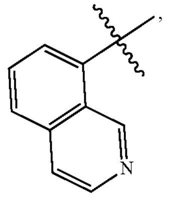
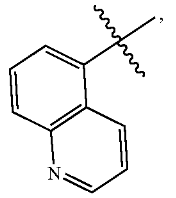
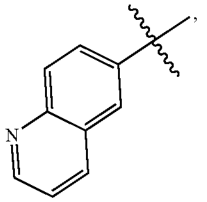
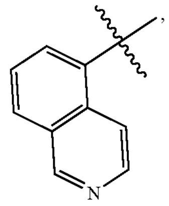
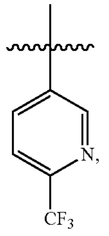
and
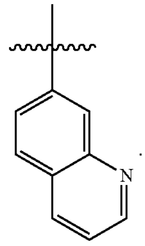
.
10. The compound of formula I, the pharmaceutically acceptable salt thereof, or the stereoisomer thereof according to claim 1, being selected from the group consisting of a compound of formula I-1 and a compound of formula I-2, a pharmaceutically acceptable salt thereof, or a stereoisomer thereof,
I-1
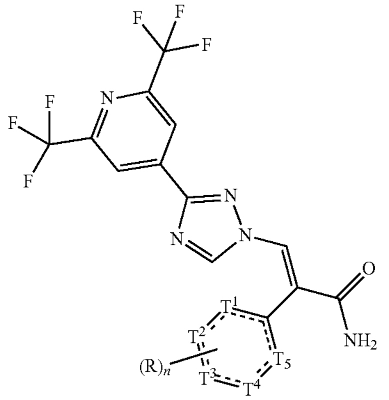

-continued

I-2

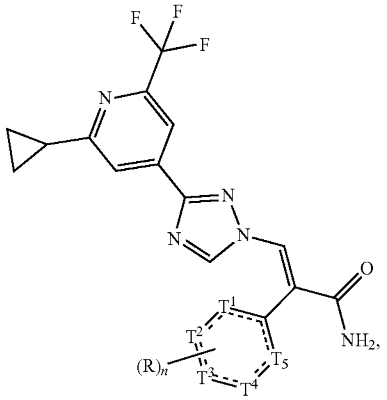

wherein $T^1$, $T^2$, $T^3$, $T^4$, and $T^5$ are each independently selected from the group consisting of a bond, O, S, N, and CH, no more than one of which is selected from a bond and at least one of which is selected from N;

 represents a single bond or a double bond;

optionally, $T^1$, $T^2$, $T^3$, $T^4$, and $T^5$ are each independently selected from the group consisting of N and CH, at least one of which is selected from N;

alternatively, $T^2$ and $T^4$ are selected from N, and $T^1$, $T^3$, and $T^5$ are selected from CH;

alternatively, $T^3$ is selected from N, and $T^1$, $T^2$, $T^4$, and $T^5$ are selected from CH;

alternatively, $T^2$ is selected from N, and $T^1$, $T^3$, $T^4$, and $T^5$ are selected from CH.

11. The compound of formula I, the pharmaceutically acceptable salt thereof, or the stereoisomer thereof according to claim 10, wherein structural unit

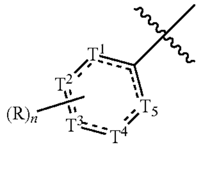

is selected from

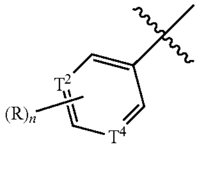
;

alternatively, structural unit

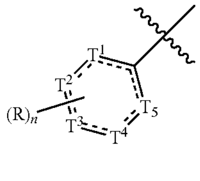

is selected from the group consisting of

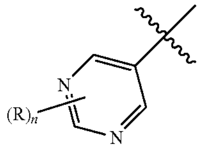
,
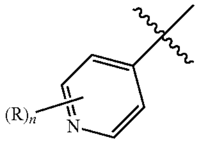
,
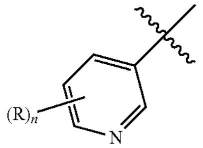
,
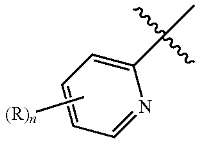
,
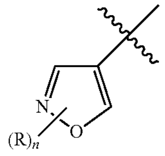
, and
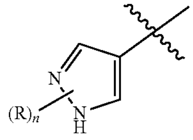
;

alternatively, structural unit

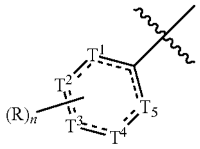

is selected from the group consisting of

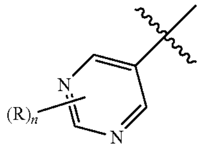
,
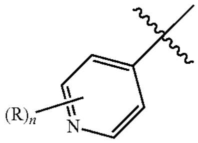
,
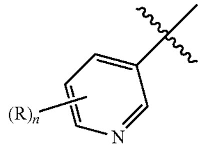
, and
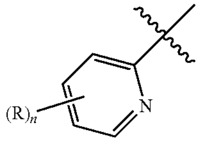
;

alternatively, structural unit

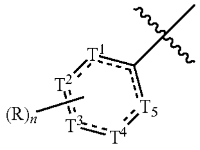

is selected from

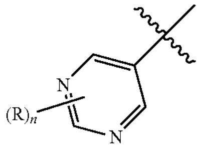
;

alternatively, structural unit
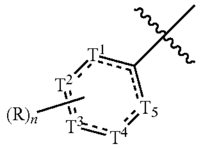
is selected from
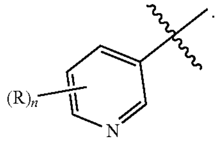
12. Compounds, pharmaceutically acceptable salts thereof, or stereoisomers thereof as follows:
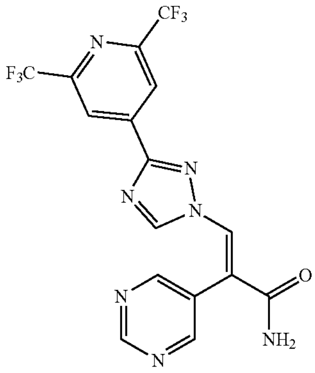
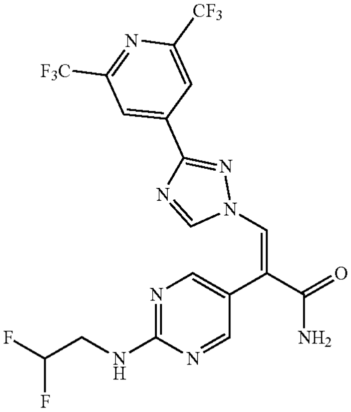
-continued
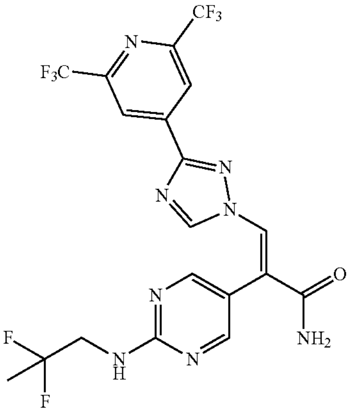
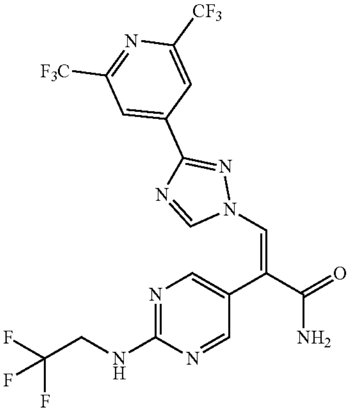
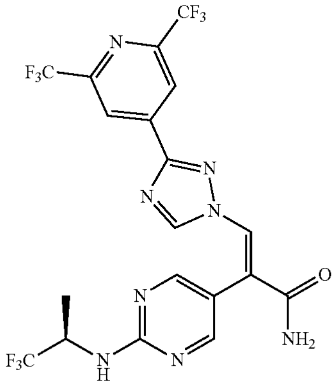
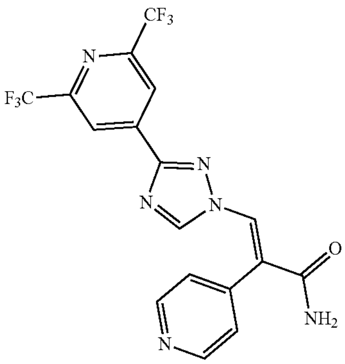

-continued
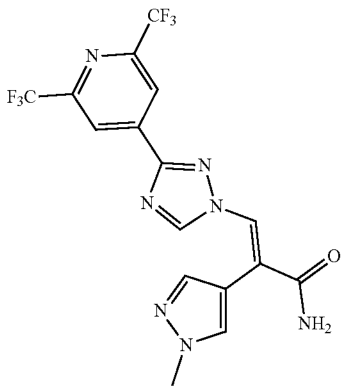
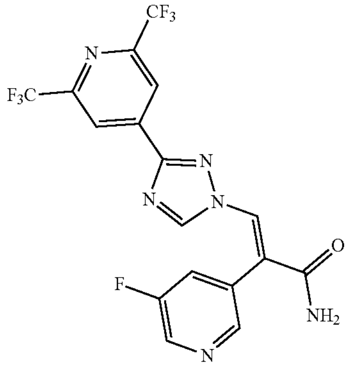
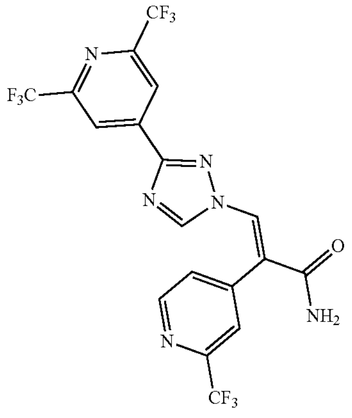
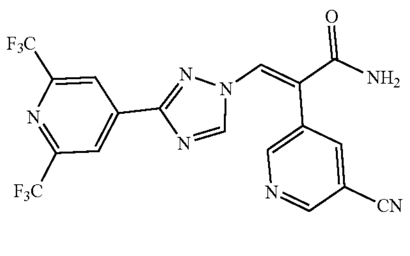
-continued
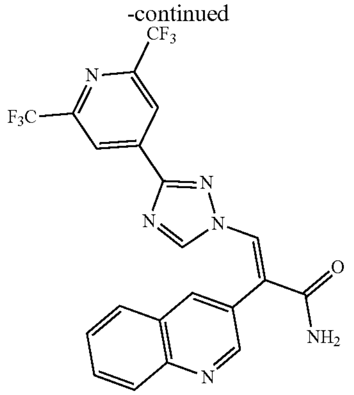
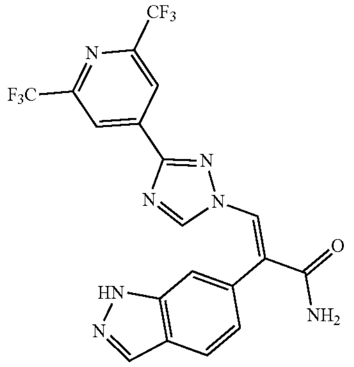
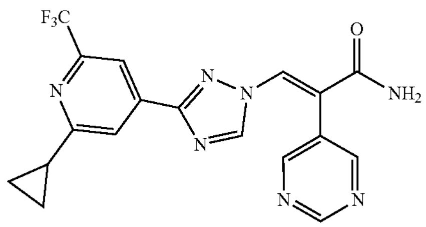
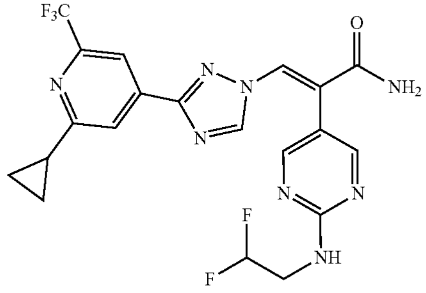
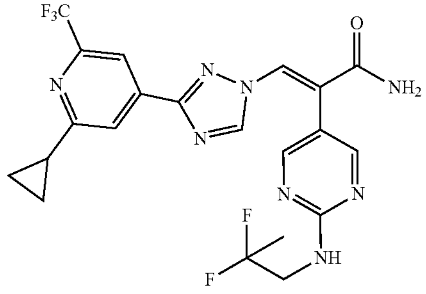

-continued
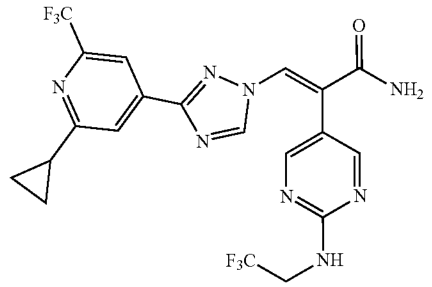
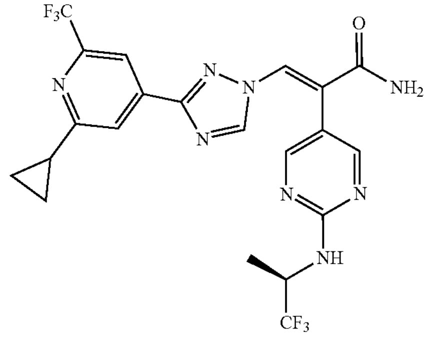
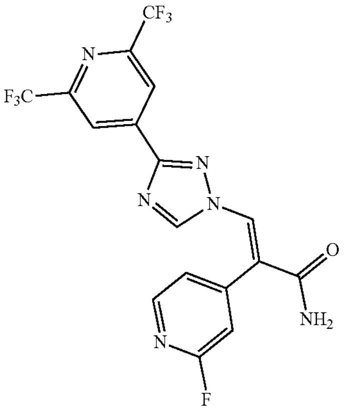
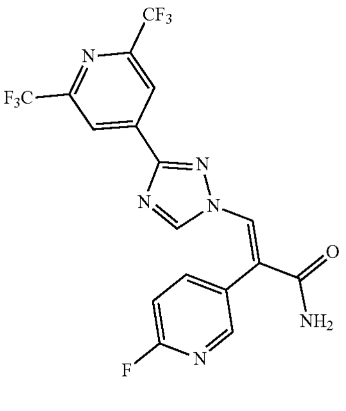
-continued
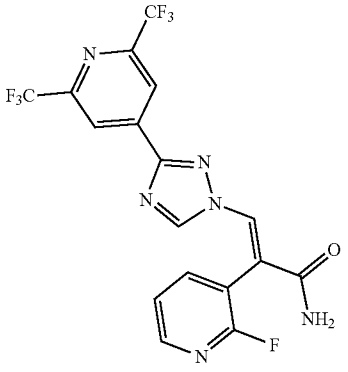
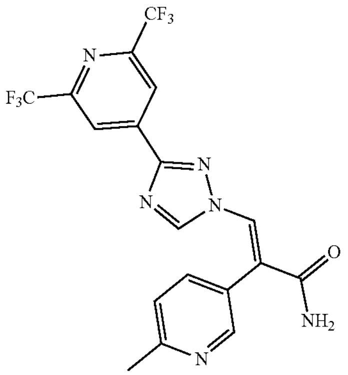
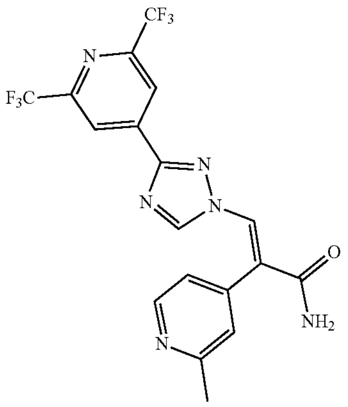
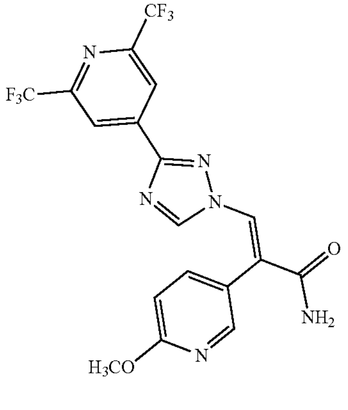

-continued
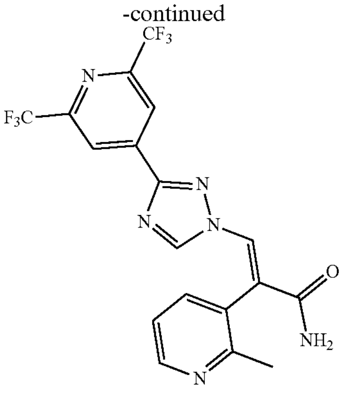
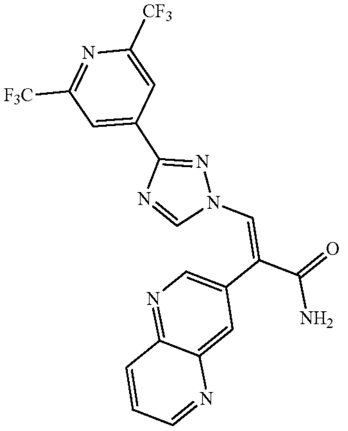
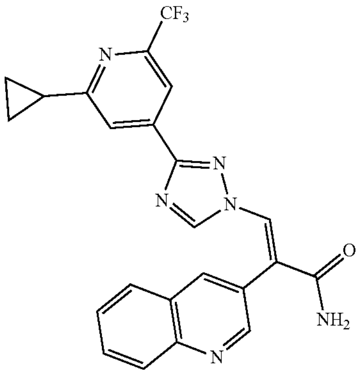
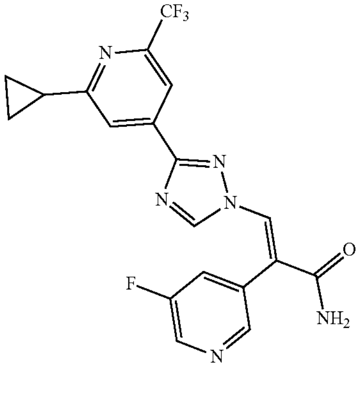
-continued
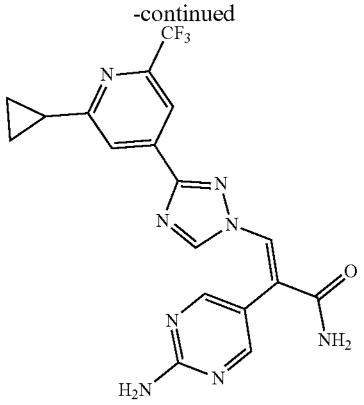
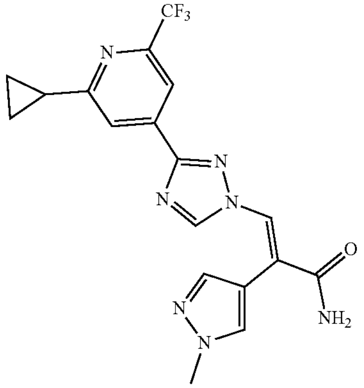
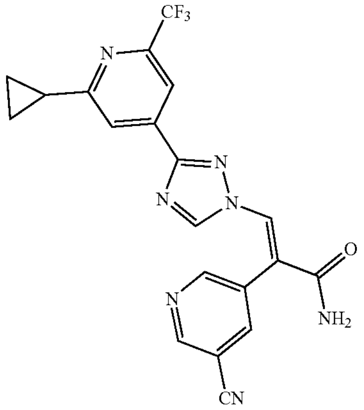
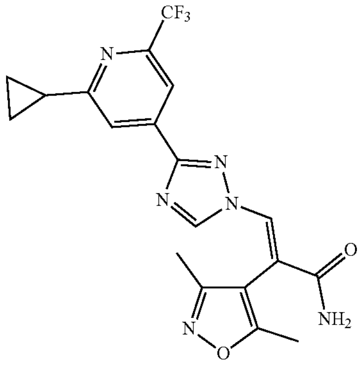

-continued
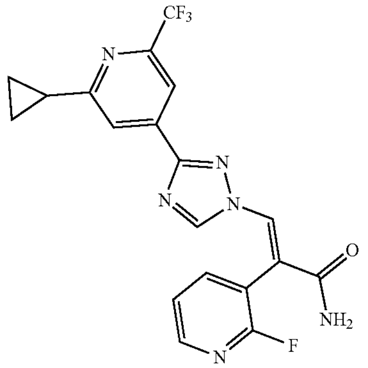
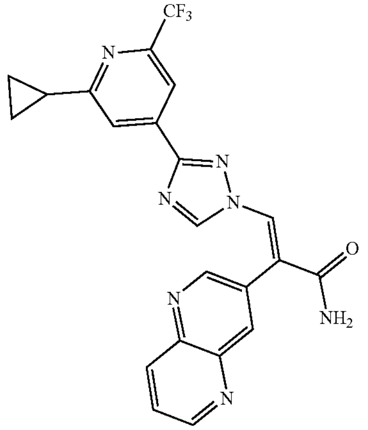
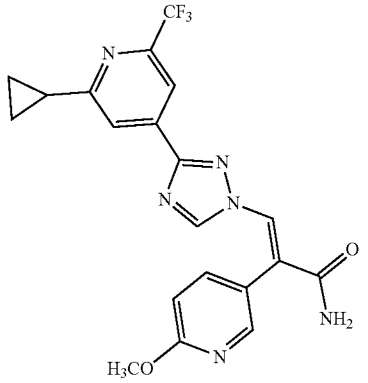
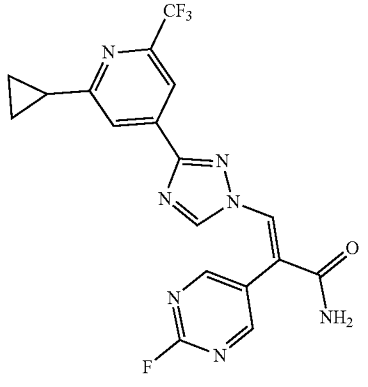
-continued
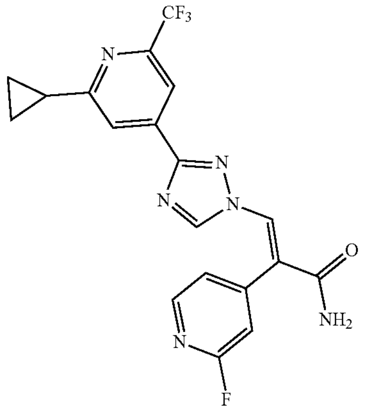
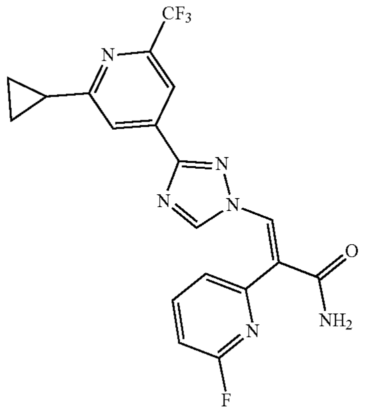
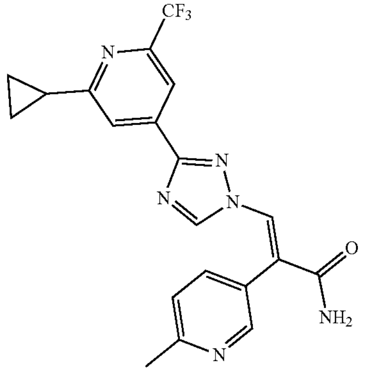
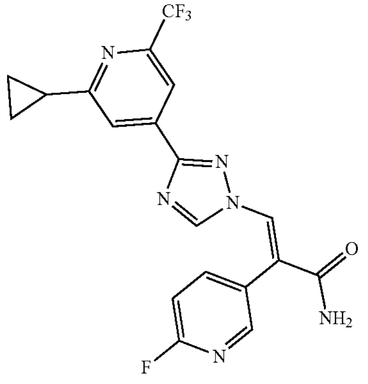

-continued
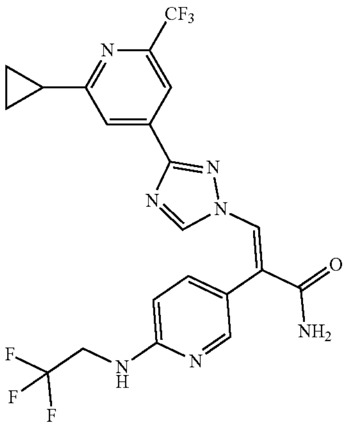
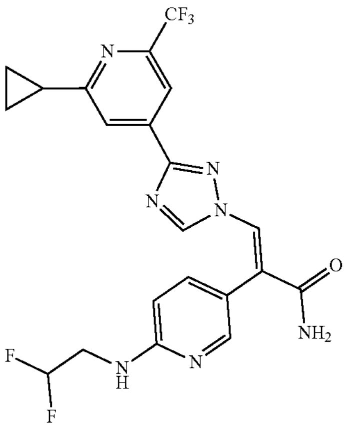
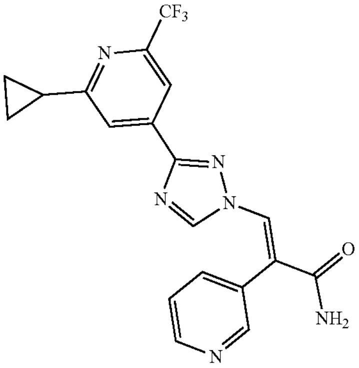
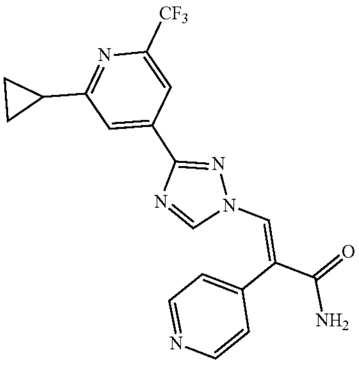
-continued
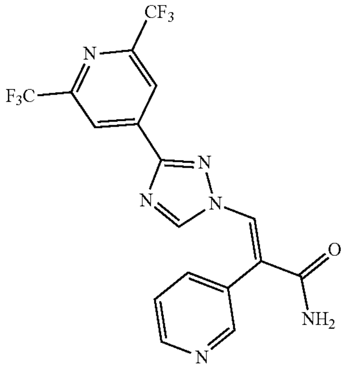
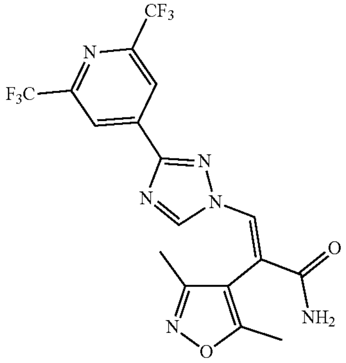
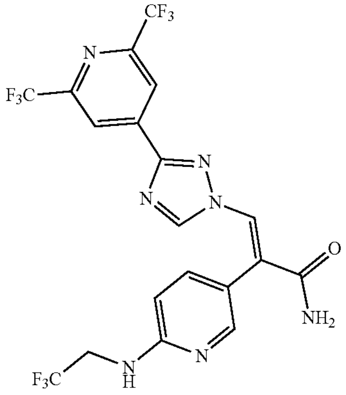
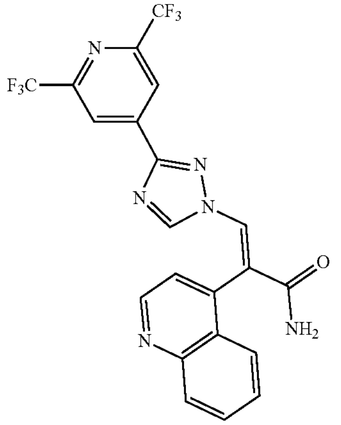

-continued
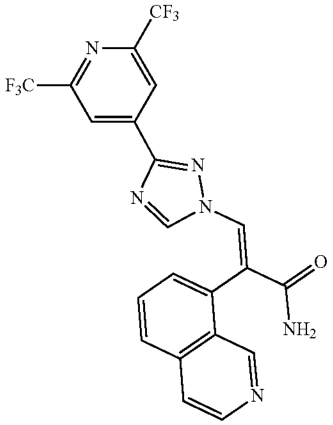
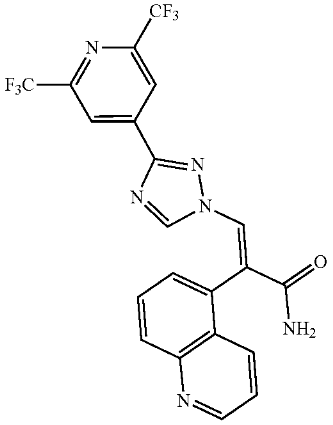
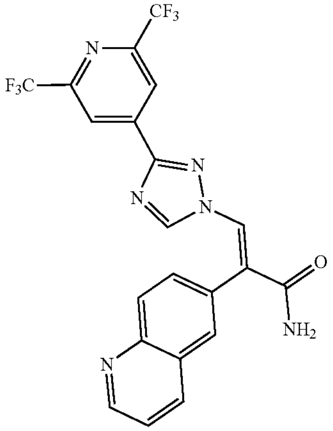
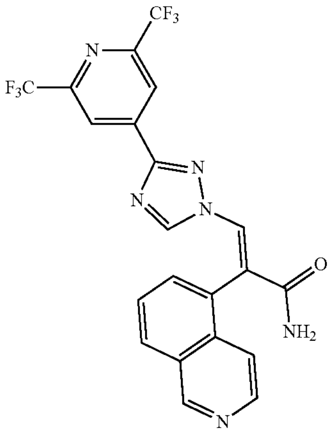
-continued
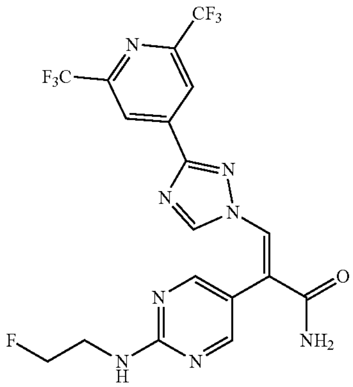
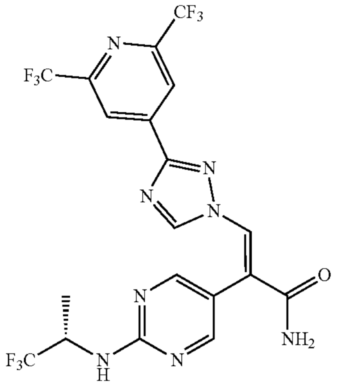
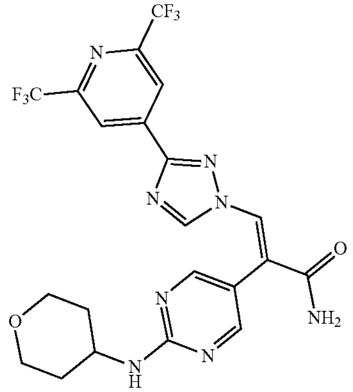
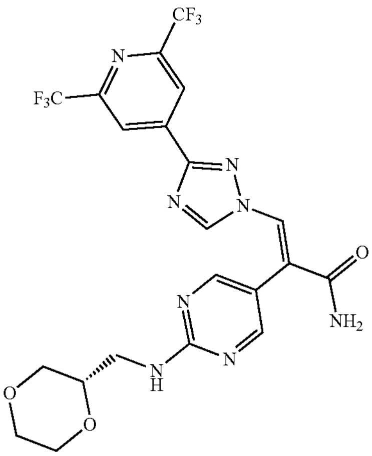

-continued
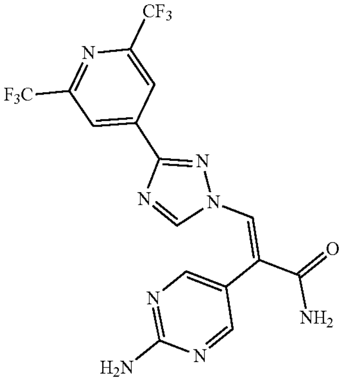
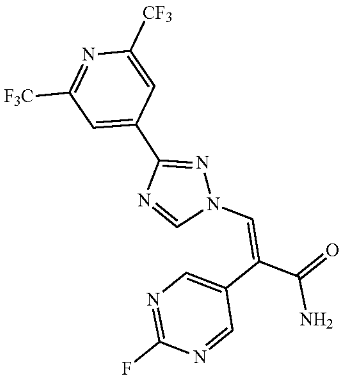
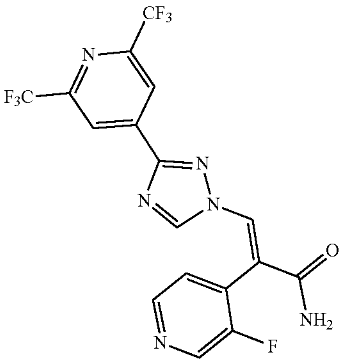
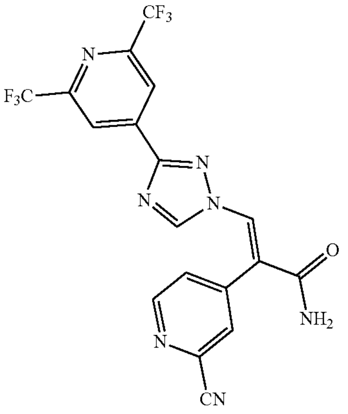
-continued
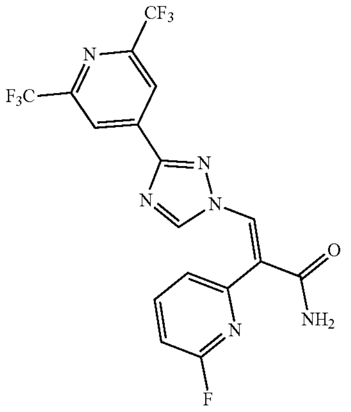
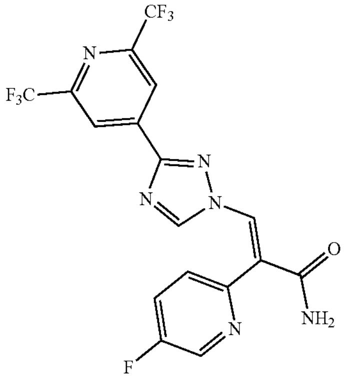
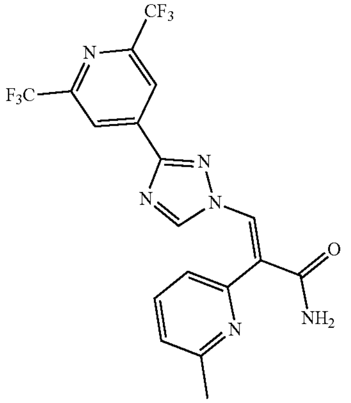
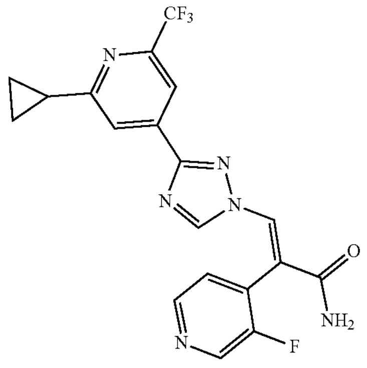

-continued
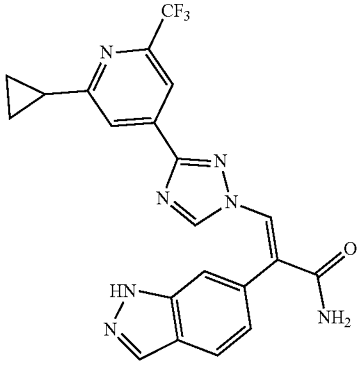
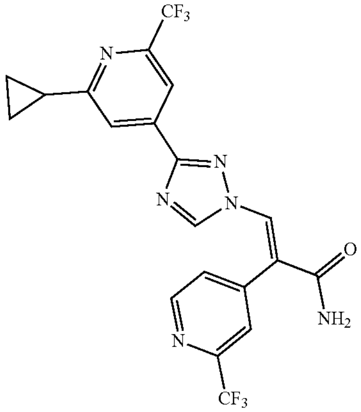
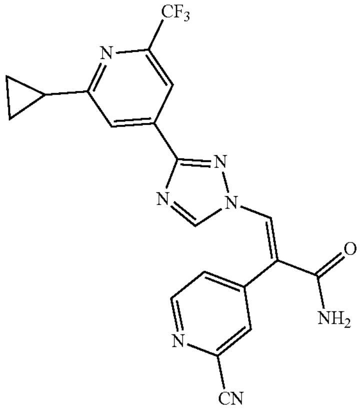
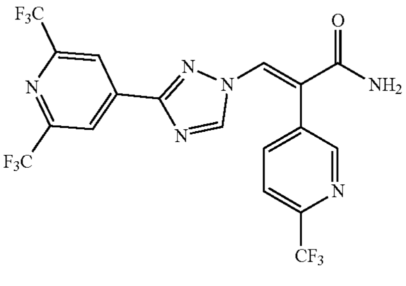
-continued
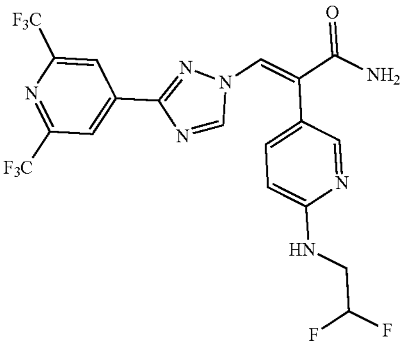
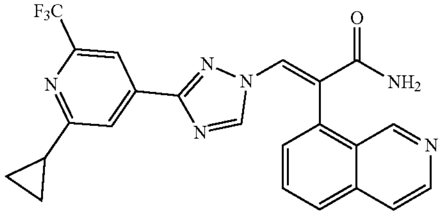
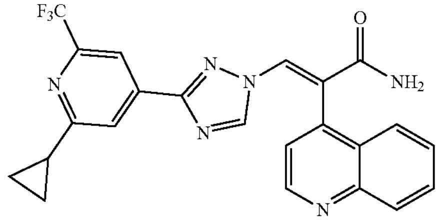
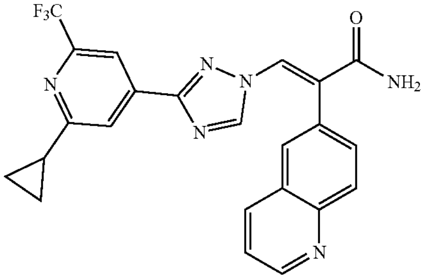
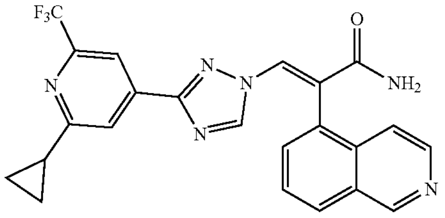
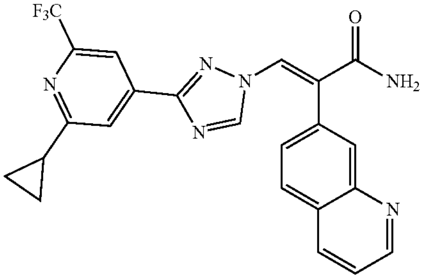

-continued

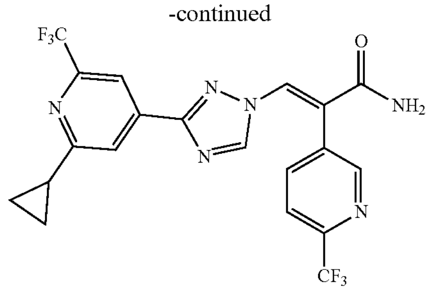

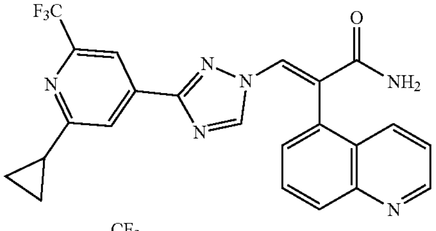

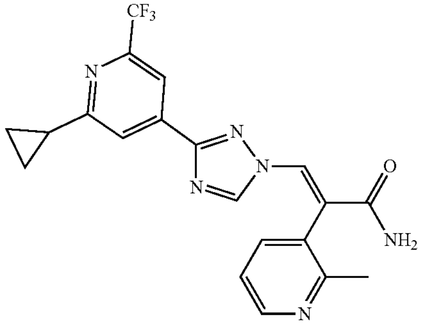

or

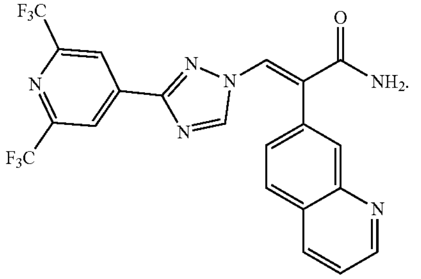

13. A pharmaceutical composition, comprising the compound, the pharmaceutically acceptable salt thereof, or the stereoisomer thereof according to claim 1.

14. A method for treating various XPO-1-related diseases, comprising administering a therapeutically effective amount of the compound, the pharmaceutically acceptable salt thereof, or the stereoisomer thereof according to claim 1 to a mammal;

optionally, the various XPO-1-related diseases are selected from the group consisting of tumors;

alternatively, the various XPO-1-related diseases are selected from the group consisting of leukemia and lymphoma.

15. The compound of formula I, the pharmaceutically acceptable salt thereof, or the stereoisomer thereof according to claim 2, wherein $R^1$ is selected from $—NH_2$.

16. The compound of formula I, the pharmaceutically acceptable salt thereof, or the stereoisomer thereof according to claim 3, wherein ring A is selected from a 6-membered heteroaromatic ring group.

17. The compound of formula I, the pharmaceutically acceptable salt thereof, or the stereoisomer thereof according to claim 1, wherein R is selected from the group consisting of fluorine, CN, $NH_2$, methyl, methoxy, trifluoromethyl,

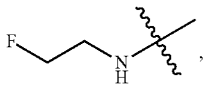 , 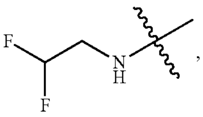 ,

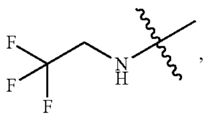 , 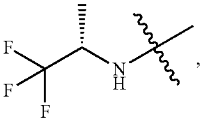 ,

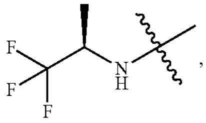 , 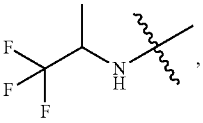 ,

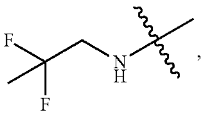 , 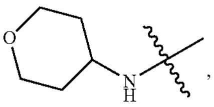 ,

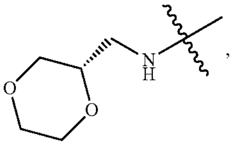 , 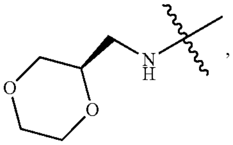 , and

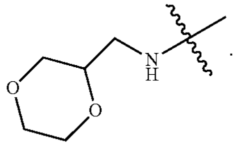 .

18. The compound of formula I, the pharmaceutically acceptable salt thereof, or the stereoisomer thereof according to claim 5, wherein $R^a$ is selected from the group consisting of $FCH_2CH_2—$, $F_2CHCH_2—$, $F_3CCH_2—$, $CF_3CH(CH_3)—$, $CH_3CF_2CH_2—$, tetrahydropyranyl, and dioxane $—CH_2—$.

19. The compound of formula I, the pharmaceutically acceptable salt thereof, or the stereoisomer thereof according to claim 1, wherein structural unit

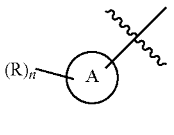

is selected from the group consisting of

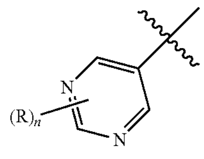 , 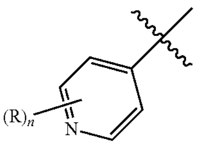 ,

-continued
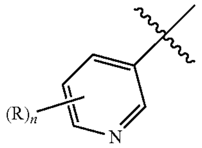
, and
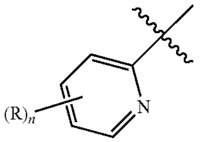
.
20. The compound of formula I, the pharmaceutically acceptable salt thereof, or the stereoisomer thereof according to claim 10, wherein structural unit
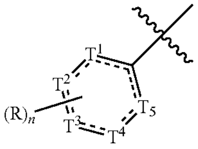
is selected from
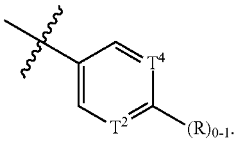
.
* * * * *